(12) United States Patent
Cai et al.

(10) Patent No.: US 10,676,468 B2
(45) Date of Patent: Jun. 9, 2020

(54) N-(3-HETEROARYLARYL)-4-ARYLARYL CARBOXAMIDES AND ANALOGS AS HEDGEHOG PATHWAY INHIBITORS AND USE THEREOF

(71) Applicant: IMPACT Therapeutics, Inc., Nanjing (CN)

(72) Inventors: Suixiong Cai, Jaingsu (CN); Ye Edward Tian, Jiangsu (CN); Sishun Kang, Jiangsu (CN); Zheng Meng, Jiangsu (CN); Chengyun Gu, Jiangsu (CN); Feng Yin, Jiangsu (CN); Shengzhi Chen, Jiangsu (CN); Yang Zhang, Jiangsu (CN); Xiuyan Zhang, Jiangsu (CN); Hongqiang Fei, Jiangsu (CN); Dongmei Wang, Jiangsu (CN)

(73) Assignee: Impact Therapeutics, Inc., Nanjing (CN)

( * ) Notice: Subject to any disclaimer, the term of this patent is extended or adjusted under 35 U.S.C. 154(b) by 277 days.

(21) Appl. No.: 14/415,293

(22) PCT Filed: Jul. 19, 2013

(86) PCT No.: PCT/CN2013/079651
§ 371 (c)(1),
(2) Date: Jan. 16, 2015

(87) PCT Pub. No.: WO2014/012511
PCT Pub. Date: Jan. 23, 2014

(65) Prior Publication Data
US 2015/0191460 A1 Jul. 9, 2015

(30) Foreign Application Priority Data

Jul. 19, 2012 (CN) .......................... 2012 1 0250565
Nov. 21, 2012 (CN) .......................... 2012 1 0475189

(51) Int. Cl.
*C07D 413/14* (2006.01)
*C07D 401/10* (2006.01)
(Continued)

(52) U.S. Cl.
CPC ........ *C07D 413/14* (2013.01); *A61K 31/4184* (2013.01); *A61K 31/454* (2013.01); *A61K 31/4725* (2013.01); *A61K 31/517* (2013.01); *A61K 31/536* (2013.01); *A61K 31/5377* (2013.01); *A61K 45/06* (2013.01); *C07D 213/40* (2013.01); *C07D 233/64* (2013.01); *C07D 235/18* (2013.01); *C07D 401/04* (2013.01); *C07D 401/10* (2013.01); *C07D 401/12* (2013.01); *C07D 401/14* (2013.01);

*C07D 403/10* (2013.01); *C07D 403/12* (2013.01); *C07D 405/12* (2013.01); *C07D 409/04* (2013.01); *C07D 409/12* (2013.01); *C07D 413/10* (2013.01); *C07D 413/12* (2013.01);
(Continued)

(58) Field of Classification Search
CPC .. C07D 413/14; C07D 213/40; C07D 233/64; C07D 235/18; C07D 401/04; C07D 401/10; C07D 401/12; C07D 401/14; C07D 403/10; C07D 403/12; C07D 405/12; C07D 409/04; C07D 409/12; C07D 413/10; C07D 413/12; C07D 471/04; C07D 487/04; A61K 31/4184; A61K 31/454; A61K 31/4725; A61K 31/517; A61K 31/536; A61K 31/5377; A61K 45/06
See application file for complete search history.

(56) References Cited

U.S. PATENT DOCUMENTS 7,888,364 B2   2/2011   Gunzner et al.
7,928,133 B2   4/2011   Cheng et al.
(Continued)

FOREIGN PATENT DOCUMENTS

CN   101072755 A   11/2007
CN   101501004 A   8/2009
(Continued)

OTHER PUBLICATIONS

STN entry for CAS RN 334502-04-4, entry date May 3, 2001.*
(Continued)

*Primary Examiner* — Rachael E Bredefeld
*Assistant Examiner* — Ibrahim D Bori
(74) *Attorney, Agent, or Firm* — Sterne, Kessler, Goldstein & Fox P.L.L.C.

(57) ABSTRACT

Disclosed are novel N-(3-heteroarylaryl)-4-arylarylcarboxamides and analogs thereof, represented by the Formula I: wherein C cyclic group, $D_1$-$D_4$, $Q_1$, $Q_2$, $R_5$ are defined herein. Compounds having Formula (I) are hedgehog pathway inhibitors. Therefore, compounds of the invention may be used to treat clinical conditions that are responsive to the inhibition of hedgehog activity, such as cancer.

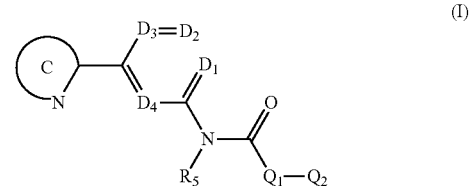

17 Claims, No Drawings

(51) Int. Cl.
| | |
|---|---|
| *C07D 235/18* | (2006.01) |
| *C07D 403/10* | (2006.01) |
| *C07D 413/10* | (2006.01) |
| *C07D 409/04* | (2006.01) |
| *C07D 401/04* | (2006.01) |
| *C07D 487/04* | (2006.01) |
| *C07D 409/12* | (2006.01) |
| *C07D 401/14* | (2006.01) |
| *C07D 401/12* | (2006.01) |
| *C07D 471/04* | (2006.01) |
| *C07D 233/64* | (2006.01) |
| *C07D 213/40* | (2006.01) |
| *C07D 403/12* | (2006.01) |
| *C07D 413/12* | (2006.01) |
| *C07D 405/12* | (2006.01) |
| *A61K 31/4184* | (2006.01) |
| *A61K 31/454* | (2006.01) |
| *A61K 31/4725* | (2006.01) |
| *A61K 31/517* | (2006.01) |
| *A61K 31/536* | (2006.01) |
| *A61K 31/5377* | (2006.01) |
| *A61K 45/06* | (2006.01) |

(52) U.S. Cl.
  CPC ......... *C07D 471/04* (2013.01); *C07D 487/04* (2013.01)

(56) References Cited

U.S. PATENT DOCUMENTS

| | | | |
|---|---|---|---|
| 8,486,945 | B2 | 7/2013 | Ivashchenko et al. |
| 2009/0281089 | A1* | 11/2009 | Gunzner .............. C07D 213/06 514/218 |
| 2010/0317699 | A1 | 12/2010 | Armstrong et al. |
| 2011/0053915 | A1 | 3/2011 | Ivaschenko et al. |
| 2012/0277233 | A1 | 11/2012 | Tao et al. |
| 2013/0045240 | A1 | 2/2013 | Tao et al. |

FOREIGN PATENT DOCUMENTS

| | | |
|---|---|---|
| CN | 101932313 A | 12/2010 |
| CN | 102573487 A | 7/2012 |
| CN | 102573832 A | 7/2012 |
| TW | 200916458 A | 4/2009 |
| WO | WO 2008/154259 A1 | 12/2008 |
| WO | WO 2009/027746 A1 | 3/2009 |
| WO | WO 2009/030952 A2 | 3/2009 |
| WO | WO2009/033281 * | 3/2009 |
| WO | WO-2009030952 A2 * | 3/2009 ........... C07D 471/04 |
| WO | WO 2009/077956 A2 | 6/2009 |
| WO | WO-2010144404 A1 * | 12/2010 ........... C07D 401/04 |
| WO | WO 2011/014888 A1 | 2/2011 |
| WO | WO 2011/025838 A1 | 3/2011 |
| WO | WO 2012/034363 A1 | 3/2012 |

OTHER PUBLICATIONS

STN entry for CAS RN 1279044-94-8 (entry date Apr. 12, 2011).*
STN entry for CAS RN 1389623-39-5 (entry date Aug. 12, 2012).*
RN1279044-94-8 (Year: 2011).*
RN1389623-39 (Year: 2012).*
DeSmaele, E. et al., "Vismodegib, a small-molecule inhibitor of the Hedgehog pathway for the treatment of advanced cancers," *Curr. Opin. Investig. Drugs* 11:707-718, Thomson Reuters (Scientific) Ltd., United Kingdom (2010).
Fukushima, N. et al., "Small-molecule Hedgehog inhibitor attenuates the leukemia-initiation potential of acute myeloid leukemia cells," *Cancer Sci.* 107:1422-1429, John Wiley & Sons Australia, Ltd. (2016).
Geng, L. and Wang, X., "New insight into hedgehog signaling in hematological malignancies," *Leuk. Lymphoma* 56:858-865, Informa Healthcare, United Kingdom (2014).
Goldgerg, L.H. et al., "Resolution of Odontogenic Keratocysts of the Jaw in Basal Cell Nevus Syndrome With GDC-0449," *Arch. Dermatol.* 147:839-841, American Medical Association (2011).
Gonnissen, A. et al., "Targeting the Hedgehog signaling pathway in cancer: beyond Smoothened," *Oncotarget* 6:13899-13913, Impact Journals, United States of America (2015).
Hui, M. et al., "The Hedgehog signaling pathway in breast development, carcinogenesis and cancer therapy," *Breast Cancer Res.* 15:203-216, BioMed Central Ltd., United Kingdom (2013).
LoRusso, P.M. et al., "Phase I Trial of Hedgehog Pathway Inhibitor Vismodegib (GDC-0449) in Patients with Refractory, Locally Advanced or Metastatic Solid Tumors," *Clin. Cancer Res.* 17:2502-2511, American Association for Cancer Research (2011).
Suzman, D.L. and Antonarakis, E.S., "Clinical Implications of Hedgehog Pathway Signaling in Prostate Cancer," *Cancers (Basel)* 7:1983-1993, MDPI, Switzerland (2015).
Xie, J. et al., "Targeting hedgehog signaling in cancer: research and clinical developments," *Onco Targets Ther.* 6:1425-1435, Dove Medical Press Limited, New Zealand (2013).

* cited by examiner

N-(3-HETEROARYLARYL)-4-ARYLARYL CARBOXAMIDES AND ANALOGS AS HEDGEHOG PATHWAY INHIBITORS AND USE THEREOF

BACKGROUND OF THE INVENTION

Field of the Invention

This invention is in the field of medicinal chemistry. In particular, the invention relates to N-(3-heteroarylaryl)-4-arylarylcarboxamides and analogs, and the use of these compounds as hedgehog pathway inhibitors and anti-cancer drugs.

Related Art

The hedgehog (Hh) proteins, a highly conserved protein family, were originally discovered in *Drosophila* and play a paramount role in the proper development of the embryo. Regarding to human, the mammalian homologues of Hh proteins include mainly three genes, Sonic hedgehog (Shh), Indian hedgehog (Ihh) and Desert hedgehog (Dhh). Of these, Shh not only is important in embryonic development, but also has been suggested to be involved in tumor genesis including basal cell carcinoma (BCC) (Caro, I. and Low, J. A., Clin Cancer Res, 2010, 16(13): 3335-9). Shh protein is produced from an approximately 45 kDa precursor. After processing, a 20 kDa N-terminal fragment is produced and this N-terminal fragment has all of the known biological activity of Shh. Although the detailed mechanism to cause cancer has not been fully understood, it is known that Shh can activate intracellular hedgehog signaling pathway that includes the following components, patched (PTCH), a 7-transmembrane G-protein coupled receptor Smoothened (SMO) as well as transcription factor Gli, etc. (Bale, A. E. and Yu, K. P., Hum Mol Genet, 2001, 10(7): 757-62). The results from mutation analysis of the Hh signal pathway in basal cell carcinoma indicate that most of the mutations occur at PTCH-1 and SMO (Von Hoff, D. D.; et al., N Engl J Med, 2009, 361(12): 1164-72). PTCH-1 is a membrane protein with a 12-transmembrane structure and it is the direct receptor of Shh. In the absence of Shh, PTCH-1 interacts with SMO and inhibits the biological activity of SMO. The binding of Shh to PTCH-1 leads to the dissociation of PTCH-1 from SMO, resulting in a dis-inhibition of SMO. The transcription factor Gli is under the control of SMO and plays an important role in turning on a transcription event. Three most important members of the Gli family include Gli1, Gli2 and Gli3. The Hh signal pathway is critically important for embryonic development. Interference of the Hh signal pathway would result in severe birth defect such as cyclopia. For example, a natural teratogenic compound cyclopamine is an Hh signal pathway inhibitor. Under normal condition, the Hh concentration is very low in adult human. Due to the low concentration of Hh, PTCH-1 binds to SMO and inhibits the activity of SMO. Therefore, the Hh signalling pathway has very low activity. When cells start to produce Hh, the secreted Hh binds to its receptor PTCH-1 and results a dissociation of PTCH-1 from SMO to remove the inhibition on SMO. The activated SMO, in turn activates transcription factor Gli-1 that regulates gene transcription and cell growth. More and more evidence indicate that most of the basal cell carcinoma is caused by mutations or other changes that cause high activity of the hedgehog signaling pathway. Therefore, inhibition of hedgehog signaling pathway may stop the growth of cancer cells, resulting to a therapeutic treatment of basal cell carcinoma and other cancers caused by similar mechanism. Series of scientific and clinic evidence indicate that hedgehog pathway inhibitors can be effectively used to treat cancers. The most recent clinical results have shown that hedgehog pathway inhibitor GDC-0449 can be used to treat basal cell carcinoma, medulloblastoma (Lorusso, P. M.; et al., Clin Cancer Res, 2011, 17(8): 2502-11) or other cancers that are caused by similar mechanisms such as basal cell nevus syndrome (BCNS) effectively (Goldberg, L. H.; et al., Arch Dermatol, 2011, 147(7): 839-41). On March of 2012, FDA approved GDC-0449 as a new targeted therapy to treat basal cell carcinoma, which validated the feasibility of using hedgehog pathway inhibitors to treat cancer. The results from biochemical research suggest that GDC-0449 interacts with SMO directly to inhibit the activity of SMO that leads to the inhibition of the entire hedgehog signaling pathway, therefore the inhibition of cancer cell growth. In addition to basal cell carcinoma and medulloblastoma there are many other cancers that are caused by high activity in hedgehog signaling pathway, such as pancreatic, gastro-intestinal, colorectal, ovarian, prostate cancers and some blood abnormality (De Smaele, E.; et al., Curr Opin Investig Drugs, 2010, 11(6): 707-18). Therefore, development of hedgehog pathway inhibitors as new type of therapeutic treatment of cancer has a great future.

Hedgehog signaling pathway is critically important for the pluripotent mesenchymal mouse embryonic cell C3H10T1/2 to differentiate into osteoblastic cells. The differentiation of C3H10T1/2 cells into osteoblastic cells accompanies with a dramatic increase in intracellular alkaline phosphatase activity which can be readily measured. Inhibition of the hedgehog signaling pathway activity can be measured as a decrease in alkaline phosphatase activity. Therefore, stimulating the hedgehog signaling pathway and measuring the alkaline phosphatase activity can be used to screen hedgehog pathway inhibitors (Peukert, S. and Miller-Moslin, K., Chem Med Chem, 2010, 5(4): 500-12; Tremblay, M. R.; et al., J Med Chem, 2009, 52(14): 4400-18).

WO2011010013 disclosed compound I [$R^{1-3}$ independently are hydrogen, halo, hydroxy, fluoroalkyl and the like; Y=monocyclic or polycyclic heteroaryl, $NHCOR^6$, $CONHR^6$, $NHCONHR^6$; $R^6$=alkyl, optionally substituted monocyclic or polycyclic heteroaryl, aryl and the like; $R^{4-5}$ independently are hydrogen, halo, alkoxy, alkylthio, nitro and the like], such as compound II, as hedgehog pathway inhibitors.

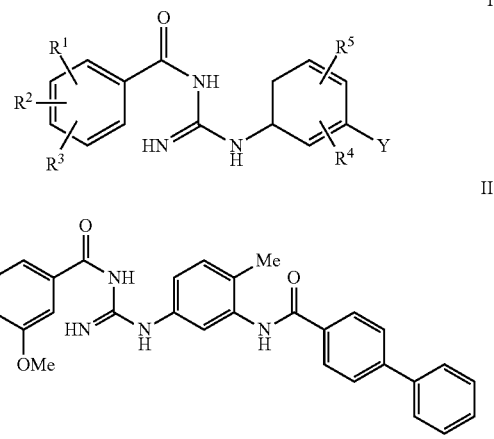

WO2008014291 disclosed compound I [n=0-2; Y¹=bond, CO; Y²=bond, CO, SO₂; R¹=hydrogen, halo, cyano, alkyl, haloalkyl; R²=hydrogen, halo, cyano, alkyl, alkoxy, haloalkyl, haloalkoxy, (substituted) aryl, arylalkyl, heteroaryl, heteroarylalkyl, cycloalkyl, cycloalkylalkyl, PhO; R³, R⁴=hydrogen, halo, cyano, alkyl, alkoxy, haloalkyl; R⁵=hydrogen, alkyl; L=phenylene, pyridinylene, naphthyridinylene, thiazolylene, (iso)quinolylene, benzothiazolylene, benzoxazolylene, benzisoxazolylene and the like] as hedgehog pathway inhibitors.

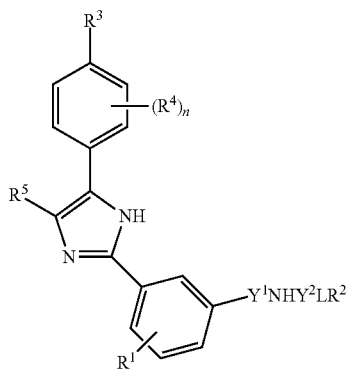

I

SUMMARY OF THE INVENTION

The invention provides novel N-(3-heteroarylaryl)-4-arylarylcarboxamides and analogs, as represented in Formulae I, II, III and IV. These compounds have hedgehog pathway inhibitory activities.

The present invention also provides pharmaceutical compositions comprising a compound of Formula I, II, III or IV in an effective amount for the treatment of cancer.

The invention also provides a pharmaceutical composition useful for the treatment of cancer, containing an effective amount of a compound of one of the Formula I, II, III or IV in admixture with one or more pharmaceutically acceptable carriers or diluents.

The invention also provides a pharmaceutical composition useful for the treatment of cancer, containing an effective amount of a compound of one of the Formula I, II, III or IV, in combination with at least one known anticancer drug or its pharmaceutically acceptable salts.

The invention also is directed to methods for the preparation of novel compounds of Formulae I, II, III and IV.

DETAILED DESCRIPTION OF THE INVENTION

The novel hedgehog pathway inhibitors of the present invention include N-(3-heteroarylaryl)-4-arylarylcarboxamides and analogs, as represented in Formulae I, II, III and IV.

Specifically, compounds of the present invention are represented by Formula I:

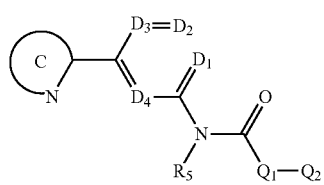

(I)

or pharmaceutically acceptable salts or prodrugs thereof, wherein:

C cyclic group is an optionally substituted nitrogen-containing heteroaryl;

$D_1$ is N or $CR_6$; $D_2$ is N or $CR_7$; $D_3$ is N or $CR_8$; $D_4$ is N or $CR_9$;

$Q_1$ and $Q_2$ independently are optionally substituted aryl, heteroaryl, a carbocyclic group, or a heterocyclic group;

$R_6$-$R_9$ independently are hydrogen, halo, optionally substituted amino, alkoxy, $C_{1-10}$ alkyl, $C_{3-8}$ cycloalkyl, haloalkyl, aryl, a carbocyclic group, a heterocyclic group, heteroaryl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, hydroxyalkoxy, aminoalkyl, aminoalkoxy, carboxyalkyl, carboxyalkoxy, nitro, cyano, acylamino, aminocarbonyl, hydroxy, thiol, acyloxy, azido, carboxy, hydroxyacylamino, alkylsulfonyl, aminosulfonyl, dialkylaminosulfonyl, alkylsulfinyl, or alkylthiol;

$R_5$ is hydrogen or $C_{1-10}$ alkyl, or $R_5$ is taken together with the N atom to which it is attached to, and other groups such as the carbon atom in C(=O) and an atom of $Q_1$ to form a heterocyclic ring.

One group of preferred compounds of Formula I includes compounds wherein the C cyclic group is an optionally substituted monocyclic or bicyclic nitrogen-containing heteroaryl. Another group of preferred compounds of Formula I includes compounds wherein the C cyclic group is an optionally substituted benzothiazolyl, pyridinyl, pyrazinyl, pyrimidinyl, pyridazinyl, indolyl, isoindolyl, 3H-indolyl, indolizinyl, indazolyl, purinyl, 4H-quinolizinyl, isoquinolyl, quinolyl, phthalzinyl, naphthyridinyl, acrindinyl, perimidinyl, phenanthrolinyl, phenazinyl, isothiazolyl, phenothiazinyl, oxazolyl, isoxazolyl, furazanyl, phenoxazinyl, 1,2-benzisoxazol-3-yl, imidazolyl, benzimidazolyl, 2-oxindolyl, thiadiazolyl, imidazo[4,5-c]pyridin-2-yl, [1,2,4]triazolo[4,3-a]pyridin-3-yl, [1,2,4]triazolo[4,3-a]pyrimidin-3-yl, [1,2,4]triazolo[4,3-a]pyrazin-3-yl, imidazo[1,2-a]pyrimidin-2-yl, imidazol[1,2-a]pyridin-2-yl, [1,2,3]triazolo[1,5-a]pyridin-2-yl or 2-oxobenzimidazolyl. Another group of preferred compounds of Formula I includes compounds wherein the C cyclic group is an optionally substituted imidazolyl, including phenylimidazolyl, pyridinylimidazolyl, furylimidazolyl, thienylimidazolyl, thiazolylimidazolyl, pyrrolylimidazolyl, alkylimidazolyl and cycloalkylimidazolyl, wherein said phenyl, pyridinyl, furyl, thienyl, thiazolyl, pyrrolyl, alkyl and cycloakyl may be optionally substituted. Another group of preferred compounds of Formula I includes compounds wherein the C cyclic group is an optionally substituted thienoimidazolyl and imidazothiazolyl. Another group of preferred compounds of Formula I includes compounds wherein one of $D_1$, $D_2$, $D_3$ and $D_4$ is N. One group of preferred compounds of Formula I includes compounds wherein the cyclic group containing $D_1$-$D_4$ is an optionally substituted phenyl or pyridinyl, of which the substituent preferably is alkyl, halo, haloalkyl and the like. Another group of preferred compounds of Formula I includes compounds wherein $Q_1$ is an optionally substituted phenyl, pyridinyl or cycloalkyl. Another group of preferred compounds of Formula I includes compounds wherein $Q_2$ is an optionally substituted phenyl, pyridinyl, pyrimidinyl, furyl, thienyl, morpholinyl, piperazinyl or piperidinyl.

One group of preferred compounds of the present invention are represented by Formulae IIa and IIb (Formula II):

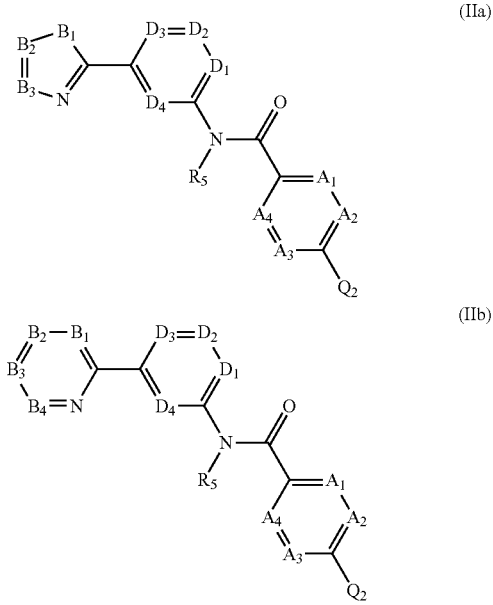

(IIa)

(IIb)

or pharmaceutically acceptable salts or prodrugs thereof, wherein:

$D_1$-$D_4$ and $Q_2$ are defined as in Formula I;

$A_1$ is N or $CR_1$; $A_2$ is N or $CR_2$; $A_3$ is N or $CR_3$; $A_4$ is N or $CR_4$;

$B_1$ is O, S, $CR_{10}$ or $NR_{14}$; $B_2$ is O, S, $CR_{11}$ or $NR_{15}$; $B_3$ is O, S, $CR_{12}$ or $NR_{16}$ for Formula IIa;

$B_1$ is N or $CR_{10}$; $B_2$ is N or $CR_{11}$; $B_3$ is N or $CR_{12}$, $B_4$ is N or $CR_{13}$ for Formula IIb;

$R_1$-$R_4$ and $R_{10}$-$R_{13}$ independently are hydrogen, halo, optionally substituted amino, alkoxy, $C_{1-10}$ alkyl, $C_{3-8}$ cycloalkyl, haloalkyl, optionally substituted aryl, a carbocyclic group, a heterocyclic group, optionally substituted heteroaryl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, hydroxyalkoxy, aminoalkyl, aminoalkoxy, carboxyalkyl, carboxyalkoxy, nitro, cyano, acylamino, aminocarbonyl, hydroxy, thiol, acyloxy, azido, carboxy, hydroxyacylamino, alkylsulfonyl, aminosulfonyl, acyl, dialkylaminosulfonyl, alkylsulfinyl, or alkylthiol;

$R_5$ is hydrogen, $C_{1-10}$ alkyl, or $R_5$ and $R_1$ or $R_4$ are taken together with other atoms, such as the carbon atom in the C(=O) group, to which they are attached to form a heterocyclic ring;

$R_{14}$-$R_{16}$ independently are hydrogen, $C_{1-10}$ alkyl, $C_{3-8}$ cycloalkyl, haloalkyl, optionally substituted aryl, a carbocyclic group, a heterocyclic group, optionally substituted heteroaryl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl; or $R_{10}$ or $R_{14}$ and $R_{11}$ or $R_{15}$, $R_{11}$ or $R_{15}$ and $R_{12}$ or $R_{16}$, or $R_{12}$ and $R_{13}$, are taken together with the C or N atom to which they are attached to form a five- or six-member aryl or heteroaryl.

One group of preferred compounds of Formulae IIa and IIb includes compounds wherein $Q_2$ is an optionally substituted phenyl, pyridyl, pyrimidinyl, funyl, thienyl, morpholinyl, piperazinyl, or piperidyl. Another group of preferred compounds of Formula IIa includes compounds wherein $B_1$ is $NR_{14}$; $B_2$ is $CR_{11}$; $R_{11}$ is an optionally substituted aryl, heteroaryl, heterocyclic group, alkyl or cycloalkyl, including phenyl, pyridyl, pyrimidinyl, funyl, thienyl, pyrrolyl, thiazolyl, methyl, ethyl, propyl, isopropyl, tert-butyl, cyclopropyl, cyclobutyl, cyclopentyl and cylohexyl.

One group of preferred compounds of the present invention are represented by Formulae IIIa and IIIb (Formula III):

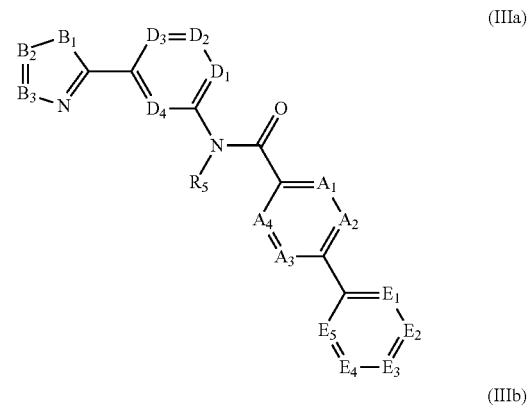

(IIIa)

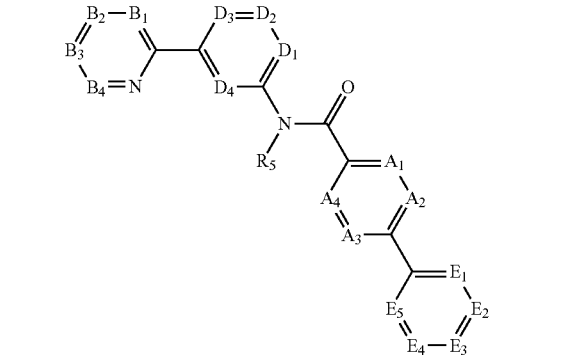

(IIIb)

or pharmaceutically acceptable salts or prodrugs thereof, wherein:

$A_1$-$A_4$, $D_1$-$D_4$, $B_1$-$B_4$ and $R_5$ are defined as in Formulae I, IIa and IIb;

$E_1$ is N or $CR_{18}$; $E_2$ is N or $CR_{19}$; $E_3$ is N or $CR_{20}$; $E_4$ is N or $CR_{21}$; $E_5$ is N or $CR_{22}$;

$R_{18}$-$R_{22}$ independently are hydrogen, halo, optionally substituted amino, alkoxy, $C_{1-10}$ alkyl, $C_{3-8}$ cycloalkyl, haloalkyl, aryl, a carbocyclic group, a heterocyclic group, heteroaryl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, hydroxyalkoxy, aminoalkyl, aminoalkoxy, carboxyalkyl, carboxyalkoxyl, nitro, cyano, acylamino, aminocarbonyl, hydroxy, thiol, acyloxy, azido, carboxy, hydroxyacylamino, alkylsulfonyl, aminosulfonyl, acyl, dialkylaminosulfonyl, alkylsulfinyl, or alkylthiol.

One group of preferred compounds of Formula IIIa includes compounds wherein $B_1$ is $NR_{14}$; $B_2$ is $CR_{11}$; $R_{11}$ is optionally substituted aryl, heteroaryl, heterocyclic group, alkyl or cycloalkyl, including phenyl, pyridyl, pyrimidinyl, furyl, pyrazinyl, thienyl, thiazolyl, pyrrolyl, methyl, ethyl, propyl, isopropyl, tert-butyl, cyclopropyl, cyclobutyl, cyclopentyl and cylohexyl. Another group of preferred compounds of Formula IIIa includes compounds wherein $B_1$ is $NR_{14}$; $B_2$ is $CR_{11}$; $B_3$ is $CR_{12}$; $R_{11}$ and $R_{12}$ are taken together with the C atoms to which they are attached to form an optionally substituted five- or six-member aryl or heteroaryl, including phenyl, pyridinyl, pyrimidinyl, furyl and thienyl.

One group of preferred compounds of the present invention are represented by Formulae IVa and IVb (Formula IV):

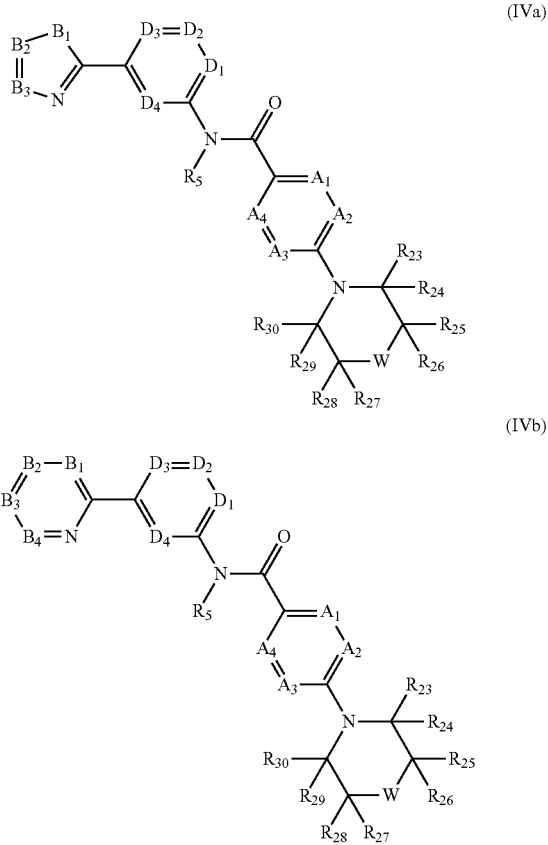

or pharmaceutically acceptable salts or prodrugs thereof, wherein:

$A_1$-$A_4$, $D_1$-$D_4$, $B_1$-$B_4$ and $R_5$ are defined as in Formulae I, IIa and IIb;

W is O, S, $CR_{31}R_{32}$ or $NR_{33}$;

$R_{23}$-$R_{32}$ independently are hydrogen, halo, optionally substituted amino, alkoxy, $C_{1-10}$ alkyl, $C_{3-8}$ cycloalkyl, haloalkyl, aryl, a carbocyclic group, a heterocyclic group, heteroaryl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, hydroxyalkoxy, aminoalkyl, aminoalkoxy, carboxyalkyl, carboxyalkoxyl, nitro, cyano, acylamino, aminocarbonyl, hydroxy, thiol, acyloxy, azido, carboxy, hydroxyacylamino, alkylsulfonyl, aminosulfonyl, acyl, dialkylaminosulfonyl, alkylsulfinyl, or alkylthiol;

$R_{33}$ is optionally substituted $C_{1-10}$ alkyl, haloalkyl, $C_{3-8}$ cycloalkyl, aryl, heteroaryl, a carbocyclic group, a heterocyclic group, alkenyl, alkynyl, acyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, alkylcarbonyl, cycloalkylcarbonyl, arylcarbonyl, heteroarylcarbonyl, heterocyclocarbonyl, aminocarbonyl, alkylsulfonyl, cycloalkylsulfonyl, or aminosulfonyl.

One group of preferred compounds of Formula IV includes compounds wherein the W-containing heterocyclic group is an optionally substituted morpholinyl, piperazinyl or piperidyl. Another group of preferred compounds of Formula IV includes compounds wherein W is O or $NR_{33}$, $R_{33}$ is an optionally substituted $C_{1-10}$ alkyl, preferably $C_{1-3}$ alkyl. Another group of preferred compounds of Formula IV includes compounds wherein the W-containing heterocyclic group is an optionally substituted (2S,6R)-2,6-dimethylmorpholinyl or (2S,6R)-2,6-dimethylpiperazinyl.

One group of compounds of Formulae I, II, III and IV of the present invention include compounds wherein $R_5$ is taken together with the N atom to which it is attached, other groups such as the carbon atom in the C(=O) group, and an atom of $Q_1$ to form a quinazolinyl, benzoxazinyl or dihydroisoquinolyl.

One group of compounds of Formulae I, II, III and IV of the present invention include compounds wherein the group corresponding to the C group (that is the C cyclic group of Formula I, and the cyclic group containing $B_1$-$B_3$ or $B_1$-$B_4$ of Formulae IIa, IIb, IIIa, IIIb, IVa and IVb) is an unsubstituted or substituted benzimidazolyl or thienoimidazolyl, or imidazolyl substituted by aryl, heteroaryl, a carbocyclic group, alkyl, cycloalkyl or a heterocyclic group; the cyclic group containing $D_1$-$D_4$ is phenyl or pyridinyl, which is optionally substituted by halo, alkyl and haloalkyl; $Q_1$ or the cyclic group containing $A_1$-$A_4$ is phenyl, pyridinyl or cycloalkyl, which is optionally substituted by alkyl, halo, nitro and amino; $Q_2$ or the cyclic group containing $E_1$-$E_5$ is phenyl, morpholinyl, pyrimidinyl, pyridinyl, piperidinyl, furyl, piperazinyl and thienyl, which is optionally substituted by alkyl, alkoxy, halo, alkylsulfonyl, cyano, nitro, acyl, haloalkyl and amino; or $Q_2$ or the W-containing cyclic group is morpholinyl, piperazinyl or piperidinyl, which is optionally substituted by alkyl, halo and haloalkyl; $R_5$ is H.

In some embodiments, compounds of the above formulae include compounds wherein the group corresponding to C group (that is the C cyclic group of Formula I, and the cyclic group containing $B_1$-$B_3$ or $B_1$-$B_4$ of Formulae IIa, IIb, IIIa, IIIb, IVa and IVb) is an unsubstituted or substituted benzimidazolyl, wherein $Q_1$ or the cyclic group containing $A_1$-$A_4$ and $Q_2$ or the cyclic group containing $E_1$-$E_5$ are not substituted by alkyl and haloalkyl at the same time. Another group of preferred compounds of Formulae I, II, III and IV of the present invention include compounds wherein at least one of $D_1$, $D_2$, $D_3$ and $D_4$ is N. Another group of preferred compounds of Formulae II, III and IV of the present invention include compounds wherein at least one of $A_1$, $A_2$, $A_3$ and $A_4$ is N. Another group of preferred compounds of Formula IV of the present invention include compounds wherein the W-containing heterocyclic group is an optionally substituted morpholinyl, piperazinyl or piperidinyl. Another group of preferred compound of Formula IV of the present invention include compounds wherein W is O or $NR_{33}$, $R_{33}$ is optionally substituted $C_{1-10}$ alkyl, preferably $C_{1-3}$ alkyl. Another group of preferred compounds of Formula IV of the present invention include compounds wherein the W-containing heterocyclic group is optionally substituted (2S,6R)-2,6-dimethylpiperazinyl.

Exemplary preferred compounds of Formulae I, II, III and IV include, without limitation:

N-(3-(1H-benzo[d]imidazol-2-yl)-4-chlorophenyl)-3-methylbiphenyl-4-carboxamide;

N-(3-(1H-benzo[d]imidazol-2-yl)-4-chlorophenyl)-3-methyl-4'-methoxybiphenyl-4-carboxamide;

N-(3-(1H-benzo[d]imidazol-2-yl)-4-chlorophenyl)-3-methyl-4'-fluorobiphenyl-4-carboxamide;

N-(3-(1H-benzo[d]imidazol-2-yl)-4-chlorophenyl)-3-methyl-4'-(methylsulfonyl)biphenyl-4-carboxamide;

N-(3-(1H-benzo[d]imidazol-2-yl)-4-chlorophenyl)-3-methyl-4'-cyanobiphenyl-4-carboxamide;
N-(3-(1H-benzo[d]imidazol-2-yl)-4-chlorophenyl)-3-methyl-4'-nitrobiphenyl-4-carboxamide;
N-(3-(1H-benzo[d]imidazol-2-yl)-4-chlorophenyl)-3-methyl-4'-chlorobiphenyl-4-carboxamide;
N-(3-(1H-benzo[d]imidazol-2-yl)-4-chlorophenyl)-3-methyl-4'-acetylbiphenyl-4-carboxamide;
N-(3-(1H-benzo[d]imidazol-2-yl)-4-chlorophenyl)-3-methyl-3'-fluorobiphenyl-4-carboxamide;
N-(3-(1H-benzo[d]imidazol-2-yl)-4-chlorophenyl)-3-methyl-3'-cyanobiphenyl-4-carboxamide;
N-(3-(1H-benzo[d]imidazol-2-yl)-4-chlorophenyl)-4'-fluorobiphenyl-4-carboxamide;
N-(3-(1H-benzo[d]imidazol-2-yl)-4-chlorophenyl)-3'-fluorobiphenyl-4-carboxamide;
N-(3-(1H-benzo[d]imidazol-2-yl)-4-chlorophenyl)-2-methyl-4'-(trifluoromethyl)biphenyl-4-carboxamide;
N-(3-(1H-benzo[d]imidazol-2-yl)-4-chlorophenyl)-3-methoxy-4'-(trifluoromethyl)biphenyl-4-carboxamide;
N-(3-(1H-benzo[d]imidazol-2-yl)-4-chlorophenyl)-3-hydroxy-4'-(trifluoromethyl)biphenyl-4-carboxamide;
N-(3-(1H-benzo[d]imidazol-2-yl)-4-chlorophenyl)-3-fluoro-4'-(trifluoromethyl)biphenyl-4-carboxamide;
N-(3-(1H-benzo[d]imidazol-2-yl)-4-chlorophenyl)-3-chloro-4'-(trifluoromethyl)biphenyl-4-carboxamide;
N-(3-(1H-benzo[d]imidazol-2-yl)-4-chlorophenyl)-3-nitro-4'-(trifluoromethyl)biphenyl-4-carboxamide;
N-(3-(1H-benzo[d]imidazol-2-yl)-4-chlorophenyl)-3,5-dimethyl-4'-(trifluoromethyl)biphenyl-4-carboxamide;
N-(3-(1H-benzo[d]imidazol-2-yl)-4-chlorophenyl)-3-methyl-4'-(trifluoromethyl)biphenyl-4-carboxamide;
N-(3-(1H-benzo[d]imidazol-2-yl)-4-chlorophenyl)-4'-(trifluoromethyl)biphenyl-4-carboxamide;
N-(3-(1H-benzo[d]imidazol-2-yl)-4-chlorophenyl)biphenyl-4-carboxamide;
N-(3-(1H-benzo[d]imidazol-2-yl)-4-chlorophenyl)-3-methyl-4'-aminobiphenyl-4-carboxamide;
N-(3-(1H-benzo[d]imidazol-2-yl)-4-chlorophenyl)-3-amino-4'-(trifluoromethyl)biphenyl-4-carboxamide;
3-(3-(1H-benzo[d]imidazol-2-yl)-4-chlorophenyl)-7-(4-(trifluoromethyl)phenyl)quinazoline-2,4(1H,3H)-dione;
3-(3-(1H-benzo[d]imidazol-2-yl)-4-chlorophenyl)-7-(4-(trifluoromethyl)phenyl)quinazolin-4(3H)-one;
3-(3-(1H-benzo[d]imidazol-2-yl)-4-chlorophenyl)-7-(4-(trifluoromethyl)phenyl)-2H-benzo[e][1,3]oxazin-4(3H)-one;
2-(3-(1H-benzo[d]imidazol-2-yl)-4-chlorophenyl)-6-phenyl-3,4-dihydroisoquinolin-1(2H)-one;
N-(3-(1H-benzo[d]imidazol-2-yl)-4-chlorophenyl)-2-methyl-4-morpholinobenzamide;
N-(3-(1H-benzo[d]imidazol-2-yl)-4-chlorophenyl)-2-methyl-4-(piperidin-1-yl)benzamide;
N-(3-(1H-benzo[d]imidazol-2-yl)-4-chlorophenyl)-2-methyl-4-((2S,6R)-2,6-dimethylmorpholino)benzamide;
N-(3-(1H-benzo[d]imidazol-2-yl)-4-chlorophenyl)-2-amino-4-((2S,6R)-2,6-dimethylmorpholino)benzamide;
3-(3-(1H-benzo[d]imidazol-2-yl)-4-chlorophenyl)-7-((2S,6R)-2,6-dimethylmorpholino)quinazolin-4(3H)-one;
N-(3-(1H-benzo[d]imidazol-2-yl)-4-chlorophenyl)-6-((2S,6R)-2,6-dimethylmorpholino)nicotinamide;
N-(3-(1H-benzo[d]imidazol-2-yl)-4-chlorophenyl)-4-chloro-6-((2S,6R)-2,6-dimethylmorpholino)nicotinamide;
N-(3-(1H-benzo[d]imidazol-2-yl)-4-chlorophenyl)-5-methyl-6-((2S,6R)-2,6-dimethylmorpholino)nicotinamide;
N-(3-(1H-benzo[d]imidazol-2-yl)-4-chlorophenyl)-2-methyl-6-((2S,6R)-2,6-dimethylmorpholino)nicotinamide;
N-(3-(1H-benzo[d]imidazol-2-yl)-4-chlorophenyl)-2-methyl-4-(2-methoxypyrimidin-5-yl)benzamide;
N-(3-(1H-benzo[d]imidazol-2-yl)-4-chlorophenyl)-2-methyl-4-(pyridin-3-yl)benzamide;
N-(3-(1H-benzo[d]imidazol-2-yl)-4-chlorophenyl)-2-methyl-4-(furan-3-yl)benzamide;
N-(3-(1H-benzo[d]imidazol-2-yl)-4-chlorophenyl)-2-methyl-4-(thiophen-3-yl)benzamide;
N-(3-(1H-benzo[d]imidazol-2-yl)-4-chlorophenyl)-2-methyl-4-(pyrimidin-5-yl)benzamide;
N-(3-(1H-benzo[d]imidazol-2-yl)-4-chlorophenyl)-4-phenylcyclohexanecarboxamide;
N-(3-(1H-benzo[d]imidazol-2-yl)phenyl)-3-methyl-4'-(trifluoromethyl)biphenyl-4-carboxamide;
N-(3-(1H-benzo[d]imidazol-2-yl)-4-methylphenyl)-3-methyl-4'-(trifluoromethyl)biphenyl-4-carboxamide;
N-(3-(1-methyl-1H-benzo[d]imidazol-2-yl)-4-chlorophenyl)-3-methyl-4'-(trifluoromethyl)biphenyl-4-carboxamide;
N-(3-(1H-benzo[d]imidazol-2-yl)-4-chlorophenyl)-N,3-dimethyl-4'-(trifluoromethyl)biphenyl-4-carboxamide;
N-(3-(1H-imidazo[4,5-c]pyridin-2-yl)-4-chlorophenyl)-3-methyl-4'-(trifluoromethyl)biphenyl-4-carboxamide;
N-(3-(5-phenyl-1H-imidazol-2-yl)-4-chlorophenyl)-3-methyl-4'-(trifluoromethyl)biphenyl-4-carboxamide;
N-(3-(5-(pyridin-3-yl)-1H-imidazol-2-yl)-4-chlorophenyl)-3-methyl-4'-(trifluoromethyl)biphenyl-4-carboxamide;
N-(3-([1,2,4]triazolo[4,3-a]pyridin-3-yl)-4-chlorophenyl)-3-methyl-4'-(trifluoromethyl)biphenyl-4-carboxamide;
N-(3-([1,2,4]triazolo[4,3-a]pyrimidin-3-yl)-4-chlorophenyl)-3-methyl-4'-(trifluoromethyl)biphenyl-4-carboxamide;
N-(3-([1,2,4]triazolo[4,3-a]pyrazin-3-yl)-4-chlorophenyl)-3-methyl-4'-(trifluoromethyl)biphenyl-4-carboxamide;
N-(3-(imidazo[1,2-a]pyrimidin-2-yl)phenyl)-3-methyl-4'-(trifluoromethyl)biphenyl-4-carboxamide;
N-(3-(imidazo[1,2-a]pyridin-2-yl)phenyl)-3-methyl-4'-(trifluoromethyl)biphenyl-4-carboxamide;
N-(3-(imidazo[1,2-a]pyrimidin-2-yl)phenyl)-6-((2S,6R)-2,6-dimethylmorpholino)nicotinamide;
N-(3-([1,2,4]triazolo[4,3-a]pyrazin-3-yl)-4-chlorophenyl)-6-((2S,6R)-2,6-dimethylmorpholino)nicotinamide;
N-(3-(pyridin-2-yl)-4-chlorophenyl)-3-methyl-4'-(trifluoromethyl)biphenyl-4-carboxamide;
N-(5-(1H-benzo[d]imidazol-2-yl)pyridin-3-yl)-3-methyl-4'-(trifluoromethyl)biphenyl-4-carboxamide;
N-(4-(1H-benzo[d]imidazol-2-yl)pyridin-2-yl)-3-methyl-4'-(trifluoromethyl)biphenyl-4-carboxamide;
N-(3-(1H-benzo[d]imidazol-2-yl)-5-(trifluoromethyl)phenyl)-3-methyl-4'-(trifluoromethyl)biphenyl-4-carboxamide;
N-(3-(1H-benzo[d]imidazol-2-yl)-5-chlorophenyl)-3-methyl-4'-(trifluoromethyl)biphenyl-4-carboxamide;
N-(3-(1H-benzo[d]imidazol-2-yl)-2-chlorophenyl)-3-methyl-4'-(trifluoromethyl)biphenyl-4-carboxamide;
N-(3-(1H-benzo[d]imidazol-2-yl)-2-methylphenyl)-6-((2S,6R)-2,6-dimethylmorpholino)nicotinamide;
N-(3-(1H-benzo[d]imidazol-2-yl)-4-chlorophenyl)-2-methyl-4-(6-methoxypyridin-3-yl)benzamide;
N-(3-(imidazo[1,2-a]pyridin-2-yl)-4-chlorophenyl)-3-methyl-4'-(trifluoromethyl)biphenyl-4-carboxamide;
N-(3-(5-(thiophen-2-yl)-1H-imidazol-2-yl)-4-chlorophenyl)-3-methyl-4'-(trifluoromethyl)biphenyl-4-carboxamide;

N-(5-(1H-benzo[d]imidazol-2-yl)-6-chloropyridin-3-yl)-3-methyl-4'-(trifluoromethyl)biphenyl-4-carboxamide;
N-(5-(1H-benzo[d]imidazol-2-yl)-6-chloropyridin-3-yl)-3-methyl-4'-cyanobiphenyl-4-carboxamide;
N-(5-(1H-benzo[d]imidazol-2-yl)-6-methylpyridin-3-yl)-3-methyl-4'-(trifluoromethyl)biphenyl-4-carboxamide;
N-(6-(1H-benzo[d]imidazol-2-yl)pyridin-2-yl)-3-methyl-4'-(trifluoromethyl)biphenyl-4-carboxamide;
N-(3-([1,2,4]triazolo[1,5-a]pyridin-2-yl)phenyl)-3-methyl-4'-(trifluoromethyl)biphenyl-4-carboxamide;
N-(3-(1H-benzo[d]imidazol-2-yl)-4-fluorophenyl)-3-methyl-4'-(trifluoromethyl)biphenyl-4-carboxamide;
N-(3-(1H-benzo[d]imidazol-2-yl)-4-bromophenyl)-3-methyl-4'-(trifluoromethyl)biphenyl-4-carboxamide;
N-(3-(1H-benzo[d]imidazol-2-yl)-4-methoxyphenyl)-3-methyl-4'-(trifluoromethyl)biphenyl-4-carboxamide;
N-(3-(5-p-tolyl-1H-imidazol-2-yl)-4-chlorophenyl)-3-methyl-4'-(trifluoromethyl)biphenyl-4-carboxamide;
N-(3-(5-(4-fluorophenyl)-1H-imidazol-2-yl)-4-chlorophenyl)-3-methyl-4'-(trifluoromethyl)biphenyl-4-carboxamide;
N-(3-(5-(furan-2-yl)-1H-imidazol-2-yl)-4-chlorophenyl)-3-methyl-4'-(trifluoromethyl)biphenyl-4-carboxamide;
N-(3-(5-p-tolyl-1H-imidazol-2-yl)-4-chlorophenyl)-2-methyl-4-((2S,6R)-2,6-dimethylmorpholino)benzamide;
N-(3-(5-(thiophen-2-yl)-1H-imidazol-2-yl)-4-chlorophenyl)-2-methyl-4-((3S,5R)-3,4,5-trimethylpiperazin-1-yl)benzamide;
N-(3-(5-(thiophen-2-yl)-1H-imidazol-2-yl)-4-chlorophenyl)-2-chloro-4-((3S,5R)-3,4,5-trimethylpiperazin-1-yl)benzamide;
N-(5-(1H-benzo[d]imidazol-2-yl)-6-chloropyridin-3-yl)-2-methyl-4-((2S,6R)-2,6-dimethylmorpholino)benzamide;
N-(5-(1H-benzo[d]imidazol-2-yl)-6-chloropyridin-3-yl)-2-methyl-6-((2S,6R)-2,6-dimethylmorpholino)nicotinamide;
N-(5-(1H-benzo[d]imidazol-2-yl)-6-chloropyridin-3-yl)-4-methyl-6-((2S,6R)-2,6-dimethylmorpholino)nicotinamide;
N-(5-(1H-benzo[d]imidazol-2-yl)-6-chloropyridin-3-yl)-6-((3S,5R)-3,4,5-trimethylpiperazin-1-yl)nicotinamide;
N-(5-(1H-benzo[d]imidazol-2-yl)-6-chloropyridin-3-yl)-2-methyl-4-((3S,5R)-3,4,5-trimethylpiperazin-1-yl)benzamide;
N-(5-(1H-benzo[d]imidazol-2-yl)-6-methylpyridin-3-yl)-2-methyl-4-((3S,5R)-3,4,5-trimethylpiperazin-1-yl)benzamide;
N-(5-(1H-benzo[d]imidazol-2-yl)-6-methylpyridin-3-yl)-3-methyl-4-((3S,5R)-3,4,5-trimethylpiperazin-1-yl)benzamide;
N-(5-(1H-benzo[d]imidazol-2-yl)-6-methylpyridin-3-yl)-6-((3S,5R)-3,4,5-trimethylpiperazin-1-yl)nicotinamide;
N-(3-(1H-benzo[d]imidazol-2-yl)-4-chlorophenyl)-4-methyl-6-((2S,6R)-2,6-dimethylmorpholino)nicotinamide;
N-(3-(1H-benzo[d]imidazol-2-yl)-4-chlorophenyl)-2-methyl-4-(4-methylpiperazin-1-yl)benzamide;
N-(3-(1H-benzo[d]imidazol-2-yl)-4-chlorophenyl)-2-methyl-4-((3S,5R)-3,4,5-trimethylpiperazin-1-yl)benzamide;
N-(3-(1H-benzo[d]imidazol-2-yl)-4-chlorophenyl)-2-chloro-4-((3S,5R)-3,4,5-trimethylpiperazin-1-yl)benzamide;
N-(3-(1H-benzo[d]imidazol-2-yl)-4-chlorophenyl)-2-fluoro-4-((3S,5R)-3,4,5-trimethylpiperazin-1-yl)benzamide;
N-(3-(6-chloro-1H-benzo[d]imidazol-2-yl)-4-chlorophenyl)-2-chloro-4-((3S,5R)-3,4,5-trimethylpiperazin-1-yl)benzamide;
N-(3-(6-chloro-1H-benzo[d]imidazol-2-yl)-4-chlorophenyl)-2-methyl-4-((3S,5R)-3,4,5-trimethylpiperazin-1-yl)benzamide;
N-(3-(6-fluoro-1H-benzo[d]imidazol-2-yl)-4-chlorophenyl)-2-methyl-4-((3S,5R)-3,4,5-trimethylpiperazin-1-yl)benzamide;
N-(3-(6-fluoro-1H-benzo[d]imidazol-2-yl)-4-chlorophenyl)-2-chloro-4-((3S,5R)-3,4,5-trimethylpiperazin-1-yl)benzamide;
N-(3-(1H-benzo[d]imidazol-2-yl)-4-chlorophenyl)-2-methyl-4-((3S,5R)-4-ethyl-3,5-dimethylpiperazin-1-yl)benzamide;
N-(3-(1H-benzo[d]imidazol-2-yl)-4-chlorophenyl)-2-methyl-4-((3S,5R)-4-isopropyl-3,5-dimethylpiperazin-1-yl)benzamide;
N-(3-(1H-benzo[d]imidazol-2-yl)-4-methylphenyl)-2-chloro-4-((3S,5R)-3,4,5-trimethylpiperazin-1-yl)benzamide;
N-(3-(1H-benzo[d]imidazol-2-yl)-4-chlorophenyl)-6-(4-methylpiperazin-1-yl)nicotinamide;
N-(3-(1H-benzo[d]imidazol-2-yl)-4-chlorophenyl)-6-((3S,5R)-3,4,5-trimethylpiperazin-1-yl)nicotinamide;
N-(3-(1H-benzo[d]imidazol-2-yl)-4-chlorophenyl)-6-((3S,5R)-4-ethyl-3,5-dimethylpiperazin-1-yl)nicotinamide;
N-(5-(1H-benzo[d]imidazol-2-yl)-6-chloropyridin-3-yl)-6-((2S,6R)-2,6-dimethylmorpholino)nicotinamide;
N-(3-(1H-benzo[d]imidazol-2-yl)-4-chlorophenyl)-4-methyl-6-((3S,5R)-3,4,5-trimethylpiperazin-1-yl)nicotinamide;
N-(3-(1H-benzo[d]imidazol-2-yl)-4-chlorophenyl)-2-methyl-4-(piperazin-1-yl)benzamide;
N-(3-(1H-benzo[d]imidazol-2-yl)-4-chlorophenyl)-2-methyl-4-((3S,5R)-3,5-dimethylpiperazin-1-yl)benzamide;
N-(3-(1-methyl-1H-benzo[d]imidazol-2-yl)-4-chlorophenyl)-2-chloro-4-((3S,5R)-3,4,5-trimethylpiperazin-1-yl)benzamide;
N-(3-(6-methyl-1H-benzo[d]imidazol-2-yl)-4-chlorophenyl)-2-chloro-4-((3S,5R)-3,4,5-trimethylpiperazin-1-yl)benzamide;
N-(3-(6-methyl-1H-benzo[d]imidazol-2-yl)-4-chlorophenyl)-2-methyl-4-((3S,5R)-3,4,5-trimethylpiperazin-1-yl)benzamide;
N-(3-(6-chloro-1H-benzo[d]imidazol-2-yl)-4-methylphenyl)-2-chloro-4-((3S,5R)-3,4,5-trimethylpiperazin-1-yl)benzamide;
N-(3-(6-fluoro-1H-benzo[d]imidazol-2-yl)-4-chlorophenyl)-2-chloro-4-((3S,5R)-4-ethyl-3,5-dimethylpiperazin-1-yl)benzamide;
N-(3-(6-fluoro-1H-benzo[d]imidazol-2-yl)-4-methylphenyl)-2-chloro-4-((3S,5R)-3,4,5-trimethylpiperazin-1-yl)benzamide;
N-(3-(1H-benzo[d]imidazol-2-yl)-4-chlorophenyl)-2-methyl-6-((3S,5R)-3,4,5-trimethylpiperazin-1-yl)nicotinamide;
N-(3-(1H-benzo[d]imidazol-2-yl)-4-chlorophenyl)-2-chloro-6-((3S,5R)-3,4,5-trimethylpiperazin-1-yl)nicotinamide;
N-(3-(1H-benzo[d]imidazol-2-yl)-4-chlorophenyl)-4-((3S,5R)-3,4,5-trimethylpiperazin-1-yl)benzamide;
N-(3-(1H-benzo[d]imidazol-2-yl)-4-chlorophenyl)-2-(trifluoromethyl)-4-((3S,5R)-3,4,5-trimethylpiperazin-1-yl)benzamide;

N-(3-(1H-benzo[d]imidazol-2-yl)-4-chlorophenyl)-3-chloro-4-((3S,5R)-3,4,5-trimethylpiperazin-1-yl)benzamide;

N-(3-(1H-benzo[d]imidazol-2-yl)-4-chlorophenyl)-3-methyl-4-((3S,5R)-3,4,5-trimethylpiperazin-1-yl)benzamide;

N-(3-(1H-benzo[d]imidazol-2-yl)-4-chlorophenyl)-2-methyl-3-fluoro-4-((3S,5R)-3,4,5-trimethylpiperazin-1-yl)benzamide;

N-(3-(1H-benzo[d]imidazol-2-yl)-4-chlorophenyl)-2-chloro-5-fluoro-4-((3S,5R)-3,4,5-trimethylpiperazin-1-yl)benzamide;

N-(3-(1H-benzo[d]imidazol-2-yl)-4-chlorophenyl)-2-chloro-4-((3S,5R)-4-ethyl-3,5-dimethylpiperazin-1-yl)benzamide;

N-(3-(1H-benzo[d]imidazol-2-yl)-4-chlorophenyl)-2-chloro-4-((3S,5R)-4-isopropyl-3,5-dimethylpiperazin-1-yl)benzamide;

(S)—N-(3-(1H-benzo[d]imidazol-2-yl)-4-chlorophenyl)-2-chloro-4-(3,4-dimethylpiperazin-1-yl)benzamide;

N-(5-(1H-benzo[d]imidazol-2-yl)-6-chloropyridin-3-yl)-2-chloro-4-((3S,5R)-3,4,5-trimethylpiperazin-1-yl)benzamide;

N-(5-(1H-benzo[d]imidazol-2-yl)-6-chloropyridin-3-yl)-2-chloro-4-((2S,6R)-2,6-dimethylmorpholino)benzamide;

N-(5-(6-fluoro-1H-benzo[d]imidazol-2-yl)-6-chloropyridin-3-yl)-2-chloro-4-((3S,5R)-3,4,5-trimethylpiperazin-1-yl)benzamide;

N-(5-(6-chloro-1H-benzo[d]imidazol-2-yl)-6-chloropyridin-3-yl)-2-chloro-4-((3S,5R)-3,4,5-trimethylpiperazin-1-yl)benzamide;

N-(3-(6-fluoro-1H-benzo[d]imidazol-2-yl)-4-chlorophenyl)-2-chloro-4-((3S,5R)-3,4,5-trimethylpiperazin-1-yl)benzamide dihydrochloride;

N-(3-(1H-benzo[d]imidazol-2-yl)-4-chlorophenyl)-2-chloro-4-((3S,5R)-3,4,5-trimethylpiperazin-1-yl)benzamide dihydrochloride;

N-(3-(1H-benzo[d]imidazol-2-yl)-4-chlorophenyl)-3-chloro-4-((3S,5R)-3,4,5-trimethylpiperazin-1-yl)benzamide dihydrochloride;

N-(3-(1H-benzo[d]imidazol-2-yl)-4-chlorophenyl)-2-cyano-4-((3S,5R)-3,4,5-trimethylpiperazin-1-yl)benzamide dihydrochloride;

N-(3-(5-(4-methylthiophen-2-yl)-1H-imidazol-2-yl)-4-chlorophenyl)-2-methyl-4-((3S,5R)-3,4,5-trimethylpiperazin-1-yl)benzamide;

N-(3-(5-(4-methylthiophen-2-yl)-1H-imidazol-2-yl)-4-chlorophenyl)-2-chloro-4-((3S,5R)-3,4,5-trimethylpiperazin-1-yl)benzamide;

N-(3-(5-(5-chlorothiophen-2-yl)-1H-imidazol-2-yl)-4-chlorophenyl)-3-chloro-4-((3S,5R)-3,4,5-trimethylpiperazin-1-yl)benzamide;

N-(3-(5-(5-chlorothiophen-2-yl)-1H-imidazol-2-yl)-4-chlorophenyl)-2-chloro-4-((3S,5R)-3,4,5-trimethylpiperazin-1-yl)benzamide;

N-(3-(5-(thiophen-3-yl)-1H-imidazol-2-yl)-4-chlorophenyl)-2-methyl-4-((3S,5R)-3,4,5-trimethylpiperazin-1-yl)benzamide;

N-(3-(5-(thiophen-3-yl)-1H-imidazol-2-yl)-4-chlorophenyl)-2-chloro-4-((3S,5R)-3,4,5-trimethylpiperazin-1-yl)benzamide;

N-(3-(5-(thiophen-3-yl)-1H-imidazol-2-yl)-4-chlorophenyl)-2-methyl-3-fluoro-4-((3S,5R)-3,4,5-trimethylpiperazin-1-yl)benzamide;

N-(3-(5-(thiophen-3-yl)-1H-imidazol-2-yl)-4-chlorophenyl)-2-chloro-5-fluoro-4-((3S,5R)-3,4,5-trimethylpiperazin-1-yl)benzamide;

N-(3-(4-methyl-5-(thiophen-2-yl)-1H-imidazol-2-yl)-4-chlorophenyl)-2-methyl-4-((3S,5R)-3,4,5-trimethylpiperazin-1-yl)benzamide;

N-(3-(5-(furan-2-yl)-1H-imidazol-2-yl)-4-chlorophenyl)-2-chloro-4-((3S,5R)-3,4,5-trimethylpiperazin-1-yl)benzamide;

N-(3-(5-(furan-2-yl)-1H-imidazol-2-yl)-4-chlorophenyl)-2-methyl-4-((3S,5R)-3,4,5-trimethylpiperazin-1-yl)benzamide;

N-(3-(5-(furan-2-yl)-1H-imidazol-2-yl)-4-chlorophenyl)-2-(trifluoromethyl)-4-((3S,5R)-3,4,5-trimethylpiperazin-1-yl)benzamide;

N-(3-(5-(furan-2-yl)-1H-imidazol-2-yl)-4-chlorophenyl)-2-cyano-4-((3S,5R)-3,4,5-trimethylpiperazin-1-yl)benzamide;

N-(3-(5-(furan-2-yl)-1H-imidazol-2-yl)-4-chlorophenyl)-2-methyl-3-fluoro-4-((3S,5R)-3,4,5-trimethylpiperazin-1-yl)benzamide;

N-(3-(5-(furan-2-yl)-1H-imidazol-2-yl)-4-chlorophenyl)-2-chloro-5-fluoro-4-((3S,5R)-3,4,5-trimethylpiperazin-1-yl)benzamide;

N-(3-(5-(furan-2-yl)-1H-imidazol-2-yl)-4-chlorophenyl)-2-chloro-4-((3S,5R)-4-ethyl-3,5-dimethylpiperazin-1-yl)benzamide;

N-(3-(5-(5-methylfuran-2-yl)-1H-imidazol-2-yl)-4-chlorophenyl)-2-chloro-4-((3S,5R)-3,4,5-trimethylpiperazin-1-yl)benzamide;

N-(3-(5-(5-methylfuran-2-yl)-1H-imidazol-2-yl)-4-chlorophenyl)-2-methyl-4-((3S,5R)-3,4,5-trimethylpiperazin-1-yl)benzamide;

N-(3-(5-(thiazol-2-yl)-1H-imidazol-2-yl)-4-chlorophenyl)-2-chloro-4-((3S,5R)-3,4,5-trimethylpiperazin-1-yl)benzamide;

N-(3-(5-(thiazol-2-yl)-1H-imidazol-2-yl)-4-chlorophenyl)-2-methyl-4-((3S,5R)-3,4,5-trimethylpiperazin-1-yl)benzamide;

N-(3-(5-(thiophen-2-yl)-1H-imidazol-2-yl)-4-chlorophenyl)-2-(trifluoromethyl)-4-((3S,5R)-3,4,5-trimethylpiperazin-1-yl)benzamide;

N-(3-(5-(thiophen-2-yl)-1H-imidazol-2-yl)-4-chlorophenyl)-2-methyl-3-fluoro-4-((3S,5R)-3,4,5-trimethylpiperazin-1-yl)benzamide;

N-(3-(5-(thiophen-2-yl)-1H-imidazol-2-yl)-4-chlorophenyl)-2-chloro-5-fluoro-4-((3S,5R)-3,4,5-trimethylpiperazin-1-yl)benzamide;

N-(3-(5-(thiophen-2-yl)-1H-imidazol-2-yl)-4-chlorophenyl)-2-chloro-4-((3S,5R)-4-ethyl-3,5-dimethylpiperazin-1-yl)benzamide;

N-(3-(5-(thiophen-2-yl)-1H-imidazol-2-yl)-4-chlorophenyl)-2-chloro-4-((3S,5R)-4-isopropyl-3,5-dimethylpiperazin-1-yl)benzamide;

N-(3-(5-(thiophen-2-yl)-1H-imidazol-2-yl)-4-chlorophenyl)-2-chloro-4-(methylsulfonyl)benzamide;

N-(3-(5-(1-methyl-1H-pyrrol-2-yl)-1H-imidazol-2-yl)-4-chlorophenyl)-2-methyl-4-((3S,5R)-3,4,5-trimethylpiperazin-1-yl)benzamide;

N-(3-(5-(1-methyl-1H-pyrrol-2-yl)-1H-imidazol-2-yl)-4-chlorophenyl)-2-chloro-4-((3S,5R)-3,4,5-trimethylpiperazin-1-yl)benzamide;

N-(3-(5-(1-methyl-1H-pyrrol-2-yl)-1H-imidazol-2-yl)-4-chlorophenyl)-2-(trifluoromethyl)-4-((3S,5R)-3,4,5-trimethylpiperazin-1-yl)benzamide;

N-(3-(5-(thiophen-3-yl)-1H-imidazol-2-yl)-4-chlorophenyl)-2-(trifluoromethyl)-4-((3S,5R)-3,4,5-trimethylpiperazin-1-yl)benzamide dihydrochloride;

N-(3-(5-(thiophen-3-yl)-1H-imidazol-2-yl)-4-chlorophenyl)-2-chloro-4-((3S,5R)-4-ethyl-3,5-dimethylpiperazin-1-yl)benzamide dihydrochloride;

N-(3-(1H-imidazol-2-yl)-4-chlorophenyl)-2-methyl-4-((3S,5R)-3,4,5-trimethylpiperazin-1-yl)benzamide;

N-(3-(5-ethyl-1H-imidazol-2-yl)-4-chlorophenyl)-2-(trifluoromethyl)-4-((3S,5R)-3,4,5-trimethylpiperazin-1-yl)benzamide;

N-(3-(5-ethyl-1H-imidazol-2-yl)-4-chlorophenyl)-2-methyl-3-fluoro-4-((3S,5R)-3,4,5-trimethylpiperazin-1-yl)benzamide;

N-(3-(5-ethyl-1H-imidazol-2-yl)-4-chlorophenyl)-2-chloro-4-((3S,5R)-4-ethyl-3,5-dimethylpiperazin-1-yl)benzamide;

N-(3-(5-isopropyl-1H-imidazol-2-yl)-4-chlorophenyl)-2-methyl-4-((3S,5R)-3,4,5-trimethylpiperazin-1-yl)benzamide;

N-(3-(5-isopropyl-1H-imidazol-2-yl)-4-chlorophenyl)-2-(trifluoromethyl)-4-((3S,5R)-3,4,5-trimethylpiperazin-1-yl)benzamide;

N-(3-(5-propyl-1H-imidazol-2-yl)-4-chlorophenyl)-2-methyl-4-((3S,5R)-3,4,5-trimethylpiperazin-1-yl)benzamide;

N-(3-(5-propyl-1H-imidazol-2-yl)-4-chlorophenyl)-2-chloro-4-((3S,5R)-3,4,5-trimethylpiperazin-1-yl)benzamide;

N-(3-(5-tert-butyl-1H-imidazol-2-yl)-4-chlorophenyl)-2-methyl-4-((3S,5R)-3,4,5-trimethylpiperazin-1-yl)benzamide;

N-(3-(5-tert-butyl-1H-imidazol-2-yl)-4-chlorophenyl)-2-chloro-4-((3S,5R)-3,4,5-trimethylpiperazin-1-yl)benzamide;

N-(3-(5-cyclopropyl-1H-imidazol-2-yl)-4-chlorophenyl)-2-chloro-4-((3S,5R)-3,4,5-trimethylpiperazin-1-yl)benzamide;

N-(3-(5-cyclopropyl-1H-imidazol-2-yl)-4-chlorophenyl)-2-methyl-4-((3S,5R)-3,4,5-trimethylpiperazin-1-yl)benzamide;

N-(3-(5-cyclopropyl-1H-imidazol-2-yl)-4-chlorophenyl)-2-(trifluoromethyl)-4-((3S,5R)-3,4,5-trimethylpiperazin-1-yl)benzamide;

N-(3-(5-cyclopropyl-1H-imidazol-2-yl)-4-chlorophenyl)-2-methyl-3-fluoro-4-((3S,5R)-3,4,5-trimethylpiperazin-1-yl)benzamide;

N-(3-(5-cyclobutyl-1H-imidazol-2-yl)-4-chlorophenyl)-2-chloro-4-((3S,5R)-3,4,5-trimethylpiperazin-1-yl)benzamide;

N-(3-(5-cyclobutyl-1H-imidazol-2-yl)-4-chlorophenyl)-2-methyl-4-((3S,5R)-3,4,5-trimethylpiperazin-1-yl)benzamide;

N-(3-(5-cyclopentyl-1H-imidazol-2-yl)-4-chlorophenyl)-2-chloro-4-((3S,5R)-3,4,5-trimethylpiperazin-1-yl)benzamide;

N-(3-(5-cyclopentyl-1H-imidazol-2-yl)-4-chlorophenyl)-2-methyl-4-((3S,5R)-3,4,5-trimethylpiperazin-1-yl)benzamide;

N-(3-(5-cyclohexyl-1H-imidazol-2-yl)-4-chlorophenyl)-2-chloro-4-((3S,5R)-3,4,5-trimethylpiperazin-1-yl)benzamide;

N-(3-(5-cyclohexyl-1H-imidazol-2-yl)-4-chlorophenyl)-2-methyl-4-((3S,5R)-3,4,5-trimethylpiperazin-1-yl)benzamide;

N-(3-(5-methyl-1H-imidazol-2-yl)-4-chlorophenyl)-2-methyl-4-((3S,5R)-3,4,5-trimethylpiperazin-1-yl)benzamide dihydrochloride;

N-(3-(5-ethyl-1H-imidazol-2-yl)-4-chlorophenyl)-2-methyl-4-((3S,5R)-3,4,5-trimethylpiperazin-1-yl)benzamide dihydrochloride;

N-(3-(5-ethyl-1H-imidazol-2-yl)-4-chlorophenyl)-2-chloro-4-((3S,5R)-3,4,5-trimethylpiperazin-1-yl)benzamide dihydrochloride;

N-(3-(5-isopropyl-1H-imidazol-2-yl)-4-chlorophenyl)-2-chloro-4-((3S,5R)-3,4,5-trimethylpiperazin-1-yl)benzamide dihydrochloride;

N-(3-(5-isopropyl-1H-imidazol-2-yl)-4-chlorophenyl)-2-methyl-3-fluoro-4-((3S,5R)-3,4,5-trimethylpiperazin-1-yl)benzamide dihydrochloride;

N-(3-(5-isopropyl-1H-imidazol-2-yl)-4-chlorophenyl)-2-chloro-5-fluoro-4-((3S,5R)-3,4,5-trimethylpiperazin-1-yl)benzamide dihydrochloride;

N-(3-(5-isopropyl-1H-imidazol-2-yl)-4-chlorophenyl)-2-chloro-4-((3S,5R)-4-ethyl-3,5-dimethylpiperazin-1-yl)benzamide dihydrochloride;

N-(3-(5-cyclopropyl-1H-imidazol-2-yl)-4-chlorophenyl)-2-chloro-5-fluoro-4-((3S,5R)-3,4,5-trimethylpiperazin-1-yl)benzamide dihydrochloride;

N-(3-(5-cyclopropyl-1H-imidazol-2-yl)-4-chlorophenyl)-2-chloro-4-((3S,5R)-4-ethyl-3,5-dimethylpiperazin-1-yl)benzamide dihydrochloride;

N-(3-(3H-imidazo[4,5-b]pyridin-2-yl)-4-chlorophenyl)-2-chloro-4-((3S,5R)-3,4,5-trimethylpiperazin-1-yl)benzamide;

N-(3-(3H-imidazo[4,5-c]pyridin-2-yl)-4-chlorophenyl)-2-chloro-4-((3S,5R)-3,4,5-trimethylpiperazin-1-yl)benzamide;

N-(3-(3H-imidazo[4,5-c]pyridin-2-yl)-4-chlorophenyl)-2-methyl-4-((3S,5R)-3,4,5-trimethylpiperazin-1-yl)benzamide;

N-(3-(1H-thieno[3,4-d]imidazol-2-yl)-4-chlorophenyl)-2-methyl-4-((3S,5R)-3,4,5-trimethylpiperazin-1-yl)benzamide;

N-(3-(1H-thieno[3,4-d]imidazol-2-yl)-4-chlorophenyl)-2-chloro-4-((3S,5R)-3,4,5-trimethylpiperazin-1-yl)benzamide;

N-(3-(1H-thieno[3,4-d]imidazol-2-yl)-4-chlorophenyl)-2-(trifluoromethyl)-4-((3S,5R)-3,4,5-trimethylpiperazin-1-yl)benzamide;

N-(3-(1H-thieno[3,4-d]imidazol-2-yl)-4-chlorophenyl)-2-methyl-3-fluoro-4-((3S,5R)-3,4,5-trimethylpiperazin-1-yl)benzamide;

N-(3-(1H-thieno[3,4-d]imidazol-2-yl)-4-chlorophenyl)-2-chloro-5-fluoro-4-((3S,5R)-3,4,5-trimethylpiperazin-1-yl)benzamide;

N-(3-(1H-thieno[3,4-d]imidazol-2-yl)-4-chlorophenyl)-2-chloro-4-((3S,5R)-4-ethyl-3,5-dimethylpiperazin-1-yl)benzamide;

N-(3-(quinoxalin-2-yl)-4-chlorophenyl)-2-chloro-4-((3S,5R)-3,4,5-trimethylpiperazin-1-yl)benzamide;

N-(3-(imidazo[2,1-b]thiazol-6-yl)-4-chlorophenyl)-2-chloro-4-((3S,5R)-3,4,5-trimethylpiperazin-1-yl)benzamide;

N-(3-(benzo[d]oxazol-2-yl)-4-chlorophenyl)-2-methyl-4-((3S,5R)-3,4,5-trimethylpiperazin-1-yl)benzamide;

N-(3-(benzo[d]thiazol-2-yl)-4-chlorophenyl)-2-chloro-4-((3S,5R)-3,4,5-trimethylpiperazin-1-yl)benzamide;

N-(3-(pyridin-2-yl)-4-chlorophenyl)-2-chloro-4-((3S,5R)-3,4,5-trimethylpiperazin-1-yl)benzamide;

N-(3-(pyrimidin-2-yl)-4-chlorophenyl)-2-chloro-4-((3S,5R)-3,4,5-trimethylpiperazin-1-yl)benzamide;

and pharmaceutically acceptable salts or prodrugs thereof.

The term "alkyl" as employed herein by itself or as part of another group refers to both straight and branched chain radicals of up to ten carbons. Useful alkyl groups include straight-chained and branched $C_{1-10}$ alkyl groups, preferably straight-chained and branched $C_{1-6}$ alkyl groups, more preferably $C_{1-3}$ alkyl groups. Typical $C_{1-10}$ alkyl groups include methyl, ethyl, propyl, isopropyl, butyl, sec-butyl, tert-butyl, 3-pentyl, hexyl and octyl groups.

The term "alkenyl" as employed herein by itself or as part of another group means a straight or branched chain radical of 2-10 carbon atoms, including at least one double bond between two of the carbon atoms in the chain. Preferred alkenyl group is $C_{2-4}$ alkenyl. Typical alkenyl groups include ethenyl, 1-propenyl, 2-methyl-1-propenyl, 1-butenyl and 2-butenyl.

The term "alkynyl" as employed herein by itself or as part of another group means a straight or branched chain radical of 2-10 carbon atoms, wherein there is at least one triple bond between two of the carbon atoms in the chain. Preferred alkynyl group is $C_{2-4}$ alkynyl. Typical alkynyl groups include ethynyl, 1-propynyl, 1-methyl-2-propynyl, 2-propynyl, 1-butynyl and 2-butynyl.

Useful alkoxy groups include oxygen substituted by alkyl, e.g., one of the $C_{1-10}$ alkyl groups mentioned above, preferably the $C_{1-6}$ alkyl groups mentioned above (that is $C_{1-6}$ alkoxy), more preferably $C_{1-3}$ alkoxy.

Useful alkylthio groups include sulfur substituted by one of the $C_{1-10}$ alkyl groups mentioned above, preferably $C_{1-6}$ alkyl, more preferably $C_{1-3}$ alkyl, which may be optionally substituted. Also included are the sulfoxides and sulfones of such alkylthio groups.

Useful amino groups include —$NH_2$, —NHR' and —NR'R", wherein R' and R" are $C_{1-10}$ alkyl or $C_{3-8}$ cycloalkyl; or R' and R" are combined with the N to form a ring structure, such as a piperidyl; or R' and R" are combined with the N and another group to form a ring, such as a piperazinyl, which are optionally substituted.

The groups as described herein, such as alkyl, alkoxy, alkylthio, alkenyl, alkynyl, cycloalkyl, carbocyclic, aryl, arylalkyl, arylalkenyl, arylalkynyl, heteroaryl and heteroarylalkyl groups and heterocyclic groups, and the like, may be optionally substituted. Generally, the term "optionally substituted" used herein indicates that the group that is "optionally substituted", such as alkyl, alkoxy, alkylthio, alkenyl, alkynyl, cycloalkyl, carbocyclic and heterocyclic groups, may be optionally substituted by one or more (such as 1, 2, 3, or 4) substituents selected from the group consisting of halo, hydroxy, carboxy, amino, amido, nitro, cyano, $C_1$-$C_6$ acylamino, $C_1$-$C_6$ acyloxy, $C_1$-$C_6$ alkoxy, aryloxy, alkylthio, $C_6$-$C_{10}$ aryl, $C_4$-$C_7$ cycloalkyl, $C_2$-$C_6$ alkenyl, $C_6$-$C_{10}$ aryl ($C_2$-$C_6$)alkenyl, —$C_6$-$C_{10}$ aryl($C_2$-$C_6$)alkynyl, saturated and unsaturated heterocyclic and heteroaryl. In one preferred embodiment, alkoxy may be substituted by one or more (such as 1~4 or 1~3) substituted selected from the group consisting of halo, morpholino, amino including alkylamino and dialkylamino, and carboxylic ester.

Optional substituents on the aryl, arylalkyl, arylalkenyl, arylalkynyl, heteroaryl and heteroarylalkyl groups may be one or more (such as 1, 2, 3, or 4) groups selected from the group consisting of $C_1$-$C_6$ alkyl, acyl, halo, methylenedioxy, $C_1$-$C_6$ haloalkyl, $C_6$-$C_{10}$ aryl, $C_4$-$C_7$ cycloalkyl, $C_2$-$C_6$ alkenyl, $C_2$-$C_6$ alkynyl, $C_6$-$C_{10}$ aryl($C_1$-$C_6$)alkyl, $C_6$-$C_{10}$ aryl ($C_2$-$C_6$)alkenyl, $C_6$-$C_{10}$ aryl($C_2$-$C_6$)alkynyl, $C_1$-$C_6$ hydroxyalkyl, nitro, amino, amido, ureido, cyano, $C_1$-$C_6$ acylamino, hydroxy, thiol, $C_1$-$C_6$ acyloxy, aminocarbonyl, azido, $C_1$-$C_6$ alkoxy, carboxy, di($C_1$-$C_{10}$ alkyl)amino, alkylsulfonyl, arylsulfonyl, dialkylaminosulfonyl, or alkylsulfinyl.

The term "aryl" as employed herein by itself or as part of another group refers to monocyclic, bicyclic or tricyclic aromatic groups containing from 6 to 14 carbons in the ring portion.

Useful aryl groups include $C_{6-14}$ aryl, preferably $C_{6-10}$ aryl. Typical $C_{6-14}$ aryl groups include phenyl, naphthyl, phenanthrenyl, anthracenyl, indenyl, biphenyl, biphenylene and fluorenyl groups.

The term "carbocycle" as employed herein include cycloalkyl and partially saturated carbocyclic groups. Useful cycloalkyl groups are $C_{3-8}$ cycloalkyl. Typical cycloalkyl groups include cyclopropyl, cyclobutyl, cyclopentyl, cyclohexyl and cycloheptyl.

Useful partially saturated carbocyclic groups are cycloalkenyl groups, such as cyclopentenyl, cycloheptenyl and cyclooctenyl.

Useful halo or halogen groups include fluorine, chlorine, bromine and iodine.

The term "arylalkyl" is used herein to mean any of the above-mentioned $C_{1-10}$ alkyl groups, preferably $C_{1-4}$ alkyl groups, substituted by any of the above-mentioned $C_{6-14}$ aryl groups. Preferably the arylalkyl group is benzyl, phenethyl or naphthylmethyl.

The term "arylalkenyl" is used herein to mean any of the above-mentioned $C_{2-10}$ alkenyl groups, preferably $C_{2-4}$ alkenyl groups, substituted by any of the above-mentioned $C_{6-14}$ aryl groups.

The term "arylalkynyl" is used herein to mean any of the above-mentioned $C_{2-10}$ alkynyl groups, preferably $C_{2-4}$ alkynyl groups, substituted by any of the above-mentioned $C_{6-14}$ aryl groups.

The term "aryloxy" is used herein to mean oxygen substituted by one of the above-mentioned $C_{6-14}$ aryl groups, which may be optionally substituted. Useful aryloxy groups include phenoxy and 4-methylphenoxy.

The term "arylalkoxy" is used herein to mean any of the above mentioned $C_{1-10}$ alkoxy groups substituted by any of the above-mentioned aryl groups, which may be optionally substituted. Useful arylalkoxy groups include benzyloxy and phenethyloxy.

Useful haloalkyl groups include $C_{1-10}$ alkyl substituted by one or more fluorine, chlorine, bromine or iodine atoms, e.g., fluoromethyl, difluoromethyl, trifluoromethyl, pentafluoroethyl, 1,1-difluoroethyl, chloromethyl, chlorofluoromethyl and trichloromethyl groups.

Acyl groups are —R—CHO groups, wherein R is $C_{1-6}$ alkylene. Useful acyl groups include $C_{1-6}$ acyl, e.g., formacyl, acetyl, and the like.

Useful acylamino (acylamido) groups are any $C_{1-6}$ acyl (alkanoyl) attached to an amino nitrogen, e.g., acetamido, chloroacetamido, propionamido, butanoylamido, pentanoylamido and hexanoylamido, as well as aryl-substituted $C_{1-6}$ acylamino groups, e.g., benzoylamido.

Useful acyloxy groups are any $C_{1-6}$ acyl (alkanoyl) attached to an oxy (—O—) group, e.g., formyloxy, acetoxy, propionoyloxy, butanoyloxy, pentanoyloxy and hexanoyloxy.

The term heterocycle is used herein to mean a saturated or partially saturated 3-7 membered monocyclic, or 7-10 membered bicyclic ring system, which consists of carbon atoms and one to four heteroatoms independently selected from the group consisting of O, N, and S, wherein the nitrogen and sulfur heteroatoms can be optionally oxidized, the nitrogen can be optionally quaternized. The term also includes any bicyclic group in which any of the above-defined heterocyclic rings is fused to a benzene ring. The heterocyclic ring of heterocycle can be substituted on carbon or on a nitrogen atom if the resulting compound is stable.

Useful saturated or partially saturated heterocyclic groups include tetrahydrofuranyl, pyranyl, piperidinyl, piperazinyl, pyrrolidinyl, imidazolidinyl, imidazolinyl, indolinyl, isoindolinyl, quinuclidinyl, morpholinyl, isochromanyl, chromanyl, pyrazolidinyl, quinazoline-2,4(1H,3H)-dione, quinazolin-4(3H)-one, benzo[e][1,3]oxazin-4(3H)-one, 3,4-dihydroisoquinolin-1(2H)-one, and pyrazolinyl. A heterocyclic group also includes heteroaryl herein.

The term "heteroaryl" as employed herein refers to groups having 5 to 14 ring atoms; 6, 10 or 14 π electrons shared in a cyclic array; and containing, as ring atom, carbon atoms and 1-3 heteroatoms selected from oxygen, nitrogen and sulfur.

Useful heteroaryl groups include quinazolinyl, thienyl, benzo[b]thienyl, benzo[d]thiazolyl, benzo[d]oxazolyl, benzo[2,3-b]thienyl, thianthrenyl, furyl (furanyl), pyranyl, isobenzopyranyl, chromenyl, xanthenyl, phenoxanthiinyl, pyrrolyl, imidazolyl, pyrazolyl, pyridyl (pyridinyl, including without limitation 2-pyridyl, 3-pyridyl, and 4-pyridyl), pyrazinyl, pyrimidinyl, pyridazinyl, indolizinyl, isoindolyl, 3H-indolyl, indolyl, indazolyl, purinyl, 4H-quinolizinyl, isoquinolyl, dihydroisoquinolyl, quinolyl, phthalzinyl, naphthyridinyl, acridinyl, perimidinyl, phenanthrolinyl, phenazinyl, thiazolyl, isothiazolyl, phenothiazinyl, isoxazolyl, furazanyl, phenoxazinyl, 1,4-dihydroquinoxaline-2,3-dione, 7-aminoisocoumarin, pyrido[1,2-a]pyrimidin-4-one, tetrahydrocyclopenta[c]pyrazol-3-yl, imidazo[1,5-a]pyrimidinyl, imidazo[4,5-c]pyridin-2-yl, [1,2,4]triazolo[4,3-a]pyridin-3-yl, [1,2,4]triazolo[4,3-a]pyrimidin-3-yl, [1,2,4]triazolo[4,3-a]pyrazin-3-yl, [1,2,4]triazolo[1,5-a]pyridin-2-yl, imidazo[1,2-a]pyrimidin-2-yl, imidazo[1,2-a]pyridin-2-yl, imidazo[4,5-b]pyridin-2-yl, imidazo[2,1-b]thiazol-6-yl, benzo[e][1,3]oxazinyl, thieno[3,4-d]imidazol-2-yl, 1,2-benzoisoxazol-3-yl, benzimidazolyl, 2-oxindolyl, thiadiazolyl, quinoxalin-2-yl and 2-oxobenzimidazolyl. Where the heteroaryl group contains a nitrogen atom in a ring, such nitrogen atom may be in the form of an N-oxide, e.g., a pyridyl N-oxide, pyrazinyl N-oxide and pyrimidinyl N-oxide.

The term "heteroaryloxy" is used herein to mean oxygen substituted by one of the above-mentioned heteroaryl groups, which may be optionally substituted. Useful heteroaryloxy groups include pyridyloxy, pyrazinyloxy, pyrrolyloxy, pyrazolyloxy, imidazolyloxy and thiophenyloxy.

The term "heteroarylalkoxy" is used herein to mean any of the above-mentioned $C_{1-10}$ alkoxy groups substituted by any of the above-mentioned heteroaryl groups, which may be optionally substituted.

Some of the compounds of the present invention may exist as stereoisomers including optical isomers. The invention includes all stereoisomers and both the racemic mixtures of such stereoisomers as well as the individual enantiomers that may be separated according to methods that are well known to those of ordinary skill in the art.

Examples of pharmaceutically acceptable addition salts include inorganic and organic acid addition salts, such as hydrochloride, hydrobromide, sulphate, citrate, lactate, tartrate, maleate, fumarate, mandelate and oxalate; and inorganic and organic base addition salts with bases, such as sodium hydroxy, tris(hydroxymethyl)aminomethane (TRIS, tromethane) and N-methylglucamine.

Examples of prodrugs of the compounds of the invention include the simple esters of carboxylic acid containing compounds (e.g., those obtained by condensation with a $C_{1-4}$ alcohol according to methods known in the art); esters of hydroxy containing compounds (e.g., those obtained by condensation with a $C_{1-4}$ carboxylic acid, $C_{3-8}$ dioic acid or anhydride thereof, such as succinic and fumaric anhydrides according to methods known in the art); imines of amino containing compounds (e.g., those obtained by condensation with a $C_{1-4}$ aldehyde or ketone according to methods known in the art); carbamate of amino containing compounds, such as those described by Leu, et. al., (J. Med. Chem. 42: 3623-3628 (1999)) and Greenwald, et al., (J. Med. Chem. 42: 3657-3667 (1999)); and acetals and ketals of alcohol containing compounds (e.g., those obtained by condensation with chloromethyl methyl ether or chloromethyl ethyl ether according to methods known in the art).

The compounds of this invention may be prepared using methods known to those skilled in the art, or the novel methods of this invention. Specifically, the compounds of this invention with Formula I, II, III or IV can be prepared as illustrated by the exemplary reaction in Scheme 1. Reaction of 4-bromo-2-methylbenzoic acid with phenylboronic acid in the presence of palladium(0)tetrakis(triphenylphosphine) and sodium carbonate in ethanol-water solution produced 3-methylbiphenyl-4-carboxylic acid. Treatment of the compound with sulfoxide chloride produced the intermediate 3-methylbiphenyl-4-carbonyl chloride. Copouling of the intermediate with 3-(1H-benzo[d]imidazol-2-yl)-4-chloroaniline in the presence of sodium carbonate in DCM produced the targeted compound N-(3-(1H-benzo[d]imidazol-2-yl)-4-chlorophenyl)-3-methylbiphenyl-4-carboxamide.

Other related compounds can be prepared similarly. For example, replacement of 4-bromo-2-methylbenzoic acid with 4-bromobenzoic acid produced the targeted compound N-(3-(1H-benzo[d]imidazol-2-yl)-4-chlorophenyl)biphenyl-4-carboxamide. Replacement of phenylboronic acid with 4-(trifluoromethyl)phenylboronic acid produced the targeted compound N-(3-(1H-benzo[d]imidazol-2-yl)-4-chlorophenyl)-3-methyl-4'-(trifluoromethyl)biphenyl-4-carboxamide. Replacement of 3-(1H-benzo[d]imidazol-2-yl)-4-chloroaniline with 4-chloro-3-(5-(phenyl-1H-imidazol-2-yl)aniline produced the targeted compound N-(3-(5-phenyl-1H-imidazol-2-yl)-4-chlorophenyl)-3-methyl-4'-(trifluoromethyl)biphenyl-4-carboxamide. Replacement of 3-(1H-benzo[d]imidazol-2-yl)-4-chloroaniline with 3-([1,2,4]triazolo[4,3-a]pyridin-3-yl)-4-chloroaniline produced N-(3-([1,2,4]triazolo[4,3-a]pyridin-3-yl)-4-chlorophenyl)-3-methyl-4'-(trifluoromethyl)biphenyl-4-carboxamide. Replacement of 3-(1H-benzo[d]imidazol-2-yl)-4-chloroaniline with 3-(imidazol[1,2-a]pyrimidin-2-yl)aniline produced the target compound N-(3-(imidazol[1,2-a]pyrimidin-2-yl)phenyl)-3-methyl-4'-(trifluoromethyl)biphenyl-4-carboxamide.

Scheme 1

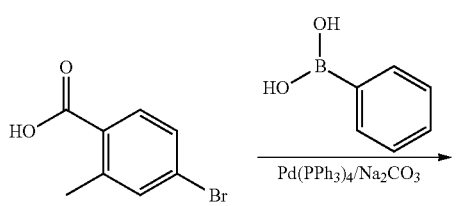

-continued

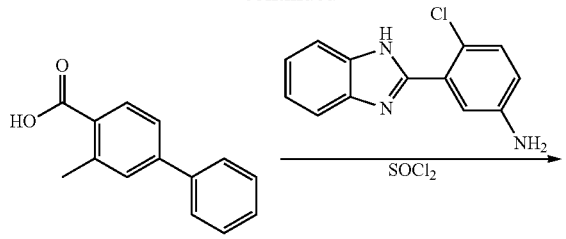

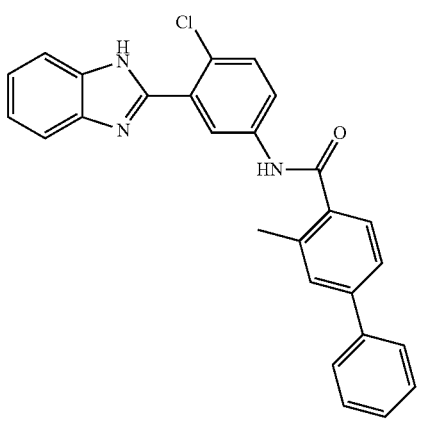

Similarly, compounds of this invention can be prepared as illustrated by the exemplary reaction in Scheme 2. Reaction of N-(3-(1H-benzo[d]imidazol-2-yl)-4-chlorophenyl)-3-amino-4'-(trifluoromethyl)biphenyl-4-carboxamide with triethyl orthoformate produced the target compound 3-(3-(1H-benzo[d]imidazol-2-yl)-4-chlorophenyl)-7-(4-(trifluoromethyl)phenyl)quinazolin-4(3H)-one. Similarly, reaction of N-(3-(1H-benzo[d]imidazol-2-yl)-4-chlorophenyl)-3-amino-4'-(trifluoromethyl)biphenyl-4-carboxamide with triphosgene in THF produced 3-(3-(1H-benzo[d]imidazol-2-yl)-4-chlorophenyl)-7-(4-(trifluoromethyl)phenyl)quinazoline-2,4(1H,3H)-dione. Reaction of N-(3-(1H-benzo[d]imidazol-2-yl)-4-chlorophenyl)-4'-trifluoromethyl-3-hydroxybiphenyl-4-carboxamide with triformol and trifluoroacetic acid produced 3-(3-(1H-benzo[d]imidazol-2-yl)-4-chlorophenyl)-7-(4-(trifluoromethyl)phenyl)-2H-benzo[e][1,3]oxazin-4(3H)-one.

Scheme 2

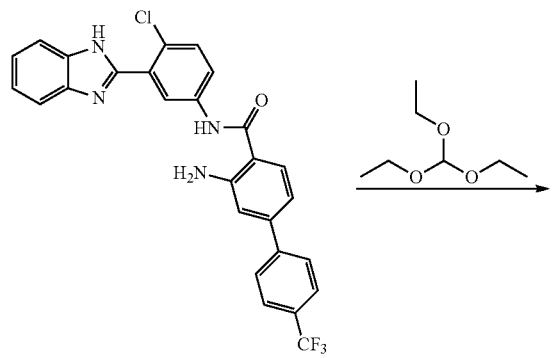

-continued

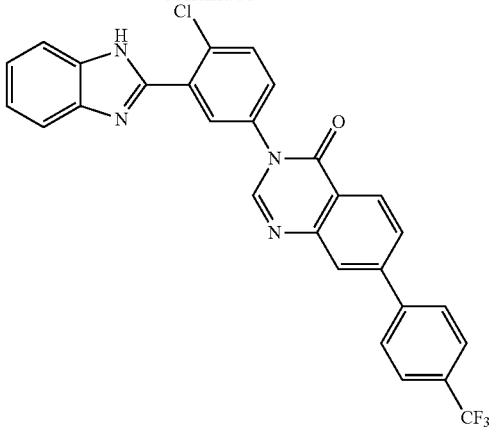

Similarly, compounds of this invention can be prepared as illustrated by the exemplary reaction in Scheme 3. Reaction of 4-bromo-2-methylbenzoic acid with sulfoxide chloride produced the intermediate 4-bromo-2-methylbenzoyl chloride. Coupling of the intermediate with 3-(1H-benzo[d]imidazol-2-yl)-4-chloroaniline in the presence of sodium carbonate in DCM produced N-(3-(1H-benzo[d]imidazol-2-yl)-4-chlorophenyl)-4-bromo-2-methylbenzamide. Treatment of the compound with 2-methoxypyrimidin-5-ylboronic acid in the presence of palladium(0)tetrakis(triphenylphosphine) and sodium carbonate in ethanol-water produced N-(3-(1H-benzo[d]imidazol-2-yl)-4-chlorophenyl)-2-methyl-4-(2-methoxypyrimidin-5-yl)benzamide.

Other related compounds can be prepared similarly. For example, replacement of 2-methoxypyrimidin-5-ylboronic acid with pyridin-3-ylboronic acid produced N-(3-(1H-benzo[d]imidazol-2-yl)-4-chlorophenyl)-2-methyl-4-(pyridin-3-yl)benzamide. Replacement of 2-methoxypyrimidin-5-ylboronic acid with furan-3-ylboronic acid produced N-(3-(1H-benzo[d]imidazol-2-yl)-4-chlorophenyl)-2-methyl-4-(furan-3-yl)benzamide. Replacement of 2-methoxypyrimidin-5-ylboronic acid with thiophen-3-ylboronic acid produced N-(3-(1H-benzo[d]imidazol-2-yl)-4-chlorophenyl)-2-methyl-4-(thiophen-3-yl)benzamide.

Scheme 3

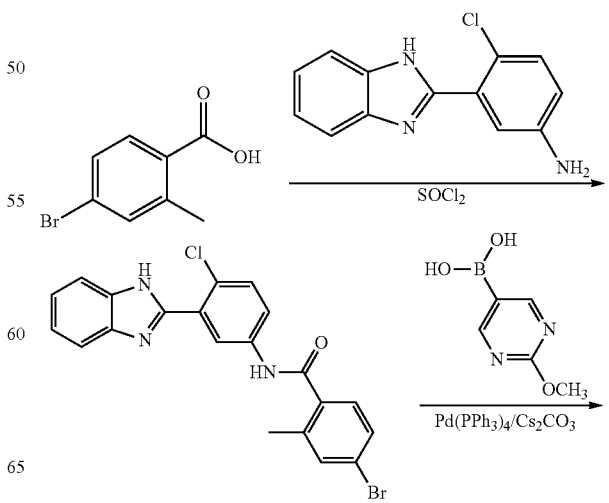

-continued

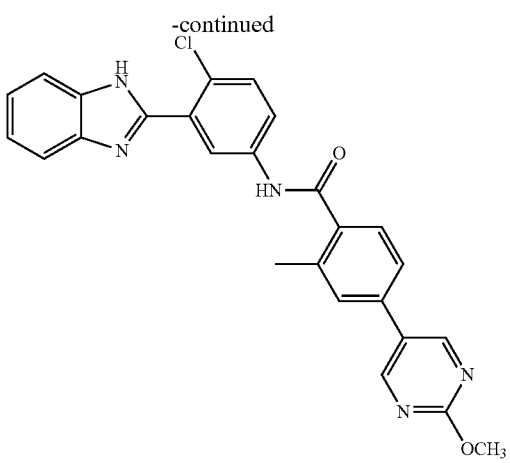

Similarly, compounds of this invention can be prepared as illustrated by the exemplary reaction in Scheme 4. Reaction of methyl 4-fluoro-2-methylbenzoate, (2S,6R)-2,6-dimethylmorpholine and potassium carbonate in ACN produced methyl 2-methyl-4-((2S,6R)-2,6-dimethylmorpholino)benzoate. Hydrolysis of the ester with sodium hydroxide in methanol-water produced 2-methyl-4-((2S,6R)-2,6-dimethylmorpholino)benzoic acid. Coupling of the acid with 3-(1H-benzo[d]imidazol-2-yl)-4-chloroaniline in the presence of HATU and TEA in DMF produced the targeted compound N-(3-(1H-benzo[d]imidazol-2-yl)-4-chlorophenyl)-2-methyl-4-((2S,6R)-2,6-dimethylmorpholino)benzamide. Other related compounds can be prepared similarly. For example, replacement of (2S,6R)-2,6-dimethylmorpholine with morpholine produced N-(3-(1H-benzo[d]imidazol-2-yl)-4-chlorophenyl)-2-methyl-4-morpholinobenzamide. Replacement of (2S,6R)-2,6-dimethylmorpholine with piperidine produced N-(3-(1H-benzo[d]imidazol-2-yl)-4-chlorophenyl)-2-methyl-4-(piperidin-4-yl)benzamide. Replacement of (2S,6R)-2,6-dimethylmorpholine with (2S,6R)-1,2,6-trimethylpiperazine produced N-(3-(1H-benzo[d]imidazol-2-yl)-4-chlorophenyl)-2-methyl-4-((3S,5R)-3,4,5-trimethylpiperazin-1-yl)benzamide. Replacement of methyl 4-fluoro-2-methylbenzoate with ethyl 4-methyl-6-chloronicotinate produced N-(3-(1H-benzo[d]imidazol-2-yl)-4-chlorophenyl)-4-methyl-6-((2S,6R)-2,6-dimethylmorpholino) nicotinamide. Replacement of 3-(1H-benzo[d]imidazol-2-yl)-4-chloroaniline with 5-(1H-benzo[d]imidazol-2-yl)-6-chloropyridin-3-amine, 3-(5-(thiophen-2-yl)-1H-imidazol-2-yl)-4-chloroaniline, 3-(5-(furan-2-yl)-1H-imidazol-2-yl)-4-chloroaniline, 3-(5-(1-methyl-1H-pyrrol-2-yl)-1H-imidazol-2-yl)-4-chloroaniline, 3-(5-cyclopropyl-1H-imidazol-2-yl)-4-chloroaniline, 3-(5-isopropyl-1H-imidazol-2-yl)-4-chloroaniline, and 3-(1H-thieno[3,4-d]imidazol-2-yl)-4-chloroaniline, produced N-(5-(1H-benzo[d]imidazol-2-yl)-6-chloropyridin-3-yl)-2-methyl-4-((2S,6R)-2,6-dimethylmorpholino)benzamide, N-(3-(5-(thiophen-2-yl)-1H-imidazol-2-yl)-4-chlorophenyl)-2-methyl-4-((3S,5R)-3,4,5-trimethylpiperazin-1-yl)benzamide, N-(3-(5-(furan-2-yl)-1H-imidazol-2-yl)-4-chlorophenyl)-2-methyl-4-((3S,5R)-3,4,5-trimethylpiperazin-1-yl)benzamide, N-(3-(5-(1-methyl-1H-pyrrol-2-yl)-1H-imidazol-2-yl)-4-chlorophenyl)-2-methyl-4-((3S,5R)-3,4,5-trimethylpiperazin-1-yl)benzamide, N-(3-(5-cyclopropyl-1H-imidazol-2-yl)-4-chlorophenyl)-2-methyl-4-((3S,5R)-3,4,5-trimethylpiperazin-1-yl)benzamide, N-(3-(5-isopropyl-1H-imidazol-2-yl)-4-chlorophenyl)-2-methyl-4-((3S,5R)-3,4,5-trimethylpiperazin-1-yl)benzamide, and N-(3-(1H-thieno[3,4-d]imidazol-2-yl)-4-chlorophenyl)-2-methyl-4-((3S,5R)-3,4,5-trimethylpiperazin-1-yl)benzamide, respectively.

Scheme 4

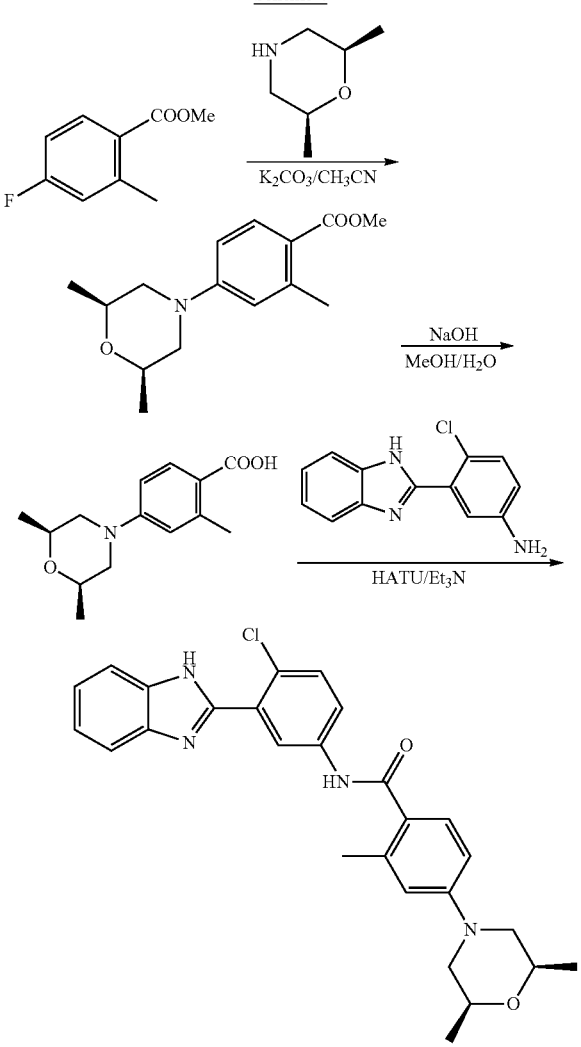

An important aspect of the present invention is the discovery that compounds having Formula I, II, III or IV are hedgehog pathway inhibitors. Therefore, these compounds are useful for the treatment of a variety of clinical conditions responsive to the inhibition of hedgehog activity, such as cancer.

The present invention also includes a therapeutic method comprising administering to a mammal an effective amount of a compound of Formula I, II, III or IV, or a pharmaceutically acceptable salt or prodrug thereof, wherein said therapeutic method is useful for the treatment of diseases due to abnormal hedgehog activity (that is hedgehog mediated diseases), such as cancer.

Various diseases that are responsive to the inhibition of hedgehog activity or hedgehog mediated diseases include cancer, but are not limited to, basal cell carcinoma, medulloblastoma cancer, basal cell nevus syndrome (BCNS), liver cancer, melanoma, Hodgkin's disease, non-Hodgkin's lymphomas, acute or chronic lymphocytic leukemia, multiple myeloma, neuroblastoma, breast carcinoma, ovarian carcinoma, lung carcinoma, Wilms' tumor, cervical carcinoma, testicular carcinoma, soft-tissue sarcoma, primary macroglobulinemia, bladder carcinoma, chronic granulocytic leukemia, primary brain carcinoma, malignant melanoma, small-cell lung carcinoma, stomach carcinoma, colon carcinoma, malignant pancreatic insulinoma, malignant carcinoid carcinoma, choriocarcinoma, mycosis fungoide, head or neck carcinoma, osteogenic sarcoma, pancreatic carcinoma, acute granulocytic leukemia, hairy cell leukemia, rhabdomyosarcoma, Kaposi's sarcoma, genitourinary carcinoma, thyroid carcinoma, esophageal carcinoma, malignant hypercalcemia, cervical hyperplasia, renal cell carcinoma, endometrial carcinoma, polycythemia vera, essential thrombocytosis, adrenal cortex carcinoma, skin cancer, and prostatic carcinoma. Preferably, diseases mentioned above are basal cell carcinoma, medulloblastoma cancer or basal cell nevus syndrome.

In practicing the therapeutic methods, effective amounts of compositions containing therapeutically effective concentrations of the compounds of Formula I, II, III or IV formulated for oral, intravenous, local or topical application, for the treatment of neoplastic diseases and other diseases, are administered to an individual exhibiting the symptoms of one or more of these disorders. The amounts are effective to ameliorate or eliminate one or more symptoms of the disorders. An effective amount of a compound for treating a particular disease is an amount that is sufficient to ameliorate, or in some manner reduce, the symptoms associated with the disease. Such amount may be administered as a single dosage or may be administered according to a regimen, whereby it is effective. The amount may cure the disease but, typically, is administered in order to ameliorate the symptoms of the disease. Typically, repeated administration is required to achieve the desired amelioration of symptom.

The present invention also includes the use of the compounds of Formula I, II, III or IV of the subject invention in the manufacture of a medicament for treating or preventing a disorder responsive to the inhibition of hedgehog activity, including cancer. In preferred embodiment, the above-mentioned diseases are selected from cancer. In more preferred embodiment, the above-mentioned diseases are selected from basal cell carcinoma, medulloblastoma cancer, basal cell nevus syndrome. In another embodiment, the above-mentioned drugs may also include other known anti-cancer drugs, but not limited to the various known anti-cancer drugs described herein.

In another embodiment, a pharmaceutical composition comprising a compound of Formula I, II, III or IV or a pharmaceutically acceptable salt thereof, which functions as hedgehog pathway inhibitor, in combination with a pharmaceutically acceptable vehicle, is provided.

Another embodiment of the present invention is directed to a composition effective to inhibit neoplasia comprising a compound of Formula I, II, III or IV, or a pharmaceutically acceptable salt or prodrug thereof, which functions as a hedgehog inhibitor, in combination with at least one known anticancer agent or a pharmaceutically acceptable salt thereof. Examples of known anticancer agents which may be used for combination therapy include, but not are limited to DNA damaging chemotherapy anti-cancer drugs, including alkylating agents, such as busulfan, melphalan, chlorambucil, cyclophosphamide, ifosfamide, temozolomide, bendamustine, cis-platin, mitomycin C, bleomycin and carboplatin; topoisomerase I inhibitors, such as camptothecin, irinotecan and topotecan; topoisomerase II inhibitors, such as doxorubicin, epirubicin, aclarubicin, mitoxantrone, ellip- tinium and etoposide; RNA/DNA antimetabolites, such as 5 azacytidine, gemcitabine, 5-fluorouracil and methotrexate; DNA antimetabolites, such as 5-fluoro-2'-deoxyuridine, fludarabine, nelarabine, ara-C, alanosine, pralatrexate, pemetrexed, hydroxyurea and thioguanine; antimitotic agents, such as colchicine, vinblastine, vincristine, vinorelbine, paclitaxel, ixabepilone, cabazitaxel, and docetaxel; antibodies, such as campath, Panitumumab, Ofatumumab, Avastin, HERCEPTIN (trastuzumab), and RITUXAN (rituximab); kinase inhibitors such as imatinib, gefitinib, erlotinib, lapatinib, sorafenib, sunitinib, nilotinib, dasatinib, pazopanib, temsirolimus and everolimus; HDAC inhibitors such as vorinostat and romidepsin. Other known anticancer agents which may be used for combination therapy include tamoxifen, letrozole, fulvestrant, mitoguazone, octreotide, retinoic acid, arsenic trioxide, zoledronic acid, bortezomib, thalidomide and lenalidomide.

In practicing the methods of the present invention, the compound of the invention may be administered together with at least one known anticancer agent as part of a unitary pharmaceutical composition. Alternatively, the compound of the invention may be administered apart from at least one known anticancer agent. In one embodiment, the compound of the invention and at least one known anticancer agent are administered substantially simultaneously, i.e. the compounds are administered at the same time or one after the other, so long as the compounds reach therapeutic levels in the blood at the same time. In another embodiment, the compound of the invention and at least one known anticancer agent are administered according to their individual dose schedule, so long as the compounds reach therapeutic levels in the blood.

Another embodiment of the present invention is directed to a composition effective to inhibit neoplasia comprising a bioconjugate of a compound described herein, in bioconjugation with at least one known therapeutically useful antibody, such as Herceptin® or Rituxan®, or growth factors, such as DGF or NGF, or cytokines, such as IL-2 or IL-4, or any molecule that binds to the cell surface. The antibodies and other molecules will deliver a compound described herein to its targets and make it an effective anticancer agent. The bioconjugates could also enhance the anticancer effect of the therapeutically useful antibodies, such as Herceptin® or Rituxan®.

Another embodiment of the present invention is directed to a composition effective to inhibit neoplasia comprising a compound of Formula I, II, III or IV, or its pharmaceutically acceptable salt or prodrug, which functions as a hedgehog pathway inhibitor, in combination with radiation therapy. In this embodiment, the compound of the invention may be administered at the same time as the radiation therapy is administered or at a different time.

Yet another embodiment of the present invention is directed to a composition effective for post-surgical treatment of cancer, comprising a compound of Formula I, II or III, or its pharmaceutically acceptable salt or prodrug, which functions as a hedgehog pathway inhibitor. The invention also relates to a method of treating cancer by surgically removing the cancer and then treating the mammal with one of the pharmaceutical compositions described herein.

Pharmaceutical compositions within the scope of this invention may also include the bioconjugate of the present invention as an active ingredient. The above-mentioned bioconjugate may form from the compound of Formula I, II or III of the subject invention with a therapeutically useful antibody. The pharmaceutical composition may also contain a pharmaceutically acceptable carrier.

Pharmaceutical compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to mammals, orally at a dose of 0.0025 to 50 mg/kg of body weight, per day, or an equivalent amount of the pharmaceutically acceptable salt thereof, to a mammal being treated. Preferably, approximately 0.01 to approximately 10 mg/kg of body weight is orally administered. If a known anticancer agent is also administered, it is administered in an amount that is effective to achieve its intended purpose. The amounts of such known anticancer agents effective for cancer are well known to those skilled in the art.

The unit oral dose may comprise from approximately 0.01 to approximately 50 mg, preferably approximately 0.1 to approximately 10 mg of the compound of the invention. The unit dose may be administered one or more times daily, as one or more tablets, each containing from approximately 0.1 to approximately 50 mg, conveniently approximately 0.25 to 10 mg of the compound or its solvates.

In a topical formulation, the compound may be present at a concentration of approximately 0.01 to 100 mg per gram of carrier.

In addition to administering the compound as a raw chemical, the compounds of the invention may be administered as part of a pharmaceutical preparation containing suitable pharmaceutically acceptable carriers comprising excipients and auxiliaries, which facilitate processing of the compounds into preparations that may be used pharmaceutically. Preferably, the preparations, particularly those preparations which may be administered orally and that may be used for the preferred type of administration, such as tablets, dragees, and capsules, as well as suitable solutions for administration by injection or orally, contain from approximately 0.01 to 99 percent, preferably from approximately 0.25 to 75 percent of active compound(s), together with the excipient.

Also included within the scope of the present invention are the non-toxic pharmaceutically acceptable salts of the compounds of the present invention. Acid addition salts are formed by mixing a solution of the compounds of the present invention with a solution of a pharmaceutically acceptable non-toxic acid, such as hydrochloric acid, fumaric acid, maleic acid, succinic acid, acetic acid, citric acid, tartaric acid, carbonic acid, phosphoric acid, oxalic acid, and the like. Base addition salts are formed by mixing a solution of the compounds of the present invention with a solution of a pharmaceutically acceptable non-toxic base, such as sodium hydroxide, potassium hydroxide, choline hydroxide, sodium carbonate, Tris, N-methylglucamine and the like.

The pharmaceutical compositions of the invention may be administered to any mammal, which may experience the beneficial effects of the compounds of the invention. Foremost among such mammals are humans and veterinary animals, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner, which is itself known, e.g., by means of conventional mixing, granulating, dragee-making, dissolving, or lyophilizing processes. Thus, pharmaceutical preparations for oral use may be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular fillers, such as saccharides, e.g. lactose or sucrose, mannitol or sorbitol; cellulose preparations or calcium phosphates, e.g. tricalcium phosphate or calcium hydrogen phosphate; as well as binders, such as starch paste, using, e.g., maize starch, wheat starch, rice starch, potato starch, gelatin, tragacanth, methyl cellulose, hydroxypropylmethylcellulose, sodium carboxymethylcellulose, or polyvinyl pyrrolidone. If desired, disintegrating agents may be added, such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, e.g., silica, talc, stearic acid or salts thereof, such as magnesium stearate, calcium stearate, stearic acid or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations, such as acetylcellulose phthalate or hydroxypropylmethylcellulose phthalate, are used. Dye stuffs or pigments may be added to the tablets or dragee coatings, e.g., for identification or in order to characterize combinations of active compound doses.

Other pharmaceutical preparations, which may be used orally, include push-fit capsules made of gelatin, as well as soft, sealed capsules made of gelatin and a plasticizer, such as glycerol or sorbitol. The push-fit capsules may contain the active compounds in the form of granules, which may be mixed with fillers, such as lactose; binders, such as starches; and/or lubricants, such as talc or magnesium stearate and, optionally, stabilizers. In soft capsules, the active compounds are preferably dissolved or suspended in suitable liquids, such as fatty oils, or liquid paraffin. In addition, stabilizers may be added.

Suitable formulations for parenteral administration include aqueous solutions of the active compounds in water-soluble form, e.g., water-soluble salts and alkaline solutions. In addition, suspensions of the active compounds as appropriate oily injection suspensions may be administered. Suitable lipophilic solvents or vehicles include fatty oils, e.g., sesame oil, or synthetic fatty acid esters, e.g., ethyl oleate, or triglycerides or polyethylene glycol-400, or cremophor, or cyclodextrins. Aqueous injection suspensions may contain substances which increase the viscosity of the suspension include, e.g., sodium carboxymethyl cellulose, sorbitol, or dextran. Optionally, the suspension may also contain stabilizers.

The topical compositions of this invention are formulated preferably as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The preferred carriers are those in which the active ingredient is soluble. Emulsifiers, stabilizers, humectants and antioxidants may also be included, as well as agents imparting color or fragrance, if desired. Additionally, transdermal penetration enhancers may be employed in these topical formulations. Examples of such enhancers are found in U.S. Pat. Nos. 3,989,816 and 4,444,762.

Creams are preferably formulated from a mixture of mineral oil, self-emulsifying beeswax and water in which mixture of the active ingredient, dissolved in a small amount of an oil, such as almond oil, is admixed. A typical example of such a cream is one which includes approximately 40 parts water, approximately 20 parts beeswax, approximately 40 parts mineral oil and approximately 1 part almond oil.

Ointments may be formulated by mixing a solution of the active ingredient in a vegetable oil, such as almond oil, with warm soft paraffin and allowing the mixture to cool. A typical example of such an ointment is one which includes approximately 30% almond oil and approximately 70% white soft paraffin by weight.

The present application also includes the use of the compounds of Formula I, II, III or IV of the subject invention in the manufacture of a composition, such as a pharmaceutical composition, for inhibiting hedgehog activity.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLES

General Remarks

All reagents were of commercial quality. Solvents were dried and purified by standard methods. Mass spectrum analyses were recorded on a Platform II (Agilent 6110) quadrupole mass spectrometer fitted with an electrospray rinterface. $^1$H NMR spectra were recorded at 300 MHz and at 300 K, on a Brücker AMX 300 apparatus. Chemical shifts were recorded as parts per million (ppm) downfield from TMS (0.00 ppm), and J coupling constants were reported in hertz (Hz).

Example 1

3-Methylbiphenyl-4-carboxylic Acid

A mixture of 4-bromo-2-methylbenzoic acid (215 mg, 1.0 mmol) and $Na_2CO_3$ (425 mg, 4.0 mmol) in ethanol (5 mL) was added water (2 mL), then the mixture was heated to reflux for 30 min, cooled to room temperature, phenylboronic acid (146 mg, 1.2 mmol) and $Pd(PPh_3)_4$ (57.8 mg, 0.05 mmol) were added to the reaction mixture. Then the mixture was heated to reflux for 8 h under nitrogen. After filtered and the residue was washed with water (5 mL). The filtrate was evaporated under reduced pressure to remove ethanol. Adjusted pH to 13~14 with sodium hydroxide and then washed with $CH_2Cl_2$ (10 mL×3), the water layer was adjusted pH to 1~2 with diluted hydrochloric acid and a lot of solid was precipitated. Filtered, the residue was washed with water (20 mL), dried to obtain the title compound as a light-yellow solid (180 mg, 85%). MS: m/z 211.1 [M−H].

Example 2

N-(3-(1H-benzo[d]imidazol-2-yl)-4-chlorophenyl)-3-methylbiphenyl-4-carboxamide A mixture of 3-methylbiphenyl-4-carboxylic acid (44.5 mg, 0.21 mmol) in $SOCl_2$ (3 mL) was heated to reflux for 2 h, then the mixture was evaporated under reduced pressure to remove solvent to get the intermediate 3-methylbiphenyl-4-carbonyl chloride.

A mixture of 3-(1H-benzo[d]imidazol-2-yl)-4-chloroaniline (51.2 mg, 0.21 mmol), $Na_2CO_3$ (44.5 mg, 0.42 mmol) in $CH_2Cl_2$ (1 mL) was stirred for 15 min in an ice-water bath. Then 3-methylbiphenyl-4-carbonyl chloride in $CH_2Cl_2$ was added dropwise to the mixture, the reaction mixture was stirred for 8 h at room temperature. After water (5 mL) was added, the mixture was extracted with EtOAc (10 mL×3), the combined organic solution was dried with anhydrous sulfate sodium, and then concentrated in vacuo to get the crude product, which was recrystallized from methanol, then purified through TLC ($CH_2Cl_2/CH_3OH$) to obtain the title compound as as an off-white solid (14.23 mg, 15.5%). $^1$H NMR (DMSO-$d_6$): 12.72 (s, 1H), 10.65 (s, 1H), 8.40 (d, J=2.4 Hz, 1H), 7.86 (dd, J=8.7 and 2.4 Hz, 1H), 7.72-7.68 (m, 3H), 7.63-7.56 (m, 5H), 7.48-7.45 (m, 2H), 7.41-7.36 (m, 1H), 7.27-7.19 (m, 2H), 2.51 (s, 3H). MS: m/z 438.1 [M+H]$^+$.

The following compounds were prepared from (un)substituted 4-bromobenzoic acid, the corresponding phenylboronic acid and 3-(1H-benzo[d]imidazol-2-yl)-4-chloroaniline using a procedure similar to those described for the syntheses of compounds of Examples 1 and 2.

Example 3

N-(3-(1H-benzo[d]imidazol-2-yl)-4-chlorophenyl)-3-methyl-4'-methoxybiphenyl-4-carboxamide Off-white solid (6.57 mg, 6.69%). $^1$H NMR (DMSO-$d_6$): 12.71 (s, 1H), 10.61 (s, 1H), 8.40 (d, J=2.4 Hz, 1H), 7.86 (dd, J=9.2 and 2.6 Hz, 1H), 7.71-7.55 (m, 8H), 7.27-7.19 (m, 2H), 7.03 (d, J=9.0 Hz, 2H), 3.79 (s, 3H), 2.51 (s, 3H). MS: m/z 468.1 [M+H]$^+$.

Example 4

N-(3-(1H-benzo[d]imidazol-2-yl)-4-chlorophenyl)-3-methyl-4'-fluorobiphenyl-4-carboxamide White solid (30.44 mg, 31.79%). $^1$H NMR (DMSO-$d_6$): 12.74 (s, 1H), 10.67 (s, 1H), 8.43 (d, J=2.4 Hz, 1H), 7.80 (dd, J=8.9 and 2.6 Hz, 1H), 7.79-7.70 (m, 3H), 7.65-7.57 (m, 4H), 7.36-7.20 (m, 4H), 2.53 (s, 3H). MS: m/z 456.1 [M+H]$^+$.

Example 5

N-(3-(1H-benzo[d]imidazol-2-yl)-4-chlorophenyl)-3-methyl-4'-(methylsulfonyl)biphenyl-4-carboxamide Off-white solid (27.03 mg, 24.94%). $^1$H NMR (DMSO-$d_6$): 12.75 (s, 1H), 10.72 (s, 1H), 8.43 (d, J=2.4 Hz, 1H), 8.05-7.99 (m, 4H), 7.88 (dd, J=8.7 and 2.6 Hz, 1H), 7.75-7.57 (m, 6H), 7.29-7.20 (m, 2H), 3.32 (s, 3H), 2.53 (s, 3H). MS: m/z 516.1 [M+H]$^+$.

Example 6

N-(3-(1H-benzo[d]imidazol-2-yl)-4-chlorophenyl)-3-methyl-4'-cyanobiphenyl-4-carboxamide Off-white solid (13.28 mg, 13.66%). $^1$H NMR (DMSO-$d_6$): 12.75 (s, 1H), 10.71 (s, 1H), 8.42 (d, J=2.4 Hz, 1H), 7.99-7.93 (m, 4H), 7.88 (dd, J=8.9 and 2.6 Hz, 1H), 7.75-7.70 (m, 3H), 7.66-7.57 (m, 3H), 7.29-7.21 (m, 2H), 2.53 (s, 3H). MS: m/z 463.1 [M+H]$^+$.

Example 7

N-(3-(1H-benzo[d]imidazol-2-yl)-4-chlorophenyl)-3-methyl-4'-nitrobiphenyl-4-carboxamide Light-yellow solid (32.07 mg, 31.6%). $^1$H NMR (DMSO-$d_6$): 12.75 (s, 1H), 10.73 (s, 1H), 8.43 (d, J=2.4 Hz, 1H), 8.34 (d, J=8.7 Hz, 2H), 8.03 (d, J=8.7 Hz, 2H), 7.88 (dd, J=9.0 and 2.6 Hz, 1H), 7.79-7.58 (m, 6H), 7.29-7.20 (m, 2H), 2.53 (s, 3H). MS: m/z 483.1 [M+H]$^+$.

Example 8

N-(3-(1H-benzo[d]imidazol-2-yl)-4-chlorophenyl)-3-methyl-4'-chlorobiphenyl-4-carboxamide White solid (8.25 mg, 8.32%). $^1$H NMR (DMSO-$d_6$): 12.72 (s, 1H), 10.66 (s, 1H), 8.41 (d, J=2.4 Hz, 1H), 7.86 (dd, J=8.1 and 1.8 Hz, 1H), 7.76-7.68 (m, 3H), 7.64-7.52 (m, 7H), 7.28-7.18 (m, 2H), 2.48 (s, 3H). MS: m/z 472.1 [M+H]$^+$.

Example 9

N-(3-(1H-benzo[d]imidazol-2-yl)-4-chlorophenyl)-3-methyl-4'-acetylbiphenyl-4-carboxamide White solid (8.62 mg, 8.55%). $^1$H NMR (DMSO-$d_6$): 12.73 (s, 1H), 10.68 (s, 1H), 8.41 (d, J=2.4 Hz, 1H), 8.05 (d, J=8.4 Hz, 2H), 7.87 (d, J=8.4 Hz, 2H), 7.85-7.83 (m, 1H), 7.72-7.54 (m, 6H), 7.27-7.19 (m, 2H), 2.61 (s, 3H), 2.48 (s, 3H). MS: m/z 480.2 [M+H]$^+$.

Example 10

N-(3-(1H-benzo[d]imidazol-2-yl)-4-chlorophenyl)-3-methyl-3'-fluorobiphenyl-4-carboxamide White solid (44.51 mg, 46.49%). $^1$H NMR (DMSO-$d_6$): 12.74 (s, 1H), 10.69 (s, 1H), 8.42 (d, J=2.4 Hz, 1H), 7.88 (dd, J=8.7 and 2.7 Hz, 1H), 7.73-7.50 (m, 9H), 7.30-7.20 (m, 3H), 2.50 (s, 3H). MS: m/z 456.2 [M+H]$^+$.

Example 11

N-(3-(1H-benzo[d]imidazol-2-yl)-4-chlorophenyl)-3-methyl-3'-cyanobiphenyl-4-carboxamide White solid (20.47 mg, 21.06%). $^1$H NMR (DMSO-$d_6$): 12.74 (s, 1H), 10.70 (s, 1H), 8.43 (d, J=2.4 Hz, 1H), 8.25 (s, 1H), 8.09 (d, J=7.8 Hz, 1H), 7.88 (d, J=7.8 Hz, 2H), 7.76-7.57 (m, 7H), 7.29-7.21 (m, 2H), 2.50 (s, 3H). MS: m/z 463.1 [M+H]$^+$.

Example 12

N-(3-(1H-benzo[d]imidazol-2-yl)-4-chlorophenyl)-4'-fluorobiphenyl-4-carboxamide

White solid (39.15 mg, 42.19%). $^1$H NMR (DMSO-$d_6$): 12.75 (brs, 1H), 10.61 (s, 1H), 8.47 (d, J=2.4 Hz, 1H), 8.10 (d, J=8.7 Hz, 2H), 8.03 (dd, J=8.9 and 2.7 Hz, 1H), 7.87-7.81 (m, 4H), 7.73-7.57 (m, 3H), 7.35 (t, J=8.9 Hz, 2H), 7.27-7.24 (m, 2H). MS: m/z 442.1 [M+H]$^+$.

Example 13

N-(3-(1H-benzo[d]imidazol-2-yl)-4-chlorophenyl)-3'-fluorobiphenyl-4-carboxamide

White solid (14.85 mg, 16.00%). $^1$H NMR (DMSO-$d_6$): 12.74 (brs, 1H), 10.63 (s, 1H), 8.47 (d, J=2.4 Hz, 1H), 8.11 (d, J=7.8 Hz, 2H), 8.03 (dd, J=8.7 and 1.2 Hz, 1H), 7.92 (d, J=7.8 Hz, 2H), 7.73-7.52 (m, 7H), 7.31-7.21 (m, 3H). MS: m/z 442.1 [M+H]$^+$.

Example 14

N-(3-(1H-benzo[d]imidazol-2-yl)-4-chlorophenyl)-2-methyl-4'-(trifluoromethyl)biphenyl-4-carboxamide White solid (46.58 mg, 43.8%). $^1$H NMR (DMSO-$d_6$): 12.74 (s, 1H), 10.60 (s, 1H), 8.46 (d, J=2.4 Hz, 1H), 8.04 (dd, J=8.7 and 2.4 Hz, 1H), 7.98 (s, 1H), 7.92 (d, J=8.4 Hz, 1H), 7.85 (d, J=8.1 Hz, 2H), 7.72 (d, J=7.5 Hz, 1H), 7.67-7.64 (m, 3H), 7.60 (d, J=7.5 Hz, 1H), 7.43 (d, J=8.1 Hz, 1H), 7.30-7.21 (m, 2H), 2.33 (s, 3H). MS: m/z 506.2 [M+H]$^+$.

Example 15

N-(3-(1H-benzo[d]imidazol-2-yl)-4-chlorophenyl)-3-methoxy-4'-(trifluoromethyl)biphenyl-4-carboxamide White solid (7.54 mg, 6.88%). $^1$H NMR (DMSO-$d_6$): 12.75 (s, 1H), 10.48 (s, 1H), 8.38 (d, J=2.4 Hz, 1H), 8.01 (d, J=8.4 Hz, 2H), 7.92 (dd, J=8.9 and 2.3 Hz, 1H), 7.87 (d, J=8.4 Hz, 2H), 7.76 (d, J=8.1 Hz, 1H), 7.72 (d, J=7.5 Hz, 1H), 7.63 (d, J=8.7 Hz, 1H), 7.59 (d, J=7.5 Hz, 1H), 7.49 (s, 1H), 7.44 (dd, J=8.1 and 1.2 Hz, 1H), 7.29-7.21 (m, 2H), 4.02 (s, 3H). MS: m/z 522.2 [M+H]$^+$.

Example 16

N-(3-(1H-benzo[d]imidazol-2-yl)-4-chlorophenyl)-3-hydroxy-4'-(trifluoromethyl)biphenyl-4-carboxamide White solid (23.26 mg, 21.81%). $^1$H NMR (DMSO-$d_6$): 12.76 (s, 1H), 11.88 (brs, 1H), 10.71 (s, 1H), 8.39 (d, J=2.4 Hz, 1H), 8.09 (d, J=8.1 Hz, 1H), 7.95-7.84 (m, 5H), 7.72 (d, J=6.9 Hz, 1H), 7.67 (d, J=8.7 Hz, 1H), 7.60 (d, J=6.9 Hz, 1H), 7.39-7.34 (m, 2H), 7.30-7.21 (m, 2H). MS: m/z 508.1 [M+H]$^+$.

Example 17

N-(3-(1H-benzo[d]imidazol-2-yl)-4-chlorophenyl)-3-fluoro-4'-(trifluoromethyl)biphenyl-4-carboxamide White solid (17.91 mg, 16.7%). $^1$H NMR (DMSO-$d_6$): 12.76 (s, 1H), 10.83 (s, 1H), 8.38 (d, J=2.4 Hz, 1H), 8.03 (d, J=8.1 Hz, 2H), 7.92-7.82 (m, 5H), 7.78-7.58 (m, 4H), 7.30-7.21 (m, 2H). MS: m/z 510.1 [M+H]$^+$.

Example 18

N-(3-(1H-benzo[d]imidazol-2-yl)-4-chlorophenyl)-3-chloro-4'-(trifluoromethyl)biphenyl-4-carboxamide White solid (19.54 mg, 17.68%). $^1$H NMR (DMSO-$d_6$): 12.72 (brs, 1H), 10.88 (s, 1H), 8.37 (d, J=2.4 Hz, 1H), 8.00-7.98 (m, 3H), 7.86-7.82 (m, 4H), 7.75 (d, J=7.8 Hz, 1H), 7.70 (d, J=6.9 Hz, 1H), 7.64 (d, J=8.7 Hz, 1H), 7.57 (d, J=6.9 Hz, 1H), 7.28-7.19 (m, 2H). MS: m/z 526.1 [M+H]$^+$.

Example 19

N-(3-(1H-benzo[d]imidazol-2-yl)-4-chlorophenyl)-3-nitro-4'-(trifluoromethyl)biphenyl-4-carboxamide White solid (250.2 mg, 51.8%). $^1$H NMR (DMSO-$d_6$): 12.74 (s, 1H), 11.06 (s, 1H), 8.48 (s, 1H), 8.32 (d, J=2.4 Hz, 1H), 8.26 (dd, J=8.0 and 1.7 Hz, 1H), 8.07 (d, J=8.1 Hz, 2H), 7.96 (d, J=7.8 Hz, 1H), 7.89 (d, J=8.4 Hz, 2H), 7.81 (dd, J=8.7 and 2.7 Hz, 1H), 7.69 (d, J=7.2 Hz, 1H), 7.65 (d, J=8.7 Hz, 1H), 7.57 (d, J=6.9 Hz, 1H), 7.28-7.19 (m, 2H). MS: m/z 537.3 [M+H]$^+$.

Example 20

N-(3-(1H-benzo[d]imidazol-2-yl)-4-chlorophenyl)-3,5-dimethyl-4'-(trifluoromethyl)biphenyl-4-carboxamide White solid (20 mg, 7.7%). $^1$H NMR (DMSO-$d_6$): 12.75 (s, 1H), 10.79 (s, 1H), 8.41 (d, J=2.4 Hz, 1H), 7.93 (d, J=8.4 Hz, 2H), 7.85-7.82 (m, 3H), 7.72 (d, J=7.2 Hz, 1H), 7.64 (d, J=9.0 Hz, 1H), 7.59 (d, J=7.2 Hz, 1H), 7.53 (s, 2H), 7.29-7.21 (m, 2H), 2.38 (s, 6H). MS: m/z 520.2 [M+H]$^+$.

Example 21

N-(3-(1H-benzo[d]imidazol-2-yl)-4-chlorophenyl)-3-methyl-4'-(trifluoromethyl)biphenyl-4-carboxamide a) 3-Methyl-4'-(trifluoromethyl)biphenyl-4-carboxylic acid: The title compound was prepared from 4-bromo-2-methylbenzoic acid and 4-(trifluoromethyl)phenylboronic acid using a procedure similar to those described for the synthesis of compound of Example 1. Brown solid (300 mg, 53.5%). MS: m/z 281.1 [M+H]$^+$.

b) N-(3-(1H-benzo[d]imidazol-2-yl)-4-chlorophenyl)-3-methyl-4'-(trifluoromethyl)biphenyl-4-carboxamide: To a solution of 3-methyl-4'-(trifluoromethyl)biphenyl-4-carboxylic acid (112 mg, 0.4 mmol) in DMF (2 mL) was added triethylamine (80 mg, 0.8 mmol), HATU (200 mg, 0.48 mmol), 3-(1H-benzo[d]imidazol-2-yl)-4-chloroaniline (100 mg, 0.4 mmol) in sequence. The reaction mixture was stirred at room temperature for 8 h, and then poured into 20 mL of water, extracted with ethyl acetate (20 mL×3). The combined organic layers were washed with 1 N hydrochloric acid (20 mL) and brine (20 mL×3), dried over anhydrous sodium sulfate, and concentrated under reduced pressure. The residue was purified by column chromatography on silica gel with ethyl acetate to give the title compound as a white solid (2 mg, 1.0%). $^1$H NMR (CD$_3$OD): 8.18 (d, J=2.4 Hz, 1H), 7.96 (dd, J=8.7 and 1.8 Hz, 1H), 7.86 (d, J=8.1 Hz, 2H), 7.77 (d, J=8.1 Hz, 2H), 7.68-7.56 (m, 6H), 7.33-7.31 (m, 2H), 2.56 (s, 3H). MS: m/z 506.1 [M+H]$^+$.

The following compounds were prepared from 3-(1H-benzo[d]imidazol-2-yl)-4-chloroaniline and the corresponding 4'-(trifluoromethyl)biphenyl-4-carboxylic acid (the compound was prepared from 4-bromobenzoic acid and 4-(trifluoromethyl)phenylboronic using a procedure similar to those described for the synthesis of compound of Example 1) or biphenyl-4-carboxylic acid using a procedure similar to those described for the synthesis of compound of Example 21b.

Example 22

N-(3-(1H-benzo[d]imidazol-2-yl)-4-chlorophenyl)-4'-(trifluoromethyl)biphenyl-4-carboxamide White solid (9 mg, 4.6%). $^1$H NMR (DMSO-$d_6$): 12.74 (s, 1H), 10.66 (s, 1H), 8.47 (d, J=1.8 Hz, 1H), 8.14 (d, J=8.1 Hz, 2H), 8.05-7.93 (m, 5H), 7.87 (d, J=8.1 Hz, 2H), 7.72 (d, J=7.5 Hz, 1H), 7.66 (d, J=8.7 Hz, 1H), 7.60 (d, J=7.2 Hz, 1H), 7.28-7.20 (m, 2H). MS: m/z 492.1 [M+H]$^+$.

Example 23

N-(3-(1H-benzo[d]imidazol-2-yl)-4-chlorophenyl)biphenyl-4-carboxamide

White solid (10.1 mg, 6.0%). $^1$H NMR (DMSO-$d_6$): 12.74 (s, 1H), 10.61 (s, 1H), 8.47 (d, J=2.4 Hz, 1H), 8.11 (d, J=8.4 Hz, 2H), 8.03 (dd, J=8.9 and 2.6 Hz, 1H), 7.86 (d, J=8.4 Hz, 2H), 7.77 (d, J=7.2 Hz, 2H), 7.72 (d, J=6.9 Hz, 1H), 7.65 (d, J=8.7 Hz, 1H), 7.59 (d, J=6.9 Hz, 1H), 7.54-7.50 (m, 2H), 7.46-7.41 (m, 1H), 7.30-7.21 (m, 2H). MS: m/z 424.1 [M+H]$^+$.

Example 24

N-(3-(1H-benzo[d]imidazol-2-yl)-4-chlorophenyl)-3-methyl-4'-aminobiphenyl-4-carboxamide To a solution of N-(3-(1H-benzo[d]imidazol-2-yl)-4-chlorophenyl)-3-methyl-4'-nitrobiphenyl-4-carboxamide (Example 7, 30.1 mg, 0.06 mmol) in methanol (5 mL) and water (1 mL) was added iron power (10.9 mg, 0.3 mmol) and NH$_4$Cl (2.1 mg, 0.04 mmol). The mixture was heated to reflux for 2 h. The cooled solution was treated with Na$_2$CO$_3$ to pH 8~9, and filtered through celite, washed with methanol (10 mL), then evaporated to remove methanol, the residue was washed with water (5 mL), and dried to give the title compound as an off-white solid (18.43 mg, 67.8%). $^1$H NMR (DMSO-$d_6$): 12.72 (s, 1H), 10.56 (s, 1H), 8.41 (d, J=2.4 Hz, 1H), 7.87 (dd, J=8.9 and 2.6 Hz, 1H), 7.71 (d, J=7.2 Hz, 1H), 7.65-7.62 (m, 7H), 7.29-7.20 (m, 2H), 6.65 (d, J=8.4 Hz, 2H), 5.32 (s, 2H), 2.45 (s, 3H). MS: m/z 453.3 [M+H]$^+$.

Example 25

N-(3-(1H-benzo[d]imidazol-2-yl)-4-chlorophenyl)-3-amino-4'-(trifluoromethyl)biphenyl-4-carboxamide The title compound was prepared from N-(3-(1H-benzo[d]imidazol-2-yl)-4-chlorophenyl)-3-nitro-4'-(trifluoromethyl)biphenyl-4-carboxamide (Example 19) using a procedure similar to those described for the synthesis of compound of Example 24. Light-yellow solid (200 mg, 91.7%). $^1$H NMR (DMSO-$d_6$): 12.71 (brs, 1H), 10.37 (s, 1H), 8.42 (d, J=2.7 Hz, 1H), 7.93 (dd, J=8.9 and 2.6 Hz, 1H), 7.88-7.82 (m, 5H), 7.73-7.56 (m, 3H), 7.26-7.25 (m, 2H), 7.13 (d, J=1.5 Hz, 1H), 6.97 (dd, J=8.1 and 1.5 Hz, 1H), 6.59 (s, 2H). MS: m/z 507.5 [M+H]$^+$.

Example 26

3-(3-(1H-benzo[d]imidazol-2-yl)-4-chlorophenyl)-7-(4-(trifluoromethyl)phenyl)quinazoline-2,4(1H,3H)-dione To a mixture of N-(3-(1H-benzo[d]imidazol-2-yl)-4-chlorophenyl)-3-amino-4'-(trifluoromethyl)biphenyl-4-carboxamide (51.1 mg, 0.1 mmol) in THF (2 mL) was added triphosgene (12.0 mg, 0.04 mmol), then the mixture was heated to reflux for 3 h, then removed the solvent in a vaccum. The residue was washed with 1N hydrochloric acid (10 mL), and purified by TLC (CH$_2$Cl$_2$/CH$_3$OH) to give the title compound as a white solid (3.86 mg, 7.2%). $^1$H NMR (DMSO-$d_6$): 12.83 (brs, 1H), 11.70 (brs, 1H), 8.08 (d, J=8.4 Hz, 1H), 7.99-7.88 (m, 5H), 7.80 (d, J=8.4 Hz, 1H), 7.69 (d, J=7.5 Hz, 1H), 7.62-7.56 (m, 3H), 7.52-7.49 (m, 1H), 7.30-7.20 (m, 2H). MS: m/z 533.2 [M+H]$^+$.

Example 27

3-(3-(1H-benzo[d]imidazol-2-yl)-4-chlorophenyl)-7-(4-(trifluoromethyl)phenyl)quinazolin-4(3H)-one N-(3-(1H-benzo[d]imidazol-2-yl)-4-chlorophenyl)-3-amino-4'-(trifluoromethyl)biphenyl-4-carboxamide (101.5 mg, 0.2 mmol) was dissolved in anhydrous triethyl orthoformate (5 mL) and the mixture was heated to reflux for 3 h, then evaporated to remove the solvent, and the residue was purified through TLC (CH$_2$Cl$_2$/CH$_3$OH) to give the title compound as a white solid (36.71 mg, 36.2%). $^1$H NMR (DMSO-$d_6$): 12.85 (brs, 1H), 8.51 (s, 1H), 8.33 (d, J=8.4 Hz, 1H), 8.17-8.09 (m, 4H), 8.01 (d, J=8.7 Hz, 1H), 7.91-7.87 (m, 3H), 7.80-7.75 (m, 1H), 7.71-7.61 (m, 2H), 7.31-7.22 (m, 2H). MS: m/z 517.2 [M+H]$^+$.

Example 28

3-(3-(1H-benzo[d]imidazol-2-yl)-4-chlorophenyl)-7-(4-(trifluoromethyl) phenyl)-2H-benzo[e][1,3]oxazin-4(3H)-one A mixture of N-(3-(1H-benzo[d]imidazol-2-yl)-4-chlorophenyl)-3-hydroxy-4'-(trifluoromethyl)biphenyl-4-carboxamide (Example 16, 20 mg, 0.04 mmol) and paraformaldehyde (3.6 mg, 0.12 mmol) in TFA (1 mL) was heated at 100° C. for 4 h. The TFA was removed under vacuum, and the residue was diluted with EtOAc (10 mL), washed with NaHCO$_3$ aqueous solution (10 mL), water (10 mL) and brine (10 mL), and dried and concentrated. The residue was purified by TLC (CH$_2$Cl$_2$/CH$_3$OH) and then recrystallized from CH$_3$OH and CH$_2$Cl$_2$ to obtain the title compound as a white solid (2.99 mg, 14.38%). $^1$H NMR (DMSO-$d_6$): 12.80 (s, 1H), 8.05-7.97 (m, 4H), 7.87 (d, J=8.4 Hz, 2H), 7.77-7.71 (m, 2H), 7.64-7.59 (m, 4H), 7.30-7.22 (m, 2H), 5.86 (s, 2H). MS: m/z 520.1 [M+H]$^+$.

Example 29

2-(3-(1H-benzo[d]imidazol-2-yl)-4-chlorophenyl)-6-phenyl-3,4-dihydroisoquinolin-1(2H)-one a) 3,4-Dihydro-6-phenyl-1H-2-benzopyran-1-one: A sealed vessel equipped with a magnetic stir bar was charged with Pd(OAc)$_2$ (56 mg, 0.25 mmol) followed by Na$_2$CO$_3$ (1.6 g, 15 mmol), 4-biphenylcarboxylic acid (1 g, 5 mmol), 1,2-dichloroethane (20 mL). The reaction mixture was heated to 140° C. over 36 h. After cooled to room temperature, the mixture was diluted with DCM (20 mL) and filtered through a short pad of celite. The filtrate was washed with brine, concentrated in vacuum, and the residue was purified by chromatography (PE/EA) to give the title compound as a yellow solid (90 mg, 7.96%). MS: m/z 225.1 [M+H]$^+$.

b) 2-(3-(1H-benzo[d]imidazol-2-yl)-4-chlorophenyl)-6-phenyl-3,4-dihydroisoquinolin-1(2H)-one: A mixture of 3-(1H-benzo[d]imidazol-2-yl)-4-chloroaniline (122 mg, 0.5 mmol), 3,4-dihydro-6-phenyl-1H-2-benzopyran-1-one (90 mg, 0.4 mmol) and Aluminum trichloride (26 mg, 0.2 mmol) was heated in a sealed vessel at 160° C. for 16 h. After cooling, to the mixture was added 1 N hydrochloric acid (4 mL), then the mixture was extracted with DMC (5 mL×2). The combined organic layers were washed with brine, dried, and evaporated. The residue was purified on silica gel column chromatography (DCM/MeOH, PE/EA) to give the title compound as a yellow solid (15 mg, 8.3%). $^1$H NMR (DMSO-$d_6$): 12.78 (s, 1H), 8.04-7.99 (m, 2H), 7.78-7.70 (m, 6H), 7.66-7.58 (m, 2H), 7.51-7.40 (m, 3H), 7.27-7.23 (m, 2H), 4.09 (t, J=6.9 Hz, 2H), 3.25 (t, J=6.9 Hz, 2H). MS: m/z 450.2 [M+H]$^+$.

Example 30

N-(3-(1H-benzo[d]imidazol-2-yl)-4-chlorophenyl)-2-methyl-4-morpholinobenzamide a) Methyl 2-methyl-4-morpholinobenzoate: A clean 50 mL flask was charged with methyl 4-fluoro-2-methylbenzoate (168 mg, 1 mmol), morpholine (870 mg, 10 mmol), potassium carbonate (276 mg, 2 mmol) and acetonitrile (10 mL). The mixture was heated to reflux overnight. After cooled to room temperature, to the suspension was added water (20 mL), filtered, and dried to give the title compound as a yellow liquid (190 mg, 80.8%). MS: m/z 236.2 [M+H]$^+$.

b) 2-Methyl-4-morpholinobenzoic acid: A mixture solution of methyl 2-methyl-4-morpholinobenzoate (190 mg, 0.8 mmol), 4 N aqueous NaOH solution (10 mL) in methanol (5 mL) was stirred at 50° C. for 2 h. Then the mixture was evaporated under reduced pressure to remove methanol. To the resulting suspension was added 10 mL of water and extracted with DCM (10 mL), acidified with 3 N hydrochloric acid to pH=3. The precipitate was filtered and dried to give the title compound as a white solid (130 mg, 73.0%). MS: m/z 222.1 [M+H]$^+$.

c) N-(3-(1H-benzo[d]imidazol-2-yl)-4-chlorophenyl)-2-methyl-4-morpholinobenzamide: The title compound was prepared from 3-(1H-benzo[d]imidazol-2-yl)-4-chloroaniline and 2-methyl-4-morpholinobenzoic acid using a procedure similar to those described for the synthesis of compound of Example 21b. White solid (10.8 mg, 6.1%). $^1$H NMR (DMSO-d$_6$): 12.72 (s, 1H), 10.36 (s, 1H), 8.38 (d, J=2.7 Hz, 1H), 7.86 (dd, J=8.9 and 2.6 Hz, 1H), 7.70 (d, J=6.9 Hz, 1H), 7.61-7.56 (m, 2H), 7.45 (d, J=9.0 Hz, 1H), 7.29-7.22 (m, 2H), 6.86-6.83 (m, 2H), 3.76-3.72 (m, 4H), 3.21-3.17 (m, 4H), 2.40 (s, 3H). MS: m/z 447.3 [M+H]$^+$.

The following compounds were prepared from methyl 4-fluoro-2-methylbenzoate, the corresponding piperidine or (2S,6R)-2,6-dimethylmorpholine, and 3-(1H-benzo[d]imidazo-2-yl)-4-chloroaniline using a procedure similar to those described for the synthesis of compound of Example 30.

Example 31

N-(3-(1H-benzo[d]imidazol-2-yl)-4-chlorophenyl)-2-methyl-4-(piperidin-1-yl)benzamide Off-white solid (1 mg, 0.6%). $^1$H NMR (CD$_3$OD): 8.11 (d, J=2.4 Hz, 1H), 7.91 (dd, J=8.7 and 2.7 Hz, 1H), 7.69-7.63 (m, 2H), 7.57 (d, J=8.7 Hz, 1H), 7.43 (d, J=9.3 Hz, 1H), 7.32-7.29 (m, 2H), 6.83-6.81 (m, 2H), 3.26-3.24 (m, 4H), 2.45 (s, 3H), 1.64-1.71 (m, 6H). MS: m/z 445.2 [M+H]$^+$.

Example 32

N-(3-(1H-benzo[d]imidazol-2-yl)-4-chlorophenyl)-2-methyl-4-((2S,6R)-2,6-dimethylmorpholino)benzamide Off-white solid (5 mg, 2.6%). $^1$H NMR (DMSO-d$_6$): 12.69 (s, 1H), 10.32 (s, 1H), 8.36 (d, J=2.4 Hz, 1H), 7.85 (dd, J=8.9 and 2.6 Hz, 1H), 7.68 (d, J=5.1 Hz, 1H), 7.58-7.55 (m, 2H), 7.42 (d, J=8.4 Hz, 1H), 7.24-7.20 (m, 2H), 6.84-6.81 (m, 2H), 3.75-3.68 (m, 4H), 2.38 (s, 3H), 2.30-2.23 (m, 2H), 1.14 (d, J=6.0 Hz, 6H). MS: m/z 475.3 [M+H]$^+$.

Example 33

N-(3-(1H-benzo[d]imidazol-2-yl)-4-chlorophenyl)-2-amino-4-((2S,6R)-2,6-dimethylmorpholino)benzamide a) Methyl 4-((2S,6R)-2,6-dimethylmorpholino)-2-nitrobenzoate: To a solution of methyl 4-bromo-2-nitrobenzoate (1 g, 3.8 mmol), (2S,6R)-2,6-dimethylmorpholine (0.88 g, 7.7 mmol) in dry dioxane (20 mL) was added cesium carbonate (2.5 g, 7.7 mmol), palladium acetate (43 mg, 0.2 mmol), (R)-(+)-2,2'-bis(diphenylphosphino)-1,1'-binaphthyl (BINAP, 23 mg, 0.04 mmol). The mixture was heated to reflux under argon overnight. After cooling to room temperature, the reaction was filtered, and the filtrate was concentrate to give the crude title compound, which was used for the next step without further purification. MS: m/z 295.2 [M+H]$^+$.

b) 4-((2S,6R)-2,6-dimethylmorpholino)-2-nitrobenzoic acid: The title compound was prepared from methyl 4-((2S,6R)-2,6-dimethylmorpholino)-2-nitrobenzoate using a procedure similar to those described for the synthesis of compound of Example 30b. Yellow solid (0.7 g). MS: m/z 281.2 [M+H]$^+$.

c) N-(3-(1H-benzo[d]imidazol-2-yl)-4-chlorophenyl)-2-nitro-4-((2S,6R)-2,6-dimethylmorpholino)benzamide: A solution of 4-((2S,6R)-2,6-dimethylmorpholino)-2-nitrobenzoic acid (84 mg, 0.3 mmol), 1H-benzotriazol-1-yloxytris(dimethylamino)phosphonium hexafluorophosphate (BOP, 158 mg, 0.36 mmol) in pyridine (10 mL) was stirred at room temperature for 30 min before the addition of 3-(1H-benzo[d]imidazol-2-yl)-4-chloroaniline (73 mg, 0.3 mmol). The reaction mixture was stirred at 80° C. overnight, and then poured into 20 mL of water, extracted with ethyl acetate (20 mL×3). The combined organic layers were washed with 1 N hydrochloric acid (20 mL) and brine (20 mL×3), and dried over anhydrous sodium sulfate, concentrated under reduced pressure. The residue was purified by column chromatography on silica gel with DCM/MeOH to give the title compound as a yellow solid (80 mg, 52.9%). MS: m/z 506.3[M+H]$^+$.

d) N-(3-(1H-benzo[d]imidazol-2-yl)-4-chlorophenyl)-2-amino-4-((2S,6R)-2,6-dimethylmorpholino)benzamide: The title compound was prepared from N-(3-(1H-benzo[d]imidazol-2-yl)-4-chlorophenyl)-2-nitro-4-((2S,6R)-2,6-dimethylmorpholino)benzamide using a procedure similar to those described for the synthesis of compound of Example 24. Gray solid (20 mg, 26.5%). $^1$H NMR (DMSO-d$_6$): 12.67 (s, 1H), 9.95 (s, 1H), 8.35 (d, J=2.4 Hz, 1H), 7.89 (dd, J=9.0 and 2.7 Hz, 1H), 7.72-7.55 (m, 4H), 7.28-7.20 (m, 2H), 6.51 (s, 2H), 6.28 (d, J=7.2 Hz, 1H), 6.19 (s, 1H), 3.64-3.60 (m, 4H), 2.34-2.26 (m, 2H), 1.15 (d, J=6.3 Hz, 6H). MS: m/z 476.2 [M+H]$^+$.

Example 34

3-(3-(1H-benzo[d]imidazol-2-yl)-4-chlorophenyl)-7-((2S,6R)-2,6-dimethylmorpholino)quinazolin-4(3H)-one The title compound was prepared from N-(3-(1H-benzo[d]imidazol-2-yl)-4-chlorophenyl)-2-amino-4-((2S,6R)-2,6-dimethylmorpholino)benzamide and triethyl orthoformate using a procedure similar to those described for the synthesis of compound of Example 27. White solid (6 mg, 12.3%). $^1$H NMR (DMSO-d$_6$): 12.83 (s, 1H), 8.32 (s, 1H), 8.08 (d, J=2.4 Hz, 1H), 8.00 (d, J=9.0 Hz, 1H), 7.84 (d, J=8.4 Hz, 1H), 7.74-7.70 (m, 2H), 7.60 (dd, J=6.8 and 1.4 Hz, 1H), 7.31-7.21 (m, 3H), 7.06 (d, J=2.1 Hz, 1H), 3.90 (d, J=11.1 Hz, 2H), 3.74-3.64 (m, 2H), 2.51-2.43 (m, 2H), 1.19 (d, J=6.0 Hz, 6H). MS: m/z 486.2 [M+H]$^+$.

Example 35

N-(3-(1H-benzo[d]imidazol-2-yl)-4-chlorophenyl)-6-((2S,6R)-2,6-dimethylmorpholino)nicotinamide a) N-(3-(1H-benzo[d]imidazol-2-yl)-4-chlorophenyl)-6-chloronicotinamide: A clean flask was charged with 6-chloronicotinic acid (79 mg, 0.5 mmol), BOP (264 mg, 0.6 mmol) and pyridine (5 mL), the solution was stirred over 10 min before the addition of 3-(1H-benzo[d]imidazol-2-yl)-4-chloroaniline (121 mg, 0.5 mmol). The mixture was stirred at room temperature overnight, poured into 30 mL of water, the resulting precipitate was collected by filtered, and dried to give the title compound as a yellow solid (100 mg, 52.3%). MS: m/z 384.1 [M+H]$^+$.

b) N-(3-(1H-benzo[d]imidazol-2-yl)-4-chlorophenyl)-6-((2S,6R)-2,6-dimethylmorpholino)nicotinamide: A mixture of N-(3-(1H-benzo[d]imidazol-2-yl)-4-chlorophenyl)-6-chloronicotinamide (100 mg, 0.26 mmol), (2S,6R)-2,6-dimethylmorpholine (30 mg, 0.52 mmol), Na$_2$CO$_3$ (55 mg, 0.52 mmol) in DMSO (5 mL) was heated to 60° C. for 10 h. After cooling to room temperature, the solution was poured into 30 mL of water, the solids was filtered and dried. The crude was purified by chromatography (PE/EA) to give the title compound as a white solid (15 mg, 12.5%). $^1$H NMR (DMSO-d$_6$): 12.66 (s, 1H), 10.27 (s, 1H), 8.74 (d, J=2.4 Hz, 1H), 8.38 (d, J=2.7 Hz, 1H), 8.11 (dd, J=9.0 and 2.7 Hz, 1H), 7.97 (d, J=8.7 and 2.7 Hz, 1H), 7.69 (d, J=6.9 Hz, 1H), 7.60-7.55 (m, 2H), 7.26-7.20 (m, 2H), 6.93 (d, J=9.3 Hz, 1H), 4.30 (d, J=12.0 Hz, 2H), 3.61-3.52 (m, 2H), 2.54-2.51 (m, 2H), 1.15 (d, J=6.0 Hz, 6H). MS: m/z 462.3 [M+H]$^+$.

The following compounds were prepared from 4,6-dichloronicotinic acid or 6-chloro-5-methylnicotinic acid, 3-(1H-benzo[d]imidazol-2-yl)-4-chloroaniline and (2S,6R)-2,6-dimethylmorpholine using a procedure similar to those described for the synthesis of compound of Example 35.

Example 36

N-(3-(1H-benzo[d]imidazol-2-yl)-4-chlorophenyl)-4-chloro-6-((2S,6R)-2,6-dimethylmorpholino)nicotinamide Gray solid (8.4 mg, 15.3%). $^1$H NMR (DMSO-d$_6$): 12.75 (brs, 1H), 10.76 (s, 1H), 8.32 (d, J=2.4 Hz, 1H), 8.21 (s, 1H), 7.84 (dd, J=8.9 and 2.4 Hz, 1H), 7.66-7.63 (m, 3H), 7.27-7.24 (m, 2H), 7.06 (s, 1H), 3.62-3.57 (m, 2H), 3.45 (d, J=12.3 Hz, 2H), 2.67-2.59 (m, 2H), 1.02 (d, J=6.3 Hz, 6H). MS: m/z 496.2 [M+H]$^+$.

Example 37

N-(3-(1H-benzo[d]imidazol-2-yl)-4-chlorophenyl)-5-methyl-6-((2S,6R)-2,6-dimethylmorpholino)nicotinamide White solid (19 mg, 26.3%). $^1$H NMR (DMSO-d$_6$): 12.69 (s, 1H), 10.42 (s, 1H), 8.67 (d, J=2.4 Hz, 1H), 8.03 (d, J=2.1 Hz, 1H), 7.96 (dd, J=8.9 and 2.6 Hz, 1H), 7.70-7.68 (m, 1H), 7.61 (d, J=9.0 Hz, 1H), 7.57 (dd, J=6.6 and 1.8 Hz, 1H), 7.28-7.18 (m, 2H), 3.76-3.66 (m, 2H), 3.53 (d, J=12.3 Hz, 2H), 2.54-2.49 (m, 2H), 2.30 (s, 3H), 1.12 (d, J=6.3 Hz, 6H). MS: m/z 476.3 [M+H]$^+$.

Example 38

N-(3-(1H-benzo[d]imidazol-2-yl)-4-chlorophenyl)-2-methyl-6-((2S,6R)-2,6-dimethylmorpholino)nicotinamide The title compound was prepared from ethyl 6-chloro-2-methylnicotinate, (2S,6R)-2,6-dimethylmorpholine and 3-(1H-benzo[d]imidazol-2-yl)-4-chloroaniline using a procedure similar to those described for the syntheses of compounds of Examples 30a, 30b and 33c. White solid (14 mg, 14.7%). $^1$H NMR (DMSO-d$_6$): 12.69 (s, 1H), 10.34 (s, 1H), 8.36 (d, J=2.4 Hz, 1H), 7.87 (dd, J=8.7 and 2.7 Hz, 1H), 7.76 (d, J=8.7 Hz, 1H), 7.70 (d, J=8.7 Hz, 1H), 7.61-7.57 (m, 2H), 7.29-7.20 (m, 2H), 6.75 (d, J=8.7 Hz, 1H), 4.26 (d, J=11.7 Hz, 2H), 3.64-3.55 (m, 2H), 3.29 (s, 3H), 2.45-2.40 (m, 2H), 1.16 (d, J=6.3 Hz, 6H). MS: m/z 476.2 [M+H]$^+$.

The following compounds were prepared from 4-bromo-2-methylbenzoic acid, 3-(1H-benzo[d]midazol-2-yl)-4-chloroaniline and the corresponding phenylboronic acid using a procedure similar to those described for the syntheses of compounds of Examples 2 and 1.

Example 39

N-(3-(1H-benzo[d]imidazol-2-yl)-4-chlorophenyl)-2-methyl-4-(2-methoxypyrimidin-5-yl)benzamide White solid (13 mg, 13.8%). $^1$H NMR (DMSO-d$_6$): 12.71 (s, 1H), 10.65 (s, 1H), 8.99 (s, 2H), 8.41 (d, J=2.4 Hz, 1H), 7.87 (dd, J=8.9 and 2.6 Hz, 1H), 7.72-7.54 (m, 6H), 7.30-7.21 (m, 2H), 3.98 (s, 3H), 2.48 (s, 3H). MS: m/z 470.2 [M+H]$^+$.

Example 40

N-(3-(1H-benzo[d]imidazol-2-yl)-4-chlorophenyl)-2-methyl-4-(pyridin-3-yl)benzamide White solid (30 mg, 34.2%). $^1$H NMR (DMSO-d$_6$): 12.74 (s, 1H), 10.68 (s, 1H), 8.94 (d, J=2.1 Hz, 1H), 8.61 (dd, J=4.8 and 1.5 Hz, 1H), 8.41 (d, J=2.4 Hz, 1H), 8.15-8.11 (m, 1H), 7.88 (dd, J=8.7 and 2.4 Hz, 1H), 7.72-7.50 (m, 6H), 7.29-7.21 (m, 2H), 2.50 (s, 3H). MS: m/z 439.2 [M+H]$^+$.

Example 41

N-(3-(1H-benzo[d]imidazol-2-yl)-4-chlorophenyl)-2-methyl-4-(furan-3-yl)benzamide White solid (10 mg, 11.7%). $^1$H NMR (DMSO-d$_6$): 12.71 (brs, 1H), 10.57 (s, 1H), 8.40 (d, J=2.4 Hz, 1H), 8.27 (s, 1H), 7.88 (dd, J=8.9 and 2.6 Hz, 1H), 7.77 (t, J=1.7 Hz, 1H), 7.70-7.52 (m, 6H), 7.26-7.24 (m, 2H), 7.03 (s, 1H), 2.45 (s, 3H). MS: m/z 428.2 [M+H]$^+$.

Example 42

N-(3-(1H-benzo[d]imidazol-2-yl)-4-chlorophenyl)-2-methyl-4-(thiophen-3-yl)benzamide White solid (15 mg, 16.9%). $^1$H NMR (DMSO-d$_6$): 12.74 (brs, 1H), 10.61 (s, 1H), 8.40 (d, J=2.4 Hz, 1H), 7.98 (d, J=1.5 Hz, 1H), 7.88 (dd, J=8.9 and 2.3 Hz, 1H), 7.70-7.54 (m, 8H), 7.26-7.23 (m, 2H), 2.46 (s, 3H). MS: m/z 444.2 [M+H]$^+$.

Example 43

N-(3-(1H-benzo[d]imidazol-2-yl)-4-chlorophenyl)-2-methyl-4-(pyrimidin-5-yl)benzamide White solid (40 mg, 20%). $^1$H NMR (DMSO-d$_6$): 12.72 (s, 1H), 10.70 (s, 1H), 9.23-9.21 (m, 3H), 8.42 (d, J=2.7 Hz, 1H), 7.89 (dd, J=8.7 and 2.7 Hz, 1H), 7.82-7.77 (m, 2H), 7.73-7.58 (m, 4H), 7.29-7.21 (m, 2H), 2.50 (s, 3H). MS: m/z 440.2 [M+H]$^+$.

Example 44

N-(3-(1H-benzo[d]imidazol-2-yl)-4-chlorophenyl)-4-phenylcyclohexanecarboxamide

The title compound was prepared from 4-phenylcyclohexanecarboxylic acid and 3-(1H-benzo[d]imidazol-2-yl)-4-chloroaniline using a procedure similar to those described for the synthesis of compound of Example 2. White solid (14.2 mg, 2.2%). $^1$H NMR (DMSO-d$_6$): 12.67 (s, 1H), 10.22 (s, 1H), 8.27 (d, J=2.7 Hz, 1H), 7.75 (dd, J=8.9 and 2.6 Hz, 1H), 7.68 (d, J=8.7 Hz, 1H), 7.56-7.53 (m, 2H), 7.27-7.16 (m, 7H), 2.79-2.38 (m, 2H), 1.93-1.85 (m, 4H), 1.62-1.46 (m, 4H). MS: m/z 430.4 [M+H]$^+$.

Example 45

N-(3-(1H-benzo[d]imidazol-2-yl)phenyl)-3-methyl-4'-(trifluoromethyl)biphenyl-4-carboxamide The title compound was prepared from 3-(1H-benzo[d]imidazol-2-yl)aniline and 3-methyl-4'-(trifluoromethyl)biphenyl-4-carboxylic acid (Example 21a) using a procedure similar to those described for the synthesis of compound of Example 2. White solid (9.59 mg, 10.2%). $^1$H NMR (DMSO-d$_6$): 12.95 (brs, 1H), 10.58 (s, 1H), 8.77 (s, 1H), 7.97 (d, J=8.1 Hz, 2H), 7.89-7.84 (m, 3H), 7.74-7.64 (m, 5H), 7.56-7.51 (m, 2H), 7.24-7.22 (m, 2H), 2.53 (s, 3H). MS: m/z 472.1 [M+H]$^+$.

Example 46

N-(3-(1H-benzo[d]imidazol-2-yl)-4-methylphenyl)-3-methyl-4'-(trifluoromethyl)biphenyl-4-carboxamide The title compound was prepared from 3-(1H-benzo[d]imidazol-2-yl)-4-methylaniline and 3-methyl-4'-(trifluoromethyl)biphenyl-4-carboxylic acid (Example 21a) using a procedure similar to those described for the synthesis of compound of Example 21b. White solid (5.15 mg, 8.3%). $^1$H NMR (CD$_3$OD): 8.03 (d, J=1.8 Hz, 1H), 7.89 (d, J=8.1 Hz, 2H), 7.81-7.77 (m, 3H), 7.71-7.60 (m, 4H), 7.43 (d, J=8.4 Hz, 2H), 7.33-7.31 (m, 2H), 2.59 (s, 3H), 2.54 (s, 3H). MS: m/z 486.2 [M+H]$^+$.

Example 47

N-(3-(1-methyl-1H-benzo[d]imidazol-2-yl)-4-chlorophenyl)-3-methyl-4'-(trifluoromethyl)biphenyl-4-carboxamide a) 2-(2-Chloro-5-nitrophenyl)-1-methylbenzo[d]imidazole: A mixture of 2-(2-chloro-5-nitrophenyl)-1H-benzo[d]imidazole (0.80 g, 2.93 mmol) and THF (50 mL) was stirred and cooled to 5° C., then was added 60% NaH (0.23 g, 5.87 mmol) in batches. The mixture was warmed to r.t. and stirred for 2 h under N$_2$. Then CH$_3$I (1.83 g, 5.87 mmol) was added dropwise to the mixture slowly, and left stirring overnight. Water (50 mL) was added, and THF was removed under evaporation. The aqueous phase was extracted with DCM (100 mL×2) and the organic phase was collected, whased with brine (30 mL), and dried with anhydrous sodium sulfate and filtered. The filtrate was concentrated to give the title compound as a yellow solid (220 mg, 26.0%). MS: m/z 288.3 [M+H]$^+$.

c) 4-Chloro-3-(1-methyl-1H-benzo[d]imidazol-2-yl)aniline: The title compound was prepared from 2-(2-chloro-5-nitrophenyl)-1-methylbenzo[d]imidazole using a procedure similar to those described for the synthesis of compound of Example 24. Yellow solid (0.18 g, 92.0%). MS: m/z 258.3 [M+H]$^+$.

e) N-(3-(1-methyl-1H-benzo[d]imidazol-2-yl)-4-chlorophenyl)-3-methyl-4'-(trifluoromethyl)biphenyl-4-carboxamide: The title compound was prepared from 3-(1-methyl-1H-benzo[d]imidazol-2-yl)-4-chloroaniline and 3-methyl-4'-(trifluoromethyl)biphenyl-4-carboxylic acid (Example 21a) using a procedure similar to those described for the synthesis of compound of Example 2. White solid (10.12 mg, 9.70%). $^1$H NMR (DMSO-d$_6$): 10.72 (s, 1H), 8.07 (d, J=1.8 Hz, 1H), 7.95-7.92 (m, 3H), 7.83 (d, J=8.4 Hz, 2H), 7.71-7.61 (m, 6H), 7.36-7.25 (m, 2H), 3.67 (s, 3H), 2.47 (s, 3H). MS: m/z 520.3 [M+H]$^+$.

Example 48

N-(3-(1H-benzo[d]imidazol-2-yl)-4-chlorophenyl)-N,3-dimethyl-4'-(trifluoromethyl)biphenyl-4-carboxamide a) Tert-butyl 2-(2-chloro-5-nitrophenyl)-1H-benzo[d]imidazole-1-carboxylate: A mixture of 2-(2-chloro-5-nitrophenyl)-1H-benzo[d]imidazole (0.50 g, 1.83 mmol), di-tert-butyl dicarbonate (0.62 g, 2.38 mmol) and 4-dimethylaminopyridine (22.4 mg, 0.18 mmol) in CH$_2$Cl$_2$ (40 mL) was stirred at room temperature overnight. The mixture was washed with 1 N hydrochloric acid (30 mL×2) and brine (30 mL). The organic layer was dried over anhydrous Na$_2$SO$_4$, filtered and concentrated to give the title compound as a white solid (0.58 g, 84.8%). MS: m/z 318.2 [M+H]$^+$.

b) Tert-butyl 2-(5-amino-2-chlorophenyl)-1H-benzo[d]imidazole-1-carboxylate: The title compound was prepared from tert-butyl 2-(2-chloro-5-nitrophenyl)-1H-benzo[d]imidazole-1-carboxylate using a procedure similar to those described for those described for the synthesis of compound of Example 24. Yellow solid (200 mg, 43.4%). MS: m/z 344.3 [M+H]$^+$.

c) Tert-butyl 2-(2-chloro-5-(methylamino)phenyl)-1H-benzo[d]imidazole-1-carboxylate: To a mixture of tert-butyl 2-(5-amino-2-chlorophenyl)-1H-benzo[d]imidazole-1-carboxylate (200 mg, 0.58 mmol) in DMF (1.5 mL) was added dropwise iodomethane (91.3 mg, 0.64 mmol), the mixture was stirred at room temperature for 3 days. The mixture was added water (60 mL) and ethyl acetate (40 mL), then the aqueous phase was extracted with ethyl acetate (30 mL), and the combined organic phases were dried over Na$_2$SO$_4$, filtered and concentrated. The residue was purified by the preparative plate of silica to give the title compound as a yellow solid (40.0 mg, 19.3%). MS: m/z 358.3 [M+H]$^+$.

d) 2-(2-Chloro-5-(N,3-dimethyl-4'-(trifluoromethyl)biphenyl-4-ylcarboxamido)phenyl)-1H-benzo[d]imidazole-1-carboxylate: The title compound was prepared from tert-butyl 2-(2-chloro-5-(methylamino)phenyl)-1H-benzo[d]imidazole-1-carboxylate and 3-methyl-4'-(trifluoromethyl)biphenyl-4-carboxylic acid (Example 21a) using a procedure similar to those described for the synthesis of compound of Example 2. Yellow solid (30 mg, 44.0%). MS: m/z 520.3 [M+H]$^+$.

e) N-(3-(1H-benzo[d]imidazol-2-yl)-4-chlorophenyl)-N,3-dimethyl-4'-(trifluoromethyl)biphenyl-4-carboxamide: 2-(2-Chloro-5-(N,3-dimethyl-4'-(trifluoromethyl)biphenyl-4-ylcarboxamido)phenyl)-1H-benzo[d]imidazole-1-carboxylate (30.0 mg, 0.05 mmol) in the solution of HCl in ethyl acetate (2 N, 5 mL, 10 mmol) was stirred at room temperature overnight. The mixture was concentrated, and Na$_2$CO$_3$ aqueous solution (2 N, 20 mL) and ethyl acetate (35 mL) were added, the organic phase was dried over Na$_2$SO$_4$, filtered and concentrated. The residue was purified by the preparative plate of silica to give the title compound as an off-white solid (7.29 mg, 28.0%). $^1$H NMR (DMSO-d$_6$): 12.69 (s, 1H), 7.97-7.93 (m, 1H), 7.85 (d, J=8.1 Hz, 2H), 7.76 (d, J=8.4 Hz, 2H), 7.69 (d, J=7.5 Hz, 1H), 7.56-7.46 (m, 4H), 7.35-7.19 (m, 4H), 3.38 (s, 3H), 2.35 (s, 3H). MS: m/z 520.3 [M+H]$^+$.

Example 49

N-(3-(1H-imidazo[4,5-c]pyridin-2-yl)-4-chlorophenyl)-3-methyl-4'-(trifluoromethyl)biphenyl-4-carboxamide The title compound was prepared from 4-chloro-3-(1H-imidazo[4,5-c]pyridin-2-yl)aniline and 3-methyl-4'-(trifluoromethyl)biphenyl-4-carboxylic acid (Example 21a) using a procedure similar to those described for the synthesis of compound of Example 21b. Off-white solid (12.88 mg, 21%). $^1$H NMR (DMSO-d$_6$): 13.41 (brs, 1H), 10.70 (s, 1H), 9.02-9.01 (m, 1H), 8.43 (s, 1H), 7.95 (d, J=8.1 Hz, 1H), 7.85-7.82 (m, 5H), 7.71-7.62 (m, 5H), 2.48 (s, 3H). MS: m/z 507.3 [M+H]$^+$.

Example 50

N-(3-(5-phenyl-1H-imidazol-2-yl)-4-chlorophenyl)-3-methyl-4'-(trifluoromethyl)biphenyl-4-carboxamide a) 2-Chloro-5-nitro-N-(2-oxo-2-phenylethyl)benzamide: The title compound was prepared from 2-amino-1-phenylethanone hydrochloride and 2-chloro-5-nitrobenzoic acid using a procedure similar to those described for the synthesis of compound of Example 21b. Yellow solid (0.9 g, 60%). MS: m/z 319.3 [M+H]$^+$.

b) 2-(2-Chloro-5-nitrophenyl)-5-phenyl-1H-imidazole: To the solution of 2-chloro-5-nitro-N-(2-oxo-2-phenylethyl) benzamide (1.5 g, 5 mmol) in AcOH (5 mL) was added NH$_4$OAc (7.2 g, 100 mmol) at r.t. under N$_2$, then the mixture was heated to reflux overnight. Until the material was consumed by LCMS, the reaction solution was cooled to r.t. and poured into water (50 mL), a solid was precipitated, collected and dried under vacuum to give the title compound as a yellow solid (300 mg), which was used for the next step without further purification. MS: m/z 300.2 [M+H]$^+$.

c) 4-Chloro-3-(5-phenyl-1H-imidazol-2-yl)aniline: To a solution of 2-(2-chloro-5-nitrophenyl)-5-phenyl-1H-imidazole (0.2 g, 0.67 mmol) in methanol (5 mL) was added SnCl$_2$.2H$_2$O (0.6 g, 2.88 mmol) at r.t. under N$_2$, then the mixture was heated to reflux and stirred overnight. After cooling, the reaction solution was concentrated under vacuum, the residue was diluted with EA (100 mL) and then saturated aqueous NaHCO$_3$ solution was added to this solution slowly until the pH of this solution is 7~8, lots of the white solid was precipitated, filtered, and the filtrate was dried over anhydrous Na$_2$SO$_4$, then concentrated to give the crude compound (150 mg), which was used for the next step without further purification. MS: m/z 270.1 [M+H]$^+$.

d) N-(3-(5-phenyl-1H-imidazol-2-yl)-4-chlorophenyl)-3-methyl-4'-(trifluoromethyl)biphenyl-4-carboxamide: The title compound was prepared from 4-chloro-3-(5-phenyl-1H-imidazol-2-yl)aniline and 3-methyl-4'-(trifluoromethyl) biphenyl-4-carboxylic acid (Example 21a) using a procedure similar to those described for the synthesis of compound of Example 21b. Off-white solid (5 mg, 5%). $^1$H NMR (CD$_3$OD): 8.08 (s, 1H), 7.92-7.75 (m, 7H), 7.65-7.63 (m, 3H), 7.57-7.54 (m, 2H), 7.39 (t, J=7.5 Hz, 2H), 7.29-7.24 (m, 1H), 2.56 (s, 3H). MS: m/z 532.2 [M+H]$^+$.

Example 51

N-(3-(5-(pyridin-3-yl)-1H-imidazol-2-yl)-4-chlorophenyl)-3-methyl-4'-(trifluoromethyl)biphenyl-4-carboxamide The title compound was prepared from 2-amino-1-(pyridin-3-yl)ethone hydrochloride, 2-chloro-5-nitrobenzoic acid, ammonium acetate and 3-methyl-4'-(trifluoromethyl) biphenyl-4-carboxylic acid (Example 21a) using a procedure similar to those described for the synthesis of compound of Example 50. Beige solid (0.72 mg, 3%). $^1$H NMR (CD$_3$OD): 9.01 (s, 1H), 8.43 (d, J=3.3 Hz, 1H), 8.27 (d, J=7.5 Hz, 1H), 8.15 (s, 1H), 7.92-7.85 (m, 3H), 7.78-7.74 (m, 3H), 7.66-7.63 (m, 3H), 7.58 (d, J=8.7 Hz, 1H), 7.50-7.46 (m, 1H), 2.56 (s, 3H). MS: m/z 533.3 [M+H]$^+$.

Example 52

N-(3-([1,2,4]triazolo[4,3-a]pyridin-3-yl)-4-chlorophenyl)-3-methyl-4'-(trifluoromethyl)biphenyl-4-carboxamide a) 2-Chloro-5-nitro-N'-(pyridin-2-yl)benzohydrazide: A mixture of 2-hydrazinylpyridine (1.0 g, 9.1 mmol), 2-chloro-5-nitrobenzoic acid (1.8 g, 9.1 mmol), BOP (11.8 mmol), 4-methylmorpholine (1.8 g, 18.2 mmol) and CH$_2$Cl$_2$ (30 mL) was stirred at room temperature overnight. The reaction mixture was filtered to give the title compound (2.1 g, 78%). MS: m/z 293.2 [M+H]$^+$.

b) 3-(2-Chloro-5-nitrophenyl)-[1,2,4]triazolo[4,3-a]pyridine: A mixture of 2-chloro-5-nitro-N'-(pyridin-2-yl)benzohydrazide (1.0 g, 3.4 mmol) and POCl$_3$ (10 mL) was heated to reflux overnight under N$_2$. After cooled to ambient temperature, the residue was concentrated, then saturated NaHCO$_3$ solution was added under stirring to adjust pH to 7~8. The solid was filtered and washed with water and then dried to give the crude title compound (0.78 g, 84%). MS: m/z 275.1 [M+H]$^+$.

c) 3-([1,2,4]Triazolo[4,3-a]pyridin-3-yl)-4-chloroaniline: A mixture of 3-(2-chloro-5-nitrophenyl)-[1,2,4]triazolo[4,3-a]pyridine (500 mg, 1.82 mmol), SnCl$_2$.2H$_2$O (1.6 g, 7.3 mmol) in MeOH (20 mL) was refluxed overnight. The mixture was cooled to room temperature, concentrated to remove the solvent, and then the residue was mixed with EA (25 mL), and adjusted pH to 7~8 with NaHCO$_3$ (a.q.). After dried over Na$_2$SO$_4$, the solvent was removed in vacuo to give the title compound (350 mg, 79%). MS: m/z 245.1 [M+H]$^+$.

d) N-(3-([1,2,4]triazolo[4,3-a]pyridin-3-yl)-4-chlorophenyl)-3-methyl-4'-(trifluoromethyl)biphenyl-4-carboxamide: The title compound was prepared from 3-([1,2,4]triazolo[4,3-a]pyridin-3-yl)-4-chloroaniline and 3-methyl-4'-(trifluoromethyl)biphenyl-4-carboxylic acid (Example 21a) using a procedure similar to those described for the synthesis of compound of Example 21b. White solid (7.31 mg, 12%). $^1$H NMR (CD$_3$OD): 8.25-8.17 (m, 3H), 8.00-7.97 (m, 3H), 7.90-7.75 (m, 3H), 7.72-7.67 (m, 4H), 7.24 (t, J=6.9 Hz, 1H), 2.67 (s, 3H). MS: m/z 507.2 [M+H]$^+$.

The following compounds were prepared from 2-hydrazinylpyrimidine or 2-hydrazinylpyrazine, 2-chloro-5-nitrobenzoic acid, and 3-methyl-4'-(trifluoromethyl)biphenyl-4-carboxylic acid (Example 21a) using a procedure similar to those described for the syntheses of compounds of Examples 52a-b, 24 and 2.

Example 53

N-(3-([1,2,4]triazolo[4,3-a]pyrimidin-3-yl)-4-chlorophenyl)-3-methyl-4'-(trifluoromethyl)biphenyl-4-carboxamide White solid (6 mg, 4.7%). $^1$H NMR (DMSO-d$_6$): 10.69 (s, 1H), 9.50 (dd, J=6.8 and 1.7 Hz, 1H), 8.93 (dd, J=4.2 and 1.8 Hz, 1H), 8.59 (d, J=2.4 Hz, 1H), 7.94 (d, J=8.1 Hz, 2H), 7.88-7.82 (m, 3H), 7.70-7.60 (m, 4H), 7.42 (dd, J=6.6 and 4.2 Hz, 1H), 2.47 (s, 3H). MS: m/z 508.2 [M+H]$^+$.

Example 54

N-(3-([1,2,4]triazolo[4,3-a]pyrazin-3-yl)-4-chlorophenyl)-3-methyl-4'-(trifluoromethyl)biphenyl-4-carboxamide White solid (10 mg, 5.5%). $^1$H NMR (DMSO-d$_6$): 10.79 (s, 1H), 9.56 (d, J=1.5 Hz, 1H), 8.28 (dd, J=4.8 and 1.5 Hz, 1H), 8.21 (d, J=2.4 Hz, 1H), 8.06-8.02 (m, 2H), 7.95 (d, J=8.1 Hz, 2H), 7.85 (d, J=8.4 Hz, 2H), 7.77 (d, J=9.0 Hz, 1H), 7.73-7.69 (m, 2H), 7.64 (d, J=7.8 Hz, 1H), 2.48 (s, 3H). MS: m/z 508.4 [M+H]$^+$.

Example 55

N-(3-(imidazo[1,2-a]pyrimidin-2-yl)phenyl)-3-methyl-4'-(trifluoromethyl)biphenyl-4-carboxamide a) 2-(3-Nitrophenyl)imidazo[1,2-a]pyrimidine: A flask was charged with 2-aminopyrimidine (475 mg, 5 mmol), 2-bromo-1-(3-nitrophenyl)ethanone (1.22 g, 5 mmol) and EtOH (20 mL). The reaction solution was heated to reflux under Nitrogen over 5 h. After cooed to room temperature, the resulting precipitate was collected by filtered to give the title compound as a yellow solid (1.1 g, 91.6%). MS: m/z 241.1 [M+H]$^+$.

b) N-(3-(imidazo[1,2-a]pyrimidin-2-yl)phenyl)-3-methyl-4'-(trifluoromethyl)biphenyl-4-carboxamide: The title compound was prepared from 2-(3-nitrophenyl)imidazo[1,2-a]pyrimidine and 3-methyl-4'-(trifluoromethyl)biphenyl-4-carboxylic acid (Example 21a) using a procedure similar to those described for the syntheses of compounds of Examples 24 and 2. White solid (21 mg, 12.5%). $^1$H NMR (DMSO-d$_6$): 10.51 (s, 1H), 8.98 (dd, J=6.8 and 2.0 Hz, 1H), 8.55-8.52 (m, 2H), 8.35 (s, 1H), 7.96 (d, J=8.1 Hz, 2H), 7.85 (d, J=8.1 Hz, 2H), 7.74-7.63 (m, 5H), 7.44 (t, J=8.1 Hz, 1H), 7.07 (dd, J=6.6 and 4.2 Hz, 1H), 2.51 (s, 3H). MS: m/z 473.4 [M+H]$^+$.

Example 56

N-(3-(imidazo[1,2-a]pyridin-2-yl)phenyl)-3-methyl-4'-(trifluoromethyl)biphenyl-4-carboxamide The title compound was prepared from 2-aminopyridine, 2-bromo-1-(3-nitrophenyl)ethone and 3-methyl-4'-(trifluoromethyl)biphenyl-4-carboxylic acid using a procedure similar to those described for the synthesis of compound of Example 55. White solid (45 mg, 37.7%). $^1$H NMR (DMSO-d$_6$): 10.46 (s, 1H), 8.57-8.51 (m, 2H), 8.38 (s, 1H), 7.96 (d, J=8.1 Hz, 2H), 7.85 (d, J=8.1 Hz, 2H), 7.72-7.57 (m, 6H), 7.41 (t, J=8.1 Hz, 1H), 7.26 (t, J=7.2 Hz, 1H), 6.91 (t, J=6.6 Hz, 1H), 2.49 (s, 3H). MS: m/z 472.3 [M+H]$^+$.

The following compounds were prepared from 6-chloronicotinic acid, the corresponding 3-(imidazo[1,2-a]pyrimidin-2-yl)aniline or 3-([1,2,4]triazolo[4,3-a]pyrazin-3-yl)-4-chloroaniline (the intermediates of compounds of Examples 55 and 54, respectively), and (2S,6R)-2,6-dimethylmorpholine using a procedure similar to those described for the syntheses of compounds of Examples 2 and 35b.

Example 57

N-(3-(imidazo[1,2-a]pyrimidin-2-yl)phenyl)-6-((2S,6R)-2,6-dimethylmorpholino)nicotinamide Beige solid (22.87 mg, 41.1%). $^1$H NMR (DMSO-d$_6$): 10.15 (s, 1H), 8.98 (dd, J=6.8 and 2.0 Hz, 1H), 8.78 (d, J=2.4 Hz, 1H), 8.54 (dd, J=4.1 and 2.0 Hz, 1H), 8.44 (s, 1H), 8.35 (s, 1H), 8.15 (dd, J=9.0 and 2.4 Hz, 1H), 7.80 (d, J=8.1 Hz, 1H), 7.69 (d, J=7.8 Hz, 1H), 7.42 (t, J=8.0 Hz, 1H), 8.07 (dd, J=6.8 and 4.1 Hz, 1H), 6.95 (d, J=9.0 Hz, 1H), 4.32 (d, J=12.0 Hz, 2H), 3.66-3.56 (m, 2H), 2.58-2.51 (m, 2H), 1.18 (d, J=6.3 Hz, 6H). MS: m/z 429.3 [M+H]$^+$.

Example 58

N-(3-([1,2,4]triazolo[4,3-a]pyrazin-3-yl)-4-chlorophenyl)-6-((2S,6R)-2,6-dimethylmorpholino)nicotinamide White solid (15.6 mg, 16.9%). $^1$H NMR (DMSO-d$_6$): 10.38 (s, 1H), 9.56 (d, J=1.5 Hz, 1H), 8.75 (d, J=2.4 Hz, 1H), 8.28 (dd, J=4.8 and 1.5 Hz, 1H), 8.17 (d, J=2.4 Hz, 1H), 8.12-8.07 (m, 2H), 8.02 (d, J=4.8 Hz, 1H), 7.75 (d, J=8.7 Hz, 1H), 6.95 (d, J=9.0 Hz, 1H), 4.32 (d, J=12.9 Hz, 2H), 3.63-3.54 (m, 2H), 2.57-2.53 (m, 2H), 1.16 (d, J=6.3 Hz, 6H). MS: m/z 464.2 [M+H]$^+$.

Example 59

N-(3-(pyridin-2-yl)-4-chlorophenyl)-3-methyl-4'-(trifluoromethyl)biphenyl-4-carboxamide The title compound was prepared from 4-chloro-3-(pyridin-2-yl)aniline and 3-methyl-4'-(trifluoromethyl)biphenyl-4-carboxylic acid (Example 21a) using a procedure similar to those described for the synthesis of compound of Example 21b. White solid (5 mg, 5%). $^1$H NMR (CDCl$_3$): 8.67 (d, J=4.5 Hz, 1H), 7.80-7.70 (m, 9H), 7.57-7.45 (m, 4H), 7.35-7.26 (m, 1H), 2.58 (s, 3H). MS: m/z 467.3 [M+H]$^+$.

Example 60

N-(5-(1H-benzo[d]imidazol-2-yl)pyridin-3-yl)-3-methyl-4'-(trifluoromethyl)biphenyl-4-carboxamide a) 5-(4-Bromo-2-methylbenzamido)nicotinic acid: The title compound was prepared from 4-bromo-2-methylbenzoic acid and methyl 5-aminonicotinate using a procedure similar to those described for the syntheses of compounds of Examples 21b and 30b. Off-white solid (380 mg, 87.3%). MS: m/z 335.0 [M+H]$^+$.

b) N-(2-aminophenyl)-5-(4-bromo-2-methylbenzamido)nicotinamide: The title compound was prepared from 5-(4-bromo-2-methylbenzamido)nicotinic acid and o-phenylenediamine using a procedure similar to those described for the synthesis of compound of Example 21b. Yellow solid (400 mg, 85.5%). MS: m/z 425.1 [M+H]$^+$.

c) N-(5-(1H-benzo[d]imidazol-2-yl)pyridin-3-yl)-4-bromo-2-methylbenzamide: A mixture of N-(2-aminophenyl)-5-(4-bromo-2-methylbenzamido)nicotinamide (400 mg, 0.94 mmol) in glacial acetic acid (5 mL) was heated to reflux for 2 h. Then water (30 mL) was added to the mixture and there were a lot of solids formed. Filtered, the residue was washed with water (20 mL), and dried to give the title compound as a yellow solid (250 mg, 61.4%). MS: m/z 407.1 [M+H]$^+$.

d) N-(5-(1H-benzo[d]imidazol-2-yl)pyridin-3-yl)-3-methyl-4'-(trifluoromethyl)biphenyl-4-carboxamide: The title compound was prepared from N-(5-(1H-benzo[d]imidazol-2-yl)pyridin-3-yl)-4-bromo-2-methylbenzamide and 4-(trifluoromethyl)phenylboronic acid using a procedure similar to those described for the synthesis of compound of Example 1. White solid (33.8 mg, 28.6%). $^1$H NMR (DMSO-d$_6$): 13.14 (brs, 1H), 10.78 (s, 1H), 9.09 (t, J=2.1 Hz, 1H), 9.05 (d, J=1.8 Hz, 1H), 8.86 (d, J=2.1 Hz, 1H), 7.96

(d, J=8.1 Hz, 2H), 7.84 (d, J=8.4 Hz, 2H), 7.74-7.63 (m, 5H), 7.25-7.22 (m, 2H), 2.52 (s, 3H). MS: m/z 473.2 [M+H]$^+$.

Example 61

N-(4-(1H-benzo[d]imidazol-2-yl)pyridin-2-yl)-3-methyl-4'-(trifluoromethyl)biphenyl-4-carboxamide The title compound was prepared from 4-bromo-2-methylbenzoic acid, methyl 2-aminoisonicotinate, o-phenylenediamine, acetic acid and 4-(trifluoromethyl)phenylboronic acid using a procedure similar to those described for the synthesis of compound of Example 60. White solid (14.3 mg, 25%). $^1$H NMR (DMSO-d$_6$): 13.31 (brs, 1H), 11.03 (s, 1H), 9.02 (s, 1H), 8.54 (d, J=5.1 Hz, 1H), 7.96 (d, J=5.1 Hz, 2H), 7.88-7.84 (m, 3H), 7.72-7.68 (m, 5H), 7.30-7.25 (m, 2H), 2.54 (s, 3H). MS: m/z 473.2 [M+H]$^+$.

The following compounds were prepared from 3-(1H-benzo[d]imidazol-2-yl)-substituted-aniline and 3-methyl-4'-(trifluoromethyl)biphenyl-4-carboxylic acid (Example 21a) using a procedure similar to those described for the synthesis of compound of Example 21b.

Example 62

N-(3-(1H-benzo[d]imidazol-2-yl)-5-(trifluoromethyl)phenyl)-3-methyl-4'-(trifluoromethyl)biphenyl-4-carboxamide White solid (1.19 mg, 5.2%). $^1$H NMR (DMSO-d$_6$): 13.22 (brs, 1H), 10.86 (s, 1H), 8.97 (s, 1H), 8.25-8.19 (m, 2H), 7.96 (d, J=8.1 Hz, 2H), 7.84 (d, J=8.1 Hz, 2H), 7.73-7.68 (m, 4H), 7.56 (d, J=6.9 Hz, 1H), 7.25-7.22 (m, 2H), 2.52 (s, 3H). MS: m/z 540.2 [M+H]$^+$.

Example 63

N-(3-(1H-benzo[d]imidazol-2-yl)-5-chlorophenyl)-3-methyl-4'-(trifluoromethyl)biphenyl-4-carboxamide White solid (2.48 mg, 7.6%). $^1$H NMR (DMSO-d$_6$): 13.02 (brs, 1H), 10.71 (s, 1H), 8.65 (s, 1H), 7.97-7.91 (m, 4H), 7.84 (d, J=8.4 Hz, 2H), 7.73 (s, 1H), 7.68 (d, J=5.7 Hz, 2H), 7.64-7.55 (m, 2H), 7.23-7.20 (m, 2H), 2.51 (s, 3H). MS: m/z 506.1 [M+H]$^+$.

Example 64

N-(3-(1H-benzo[d]imidazol-2-yl)-2-chlorophenyl)-3-methyl-4'-(trifluoromethyl)biphenyl-4-carboxamide White solid (12.69 mg, 15.3%). $^1$H NMR (DMSO-d$_6$): 7.85-7.80 (m, 5H), 7.62-7.59 (m, 1H), 7.52 (s, 1H), 7.44-7.40 (m, 4H), 6.89 (t, J=7.8 Hz, 1H), 6.67 (dd, J=7.5 and 2.0 Hz, 1H), 6.61 (dd, J=8.1 and 2.0 Hz, 1H), 2.34 (s, 3H). MS: m/z 506.1 [M+H]$^+$.

Example 65

N-(3-(1H-benzo[d]imidazol-2-yl)-2-methylphenyl)-6-((2S,6R)-2,6-dimethylmorpholino)nicotinamide The title compound was prepared from 6-chloronicotinic acid, 3-(1H-benzo[d]imidazol-2-yl)-2-methylaniline and (2S,6R)-2,6-dimethylmorpholine using a procedure similar to those described for the synthesis of compound of Example 35. White solid (19.52 mg, 21.3%). $^1$H NMR (DMSO-d$_6$): 12.65 (brs, 1H), 9.82 (s, 1H), 8.76 (d, J=2.1 Hz, 1H), 8.12 (dd, J=9.0 and 2.4 Hz, 1H), 7.68-7.52 (m, 3H), 7.45 (d, J=7.2 Hz, 1H), 7.36 (t, J=7.7 Hz, 1H), 7.21-7.18 (m, 2H), 6.94 (d, J=9.0 Hz, 1H), 4.31 (d, J=12.0 Hz, 2H), 3.62-3.54 (m, 2H), 2.53-2.50 (m, 2H), 2.41 (s, 3H), 1.15 (d, J=6.0 Hz, 6H). MS: m/z 442.3 [M+H]$^+$.

Example 66

N-(3-(1H-benzo[d]imidazol-2-yl)-4-chlorophenyl)-2-methyl-4-(6-methoxypyridin-3-yl)benzamide The title compound was prepared from 4-bromo-2-methylbenzoic acid, 3-(1H-benzo[d]imidazol-2-yl)-4-chloroaniline and 2-methoxy-5-pyridineboronic acid using a procedure similar to those described for the syntheses of compounds of Examples 2 and 1. White solid (11.7 mg, 11.4%). $^1$H NMR (DMSO-d$_6$): 12.70 (s, 1H), 10.62 (s, 1H), 8.53 (s, 1H), 8.40 (s, 1H), 8.05 (d, J=7.8 Hz, 1H), 7.86 (d, J=7.8 Hz, 1H), 7.70-7.59 (m, 6H), 7.24-7.22 (m, 2H), 6.92 (d, J=8.7 Hz, 1H), 3.89 (s, 3H), 2.48 (s, 3H). MS: m/z 469.2 [M+H]$^+$.

Example 67

N-(3-(imidazo[1,2-a]pyridin-2-yl)-4-chlorophenyl)-3-methyl-4'-(trifluoromethyl)biphenyl-4-carboxamide The title compound was prepared from 2-aminopyridine, 2-bromo-1-(4-chloro-3-nitrophenyl)ethone and 3-methyl-4'-(trifluoromethyl)biphenyl-4-carboxylic acid using a procedure similar to those described for the synthesis of compound of Example 55. Yellow solid (1 mg, 0.8%). $^1$H NMR (CD$_3$OD): 8.93 (dd, J=6.9 and 1.8 Hz, 1H), 8.62 (dd, J=4.2 and 1.8 Hz, 1H), 8.49 (s, 1H), 8.23 (d, J=2.4 Hz, 1H), 8.00-7.96 (m, 1H), 7.88 (d, J=8.4 Hz, 2H), 7.78 (d, J=8.4 Hz, 2H), 7.58-7.55 (m, 3H), 7.56 (d, J=8.4 Hz, 2H), 7.10 (dd, J=6.9 and 4.2 Hz, 1H), 2.58 (s, 3H). MS: m/z 507.2 [M+H]$^+$.

Example 68

N-(3-(5-(thiophen-2-yl)-1H-imidazol-2-yl)-4-chlorophenyl)-3-methyl-4'-(trifluoromethyl)biphenyl-4-carboxamide The title compound was prepared from 2-amino-1-(thiophen-2-yl)ethone hydrochloride, 2-chloro-5-nitrobenzoic acid, ammonium acetate and 3-methyl-4'-(trifluoromethyl)biphenyl-4-carboxylic acid using a procedure similar to those described for the synthesis of compound of Example 50. White solid (1.41 mg, 2.5%). $^1$H NMR (CDCl$_3$): 8.32-8.22 (m, 3H), 7.76-7.67 (m, 4H), 7.51-7.42 (m, 4H), 7.22-7.21 (m, 2H), 7.05-7.02 (m, 1H), 2.08 (s, 3H). MS: m/z 538.1 [M+H]$^+$.

Example 69

N-(5-(1H-benzo[d]imidazol-2-yl)-6-chloropyridin-3-yl)-3-methyl-4'-(trifluoromethyl)biphenyl-4-carboxamide The title compound was prepared from 5-(1H-benzo[d]imidazol-2-yl)-6-chloropyridin-3-carboxamide and 3-methyl-4'-(trifluoromethyl)biphenyl-4-carboxylic acid using a procedure similar to those described for the synthesis of compound of Example 2. White solid (0.94 mg, 1.03%). $^1$H NMR (DMSO-d$_6$): 12.84 (s, 1H), 10.89 (s, 1H), 8.89-8.83 (s, 2H), 7.95 (d, J=8.1 Hz, 2H), 7.83 (d, J=8.1 Hz, 2H), 7.73-7.70 (m, 4H), 7.61 (d, J=6.9 Hz, 1H), 7.31-7.21 (m, 2H), 2.50 (s, 3H). MS: m/z 507.1 [M+H]$^+$.

The following compounds were prepared from 5-(1H-benzo[d]imidazol-2-yl)-6-substituted-pyridin-3-amine and the corresponding 3-methyl-4'-substituted-biphenyl-4-carboxylic acid using a procedure similar to those described for the synthesis of compound of Example 2.

Example 70

N-(5-(1H-benzo[d]imidazol-2-yl)-6-chloropyridin-3-yl)-3-methyl-4'-cyanobiphenyl-4-carboxamide White solid (4.22 mg, 4.8%). $^1$H NMR (DMSO-d$_6$): 12.86 (s, 1H), 10.91 (s, 1H), 8.87 (d, J=2.1 Hz, 2H), 8.00-7.94 (m, 4H), 7.76-7.72 (m, 4H), 7.63 (d, J=7.2 Hz, 1H), 7.33-7.23 (m, 2H), 2.50 (s, 3H). MS: m/z 464.1 [M+H]$^+$.

Example 71

N-(5-(1H-benzo[d]imidazol-2-yl)-6-methylpyridin-3-yl)-3-methyl-4'-(trifluoromethyl)biphenyl-4-carboxamide Off-white solid (14.01 mg, 16.0%). $^1$H NMR (DMSO-d$_6$): 12.82 (s, 1H), 10.71 (s, 1H), 8.82 (s, 1H), 8.63 (s, 1H), 7.96 (d, J=7.8 Hz, 2H), 7.85 (d, J=8.1 Hz, 2H), 7.74-7.68 (m, 4H), 7.58 (d, J=7.2 Hz, 1H), 7.31-7.19 (m, 2H), 2.76 (s, 3H), 2.52 (s, 3H). MS: m/z 487.3 [M+H]$^+$.

Example 72

N-(6-(1H-benzo[d]imidazol-2-yl)pyridin-2-yl)-3-methyl-4'-(trifluoromethyl)biphenyl-4-carboxamide The title compound was prepared from 4-bromo-2-methylbenzoic acid, methyl 5-aminonicotinate, o-phenylenediamine, acetic acid, and 4-(trifluoromethyl)phenylboronic acid using a procedure similar to those described for the synthesis of compound of Example 60. White solid (10.6 mg, 9.0%). $^1$H NMR (DMSO-d$_6$): 12.58 (s, 1H), 10.61 (s, 1H), 8.88 (dd, J=6.6 and 2.4 Hz, 1H), 8.09-8.05 (m, 2H), 7.98 (d, J=8.1 Hz, 2H), 7.86 (d, J=8.1 Hz, 2H), 7.75-7.71 (m, 4H), 7.58 (d, J=6.9 Hz, 1H), 7.28-7.19 (m, 2H), 2.55 (s, 3H). MS: m/z 473.2 [M+H]$^+$.

Example 73

N-(3-([1,2,4]triazolo[1,5-a]pyridin-2-yl)phenyl)-3-methyl-4'-(trifluoromethyl)biphenyl-4-carboxamide The title compound was prepared from 3-([1,2,4]triazolo[1,5-a]pyridin-2-yl)aniline and 3-methyl-4'-(trifluoromethyl)biphenyl-4-carboxylic acid using a procedure similar to those described for the synthesis of compound of Example 2. Yellow solid (6 mg, 50%). $^1$H NMR (DMSO-d$_6$): 10.56 (s, 1H), 9.03 (s, 1H), 8.96-8.94 (m, 1H), 8.62 (s, 1H), 7.94 (d, J=8.4 Hz, 2H), 7.87-7.82 (m, 3H), 7.72-7.62 (m, 3H), 7.53-7.48 (m, 2H), 7.20 (d, J=9.3 Hz, 1H), 6.81 (t, J=6.6 Hz, 1H), 2.51 (s, 3H). MS: m/z 473.2 [M+H]$^+$.

The following compounds were prepared from the corresponding 3-(1H-benzo[d]imidazol-2-yl)-4-substituted-aniline and 3-methyl-4'-(trifluoromethyl)biphenyl-4-carboxylic acid (Example 21a) using a procedure similar to those described for the synthesis of compound of Example 21b.

Example 74

N-(3-(1H-benzo[d]imidazol-2-yl)-4-fluorophenyl)-3-methyl-4'-(trifluoromethyl)biphenyl-4-carboxamide Off-white solid (36.52 mg, 34%). $^1$H NMR (DMSO-d$_6$): 12.54 (s, 1H), 10.58 (s, 1H), 8.75 (dd, J=6.5 and 2.6 Hz, 1H), 7.94 (d, J=8.4 Hz, 2H), 7.85-7.82 (m, 3H), 7.71-7.63 (m, 5H), 7.43 (t, J=9.1 Hz, 1H), 7.23-7.21 (m, 2H), 2.49 (s, 3H). MS: m/z 490.2 [M+H]$^+$.

Example 75

N-(3-(1H-benzo[d]imidazol-2-yl)-4-bromophenyl)-3-methyl-4'-(trifluoromethyl)biphenyl-4-carboxamide White solid (5.27 mg, 13%). $^1$H NMR (DMSO-d$_6$): 12.74 (s, 1H), 10.68 (s, 1H), 8.26 (s, 1H), 7.95 (d, J=8.1 Hz, 2H), 7.86-7.80 (m, 4H), 7.72-7.56 (m, 5H), 7.29-7.20 (m, 2H), 2.50 (s, 3H). MS: m/z 552.1 [M+H]$^+$.

Example 76

N-(3-(1H-benzo[d]imidazol-2-yl)-4-methoxyphenyl)-3-methyl-4'-(trifluoromethyl)biphenyl-4-carboxamide Off-white solid (5.16 mg, 11%). $^1$H NMR (DMSO-d$_6$): 12.14 (s, 1H), 10.39 (s, 1H), 8.79 (s, 1H), 7.96 (d, J=7.8 Hz, 2H), 7.86-7.84 (m, 3H), 7.72-7.65 (m, 5H), 7.27-7.20 (m, 3H), 4.03 (s, 3H), 2.50 (s, 3H). MS: m/z 502.2 [M+H]$^+$.

The following compounds were prepared from the corresponding 2-amino-1-p-substituted-phenylethanone hydrochloride or 2-amino-1-(furan-2-yl)ethanone hydrochloride or 2-amino-1-(thiophen-2-yl)ethanone hydrochloride, 2-chloro-5-nitrobenzoic acid, ammonium acetate and the corresponding 3-methyl-4'-(trifluoromethyl)biphenyl-4-carboxylic acid or 2-methyl-4-((2S,6R)-2,6-dimethylmorpholino)benzoic acid or 2-substituted-4-((3S,5R)-3,4,5-trimethylpiperazin-1-yl)benzoic acid (the compounds were prepared from methyl 4-halo-2-substituted-benzoate and (2S,6R)-1,2,6-trimethylpiperazine hydrochloride using a procedure similar to those described for the syntheses of compounds of Examples 30a-b) using a procedure similar to those described for the synthesis of compound of Example 50.

Example 77

N-(3-(5-p-tolyl-1H-imidazol-2-yl)-4-chlorophenyl)-3-methyl-4'-(trifluoromethyl)biphenyl-4-carboxamide White solid (2.98 mg, 5.0%). $^1$H NMR (CDCl$_3$): 8.54 (s, 1H), 8.32 (s, 1H), 8.25 (d, J=8.7 Hz, 1H), 7.73-7.65 (m, 4H), 7.58-7.53 (m, 1H), 7.48 (d, J=9.0 Hz, 1H), 7.42-7.40 (m, 3H), 7.27 (s, 1H), 7.17 (d, J=7.8 Hz, 2H), 2.45 (s, 3H), 2.35 (s, 3H). MS: m/z 546.2 [M+H]$^+$.

Example 78

N-(3-(5-(4-fluorophenyl)-1H-imidazol-2-yl)-4-chlorophenyl)-3-methyl-4'-(trifluoromethyl)biphenyl-4-carboxamide White solid (2.16 mg, 3.0%). $^1$H NMR (CDCl$_3$): 10.30 (brs, 1H), 8.30 (d, J=15.6 Hz, 2H), 8.20 (dd, J=8.7 and 1.5 Hz, 1H), 7.74-7.67 (m, 5H), 7.50-7.41 (m, 4H), 7.30 (s, 1H), 7.09-7.04 (m, 2H), 2.49 (s, 3H). MS: m/z 550.1 [M+H]$^+$.

Example 79

N-(3-(5-(furan-2-yl)-1H-imidazol-2-yl)-4-chlorophenyl)-3-methyl-4'-(trifluoromethyl)biphenyl-4-carboxamide White solid (0.43 mg, 1.0%). $^1$H NMR (CDCl$_3$): 10.30 (brs, 1H), 8.27-8.18 (m, 2H), 7.93 (s, 1H), 7.75-7.69 (m, 3H), 7.56 (d, J=7.5 Hz, 1H), 7.50-7.47 (m, 3H), 7.42 (s, 1H), 7.36 (s, 1H), 6.68-6.64 (m, 1H), 6.47-6.44 (m, 1H), 2.57 (s, 3H). MS: m/z 522.1 [M+H]$^+$.

Example 80

N-(3-(5-p-tolyl-1H-imidazol-2-yl)-4-chlorophenyl)-2-methyl-4-((2S,6R)-2,6-dimethylmorpholino)benzamide White solid (4.68 mg, 17%). $^1$H NMR (DMSO-d$_6$): 12.33 (s, 1H), 10.27 (s, 1H), 8.26 (d, J=2.4 Hz, 1H), 7.82 (dd, J=8.9 and 2.6 Hz, 1H), 7.74 (d, J=8.1 Hz, 2H), 7.71-7.68 (m, 1H), 7.50 (d, J=8.7 Hz, 1H), 7.45-7.42 (m, 1H), 7.18 (d, J=8.1 Hz, 2H), 6.86-6.82 (m, 2H), 3.72-3.65 (m, 4H), 2.40 (s, 3H), 2.34-2.26 (m, 5H), 1.17 (d, J=6.0 Hz, 6H). MS: m/z 515.4 [M+H]$^+$.

Example 81

N-(3-(5-(thiophen-2-yl)-1H-imidazol-2-yl)-4-chlorophenyl)-2-methyl-4-((3S,5R)-3,4,5-trimethylpiperazin-1-yl)benzamide White solid (12 mg, 8%). $^1$H NMR (CD$_3$OD): 8.00 (s, 1H), 7.85 (dd, J=8.7 and 2.4 Hz, 1H), 7.52 (d, J=9.0 Hz, 1H), 7.47-7.44 (m, 2H), 7.35 (d, J=3.3 Hz, 1H), 7.30-7.29 (m, 1H), 7.06 (t, J=4.1 Hz, 1H), 6.86-6.82 (m, 2H), 3.70 (d, J=11.7 Hz, 2H), 2.59 (t, J=11.4 Hz, 2H), 2.52-2.48 (m, 2H), 2.47 (s, 3H), 2.38 (s, 3H), 1.22 (d, J=6.0 Hz, 6H). MS: m/z 520.1 [M+H]$^+$.

Example 82

N-(3-(5-(thiophen-2-yl)-1H-imidazol-2-yl)-4-chlorophenyl)-2-chloro-4-((3S,5R)-3,4,5-trimethylpiperazin-1-yl)benzamide Off-white solid (15.8 mg, 11.5%). $^1$H NMR (CD$_3$OD): 8.03 (s, 1H), 7.89-7.85 (m, 1H), 7.55-7.48 (m, 3H), 7.35 (d, J=3.0 Hz, 1H), 7.30-7.28 (m, 1H), 7.07-7.03 (m, 2H), 6.97 (dd, J=8.7 and 2.4 Hz, 1H), 3.72 (d, J=12.0 Hz, 2H), 2.62 (t, J=11.4 Hz, 2H), 2.49-2.40 (m, 2H), 2.36 (s, 3H), 1.22 (d, J=6.0 Hz, 6H). MS: m/z 542.0 [M+H]$^+$.

Example 83

N-(5-(1H-benzo[d]imidazol-2-yl)-6-chloropyridin-3-yl)-2-methyl-4-((2S,6R)-2,6-dimethylmorpholino)benzamide To a solution of 5-(1H-benzo[d]imidazol-2-yl)-6-chloropyridin-3-amine (50 mg, 0.2 mmol) and 2-methyl-4-((2S,6R)-2,6-dimethylmorpholino)benzoic acid (the intermediate of Example 32, 50 mg, 0.2 mmol) in pyridine (3 mL) was added EDCI (80 mg, 0.4 mmol), the resulting mixture was stirred over night at room temperature. Then the mixture concentrated under reduced pressure, water (5 mL) was added and extracted with ethyl acetate (5 mL×3), the organic layer was dried over anhydrous sodium sulfate and evaporated in vacuo to get the crude product, which was purified through TLC (CH$_2$Cl$_2$/CH$_3$OH) to give the title compound as a white solid (12.47 mg, 13.1%). $^1$H NMR (DMSO-d$_6$): 12.81 (brs, 1H), 10.53 (s, 1H), 8.86-8.84 (m, 2H), 7.74-7.62 (m, 2H), 7.52 (d, J=8.7 Hz, 1H), 7.29-7.26 (m, 2H), 6.88-6.85 (m, 2H), 3.75-3.66 (m, 4H), 2.43 (s, 3H), 2.35-2.28 (m, 2H), 1.17 (d, J=6.0 Hz, 6H). MS: m/z 476.3 [M+H]$^+$.

The following compounds were prepared from 5-(1H-benzo[d]imidazol-2-yl)-6-substituted-pyridin-3-amine and the corresponding 2- or 4-methyl-6-((2S,6R)-2,6-dimethylmorpholino)nicotinic acid (the compounds were prepared from ethyl 2- or 4-methyl-6-chloronicotinate and (2S,6R)-2,6-dimethylmorpholine using a procedure similar to those described for the syntheses of compounds of Examples 30a-b) or 6-((3S,5R)-3,4,5-trimethylpiperazin-1-yl)nicotinic acid (the compound was prepared from methyl 6-chloronicotinate and (2S,6R)-1,2,6-trimethylpiperazine hydrochloride using a procedure similar to those described for the syntheses of compounds of Examples 30a-b) or 2- or 3-methyl-4-((3S,5R)-3,4,5-trimethylpiperazin-1-yl)benzoic acid (the compounds were prepared from methyl 2- or 3-methyl-4-halobenzoate and (2S,6R)-1,2,6-trimethylpiperazine hydrochloride using a procedure similar to those described for the syntheses of compounds of Examples 30a or 33a, and 30b) using a procedure similar to those described for the synthesis of compound of Example 83.

Example 84

N-(5-(1H-benzo[d]imidazol-2-yl)-6-chloropyridin-3-yl)-2-methyl-6-((2S,6R)-2,6-dimethylmorpholino)nicotinamide Light-yellow solid (18.35 mg, 19.2%). $^1$H NMR (DMSO-d$_6$): 12.83 (brs, 1H), 10.54 (s, 1H), 8.84 (d, J=5.7 Hz, 2H), 7.83 (d, J=8.7 Hz, 1H), 7.76-7.58 (m, 2H), 7.33-7.20 (m, 2H), 6.77 (d, J=9.0 Hz, 1H), 4.28 (d, J=12.6 Hz, 2H), 3.61-3.57 (m, 2H), 2.50 (s, 3H), 2.46-2.39 (m, 2H), 1.17 (d, J=6.0 Hz, 6H). MS: m/z 477.1 [M+H]$^+$.

Example 85

N-(5-(1H-benzo[d]imidazol-2-yl)-6-chloropyridin-3-yl)-4-methyl-6-((2S,6R)-2,6-dimethylmorpholino)nicotinamide Light-yellow solid (20.64 mg, 21.6%). $^1$H NMR (DMSO-d$_6$): 12.81 (brs, 1H), 10.63 (s, 1H), 8.82 (dd, J=5.3 and 2.6 Hz, 2H), 8.39 (s, 1H), 7.73-7.61 (m, 2H), 7.27-7.24 (m, 2H), 6.78 (s, 1H), 4.26 (d, J=12.0 Hz, 2H), 3.62-3.52 (m, 2H), 2.46-2.42 (m, 2H), 2.40 (s, 3H), 1.15 (d, J=6.3 Hz, 6H). MS: m/z 477.1 [M+H]$^+$.

Example 86

N-(5-(1H-benzo[d]imidazol-2-yl)-6-chloropyridin-3-yl)-6-((3S,5R)-3,4,5-trimethylpiperazin-1-yl)nicotinamide Brown solid (9.66 mg, 5.1%). $^1$H NMR (DMSO-d$_6$): 12.82 (s, 1H), 10.50 (s, 1H), 8.96 (d, J=2.7 Hz, 1H), 8.85 (d, J=2.7 Hz, 1H), 8.77 (d, J=2.1 Hz, 1H), 8.14 (d, J=8.1 Hz, 1H), 7.72 (d, J=7.2 Hz, 1H), 7.61 (d, J=6.9 Hz, 1H), 7.30-7.21 (m, 2H), 7.01-6.95 (m, 1H), 4.47-4.29 (m, 2H), 2.85-2.62 (m, 2H), 2.41-1.98 (m, 5H), 1.32-1.01 (m, 6H). MS: m/z 476.0 [M+H]$^+$.

Example 87

N-(5-(1H-benzo[d]imidazol-2-yl)-6-chloropyridin-3-yl)-2-methyl-4-(3S,5R)-3,4,5-trimethylpiperazin-1-yl)benzamide Yellow solid (17.08 mg, 9.5%). $^1$H NMR (DMSO-d$_6$): 12.85 (s, 1H), 10.55 (s, 1H), 8.86-8.83 (m, 2H), 7.72 (d, J=6.9 Hz, 1H), 7.61 (d, J=7.5 Hz, 1H), 7.50 (d, J=8.7 Hz, 1H), 7.29-7.21 (m, 2H), 6.86-6.84 (m, 2H), 3.76 (d, J=11.4 Hz, 2H), 2.59-2.53 (m, 4H), 2.48 (s, 3H), 2.29 (s, 3H), 1.13 (d, J=5.7 Hz, 6H). MS: m/z 489.1 [M+H]$^+$.

Example 88

N-(5-(1H-benzo[d]imidazol-2-yl)-6-methylpyridin-3-yl)-2-methyl-4-((3S,5R)-3,4,5-trimethylpiperazin-1-yl)benzamide White solid (9.3 mg, 18.0%). $^1$H NMR (DMSO-d$_6$): 12.81 (s, 1H), 10.36 (s, 1H), 8.81 (d, J=2.1 Hz, 1H), 8.58 (d, J=2.1 Hz, 1H), 7.71 (d, J=6.9 Hz, 1H), 7.57 (d, J=7.2 Hz, 1H), 7.49 (d, J=8.7 Hz, 1H), 7.28-7.20 (m, 2H), 6.90-6.87 (m, 2H), 3.82-3.80 (m, 2H), 2.74 (s, 3H), 2.69-2.57 (m, 4H), 2.46-2.35 (m, 6H), 1.28-1.14 (m, 6H). MS: m/z 469.3 [M+H]$^+$.

Example 89

N-(5-(1H-benzo[d]imidazol-2-yl)-6-methylpyridin-3-yl)-3-methyl-4-((3S,5R)-3,4,5-trimethylpiperazin-1-yl)benzamide Light-yellow solid (15.6 mg, 8.8%). $^1$H NMR (CD$_3$OD): 8.92 (d, J=2.4 Hz, 1H), 8.52 (d, J=2.4 Hz, 1H), 7.85-7.82 (m, 2H), 7.72-7.63 (m, 2H), 7.36-7.31 (m, 2H), 7.15 (d, J=8.1 Hz, 1H), 3.23 (d, J=12.0 Hz, 2H), 3.01-2.86 (m, 2H), 2.81-2.74 (m, 2H), 2.72 (s, 3H), 2.62 (s, 3H), 2.41 (s, 3H), 1.30 (d, J=6.3 Hz, 6H). MS: m/z 469.3 [M+H]$^+$.

Example 90

N-(5-(1H-benzo[d]imidazol-2-yl)-6-methylpyridin-3-yl)-6-((3S,5R)-3,4,5-trimethylpiperazin-1-yl)nicotinamide White solid (8.74 mg, 9%). $^1$H NMR (DMSO-d$_6$): 12.81 (s, 1H), 10.39 (s, 1H), 8.89 (d, J=2.4 Hz, 1H), 8.81 (d, J=2.1 Hz, 1H), 8.60 (d, J=2.1 Hz, 1H), 8.18 (dd, J=8.7 and 1.8 Hz, 1H), 7.73-7.56 (m, 2H), 7.25-7.24 (m, 2H), 7.04 (d, J=8.7 Hz, 1H), 4.44 (d, J=12.0 Hz, 2H), 3.22-3.14 (m, 2H), 2.97-2.82 (m, 2H), 2.76 (s, 3H), 2.45-2.41 (m, 3H), 1.30-1.17 (m, 6H). MS: m/z 456.2 [M+H]$^+$.

The following compounds were prepared from 3-(6-(un)substituted-1H-benzo[d]imidazol-2-yl)-4-substituted-aniline and the corresponding 4-methyl-6-((2S,6R)-2,6-dimethylmorpholino)nicotinic acid (the intermediate of Example 85) or 2-methyl-4-(4-methylpiperazin-1-yl)benzoic acid hydrochloride (the compound was prepared from methyl 4-fluoro-2-methylbenzoate and 1-methylpiperazine using a procedure similar to those described for the syntheses of compounds of Examples 30a-b) or 2-substituted-4-((3S,5R)-3,4,5-trimethylpiperazin-1-yl)benzoic acid (the compounds were prepared from methyl 4-halo-2-substituted-benzoate and (2S,6R)-1,2,6-trimethylpiperazine hydrochloride using a procedure similar to those described for the syntheses of compounds of Examples 30a-b) or 2-methyl-4-((3S,5R)-4-alkyl-3,5-dimethylpiperazin-1-yl)benzoic acid (the compounds were prepared from methyl 4-fluoro-2-methylbenzoate and (2S,6R)-1-alkyl-2,6-dimethylpiperazine hydrochloride using a procedure similar to those described for the syntheses of compounds of Examples 30a-b) using a procedure similar to those described for the synthesis of compound of Example 83.

Example 91

N-(3-(1H-benzo[d]imidazol-2-yl)-4-chlorophenyl)-4-methyl-6-((2S,6R)-2,6-dimethylmorpholino)nicotinamide Off-white solid (10 mg, 6.4%). $^1$H NMR (DMSO-d$_6$): 12.72 (brs, 1H), 10.41 (s, 1H), 8.37-8.34 (m, 2H), 7.83 (dd, J=8.7 and 2.7 Hz, 1H), 7.58-7.55 (m, 3H), 7.22-7.13 (m, 2H), 6.78 (s, 1H), 4.28 (d, J=11.7 Hz, 2H), 3.61-3.56 (m, 2H), 2.48-2.42 (m, 2H), 2.39 (s, 3H), 1.17 (d, J=6.3 Hz, 6H). MS: m/z 476.2 [M+H]$^+$.

Example 92

N-(3-(1H-benzo[d]imidazol-2-yl)-4-chlorophenyl)-2-methyl-4-(4-methylpiperazin-1-yl)benzamide White solid (6.0 mg, 13.0%). $^1$H NMR (DMSO-d$_6$): 12.67 (s, 1H), 10.31 (s, 1H), 8.37 (d, J=2.7 Hz, 1H), 7.87-7.83 (m, 1H), 7.68 (d, J=6.0 Hz, 1H), 7.58-7.55 (m, 2H), 7.43 (d, J=8.4 Hz, 1H), 7.23-7.22 (m, 2H), 6.85-6.82 (m, 2H), 3.46-3.41 (m, 4H), 2.68-2.62 (m, 4H), 2.41-2.36 (m, 6H). MS: m/z 460.2 [M+H]$^+$.

Example 93

N-(3-(1H-benzo[d]imidazol-2-yl)-4-chlorophenyl)-2-methyl-4-((3S,5R)-3,4,5-trimethylpiperazin-1-yl)benzamide White solid (3.85 mg, 5.80%). $^1$H NMR (DMSO-d$_6$): 12.69 (brs, 1H), 10.35 (s, 1H), 8.36 (d, J=2.7 Hz, 1H), 7.86 (dd, J=8.9 and 2.6 Hz, 1H), 7.70-7.56 (m, 3H), 7.46 (d, J=8.4 Hz, 1H), 7.23-7.22 (m, 2H), 6.93-6.91 (m, 2H), 4.01 (d, J=13.2 Hz, 2H), 2.93 (t, J=12.0 Hz, 2H), 2.82-2.74 (m, 2H), 2.48-2.45 (m, 3H), 2.40 (s, 3H), 1.37 (d, J=5.1 Hz, 6H). MS: m/z 488.2 [M+H]$^+$.

Example 94

N-(3-(1H-benzo[d]imidazol-2-yl)-4-chlorophenyl)-2-chloro-4-((3S,5R)-3,4,5-trimethylpiperazin-1-yl)benzamide Off-white solid (37.27 mg, 15.3%). $^1$H NMR (DMSO-d$_6$): 12.73 (s, 1H), 10.55 (s, 1H), 8.34 (d, J=2.1 Hz, 1H), 7.85 (dd, J=8.9 and 2.3 Hz, 1H), 7.70 (d, J=7.5 Hz, 1H), 7.62-7.57 (m, 2H), 7.45 (d, J=8.4 Hz, 1H), 7.27-7.24 (m, 2H), 7.04 (s, 1H), 6.98 (d, J=8.7 Hz, 1H), 3.73 (d, J=11.7 Hz, 2H), 2.47-2.44 (m, 2H), 2.26-2.13 (m, 5H), 1.08 (d, J=6.0 Hz, 6H). MS: m/z 508.1 [M+H]$^+$.

Example 95

N-(3-(1H-benzo[d]imidazol-2-yl)-4-chlorophenyl)-2-fluoro-4-((3S,5R)-3,4,5-trimethylpiperazin-1-yl)benzamide Light-yellow solid (60.51 mg, 16.4%). $^1$H NMR (DMSO-d$_6$): 12.70 (s, 1H), 10.22 (s, 1H), 8.32 (d, J=2.7 Hz, 1H), 7.89 (dd, J=9.0 and 2.7 Hz, 1H), 7.69 (d, J=7.2 Hz, 1H), 7.61-7.54 (m, 3H), 7.28-7.19 (m, 2H), 6.86-6.84 (m, 2H), 3.86-3.78 (m, 2H), 2.61-2.53 (m, 2H), 2.33-2.13 (m, 5H), 1.22-1.01 (m, 6H). MS: m/z 246.6 [M/2+H]$^+$.

Example 96

N-(3-(6-chloro-1H-benzo[d]imidazol-2-yl)-4-chlorophenyl)-2-chloro-4-((3S,5R)-3,4,5-trimethylpiperazin-1-yl)benzamide Off-white solid (65 mg, 26.7%). $^1$H NMR (DMSO-d$_6$): 12.91 (d, J=2.1 Hz, 1H), 10.56 (s, 1H), 8.36 (s, 1H), 7.85 (d, J=8.7 Hz 1H), 7.77-7.71 (m, 1H), 7.63-7.61 (m, 2H), 7.56 (d, J=8.7 Hz, 1H), 7.27 (t, J=9.2 Hz, 1H), 7.06 (s, 1H), 6.98 (d, J=8.1 Hz, 1H), 3.76 (d, J=10.5 Hz, 2H), 2.44-2.38 (m, 2H), 2.31-2.15 (m, 5H), 1.18-1.03 (m, 6H). MS: m/z 542.0 [M+H]$^+$.

Example 97

N-(3-(6-chloro-1H-benzo[d]imidazol-2-yl)-4-chlorophenyl)-2-methyl-4-((3S,5R)-3,4,5-trimethylpiperazin-1-yl)benzamide Off-white solid (37.52 mg, 14.9%). $^1$H NMR (DMSO-d$_6$): 12.91 (d, J=13.5 Hz, 1H), 10.35 (s, 1H), 8.40 (s, 1H), 7.87 (d, J=11.7 Hz 1H), 7.77-7.71 (m, 1H), 7.61-7.58 (m, 2H), 7.44 (d, J=8.1 Hz, 1H), 7.31-7.24 (m, 1H), 6.87-6.85 (m, 2H), 3.82-3.70 (m, 2H), 2.65-2.54 (m, 2H), 2.40-2.19 (m, 8H), 1.21-1.08 (m, 6H). MS: m/z 522.1 [M+H]$^+$.

Example 98

N-(3-(6-fluoro-1H-benzo[d]imidazol-2-yl)-4-chlorophenyl)-2-methyl-4-((3S,5R)-3,4,5-trimethylpiperazin-1-yl)benzamide White solid (46.01 mg, 18.7%). $^1$H NMR (DMSO-d$_6$): 12.82 (brs, 1H), 10.32 (s, 1H), 8.39 (d, J=2.4 Hz, 1H), 7.85 (dd, J=8.9 and 2.6 Hz, 1H), 7.70-7.54 (m, 2H), 7.50-7.35 (m, 2H), 7.11 (t, J=9.0 Hz, 1H), 6.84-6.82 (m, 2H), 3.69 (d, J=11.1 Hz, 2H), 2.48-2.44 (m, 2H), 2.39 (s, 3H), 2.24-2.21 (m, 2H), 2.18 (s, 3H), 1.08 (d, J=6.0 Hz, 6H). MS: m/z 506.1 [M+H]$^+$.

Example 99

N-(3-(6-fluoro-1H-benzo[d]imidazol-2-yl)-4-chlorophenyl)-2-chloro-4-((3S,5R)-3,4,5-trimethylpiperazin-1-yl)benzamide Off-white solid (58.06 mg, 21.0%). $^1$H NMR (DMSO-d$_6$): 12.85 (s, 1H), 10.55 (s, 1H), 8.36 (s, 1H), 7.84 (d, J=8.7 Hz, 1H), 7.71-7.35 (m, 4H), 7.13-6.97 (m, 3H), 3.74 (d, J=12.0 Hz, 2H), 2.46-2.41 (m, 2H), 2.28-2.13 (m, 5H), 1.08 (d, J=5.7 Hz, 6H). MS: m/z 526.0 [M+H]$^+$.

Example 100

N-(3-(1H-benzo[d]imidazol-2-yl)-4-chlorophenyl)-2-methyl-4-((3S,5R)-4-ethyl-3,5-dimethylpiperazin-1-yl)benzamide White solid (36.0 mg, 15.3%). $^1$H NMR (DMSO-d$_6$): 12.69 (s, 1H), 10.32 (s, 1H), 8.36 (d, J=2.7 Hz, 1H), 7.84 (dd, J=8.9 and 2.6 Hz, 1H), 7.68 (d, J=6.9 Hz, 1H), 7.59-7.55 (m, 2H), 7.42 (d, J=8.7 Hz, 1H), 7.27-7.18 (m, 2H), 6.88-6.81 (m, 2H), 3.79-3.63 (m, 2H), 3.12-2.55 (m, 6H), 2.38 (s, 3H), 1.33-0.80 (m, 9H). MS: m/z 502.1 [M+H]$^+$.

Example 101

N-(3-(1H-benzo[d]imidazol-2-yl)-4-chlorophenyl)-2-methyl-4-((3S,5R)-4-isopropyl-3,5-dimethylpiperazin-1-yl)benzamide Off-white solid (7.5 mg, 12.1%). $^1$H NMR (DMSO-d$_6$): 12.70 (s, 1H), 10.29 (brs, 1H), 8.37 (d, J=2.7 Hz, 1H), 7.85 (dd, J=8.9 and 2.3 Hz, 1H), 7.68 (d, J=7.5 Hz, 1H), 7.57 (d, J=8.7 Hz, 2H), 7.45-7.43 (m, 1H), 7.27-7.18 (m, 2H), 6.76-6.58 (m, 2H), 3.84-3.64 (m, 2H), 3.24-2.98 (m, 4H), 2.58-2.48 (m, 2H), 2.39 (s, 3H), 1.47-1.25 (m, 6H), 1.13-0.88 (m, 6H). MS: m/z 516.1 [M+H]$^+$.

Example 102

N-(3-(1H-benzo[d]imidazol-2-yl)-4-methylphenyl)-2-chloro-4-((3S,5R)-3,4,5-trimethylpiperazin-1-yl)benzamide Yellow solid (45.97 mg, 12.1%). $^1$H NMR (CD$_3$OD): 7.96 (d, J=1.8 Hz, 1H), 7.71 (dd, J=8.4 and 2.1 Hz, 1H), 7.64-7.61 (m, 2H), 7.48 (d, J=8.4 Hz, 1H), 7.38 (d, J=8.4 Hz, 1H), 7.30-7.27 (m, 2H), 7.03 (d, J=2.1 Hz, 1H), 6.97 (dd, J=8.7 and 2.1 Hz, 1H), 3.73 (d, J=12.0 Hz, 2H), 2.64 (t, J=11.6 Hz, 2H), 2.56-2.53 (m, 2H), 2.49 (s, 3H), 2.41 (s, 3H), 1.24 (d, J=6.3 Hz, 6H). MS: m/z 488.1 [M+H]$^+$.

The following compounds were prepared from N-(3-(1H-benzo[d]imidazol-2-yl)-4-chlorophenyl)-6-chloronicotinamide (Example 35a) and the corresponding 1-methylpiperazine or (2S,6R)-1,2,6-trimethylpiperazine trifluoroacetate or (2S,6R)-1-ethyl-2,6-dimethylpiperazine trifluoroacetate using a procedure similar to those described for the synthesis of compound of Example 35b.

Example 103

N-(3-(1H-benzo[d]imidazol-2-yl)-4-chlorophenyl)-6-(4-methylpiperazin-1-yl)nicotinamide Off-white solid (9.1 mg, 15.6%). $^1$H NMR (DMSO-d$_6$): 12.66 (s, 1H), 10.25 (s, 1H), 8.74 (d, J=2.1 Hz, 1H), 8.38 (d, J=2.4 Hz, 1H), 8.09 (dd, J=9.0 and 2.4 Hz, 1H), 7.96 (dd, J=8.9 and 2.6 Hz, 1H), 7.69 (d, J=7.5 Hz, 1H), 7.60-7.57 (m, 2H), 7.27-7.18 (m, 2H), 6.90 (d, J=9.0 Hz, 1H), 3.62 (t, J=4.8 Hz, 4H), 2.38 (t, J=4.8 Hz, 4H), 2.21 (s, 3H). MS: m/z 447.2 [M+H]$^+$.

Example 104

N-(3-(1H-benzo[d]imidazol-2-yl)-4-chlorophenyl)-6-((3S,5R)-3,4,5-trimethylpiperazin-1-yl)nicotinamide Light-yellow solid (5.86 mg, 9.5%). $^1$H NMR (DMSO-d$_6$): 12.78 (s, 1H), 10.35 (s, 1H), 8.84 (d, J=2.4 Hz, 1H), 8.49 (d, J=2.7 Hz, 1H), 8.19 (dd, J=9.2 and 2.3 Hz, 1H), 8.08 (dd, J=8.9 and 2.6 Hz, 1H), 7.80 (d, J=7.8 Hz, 1H), 7.72-7.69 (m, 2H), 7.39-7.30 (m, 2H), 7.05 (d, J=9.0 Hz, 1H), 4.39 (d, J=12.9 Hz, 2H), 2.74 (t, J=11.9 Hz, 2H), 2.28 (s, 3H), 2.24-2.19 (m, 2H), 1.19 (d, J=6.3 Hz, 6H). MS: m/z 475.2 [M+H]$^+$.

Example 105

N-(3-(1H-benzo[d]imidazol-2-yl)-4-chlorophenyl)-6-((3S,5R)-4-ethyl-3,5-dimethylpiperazin-1-yl)nicotinamide Brown solid (18.0 mg, 18.4%). $^1$H NMR (DMSO-d$_6$): 12.71 (s, 1H), 10.37 (s, 1H), 8.79 (d, J=2.1 Hz, 1H), 8.41 (d, J=2.7 Hz, 1H), 8.17 (dd, J=9.0 and 2.1 Hz, 1H), 8.00 (dd, J=8.9 and 2.6 Hz, 1H), 7.76-7.65 (m, 1H), 7.61 (d, J=9.0 Hz, 2H), 7.26-7.24 (m, 2H), 7.02 (d, J=9.0 Hz, 1H), 4.46 (d, J=11.7 Hz, 2H), 3.17-2.89 (m, 6H), 1.26 (d, J=5.1 Hz, 6H), 1.02 (t, J=6.3 Hz, 3H). MS: m/z 489.2 [M+H]$^+$.

Example 106

N-(5-(1H-benzo[d]imidazol-2-yl)-6-chloropyridin-3-yl)-6-((2S,6R)-2,6-dimethylmorpholino)nicotinamide The title compound was prepared from 6-chloronicotinic acid, 5-(1H-benzo[d]imidazol-2-yl)-6-chloropyridin-3-carboxamide and (2S,6R)-2,6-dimethylmorpholine using a procedure similar to those described for the synthesis of compound of Example 35. White solid (16 mg, 18.2%). $^1$H NMR (DMSO-d$_6$): 12.73 (brs, 1H), 10.49 (brs, 1H), 8.93 (d, J=2.7 Hz, 1H), 8.82 (d, J=2.7 Hz, 1H), 8.76 (d, J=2.1 Hz, 1H), 8.12 (dd, J=9.0 and 2.4 Hz, 1H), 7.67-7.65 (m, 2H), 7.27-7.24 (m, 2H), 6.94 (d, J=9.0 Hz, 1H), 4.30 (d, J=12.3 Hz, 2H), 3.80-3.71 (m, 2H), 2.60-2.55 (m, 2H), 1.15 (d, J=6.3 Hz, 6H). MS: m/z 463.2 [M+H]$^+$.

Example 107

N-(3-(1H-benzo[d]imidazol-2-yl)-4-chlorophenyl)-4-methyl-6-((3S,5R)-3,4,5-trimethylpiperazin-1-yl)nicotinamide a) N-(3-(1H-benzo[d]imidazol-2-yl)-4-chlorophenyl)-6-chloro-4-methylnicotinamide: A solution of 6-hydroxy-4-methylnicotinic acid (85 mg, 0.53 mmol) in phosphorus oxychloride (2 mL) was heated to reflux over 5 hours. After cooled to room temperature, the mixture was concentrated to give 6-chloro-4-methylnicotinoyl chloride, which used in the next step without purification. To a solution of 3-(1H-benzo[d]imidazol-2-yl)-4-chloroaniline (130 mg, 0.53 mmol), Et$_3$N (210 mg, 2.1 mmol) in DCM (10 mL) was added dropwise the solution of 6-chloro-4-methylnicotinoyl chloride in DCM (3 mL) at ice-bath. The mixture was stirred at r.t. overnight, then concentrated to give the crude product as a yellow solid (130 mg, 61.9%). MS: m/z 397.1 [M+H]$^+$.

b) N-(3-(1H-benzo[d]imidazol-2-yl)-4-chlorophenyl)-4-methyl-6-((3S,5R)-3,4,5-trimethylpiperazin-1-yl)nicotinamide: The title compound was prepared from N-(3-(1H-benzo[d]imidazol-2-yl)-4-chlorophenyl)-6-chloro-4-methylnicotinamide and (2S,6R)-1,2,6-trimethylpiperazine hydrochloride using a procedure similar to those described for the synthesis of compound of Example 35b. White solid (15 mg, 9.6%). $^1$H NMR (DMSO-d$_6$): 12.70 (s, 1H), 10.43 (s, 1H), 8.35 (d, J=12.0 Hz, 2H), 7.86 (d, J=8.7 Hz, 1H), 7.71 (d, J=7.2 Hz, 1H), 7.61-7.57 (m, 2H), 7.29-7.20 (m, 2H), 6.81 (s, 1H), 4.29-4.23 (m, 2H), 2.64-2.57 (m, 2H), 2.39 (s, 3H), 2.29-2.00 (m, 5H), 1.23-1.01 (m, 6H). MS: m/z 489.1 [M+H]$^+$.

Example 108

N-(3-(1H-benzo[d]imidazol-2-yl)-4-chlorophenyl)-2-methyl-4-(piperazin-1-yl)benzamide a) Methyl 2-methyl-4-(piperazin-1-yl)benzoate: A mixture of methyl 4-fluoro-2-methylbenzoate (150 mg, 0.89 mmol) and piperazine (230 mg, 2.67 mmol) in dimethyl sulfoxide (2 mL) was stirred at 80° C. overnight. The reaction mixture was cooled to room temperature, added water (50 mL) and stirred. The aqueous phase was extracted with ethyl acetate (50 mL×3), the combined organic phases were dried over Na$_2$SO$_4$, filtered and concentrated to give the title compound as a yellow oil (122 mg, 58.3%). MS: m/z 235.2 [M+H]$^+$.

b) 2-Methyl-4-(4-(tert-butoxycarbonyl)piperazin-1-yl)benzoic acid: A mixture of methyl 2-methyl-4-(piperazin-1-yl)benzoate (122 mg, 0.52 mmol), 2 N NaOH aqueous solution (0.78 mL, 1.56 mmol) in methanol (10 mL) was stirred at 60° C. overnight. The reaction mixture was concentrated to move methanol, added water (1.5 mL) and dioxane (5 mL), stirred and added di-tert-butyl dicarbonate (170 mg, 0.78 mmol). The mixture was stirred at room temperature overnight, concentrated and added water (40 mL). The aqueous phase was acidified to pH=1 with 1 N hydrochloric acid and extracted with ethyl acetate (50 mL×2), the combined organic phases were dried over Na$_2$SO$_4$, filtered and concentrated to give the title compound as a yellow solid (103 mg, 62.1%). MS: m/z 321.2 [M+H]$^+$.

c) N-(3-(1H-benzo[d]imidazol-2-yl)-4-chlorophenyl)-2-methyl-4-(4-(tert-butoxycarbonyl)piperazin-1-yl)benzamide: The title compound was prepared from 3-(1H-benzo[d]imidazol-2-yl)-4-chloroaniline and 2-methyl-4-(4-(tert-butoxycarbonyl)piperazin-1-yl)benzoic acid using a procedure similar to those described for the synthesis of compound of Example 83. White solid (70 mg, 61.1%). MS: m/z 546.3 [M+H]$^+$.

d) N-(3-(1H-benzo[d]imidazol-2-yl)-4-chlorophenyl)-2-methyl-4-(piperazin-1-yl)benzamide: A mixture of N-(3-(1H-benzo[d]imidazol-2-yl)-4-chlorophenyl)-2-methyl-4-(4-(tert-butoxycarbonyl)piperazin-1-yl)benzamide (70 mg, 0.13 mmol) in 2,2,2-trifluoroacetic acid (1 mL) and CH$_2$Cl$_2$ (3 mL) was stirred at room temperature overnight. The mixture was concentrated, to the residue was added ethyl acetate (50 mL) and saturated aqueous NaHCO$_3$ solution, stirred and separated. The organic phase was dried over Na$_2$SO$_4$, filtered and concentrated, and the residue was purified by the preparative plate of silica to give the title compound as an off-white solid (4.8 mg, 8.3%). $^1$H NMR (DMSO-$d_6$): 12.67 (brs, 1H), 10.32 (s, 1H), 8.37 (d, J=1.5 Hz, 1H), 7.87-7.84 (m, 1H), 7.66-7.63 (m, 3H), 7.57 (d, J=8.7 Hz, 1H), 7.46-7.43 (m, 2H), 6.86-6.84 (m, 2H), 3.50-3.44 (m, 4H), 3.07-3.03 (m, 4H), 2.39 (s, 3H). MS: m/z 446.2 [M+H]$^+$.

Example 109

N-(3-(1H-benzo[d]imidazol-2-yl)-4-chlorophenyl)-2-methyl-4-((3S,5R)-3,5-dimethylpiperazin-1-yl)benzamide The title compound was prepared from methyl 4-fluoro-2-methylbenzoate, (2S,6R)-2,6-dimethylpiperazine, di-tert-butyl dicarbonate and 3-(1H-benzo[d]imidazol-2-yl)-4-chloroaniline using a procedure similar to those described for the synthesis of compound of Example 108. White solid (3.8 mg, 3.8%). $^1$H NMR (DMSO-$d_6$): 12.69 (s, 1H), 10.32 (s, 1H), 8.38 (d, J=2.7 Hz, 1H), 7.87 (dd, J=8.9 and 2.6 Hz, 1H), 7.71-7.69 (m, 1H), 7.60-7.57 (m, 2H), 7.45 (d, J=8.7 Hz, 1H), 7.29-7.20 (m, 2H), 6.86-6.84 (m, 2H), 3.80 (d, J=11.1 Hz, 2H), 3.16-2.96 (m, 4H), 2.40 (s, 3H), 1.14 (d, J=6.3 Hz, 6H). MS: m/z 474.2 [M+H]$^+$.

Example 110

N-(3-(1-methyl-1H-benzo[d]imidazol-2-yl)-4-chlorophenyl)-2-chloro-4-((3S,5R)-3,4,5-trimethylpiperazin-1-yl)benzamide The title compound was prepared from 3-(1-methyl-1H-benzo[d]imidazol-2-yl)-4-chloroaniline (Example 47b) and 2-chloro-4-((3S,5R)-3,4,5-trimethylpiperazin-1-yl)benzoic acid using a procedure similar to those described for the synthesis of compound of Example 83. Light-yellow solid (22.0 mg, 23.4%). $^1$H NMR (DMSO-$d_6$): 10.57 (s, 1H), 7.99 (d, J=2.4 Hz, 1H), 7.89 (dd, J=8.9 and 2.6 Hz, 2H), 7.70-7.61 (m, 3H), 7.43 (d, J=8.4 Hz, 1H), 7.35-7.24 (m, 2H), 7.03 (s, 1H), 6.97 (d, J=8.7 Hz, 1H), 3.76-3.72 (m, 2H), 3.65 (s, 3H), 2.58-2.52 (m, 2H), 2.30-2.10 (m, 5H), 1.09-1.07 (m, 6H). MS: m/z 522.1 [M+H]$^+$.

The following compounds were prepared from 3-(6-substituted-1H-benzo[d]imidazol-2-yl)-4-substituted-aniline and the corresponding 2-substituted-4-((3S,5R)-3,4,5-trimethylpiperazin-1-yl)benzoic acid or 2-chloro-4-((3S,5R)-4-ethyl-3,5-dimethylpiperazin-1-yl)benzoic acid (the compound was prepared from methyl 2-chloro-4-fluorobenzoate and (2S,6R)-1-ethyl-2,6-dimethylpiperazine dihydrochloride using a procedure similar to those described for the syntheses of compounds of Examples 30a and 30b) using a procedure similar to those described for the synthesis of compound of Example 83.

Example 111

N-(3-(6-methyl-1H-benzo[d]imidazol-2-yl)-4-chlorophenyl)-2-chloro-4-((3S,5R)-3,4,5-trimethylpiperazin-1-yl)benzamide White solid (16.46 mg, 9.0%). $^1$H NMR (CD$_3$OD): 8.12 (d, J=2.4 Hz, 1H), 7.94 (dd, J=9.0 and 2.4 Hz, 1H), 7.62-7.51 (m, 3H), 7.47 (s, 1H), 7.18 (d, J=8.4 Hz, 1H), 7.12 (d, J=1.8 Hz, 1H), 7.04 (dd, J=8.4 and 2.4 Hz, 1H), 3.89 (d, J=11.4 Hz, 2H), 2.97-2.73 (m, 4H), 2.66 (s, 3H), 2.52 (s, 3H), 1.36 (d, J=5.7 Hz, 6H). MS: m/z 522.0 [M+H]$^+$.

Example 112

N-(3-(6-methyl-1H-benzo[d]imidazol-2-yl)-4-chlorophenyl)-2-methyl-4-((3S,5R)-3,4,5-trimethylpiperazin-1-yl)benzamide White solid (14.16 mg, 6.7%). $^1$H NMR (CD$_3$OD): 8.09 (d, J=2.7 Hz, 1H), 7.92 (dd, J=9.0 and 2.7 Hz, 1H), 7.58 (d, J=8.7 Hz, 1H), 7.55-7.48 (m, 2H), 7.45 (s, 1H), 7.16 (d, J=8.4 Hz, 1H), 6.95-6.92 (m, 2H), 3.96 (d, J=13.5 Hz, 2H), 3.28-3.25 (m, 2H), 2.92-2.76 (m, 5H), 2.50 (s, 3H), 2.48 (s, 3H), 1.44 (d, J=6.6 Hz, 6H). MS: m/z 251.6 [M/2+H]$^+$.

Example 113

N-(3-(6-chloro-1H-benzo[d]imidazol-2-yl)-4-methylphenyl)-2-chloro-4-((3S,5R)-3,4,5-trimethylpiperazin-1-yl)benzamide White solid (36 mg, 15.3%). $^1$H NMR (CD$_3$OD): 7.99 (d, J=2.1 Hz, 1H), 7.71 (dd, J=8.3 and 1.7 Hz, 1H), 7.68-7.62 (m, 1H), 7.61-7.55 (m, 1H), 7.49 (d, J=8.7 Hz, 1H), 7.40 (d, J=8.4 Hz, 1H), 7.29 (d, J=8.1 Hz, 1H), 7.04 (d, J=1.8 Hz, 1H), 6.98 (dd, J=8.7 and 2.1 Hz, 1H), 3.73 (d, J=11.7 Hz, 2H), 2.67-2.59 (m, 2H), 2.58-2.45 (m, 5H), 1.24 (d, J=6.0 Hz, 6H). MS: m/z 522.0 [M+H]$^+$.

Example 114

N-(3-(6-fluoro-1H-benzo[d]imidazol-2-yl)-4-chlorophenyl)-2-chloro-4-((3S,5R)-4-ethyl-3,5-dimethylpiperazin-1-yl)benzamide Off-white solid (30.15 mg, 24.30%). $^1$H NMR (CD$_3$OD): 8.14 (d, J=2.4 Hz, 1H), 7.91 (d, J=8.7 Hz, 1H), 7.61-7.58 (m, 2H), 7.51 (d, J=8.7 Hz, 1H), 7.37-7.34 (m, 1H), 7.14-7.06 (m, 2H), 6.99 (dd, J=8.9 and 2.3 Hz, 1H), 3.83 (d, J=12.3 Hz, 2H), 3.22-3.15 (m, 4H), 2.71 (t, J=11.9 Hz, 2H), 1.29 (d, J=6.3 Hz, 6H), 1.11 (t, J=7.2 Hz, 3H). MS: m/z 540.0 [M+H]$^+$.

Example 115

N-(3-(6-fluoro-1H-benzo[d]imidazol-2-yl)-4-methylphenyl)-2-chloro-4-((3S,5R)-3,4,5-trimethylpiperazin-1-yl)benzamide White solid (16.36 mg, 10.40%). $^1$H NMR (CD$_3$OD): 7.98 (s, 1H), 7.71 (d, J=8.4 Hz, 1H), 7.62-7.58 (m, 1H), 7.48 (d, J=8.4 Hz, 1H), 7.40-7.31 (m, 2H), 7.12-7.04 (m, 2H), 6.97 (d, J=8.7 Hz, 1H), 3.74 (d, J=11.7 Hz, 2H), 2.64 (t, J=11.6 Hz, 2H), 2.56-2.52 (m, 2H), 2.49 (s, 3H), 2.42 (s, 3H), 1.24 (d, J=6.0 Hz, 6H). MS: m/z 506.0 [M+H]$^+$.

The following compounds were prepared from 3-(1H-benzo[d]imidazol-2-yl)-4-chloroaniline and the corresponding substituted 6-((3S,5R)-3,4,5-trimethylpiperazin-1-yl)nicotinic acid (the compounds were prepared from ethyl substituted 6-chloronicotinate and (2S,6R)-1,2,6-trimethylpiperazine dihydrochloride using a procedure similar to those described for the syntheses of compounds of Examples 30a-b) or (un)substituted-4-((3S,5R)-3,4,5-trimethylpiperazin-1-yl)benzoic acid (the compounds were prepared from methyl (un)substituted-4-halobenzoate and (2S,6R)-1,2,6-trimethylpiperazine dihydrochloride using a procedure similar to those described for the syntheses of compounds of Examples 30a or 33a and 30b) or 2-chloro-4-((3S,5R)-4-alkyl-3,5-dimethylpiperazin-1-yl)benzoic acid (the compounds were prepared from methyl 2-chloro-4-fluorobenzoate and (2S,6R)-1-alkyl-2,6-dimethylpiperazine dihydrochloride using a procedure similar to those described for the syntheses of compounds of Examples 30a-b) or (S)-2-chloro-4-(3,4-dimethylpiperazin-1-yl)benzoic acid (the compound was prepared from methy 2-chloro-4-fluorobenzoate and (S)-1,2-dimethylpiperazine dihydrochloride using a procedure similar to those described for the syntheses of compounds of Examples 30a-b) using a procedure similar to those described for the synthesis of compound of Example 83.

Example 116

N-(3-(1H-benzo[d]imidazol-2-yl)-4-chlorophenyl)-2-methyl-6-((3S,5R)-3,4,5-trimethylpiperazin-1-yl)nicotinamide Brown solid (50.32 mg, 25.1%). $^1$H NMR (CD$_3$OD): 8.12 (d, J=2.7 Hz, 1H), 7.92 (dd, J=8.7 and 2.7 Hz, 1H), 7.79 (d, J=8.7 Hz, 1H), 7.67-7.65 (m, 2H), 7.60 (d, J=8.7 Hz, 1H), 7.35-7.29 (m, 2H), 6.80 (d, J=8.7 Hz, 1H), 4.56 (d, J=12.0 Hz, 2H), 3.18-3.03 (m, 2H), 2.97-2.89 (m, 2H), 2.78 (s, 3H), 2.57 (s, 3H), 1.42 (d, J=6.3 Hz, 6H). MS: m/z 489.0 [M+H]$^+$.

Example 117

N-(3-(1H-benzo[d]imidazol-2-yl)-4-chlorophenyl)-2-chloro-6-((3S,5R)-3,4,5-trimethylpiperazin-1-yl)nicotinamide Off-white solid (45.12 mg, 24%). $^1$H NMR (CD$_3$OD): 8.12 (d, J=2.7 Hz, 1H), 7.90 (dd, J=9.0 and 2.7 Hz, 1H), 7.77 (d, J=8.4 Hz, 1H), 7.72-7.62 (m, 2H), 7.59 (d, J=9.0 Hz, 1H), 7.34-7.28 (m, 2H), 6.82 (d, J=8.7 Hz, 1H), 4.28 (d, J=12.9 Hz, 2H), 2.80-2.72 (m, 2H), 2.48-2.32 (m, 5H), 1.23 (d, J=6.0 Hz, 6H). MS: m/z 509.2 [M+H]$^+$.

Example 118

N-(3-(1H-benzo[d]imidazol-2-yl)-4-chlorophenyl)-4-((3S,5R)-3,4,5-trimethylpiperazin-1-yl)benzamide Off-white solid (28.08 mg, 17.9%). $^1$H NMR (CD$_3$OD): 8.13 (d, J=2.4 Hz, 1H), 7.93 (dd, J=8.9 and 2.6 Hz, 3H), 7.89 (d, J=9.0 Hz, 2H), 7.71-7.62 (m, 2H), 7.57 (d, J=8.7 Hz, 1H), 7.32-7-29 (m, 2H), 7.03 (d, J=9.0 Hz, 2H), 3.80 (d, J=12.0 Hz, 2H), 2.71-2.63 (m, 2H), 2.59-2.48 (m, 2H), 2.42 (s, 3H), 1.25 (d, J=6.0 Hz, 6H). MS: m/z 474.2 [M+H]$^+$.

Example 119

N-(3-(1H-benzo[d]imidazol-2-yl)-4-chlorophenyl)-2-(trifluoromethyl)-4-((3S,5R)-3,4,5-trimethylpiperazin-1-yl)benzamide White solid (27.12 mg, 20.0%). $^1$H NMR (CD$_3$OD): 8.09 (d, J=1.8 Hz, 1H), 7.89 (dd, J=9.3 and 1.5 Hz, 1H), 7.72-7.54 (m, 4H), 7.32-7.22 (m, 4H), 3.75 (d, J=11.1 Hz, 2H), 2.68-2.60 (m, 2H), 2.46-2.43 (m, 2H), 2.36 (s, 3H), 1.23 (d, J=6.3 Hz, 6H). MS: m/z 542.2 [M+H]$^+$.

Example 120

N-(3-(1H-benzo[d]imidazol-2-yl)-4-chlorophenyl)-3-chloro-4-((3S,5R)-3,4,5-trimethylpiperazin-1-yl)benzamide Off-white solid (120 mg, 57.6%). $^1$H NMR (CD$_3$OD): 8.17 (d, J=2.7 Hz, 1H), 8.08 (d, J=1.8 Hz, 1H), 7.97 (dd, J=8.9 and 2.6 Hz, 2H), 7.69-7.66 (m, 2H), 7.61 (d, J=8.7 Hz, 1H), 7.36-7.30 (m, 3H), 3.74-3.62 (m, 2H), 3.60-3.46 (m, 2H), 3.06-2.88 (m, 5H), 1.46 (d, J=6.6 Hz, 6H). MS: m/z 508.0 [M+H]$^+$.

Example 121

N-(3-(1H-benzo[d]imidazol-2-yl)-4-chlorophenyl)-3-methyl-4-((3S,5R)-3,4,5-trimethylpiperazin-1-yl)benzamide White solid (19.07 mg, 18.6%). $^1$H NMR (DMSO-d$_6$): 12.74 (s, 1H), 10.41 (s, 1H), 8.42 (d, J=2.1 Hz, 1H), 8.02 (dd, J=8.9 and 2.3 Hz, 1H), 7.86-7.83 (m, 2H), 7.71 (d, J=7.2 Hz, 1H), 7.64-7.58 (m, 2H), 7.29-7.21 (m, 2H), 7.11 (d, J=8.1 Hz, 1H), 3.17-3.16 (m, 2H), 2.70-2.60 (m, 4H), 2.50 (s, 3H), 2.34 (s, 3H), 1.32-1.12 (m, 6H). MS: m/z 488.0 [M+H]$^+$.

Example 122

N-(3-(1H-benzo[d]imidazol-2-yl)-4-chlorophenyl)-2-methyl-3-fluoro-4-((3S,5R)-3,4,5-trimethylpiperazin-1-yl)benzamide White solid (56.21 mg, 27.8%). $^1$H NMR (DMSO-d$_6$): 12.74 (s, 1H), 10.60 (s, 1H), 8.38 (d, J=2.4 Hz, 1H), 7.86 (dd, J=9.0 and 2.1 Hz, 1H), 7.70 (d, J=6.9 Hz, 1H), 7.64-7.57 (m, 2H), 7.36-7.20 (m, 3H), 7.09-7.01 (m, 1H), 3.70-3.40 (m, 4H), 3.04-2.91 (m, 2H), 2.87 (s, 3H), 2.31 (s, 3H), 1.48-0.98 (m, 6H). MS: m/z 506.2 [M+H]$^+$.

Example 123

N-(3-(1H-benzo[d]imidazol-2-yl)-4-chlorophenyl)-2-chloro-5-fluoro-4-((3S,5R)-3,4,5-trimethylpiperazin-1-yl)benzamide White solid (10.68 mg, 5.1%). $^1$H NMR (DMSO-d$_6$): 12.72 (s, 1H), 10.71 (s, 1H), 8.35 (d, J=2.7 Hz, 1H), 7.83 (dd, J=9.0 and 2.7 Hz, 1H), 7.71 (d, J=7.8 Hz, 1H), 7.63 (d, J=8.7 Hz, 1H), 7.60-7.52 (m, 2H), 7.29-7.16 (m, 3H), 3.52-3.40 (m, 2H), 2.81-2.62 (m, 4H), 2.47-2.27 (m, 3H), 1.25-1.09 (m, 6H). MS: m/z 526.1 [M+H]$^+$.

Example 124

N-(3-(1H-benzo[d]imidazol-2-yl)-4-chlorophenyl)-2-chloro-4-((3S,5R)-4-ethyl-3,5-dimethylpiperazin-1-yl)benzamide White solid (45.2 mg, 21.1%). $^1$H NMR (CD$_3$OD): 8.13 (d, J=2.4 Hz, 1H), 7.94 (dd, J=8.7 and 2.4 Hz, 1H), 7.68-7.65 (m, 2H), 7.60 (d, J=8.7 Hz, 1H), 7.54 (d, J=8.7 Hz, 1H), 7.34-7.30 (m, 2H), 7.15 (d, J=2.1 Hz, 1H), 7.05 (dd, J=8.7 and 2.4 Hz, 1H), 3.99 (d, J=12.9 Hz, 2H), 3.46-3.40 (m, 4H), 2.92-2.84 (m, 2H), 1.41 (d, J=6.3 Hz, 6H), 1.25 (t, J=7.4 Hz, 3H). MS: m/z 522.0 [M+H]$^+$.

Example 125

N-(3-(1H-benzo[d]imidazol-2-yl)-4-chlorophenyl)-2-chloro-4-((3S,5R)-4-isopropyl-3,5-dimethylpiperazin-1-yl)benzamide Off-white solid (23.50 mg, 15.10%). $^1$H NMR (CD$_3$OD): 8.14 (d, J=2.4 Hz, 1H), 7.94 (dd, J=8.9 and 2.3 Hz, 1H), 7.73-7.64 (m, 2H), 7.61 (d, J=9.0 Hz, 1H), 7.53 (d, J=8.4 Hz, 1H), 7.35-7.32 (m, 2H), 6.91 (d, J=1.8 Hz, 1H), 6.84 (dd, J=8.7 and 2.1 Hz, 1H), 3.62-3.58 (m, 5H), 3.38-3.34 (m, 2H), 1.31-1.27 (m, 12H). MS: m/z 536.2 [M+H]$^+$.

Example 126

(S)—N-(3-(1H-benzo[d]imidazol-2-yl)-4-chlorophenyl)-2-chloro-4-(3,4-dimethylpiperazin-1-yl)benzamide Light-yellow solid (23.31 mg, 29.6%). $^1$H NMR (CD$_3$OD): 8.13 (d, J=2.4 Hz, 1H), 7.92 (dd, J=8.9 and 2.3 Hz, 1H), 7.67-7.64 (m, 2H), 7.59 (d, J=8.7 Hz, 1H), 7.49 (d, J=8.7 Hz, 1H), 7.33-7.30 (m, 2H), 7.03 (d, J=2.1 Hz, 1H), 6.97 (dd, J=8.7 and 2.4 Hz, 1H), 3.75-3.67 (m, 2H), 3.00-2.93 (m, 2H), 2.64-2.57 (m, 1H), 2.50-39 (m, 5H), 1.19 (d, J=6.3 Hz, 3H). MS: m/z 494.1 [M+H]$^+$.

The following compounds were prepared from 5-(6-(un)substituted-1H-benzo[d]imidazol-2-yl)-6-chloropyridine-3-amine and the corresponding 2-chloro-4-((3S,5R)-3,4,5-trimethylpiperazin-1-yl)benzoic acid or 2-chloro-4-((2S,6R)-2,6-dimethylmorpholino)benzoic acid (the compound was prepared from methyl 4-bromo-2-chlorobenzoate and (2S,6R)-2,6-dimethylmorpholine using a procedure similar to those described for the syntheses of compounds of Examples 33a and 30b) using a procedure similar to those described for the synthesis of compound of Example 83.

Example 127

N-(5-(1H-benzo[d]imidazol-2-yl)-6-chloropyridin-3-yl)-2-chloro-4-((3S,5R)-3,4,5-trimethylpiperazin-1-yl)benzamide Off-white (18.11 mg, 8.7%). $^1$H NMR (CD$_3$OD): 8.88 (d, J=2.4 Hz, 1H), 8.66 (d, J=2.7 Hz, 1H), 7.70-7.67 (m, 2H), 7.53 (d, J=8.7 Hz, 1H), 7.37-7.31 (m, 2H), 7.07 (d, J=2.4 Hz, 1H), 6.98 (dd, J=8.7 and 2.4 Hz, 1H), 3.83 (d, J=10.8 Hz, 2H), 2.81-2.70 (m, 4H), 2.56 (s, 3H), 1.31 (d, J=5.7 Hz, 6H). MS: m/z 509.0 [M+H]$^+$.

Example 128

N-(5-(1H-benzo[d]imidazol-2-yl)-6-chloropyridin-3-yl)-2-chloro-4-((2S,6R)-2,6-dimethylmorpholino)benzamide Off-white solid (41.72 mg, 20.5%). $^1$H NMR (DMSO-d$_6$): 12.85 (s, 1H), 10.79 (s, 1H), 8.80 (d, J=1.8 Hz, 2H), 7.71 (d, J=7.8 Hz, 1H), 7.59 (d, J=7.5 Hz, 1H), 7.51 (d, J=8.4 Hz, 1H), 7.29-7.20 (m, 2H), 7.05 (d, J=2.1 Hz, 1H), 6.99 (dd, J=9.0 and 2.4 Hz, 1H), 3.75 (d, J=12.9 Hz, 2H), 3.67-3.60 (m, 2H), 2.32 (t, J=11.3 Hz, 2H), 1.14 (d, J=6.0 Hz, 6H). MS: m/z 495.9 [M+H]$^+$.

Example 129

N-(5-(6-fluoro-1H-benzo[d]imidazol-2-yl)-6-chloropyridin-3-yl)-2-chloro-4-((3S,5R)-3,4,5-trimethylpiperazin-1-yl)benzamide Light-yellow solid (17.50 mg, 14.0%). $^1$H NMR (CD$_3$OD): 8.84 (d, J=2.7 Hz, 1H), 8.68 (d, J=2.4 Hz, 1H), 7.67-7.62 (m, 1H), 7.49 (d, J=8.7 Hz, 1H), 7.36 (dd, J=9.0 and 1.8 Hz, 1H), 7.15-7.08 (m, 1H), 7.00 (d, J=2.1 Hz, 1H), 6.92 (dd, J=8.7 and 2.4 Hz, 1H), 3.72 (d, J=11.7 Hz, 2H), 2.68-2.60 (m, 2H), 2.55-2.53 (m, 2H), 2.41 (s, 3H), 1.23 (d, J=6.3 Hz, 6H). MS: m/z 527.0 [M+H]$^+$.

Example 130

N-(5-(6-chloro-1H-benzo[d]imidazol-2-yl)-6-chloropyridin-3-yl)-2-chloro-4-((3S,5R)-3,4,5-trimethylpiperazin-1-yl)benzamide Beige solid (19.01 mg, 9.7%). $^1$H NMR (CD$_3$OD): 8.87 (d, J=2.4 Hz, 1H), 8.69 (d, J=2.4 Hz, 1H), 7.73-7.60 (m, 2H), 7.53 (d, J=8.7 Hz, 1H), 7.33 (d, J=8.7 Hz, 1H), 7.05 (s, 1H), 6.98 (dd, J=9.0 and 1.8 Hz, 1H), 3.76 (d, J=12.0 Hz, 2H), 2.66 (t, J=11.7 Hz, 2H), 2.60-2.48 (m, 2H), 2.42 (s, 3H), 1.25 (d, J=6.0 Hz, 6H). MS: m/z 543.0 [M+H]$^+$.

Example 131

N-(3-(6-fluoro-1H-benzo[d]imidazol-2-yl)-4-chlorophenyl)-2-chloro-4-((3S,5R)-3,4,5-trimethylpiperazin-1-yl)benzamide Dihydrochloride A mixture of N-(3-(6-fluoro-1H-benzo[d]imidazol-2-yl)-4-chlorophenyl)-2-chloro-4-((3S,5R)-3,4,5-trimethylpiperazin-1-yl)benzamide (Example 99, 23.0 mg, 0.044 mmol) in HCl/EA solution (7 M, 5 mL) was stirred at room temperature overnight. The mixture was filtered, the solids were washed with diethyl ether (5 mL) and dried in vacuo to give the title compound as a white solid (12.0 mg, 45.4%). $^1$H NMR (DMSO-d$_6$): 10.73 (s, 1H), 10.61 (brs, 1H), 8.42 (d, J=2.1 Hz, 1H), 7.87 (dd, J=8.7 and 2.4 Hz, 1H), 7.76-7.72 (m, 1H), 7.68 (d, J=8.7 Hz, 1H), 7.56-7.51 (m, 2H), 7.28-7.22 (m, 2H), 7.10 (d, J=8.7 Hz, 1H), 4.10 (d, J=13.2 Hz, 2H), 3.31-3.23 (m, 2H), 3.07-2.98 (m, 2H), 2.81 (s, 3H), 1.40 (d, J=6.0 Hz, 6H). MS: m/z 526.1 [M+H]$^+$.

The following compounds were prepared from the corresponding N-(3-(1H-benzo[d]imidazol-2-yl)-4-chlorophenyl)-2-chloro-4-((3S,5R)-3,4,5-trimethylpiperazin-1-yl)benzamide (Example 94) or N-(3-(1H-benzo[d]imidazol-2-yl)-4-chlorophenyl)-3-chloro-4-((3S,5R)-3,4,5-trimethylpiperazin-1-yl)benzamide (Example 120) using a procedure similar to those described for the synthesis of compound of Example 131.

Example 132

N-(3-(1H-benzo[d]imidazol-2-yl)-4-chlorophenyl)-2-chloro-4-((3S,5R)-3,4,5-trimethylpiperazin-1-yl)benzamide Dihydrochloride White solid (518 mg, 72%). $^1$H NMR (DMSO-d$_6$): 10.99 (brs, 1H), 10.84 (s, 1H), 8.49 (d, J=2.4 Hz, 1H), 7.93 (dd, J=8.9 and 2.6 Hz, 1H), 7.88-7.85 (m, 2H), 7.77 (d, J=8.7 Hz, 1H), 7.59-7.51 (m, 3H), 7.22 (d, J=2.4 Hz, 1H), 7.10 (dd, J=8.7 and 2.4 Hz, 1H), 4.08 (d, J=12.9 Hz, 2H), 3.42-3.30 (m, 2H), 3.13-3.04 (m, 2H), 2.51-2.49 (m, 3H), 1.42 (d, J=6.3 Hz, 6H). MS: m/z 508.2 [M+H]$^+$.

Example 133

N-(3-(1H-benzo[d]imidazol-2-yl)-4-chlorophenyl)-3-chloro-4-((3S,5R)-3,4,5-trimethylpiperazin-1-yl)benzamide Dihydrochloride Light-yellow solid (31.1 mg, 53.5%). $^1$H NMR (CD$_3$OD): 8.58 (d, J=2.4 Hz, 1H), 8.13 (d, J=2.1 Hz, 1H), 8.04-7.90 (m, 4H), 7.81 (d, J=8.7 Hz, 1H), 7.76-7.70 (m, 2H), 7.36 (d, J=8.4 Hz, 1H), 3.74 (d, J=13.5 Hz, 2H), 3.69-3.61 (m, 2H), 3.11-3.03 (m, 5H), 1.53 (d, J=6.3 Hz, 6H). MS: m/z 508.3 [M+H]$^+$.

Example 134

N-(3-(1H-benzo[d]imidazol-2-yl)-4-chlorophenyl)-2-cyano-4-((3S,5R)-3,4,5-trimethylpiperazin-1-yl)benzamide Dihydrochloride The compound was prepared from 3-(1H-benzo[d]imidazol-2-yl)-4-chloroaniline and 2-cyano-4-((3S,5R)-3,4,5-trimethylpiperazin-1-yl)benzoic acid (the compound was prepared from methyl 2-cyano-4-fluorobenzoate and (2S,6R)-1,2,6-trimethylpiperazine dihydrochloride using a procedure similar to those described for the syntheses of compounds of Examples 30a-b) using a procedure similar to those described for the syntheses of compounds of Examples 83 and 131. Yellow solid (2.64 mg, 46.2%). $^1$H NMR (DMSO-d$_6$): 12.80 (s, 1H), 8.00 (d, J=2.4 Hz, 1H), 7.81 (d, J=8.7 Hz, 1H), 7.76-7.70 (m, 2H), 7.64-7.58 (m, 2H), 7.45 (s, 1H), 7.34-7.23 (m, 3H), 3.99 (d, J=13.8 Hz, 2H), 2.71-2.63 (m, 2H), 2.38-2.12 (m, 5H), 1.11 (d, J=5.7 Hz, 6H). MS: m/z 500.2 [M+H]$^+$.

Example 135

N-(3-(5-(4-methylthiophen-2-yl)-1H-imidazol-2-yl)-4-chlorophenyl)-2-methyl-4-((3S,5R)-3,4,5-trimethylpiperazin-1-yl)benzamide a) 2-(2-Chloro-5-nitrophenyl)-5-(4-methylthiophen-2-yl)-1H-imidazole: A solution of 2-chloro-5-nitrobenzimidamide hydrochloride (0.05 g, 0.212 mmol) and potassium carbonate (0.088 g, 0.635 mmol) in tetrahydrofuran/water (6 mL/1.5 mL) was stirred at 75° C., then 2-bromo-1-(4-methylthiophen-2-yl)ethanone (0.046 g, 0.212 mol) in tetrahydrofuran (2 mL) was added dropwise. The reaction mixture was stirred at the same temperature for additional 2 h, and then it was quenched with water and extracted with dichloromethane (15 mL×3). The combined organic layers were washed with water (5 mL×2) and brine (5 mL), dried over anhydrous sodium sulfate and concentrated. Then the crude product was purified by flash column chromatograph to give the title compound as a yellow solid (0.06 g, 74%). MS: m/z 319.9 [M+H]$^+$.

b) 4-Chloro-3-(5-(4-methylthiophen-2-yl)-1H-imidazol-2-yl)aniline: The title compound was prepared from 2-(2-chloro-5-nitrophenyl)-5-(4-methylthiophen-2-yl)-1H-imidazole using a procedure similar to those described for the synthesis of compound of Example 24. Yellow solid (0.05 g, 92%). MS: m/z 289.9 [M+H]$^+$.

c) N-(3-(5-(4-methylthiophen-2-yl)-1H-imidazol-2-yl)-4-chlorophenyl)-2-methyl-4-((3S,5R)-3,4,5-trimethylpiperazin-1-yl)benzamide: The title compound was prepared from 4-chloro-3-(5-(4-methylthiophen-2-yl)-1H-imidazol-2-yl)aniline and 2-methyl-4-((3S,5R)-3,4,5-trimethylpiperazin-1-yl)benzoic acid using a procedure similar to those described for the synthesis of compound of Example 83. Yellow solid (9.27 mg, 10%). $^1$H NMR (CD$_3$OD): 7.99 (d, J=2.4 Hz, 1H), 7.85 (dd, J=8.7 and 2.4 Hz, 1H), 7.52 (d, J=8.7 Hz, 1H), 7.46 (d, J=9.0 Hz, 1H), 7.39 (s, 1H), 7.17 (s, 1H), 6.88-6.85 (m, 3H), 3.76 (d, J=9.3 Hz, 2H), 2.67-2.60 (m, 4H), 2.49 (s, 3H), 2.47 (s, 3H), 2.27 (s, 3H), 1.28 (d, J=5.7 Hz, 6H). MS: m/z 534.1 [M+H]$^+$.

Example 136

N-(3-(5-(4-methylthiophen-2-yl)-1H-imidazol-2-yl)-4-chlorophenyl)-2-chloro-4-((3S,5R)-3,4,5-trimethylpiperazin-1-yl)benzamide The compound was prepared from 4-chloro-3-(5-(4-methylthiophen-2-yl)-1H-imidazol-2-yl)aniline (Example 135b) and 2-chloro-4-((3S,5R)-3,4,5-trimethylpiperazin-1-yl)benzoic acid using a procedure similar to those described for the synthesis of compound of Example 83. Off-white solid (58.05 mg, 20.1%). $^1$H NMR (CD$_3$OD): 8.02 (d, J=2.4 Hz, 1H), 7.88 (dd, J=8.7 and 2.4 Hz, 1H), 7.56-7.50 (m, 2H), 7.41 (s, 1H), 7.19 (d, J=0.9 Hz, 1H), 7.07 (d, J=2.4 Hz, 1H), 7.01 (dd, J=8.7 and 2.4 Hz, 1H), 6.89 (s, 1H), 3.79 (d, J=10.5 Hz, 2H), 2.74-2.62 (m, 4H), 2.49 (s, 3H), 2.29 (s, 3H), 1.29 (d, J=6.0 Hz, 6H). MS: m/z 554.2 [M+H]$^+$.

The following compounds were prepared from 2-chloro-5-nitrobenzimidamide hydrochloride, the corresponding 2-bromo-1-(5-chlorothiophen-2-yl)ethanone or 2-bromo-1-(thiophen-3-yl)ethanone or 2-bromo-1-(thiophen-2-yl)propan-1-one, and the corresponding 3-chloro-4-((2S,6R)-3,4,5-trimethylpiperazin-1-yl)benzoic acid (the intermediate of Example 120) or substituted-4-((3S,5R)-4-alkyl-3,5-dimethylpiperazin-1-yl)benzoic acid using a procedure similar to those described for the synthesis of compound of Example 135.

Example 137

N-(3-(5-(5-chlorothiophen-2-yl)-1H-imidazol-2-yl)-4-chlorophenyl)-3-chloro-4-((3S,5R)-3,4,5-trimethylpiperazin-1-yl)benzamide Yellow solid (22.36 mg, 8.1%). $^1$H NMR (CD$_3$OD): 8.07-8.05 (m, 2H), 7.95-7.88 (m, 2H), 7.53 (d, J=8.7 Hz, 1H), 7.48 (s, 1H), 7.27 (d, J=8.4 Hz, 1H), 7.16 (d, J=3.9 Hz, 1H), 6.93 (d, J=3.9 Hz, 1H), 3.59 (d, J=12.6 Hz, 2H), 3.27-3.19 (m, 2H), 2.89 (t, J=11.7 Hz, 2H), 2.80 (s, 3H), 1.39 (d, J=6.3 Hz, 6H). MS: m/z 573.9 [M+H]$^+$.

Example 138

N-(3-(5-(5-chlorothiophen-2-yl)-1H-imidazol-2-yl)-4-chlorophenyl)-2-chloro-4-((3S,5R)-3,4,5-trimethylpiperazin-1-yl)benzamide Brown solid (47.08 mg, 16.4%). $^1$H NMR (CD$_3$OD): 8.02 (d, J=2.4 Hz, 1H), 7.85 (dd, J=8.7 and 2.4 Hz, 1H), 7.53-7.46 (m, 3H), 7.14 (d, J=3.9 Hz, 1H), 7.05 (d, J=2.1 Hz, 1H), 6.98 (dd, J=8.7 and 2.4 Hz, 1H), 6.92 (d, J=3.9 Hz, 1H), 3.82-3.73 (m, 2H), 2.74-2.62 (m, 4H), 2.49 (s, 3H), 1.27 (d, J=5.7 Hz, 6H). MS: m/z 574.1 [M+H]$^+$.

Example 139

N-(3-(5-(thiophen-3-yl)-1H-imidazol-2-yl)-4-chlorophenyl)-2-methyl-4-((3S,5R)-3,4,5-trimethylpiperazin-1-yl)benzamide Off-white solid (5.92 mg, 3.2%). $^1$H NMR (CD$_3$OD): 7.99 (d, J=2.4 Hz, 1H), 7.85 (dd, J=8.9 and 2.6 Hz, 1H), 7.65-7.64 (m, 1H), 7.53 (d, J=8.7 Hz, 1H), 7.49-7.44 (m, 4H), 6.90-6.87 (m, 2H), 3.82 (d, J=9.0 Hz, 2H), 2.91-2.78 (m, 2H), 2.70 (t, J=12.0 Hz, 2H), 2.59 (s, 3H), 2.47 (s, 3H), 1.32 (d, J=6.3 Hz, 6H). MS: m/z 520.2 [M+H]$^+$.

Example 140

N-(3-(5-(thiophen-3-yl)-1H-imidazol-2-yl)-4-chlorophenyl)-2-chloro-4-((3S,5R)-3,4,5-trimethylpiperazin-1-yl)benzamide White solid (14.39 mg, 6.1%). $^1$H NMR (CD$_3$OD): 8.00 (d, J=2.1 Hz, 1H), 7.85 (dd, J=8.6 and 2.0 Hz, 1H), 7.64-7.63 (m, 1H), 7.54-7.47 (m, 5H), 7.03 (d, J=2.4 Hz, 1H), 6.97 (dd, J=8.7 and 2.4 Hz, 1H), 3.72 (d, J=6.0 Hz, 2H), 2.63 (t, J=11.7 Hz, 2H), 2.53-2.45 (m, 2H), 2.38 (s, 3H), 1.23 (d, J=6.0 Hz, 6H). MS: m/z 540.2 [M+H]$^+$.

Example 141

N-(3-(5-(thiophen-3-yl)-1H-imidazol-2-yl)-4-chlorophenyl)-2-methyl-3-fluoro-4-((3S,5R)-3,4,5-trimethylpiperazin-1-yl)benzamide Gray solid (1.73 mg, 1.8%). $^1$H NMR (CD$_3$OD): 8.10 (d, J=2.1 Hz, 1H), 7.86 (dd, J=8.7 and 2.1 Hz, 1H), 7.65-7.64 (m, 1H), 7.54 (d, J=8.7 Hz, 1H), 7.46-7.45 (m, 3H), 7.31 (d, J=8.1 Hz, 1H), 6.98-6.93 (m, 1H), 3.45 (d, J=9.6 Hz, 2H), 2.70-2.63 (m, 4H), 2.48 (s, 3H), 2.37 (d, J=2.7 Hz, 3H), 1.25 (d, J=5.7 Hz, 6H). MS: m/z 538.2 [M+H]$^+$.

Example 142

N-(3-(5-(thiophen-3-yl)-1H-imidazol-2-yl)-4-chlorophenyl)-2-chloro-5-fluoro-4-((3S,5R)-3,4,5-trimethylpiperazin-1-yl)benzamide Pale-yellow solid (4.58 mg, 4.6%). $^1$H NMR (CD$_3$OD): 7.19 (d, J=2.1 Hz, 1H), 7.03 (dd, J=8.9 and 2.6 Hz, 1H), 6.83-6.81 (m, 1H), 6.72 (d, J=8.7 Hz, 1H), 6.64-6.62 (m, 3H), 6.53 (d, J=12.6 Hz, 1H), 6.27 (d, J=7.5 Hz, 1H), 2.64 (d, J=10.8 Hz, 2H), 1.89-1.75 (m, 4H), 1.60 (s, 3H), 0.39 (d, J=5.7 Hz, 6H). MS: m/z 558.2 [M+H]$^+$.

Example 143

N-(3-(4-methyl-5-(thiophen-2-yl)-1H-imidazol-2-yl)-4-chlorophenyl)-2-methyl-4-((3S,5R)-3,4,5-trimethylpiperazin-1-yl)benzamide Off-white solid (6.77 mg, 7.5%). $^1$H NMR (CD$_3$OD): 7.98 (d, J=2.4 Hz, 1H), 7.88 (dd, J=8.7 and 2.4 Hz, 1H), 7.56-7.49 (m, 2H), 7.39 (d, J=5.4 Hz, 1H), 7.32-7.31 (m, 1H), 7.14 (dd, J=5.1 and 3.6 Hz, 1H), 6.94-6.91 (m, 2H), 3.89-3.84 (m, 2H), 2.98-2.84 (m, 2H), 2.79-2.70 (m, 2H), 2.65 (s, 3H), 2.53 (s, 3H), 2.51 (s, 3H), 1.37 (d, J=6.0 Hz, 6H). MS: m/z 534.3 [M+H]$^+$.

The following compounds were prepared from 2-chloro-5-nitrobenzimidamide hydrochloride, the corresponding 2-bromo-1-(furan-2-yl)ethanone or 2-bromo-1-(5-methyl-furan-2-yl)ethanone or 2-bromo-1-(thiazol-2-yl)ethanone or 2-bromo-1-(thiophen-2-yl)ethanone or 2-bromo-1-(1-methyl-1H-pyrrol-2-yl)ethanone and the corresponding substituted-4-((3S,5R)-4-alkyl-3,5-dimethylpiperazin-1-yl)benzoic acid or 2-chloro-4-(methylsulfonyl)benzoic acid using a procedure similar to those described for the syntheses of compounds of Examples 135a, 50c and 83.

Example 144

N-(3-(5-(furan-2-yl)-1H-imidazol-2-yl)-4-chlorophenyl)-2-chloro-4-((3S,5R)-3,4,5-trimethylpiperazin-1-yl)benzamide White solid (11.68 mg, 11.7%). $^1$H NMR (CD$_3$OD): 8.00 (d, J=1.8 Hz, 1H), 7.87 (dd, J=8.9 and 2.3 Hz, 1H), 7.55-7.43 (m, 4H), 7.06 (d, J=2.1 Hz, 1H), 6.99 (dd, J=8.7 and 2.1 Hz, 1H), 6.67 (d, J=3.3 Hz, 1H), 6.50-6.49 (m, 1H), 3.79 (d, J=9.0 Hz, 2H), 2.75-2.60 (m, 4H), 2.49 (s, 3H), 1.27 (d, J=6.0 Hz, 6H). MS: m/z 524.1 [M+H]$^+$.

Example 145

N-(3-(5-(furan-2-yl)-1H-imidazol-2-yl)-4-chlorophenyl)-2-methyl-4-((3S,5R)-3,4,5-trimethylpiperazin-1-yl)benzamide Light-yellow solid (35.03 mg, 18%). $^1$H NMR (CD$_3$OD): 8.00 (d, J=2.4 Hz, 1H), 7.86 (dd, J=8.7 and 2.4 Hz, 1H), 7.53-7.38 (m, 4H), 7.16 (s, 1H), 7.04 (d, J=2.1 Hz, 1H), 6.97 (dd, J=8.7 and 2.4 Hz, 1H), 6.86 (s, 1H), 3.76 (d, J=10.5 Hz, 2H), 2.71-2.64 (m, 4H), 2.46 (s, 3H), 2.26 (s, 3H), 1.26 (d, J=5.7 Hz, 6H). MS: m/z 504.3 [M+H]$^+$.

Example 146

N-(3-(5-(furan-2-yl)-1H-imidazol-2-yl)-4-chlorophenyl)-2-(trifluoro-methyl)-4-((3S,5R)-3,4,5-trimethyl-piperazin-1-yl)benzamide White solid (3.5 mg, 3.5%). $^1$H NMR (CD$_3$OD): 7.96 (d, J=2.4 Hz, 1H), 7.84 (dd, J=8.7 and 2.4 Hz, 1H), 7.58-7.48 (m, 3H), 7.43 (s, 1H), 7.31-7.22 (m, 2H), 6.67 (d, J=3.3 Hz, 1H), 6.51-6.47 (m, 1H), 3.88-3.78 (m, 2H), 2.77-2.67 (m, 4H), 2.52 (s, 3H), 1.30 (d, J=5.4 Hz, 6H). MS: m/z 558.2 [M+H]$^+$.

Example 147

N-(3-(5-(furan-2-yl)-1H-imidazol-2-yl)-4-chlorophenyl)-2-cyano-4-((3S,5R)-3,4,5-trimethylpiperazin-1-yl)benzamide Yellow solid (3.27 mg, 5.3%). $^1$H NMR (CD$_3$OD): 7.87 (d, J=2.4 Hz, 1H), 7.76 (d, J=8.7 Hz, 1H), 7.69 (d, J=8.4 Hz, 1H), 7.56 (dd, J=8.4 and 2.4 Hz, 1H), 7.50-7.45 (m, 3H), 7.31 (dd, J=8.6 and 2.0 Hz, 1H), 6.68 (d, J=3.3 Hz, 1H), 6.50-6.48 (m, 1H), 3.96 (d, J=12.9 Hz, 2H), 2.87-2.79 (m, 2H), 2.71-2.59 (m, 2H), 2.48 (s, 3H), 1.28 (d, J=6.3 Hz, 6H). MS: m/z 516.3 [M+H]$^+$.

Example 148

N-(3-(5-(furan-2-yl)-1H-imidazol-2-yl)-4-chlorophenyl)-2-methyl-3-fluoro-4-((3S,5R)-3,4,5-trimethyl-piperazin-1-yl)benzamide White solid (3.5 mg, 3.5%). $^1$H NMR (CD$_3$OD): 8.00 (s, 1H), 7.87 (d, J=8.4 Hz, 1H), 7.54 (d, J=8.7 Hz, 1H), 7.50-7.45 (m, 2H), 7.31 (d, J=8.4 Hz, 1H), 6.97 (t, J=8.4 Hz, 1H), 6.67 (d, J=3.3 Hz, 1H), 6.50 (s, 1H), 3.47 (d, J=10.5 Hz, 2H), 2.80-2.65 (m, 4H), 2.53 (s, 3H), 2.36 (d, J=3.0 Hz, 3H), 1.26 (d, J=5.4 Hz, 6H). MS: m/z 522.2 [M+H]$^+$.

Example 149

N-(3-(5-(furan-2-yl)-1H-imidazol-2-yl)-4-chlorophenyl)-2-chloro-5-fluoro-4-((3S,5R)-3,4,5-trimethylpiperazin-1-yl)benzamide White solid (4.53 mg, 12.7%). $^1$H NMR (CD$_3$OD): 8.00 (d, J=1.8 Hz, 1H), 7.86 (dd, J=8.7 and 2.4 Hz, 1H), 7.55 (d, J=9.0 Hz, 1H), 7.50-7.44 (m, 2H), 7.38 (d, J=12.9 Hz, 1H), 7.12 (d, J=7.5 Hz, 1H), 6.67 (d, J=3.3 Hz, 1H), 6.51-6.49 (m, 1H), 3.55-3.50 (m, 2H), 2.80-2.68 (m, 4H), 2.54 (s, 3H), 1.27 (d, J=5.1 Hz, 6H). MS: m/z 542.2 [M+H]$^+$.

Example 150

N-(3-(5-(furan-2-yl)-1H-imidazol-2-yl)-4-chlorophenyl)-2-chloro-4-((3S,5R)-4-ethyl-3,5-dimethylpiperazin-1-yl)benzamide Pale-yellow solid (22.41 mg, 24%). $^1$H NMR (CD$_3$OD): 8.00 (d, J=2.1 Hz, 1H), 7.87 (dd, J=8.9 and 2.3 Hz, 1H), 7.55-7.50 (m, 3H), 7.43 (s, 1H), 7.11 (d, J=2.1 Hz, 1H), 7.03 (dd, J=8.7 and 2.1 Hz, 1H), 6.67 (d, J=3.3 Hz, 1H), 6.51-6.49 (m, 1H), 3.93 (d, J=12.3 Hz, 2H), 3.41-3.29 (m, 4H), 2.88-2.80 (m, 2H), 1.38 (d, J=6.6 Hz, 6H), 1.21 (t, J=7.4 Hz, 3H). MS: m/z 538.1 [M+H]$^+$.

Example 151

N-(3-(5-(5-methylfuran-2-yl)-1H-imidazol-2-yl)-4-chlorophenyl)-2-chloro-4-((3S,5R)-3,4,5-trimethylpiperazin-1-yl)benzamide White solid (12.6 mg, 6.4%). $^1$H NMR (CD$_3$OD): 7.98 (d, J=2.4 Hz, 1H), 7.86 (dd, J=8.7 and 2.1 Hz, 1H), 7.54-7.45 (m, 2H), 7.36 (s, 1H), 7.04 (d, J=2.1 Hz, 1H), 6.98 (dd, J=8.7 and 2.4 Hz, 1H), 6.53 (d, J=3.0 Hz, 1H), 6.07 (d, J=2.4 Hz, 1H), 3.74 (d, J=12 Hz, 1H), 2.70-2.60 (m, 2H), 2.58-2.48 (m, 2H), 2.41 (s, 3H), 2.35 (s, 3H), 1.23 (d, J=6.3 Hz, 6H). MS: m/z 538.2 [M+H]$^+$.

Example 152

N-(3-(5-(5-methylfuran-2-yl)-1H-imidazol-2-yl)-4-chlorophenyl)-2-methyl-4-((3S,5R)-3,4,5-trimethylpiperazin-1-yl)benzamide Yellow solid (22.6 mg, 11.9%). $^1$H NMR (CD$_3$OD): 7.99 (d, J=2.4 Hz, 1H), 7.87 (dd, J=8.7 and 2.7 Hz, 1H), 7.53 (d, J=8.7 Hz, 1H), 7.48 (d, J=9.0 Hz, 1H), 7.38 (s, 1H), 6.92-6.88 (m, 2H), 6.56 (d, J=3.0 Hz, 1H), 6.10 (d, J=2.1 Hz, 1H), 3.83 (d, J=12.0 Hz, 1H), 2.93-2.79 (m, 2H), 2.75-2.64 (m, 2H), 2.60 (s, 3H), 2.49 (s, 3H), 2.37 (s, 3H), 1.33 (d, J=6.0 Hz, 6H). MS: m/z 518.3 [M+H]$^+$.

Example 153

N-(3-(5-(thiazol-2-yl)-1H-imidazol-2-yl)-4-chlorophenyl)-2-chloro-4-((3S,5R)-3,4,5-trimethylpiperazin-1-yl)benzamide Light-yellow solid (28.03 mg, 14.3%). $^1$H NMR (CD$_3$OD): 8.14 (s, 1H), 7.91-7.84 (m, 3H), 7.58-7.52 (m, 3H), 7.12 (d, J=2.1 Hz, 1H), 7.03 (dd, J=8.7 and 2.4 Hz, 1H), 3.89 (d, J=12.9 Hz, 2H), 3.05-2.91 (m, 2H), 2.80 (t, J=12.0 Hz, 2H), 2.67 (s, 3H), 1.37 (d, J=6.3 Hz, 6H). MS: m/z 541.2 [M+H]$^+$.

Example 154

N-(3-(5-(thiazol-2-yl)-1H-imidazol-2-yl)-4-chlorophenyl)-2-methyl-4-((3S,5R)-3,4,5-trimethylpiperazin-1-yl)benzamide White solid (17.6 mg, 9.4%). $^1$H NMR (CD$_3$OD): 8.11 (d, J=2.1 Hz, 1H), 7.86 (dd, J=8.9 and 2.6 Hz, 1H), 7.81-7.80 (m, 2H), 7.54-7.51 (m, 2H), 7.46 (d, J=9.0 Hz, 1H), 6.88-6.86 (m, 2H), 3.78 (d, J=10.8 Hz, 2H), 2.85-2.60 (m, 4H), 2.53 (s, 3H), 2.46 (s, 3H), 1.29 (d, J=6 Hz, 6H). MS: m/z 521.2 [M+H]$^+$.

Example 155

N-(3-(5-(thiophen-2-yl)-1H-imidazol-2-yl)-4-chlorophenyl)-2-(trifluoro-methyl)-4-((3S,5R)-3,4,5-trimethylpiperazin-1-yl)benzamide Yellow solid (26 mg, 12.5%). $^1$H NMR (CD$_3$OD): 8.01 (d, J=2.1 Hz, 1H), 7.85 (dd, J=8.7 and 2.4 Hz, 1H), 7.60-7.54 (m, 2H), 7.49-7.43 (m, 1H), 7.37 (d, J=3.6 Hz, 1H), 7.33-7.27 (m, 3H), 7.10-7.07 (m, 1H), 3.88-3.85 (m, 2H), 2.86-2.67 (m, 4H), 2.55 (s, 3H), 1.32 (d, J=4.5 Hz, 6H). MS: m/z 574.2 [M+H]$^+$.

Example 156

N-(3-(5-(thiophen-2-yl)-1H-imidazol-2-yl)-4-chlorophenyl)-2-methyl-3-fluoro-4-((3S,5R)-3,4,5-trimethylpiperazin-1-yl)benzamide White solid (17.01 mg, 17.3%). $^1$H NMR (CD$_3$OD): 8.02 (d, J=1.8 Hz, 1H), 7.70 (dd, J=9.0 and 2.4 Hz, 1H), 7.54 (d, J=9.0 Hz, 1H), 7.44 (s, 1H), 7.36-7.30 (m, 3H), 7.06 (dd, J=5.1 and 3.6 Hz, 1H), 6.97 (t, J=8.4 Hz, 1H), 3.51 (d, J=11.7 Hz, 2H), 3.04-2.85 (m, 2H), 2.78-2.70 (m, 2H), 2.61 (s, 3H), 2.36 (d, J=2.7 Hz, 3H), 1.30 (d, J=6.3 Hz, 6H). MS: m/z 538.2 [M+H]$^+$.

Example 157

N-(3-(5-(thiophen-2-yl)-1H-imidazol-2-yl)-4-chlorophenyl)-2-chloro-5-fluoro-4-((3S,5R)-3,4,5-trimethylpiperazin-1-yl)benzamide White solid (8.16 mg, 22.2%). $^1$H NMR (CD$_3$OD): 8.02 (d, J=2.1 Hz, 1H), 7.87 (dd, J=9.0 and 2.4 Hz, 1H), 7.54 (d, J=8.7 Hz, 1H), 7.44 (s, 1H), 7.42-7.30 (m, 3H), 7.14 (d, J=7.5 Hz, 1H), 7.06 (dd, J=5.1 and 3.6 Hz, 1H), 3.55 (d, J=11.4 Hz, 2H), 3.00-2.83 (m, 2H), 2.81-2.73 (m, 2H), 2.60 (s, 3H), 1.30 (d, J=6.0 Hz, 6H). MS: m/z 558.1 [M+H]$^+$.

Example 158

N-(3-(5-(thiophen-2-yl)-1H-imidazol-2-yl)-4-chlorophenyl)-2-chloro-4-((3S,5R)-4-ethyl-3,5-dimethylpiperazin-1-yl)benzamide White solid (6.16 mg, 15%). $^1$H NMR (CD$_3$OD): 8.01 (s, 1H), 7.85 (dd, J=8.9 and 1.4 Hz, 1H), 7.54-7.43 (m, 3H), 7.35 (dd, J=3.6 and 0.9 Hz, 1H), 7.30 (d, J=4.8 Hz, 1H), 7.07-7.03 (m, 2H), 6.97 (dd, J=8.7 and 2.4 Hz, 1H), 3.75 (d, J=11.7 Hz, 2H), 3.12-3.04 (m, 2H), 3.00-2.89 (m, 2H), 2.63 (t, J=11.6 Hz, 2H), 1.23 (d, J=6.0 Hz, 6H), 1.03 (t, J=7.1 Hz, 3H). MS: m/z 554.2 [M+H]$^+$.

Example 159

N-(3-(5-(thiophen-2-yl)-1H-imidazol-2-yl)-4-chlorophenyl)-2-chloro-4-((3S,5R)-4-isopropyl-3,5-dimethylpiperazin-1-yl)benzamide White solid (2.46 mg, 5.8%). $^1$H NMR (CD$_3$OD): 8.01 (s, 1H), 7.86 (dd, J=9.0 and 1.8 Hz, 1H), 7.54-7.48 (m, 3H), 7.35 (d, J=3.0 Hz, 1H), 7.30 (d, J=3.6 Hz, 1H), 7.07-7.04 (m, 1H), 6.86 (s, 1H), 6.81 (dd, J=8.6 and 2.0 Hz, 1H), 3.62-3.42 (m, 5H), 3.30-3.15 (m, 2H), 1.29-1.15 (m, 12H). MS: m/z 568.2 [M+H]$^+$.

Example 160

N-(3-(5-(thiophen-2-yl)-1H-imidazol-2-yl)-4-chlorophenyl)-2-chloro-4-(methylsulfonyl)benzamide White solid (9.4 mg, 26%). $^1$H NMR (CD$_3$OD): 8.12 (d, J=1.8 Hz, 1H), 8.05-8.00 (m, 2H), 7.88 (dd, J=8.7 and 2.4 Hz, 1H), 7.84 (d, J=7.8 Hz, 1H), 7.57 (d, J=8.7 Hz, 1H), 7.48-7.42 (m, 1H), 7.35 (d, J=3.3 Hz, 1H), 7.30 (d, J=4.5 Hz, 1H), 7.07-7.04 (m, 1H), 3.20 (s, 3H). MS: m/z 492.1 [M+H]$^+$.

Example 161

N-(3-(5-(1-methyl-1H-pyrrol-2-yl)-1H-imidazol-2-yl)-4-chlorophenyl)-2-methyl-4-((3S,5R)-3,4,5-trimethylpiperazin-1-yl)benzamide Gray solid (12.96 mg, 12.6%). $^1$H NMR (CD$_3$OD): 7.96 (d, J=2.4 Hz, 1H), 7.86 (dd, J=8.7 and 2.4 Hz, 1H), 7.52 (d, J=9.0 Hz, 1H), 7.47 (d, J=8.7 Hz, 1H), 7.23 (s, 1H), 6.90-6.87 (m, 2H), 6.75-6.73 (m, 1H), 6.33-6.63 (m, 1H), 6.09 (t, J=3.2 Hz, 1H), 3.83 (d, J=12.0 Hz, 1H), 3.77 (s, 3H), 2.96-2.83 (m, 2H), 2.76-2.68 (m, 2H), 2.62 (s, 3H), 2.47 (s, 3H), 1.33 (d, J=6.3 Hz, 6H). MS: m/z 517.3 [M+H]$^+$.

Example 162

N-(3-(5-(1-methyl-1H-pyrrol-2-yl)-1H-imidazol-2-yl)-4-chlorophenyl)-2-chloro-4-((3S,5R)-3,4,5-trimethylpiperazin-1-yl)benzamide Gray solid (18.7 mg, 19.1%). $^1$H NMR (CD$_3$OD): 8.00 (d, J=2.4 Hz, 1H), 7.88 (dd, J=8.9 and 2.0 Hz, 1H), 7.56-7.50 (m, 2H), 7.25 (s, 1H), 7.06 (d, J=2.1 Hz, 1H), 7.00 (dd, J=8.7 and 2.4 Hz, 1H), 6.76 (t, J=2.0 Hz, 1H), 6.35-6.33 (m, 1H), 6.12-6.09 (m, 1H), 3.79-3.73 (m, 5H), 2.72-2.64 (m, 2H), 2.62-2.54 (m, 2H), 2.45 (s, 3H), 1.32 (s, 3H), 1.27 (d, J=6.0 Hz, 6H). MS: m/z 537.1 [M+H]$^+$.

Example 163

N-(3-(5-(1-methyl-1H-pyrrol-2-yl)-1H-imidazol-2-yl)-4-chlorophenyl)-2-(trifluoromethyl)-4-((3S,5R)-3,4,5-trimethylpiperazin-1-yl)benzamide Pale-yellow solid (19.66 mg, 19.23%). $^1$H NMR (CD$_3$OD): 7.95 (d, J=2.7 Hz, 1H), 7.84 (dd, J=8.9 and 2.6 Hz, 1H), 7.58-7.52 (m, 2H), 7.32-7.23 (m, 3H), 6.74 (t, J=2.1 Hz, 1H), 6.33-6.32 (m, 1H), 6.10-6.08 (m, 1H), 3.87 (d, J=12.0 Hz, 2H), 3.76 (s, 3H), 2.90-2.81 (m, 2H), 2.80-2.72 (m, 2H), 2.58 (s, 3H), 1.33 (d, J=6.0 Hz, 6H). MS: m/z 571.1 [M+H]$^+$.

The compounds were prepared from 3-(5-(thiophen-3-yl)-1H-imidazol-2-yl)-4-chloroaniline and 2-(trifluoromethyl)-4-((3S,5R)-3,4,5-trimethylpiperazin-1-yl)benzoic acid or 2-chloro-4-((3S,5R)-4-ethyl-3,5-dimethylpiperazin-1-yl)benzoic acid using a procedure similar to those described for the syntheses of compounds of Examples 83 and 131.

Example 164

N-(3-(5-(thiophen-3-yl)-1H-imidazol-2-yl)-4-chlorophenyl)-2-(trifluoromethyl)-4-((3S,5R)-3,4,5-trimethylpiperazin-1-yl) benzamide Dihydrochloride Yellow solid (9.06 mg, 4.2%). $^1$H NMR (CD$_3$OD): 7.99 (d, J=2.4 Hz, 1H), 7.85 (dd, J=8.7 and 2.4 Hz, 1H), 7.67-7.65 (m, 1H), 7.60-7.54 (m, 2H), 7.48-7.46 (m, 3H), 7.32-7.26 (m, 2H), 3.91-3.81 (m, 2H), 2.81-2.71 (m, 4H), 2.55 (s, 3H), 1.32 (d, J=5.7 Hz, 6H). MS: m/z 574.3 [M+H]$^+$.

Example 165

N-(3-(5-(thiophen-3-yl)-1H-imidazol-2-yl)-4-chlorophenyl)-2-chloro-4-((3S,5R)-4-ethyl-3,5-dimethylpiperazin-1-yl)benzamide Dihydrochloride Gray solid (4 mg, 4.0%). $^1$H NMR (CD$_3$OD): 8.04 (d, J=1.8 Hz, 1H), 7.86 (dd, J=8.7 and 1.8 Hz, 1H), 7.66 (s, 1H), 7.55-7.46 (m, 5H), 7.08 (d, J=1.8 Hz, 1H), 6.99 (dd, J=8.7 and 1.8 Hz, 1H), 3.84 (d, J=12.3 Hz, 2H), 3.24-3.14 (m, 4H), 2.79-2.71 (m, 2H), 1.31 (d, J=6.3 Hz, 6H), 1.12 (t, J=7.2 Hz, 3H). MS: m/z 554.2 [M+H]$^+$.

The following compounds were prepared from 2-chloro-5-nitrobenzimidamide hydrochloride, the corresponding 2-bromoacetaldehyde or 2-bromobutanol or 2-bromo-3-methylbutanal or 2-bromopentanal or 1-bromo-3,3-dimethylbutan-2-one or 2-bromo-1-cycloalkylethanone and the corresponding substituted 4-((3S,5R)-4-alkyl-3,5-dimethylpiperazin-1-yl)benzoic acid using a procedure similar to those described for the synthesis of compound of Example 135.

Example 166

N-(3-(1H-imidazol-2-yl)-4-chlorophenyl)-2-methyl-4-((3S,5R)-3,4,5-trimethylpiperazin-1-yl)benzamide Off-white solid (16.76 mg, 7.36%). $^1$H NMR (CD$_3$OD): 7.95 (s, 1H), 7.88 (d, J=9.3 Hz, 1H), 7.54-7.47 (m, 2H), 7.23 (s, 2H), 6.97-6.87 (m, 2H), 3.84 (d, J=12.3 Hz, 2H), 2.99-2.81 (m, 2H), 2.76-2.69 (m, 2H), 2.62 (s, 3H), 2.48 (s, 3H), 1.35 (d, J=6.3 Hz, 6H). MS: m/z 438.2 [M+H]$^+$.

Example 167

N-(3-(5-ethyl-1H-imidazol-2-yl)-4-chlorophenyl)-2-(trifluoromethyl)-4-((3S,5R)-3,4,5-trimethylpiperazin-1-yl)benzamide Off-white solid (1.04 mg, 1.42%). $^1$H NMR (DMSO-d$_6$): 10.60 (s, 1H), 7.92 (d, J=2.4 Hz, 1H), 7.68 (dd, J=8.9 and 2.3 Hz, 1H), 7.56-7.49 (m, 1H), 7.41 (d, J=8.7 Hz, 1H), 7.30-7.24 (m, 2H), 7.19-7.12 (m, 1H), 3.88-3.77 (m, 2H), 2.69-2.47 (m, 6H), 2.22-2.21 (m, 3H), 1.23-1.09 (m, 9H). MS: m/z 520.1 [M+H]$^+$.

Example 168

N-(3-(5-ethyl-1H-imidazol-2-yl)-4-chlorophenyl)-2-methyl-3-fluoro-4-((3S,5R)-3,4,5-trimethylpiperazin-1-yl)benzamide Pale-yellow solid (2.48 mg, 3.79%). $^1$H NMR (CD$_3$OD): 7.94 (d, J=2.7 Hz, 1H), 7.84 (dd, J=9.0 and 2.4 Hz, 1H), 7.52 (d, J=8.7 Hz, 1H), 7.32 (d, J=8.4 Hz, 1H), 7.01-6.93 (m, 2H), 3.50 (d, J=12.0 Hz, 2H), 2.90-2.81 (m, 2H), 2.78-2.67 (m, 4H), 2.58 (s, 3H), 2.38 (d, J=3.0 Hz, 3H), 1.34-1.29 (m, 9H). MS: m/z 484.1 [M+H]$^+$.

Example 169

N-(3-(5-ethyl-1H-imidazol-2-yl)-4-chlorophenyl)-2-chloro-4-((3S,5R)-4-ethyl-3,5-dimethylpiperazin-1-yl)benzamide Pale-yellow solid (1.72 mg, 2.54%). $^1$H NMR (CD$_3$OD): 7.94 (d, J=2.7 Hz, 1H), 7.84 (dd, J=8.6 and 2.3 Hz, 1H), 7.52-7.50 (m, 2H), 7.07 (d, J=2.1 Hz, 1H), 7.00 (dd, J=8.7 and 2.1 Hz, 1H), 6.92 (s, 1H), 3.82 (d, J=12.3 Hz, 2H), 3.18 (q, J=7.2 Hz, 2H), 3.12-3.06 (m, 2H), 2.76-2.67 (m, 4H), 1.34-1.29 (m, 9H), 1.11 (t, J=7.2 Hz, 3H). MS: m/z 500.1 [M+H]$^+$.

Example 170

N-(3-(5-isopropyl-1H-imidazol-2-yl)-4-chlorophenyl)-2-methyl-4-((3S,5R)-3,4,5-trimethylpiperazin-1-yl)benzamide Yellow solid (9.12 mg, 3.5%). $^1$H NMR (CD$_3$OD): 7.88 (d, J=2.4 Hz, 1H), 7.81 (dd, J=8.6 and 2.6 Hz, 1H), 7.49-7.43 (m, 2H), 6.88-6.84 (m, 3H), 3.73 (d, J=9.9 Hz, 2H), 3.03-2.94 (m, 1H), 2.66-2.55 (m, 4H), 2.45 (s, 3H), 2.44 (s, 3H), 1.31 (d, J=6.9 Hz, 6H), 1.25 (d, J=5.7 Hz, 6H). MS: m/z 480.3 [M+H]$^+$.

Example 171

N-(3-(5-isopropyl-1H-imidazol-2-yl)-4-chlorophenyl)-2-(trifluoro-methyl)-4-((3S,5R)-3,4,5-trimethyl-piperazin-1-yl)benzamide Gray solid (19.99 mg, 9.9%). $^1$H NMR (CD$_3$OD): 7.90 (d, J=2.7 Hz, 1H), 7.81 (dd, J=8.7 and 2.7 Hz, 1H), 7.59-7.51 (m, 2H), 7.32-7.26 (m, 2H), 6.92 (s, 1H), 3.90-3.80 (m, 2H), 3.05-3.29 (m, 1H), 2.80-2.70 (m, 4H), 2.54 (s, 3H), 1.35-1.31 (m, 12H). MS: m/z 534.4 [M+H]$^+$.

Example 172

N-(3-(5-propyl-1H-imidazol-2-yl)-4-chlorophenyl)-2-methyl-4-((3S,5R)-3,4,5-trimethylpiperazin-1-yl)benzamide Off-white solid (4.43 mg, 3.1%). $^1$H NMR (CD$_3$OD): 7.94 (d, J=2.7 Hz, 1H), 7.84 (dd, J=8.7 and 2.4 Hz, 1H), 7.54-7.48 (m, 2H), 6.96-6.94 (m, 2H), 6.92-6.85 (m, 1H), 3.93 (d, J=12.6 Hz, 2H), 3.25-3.08 (m, 2H), 2.89-2.82 (m, 2H), 2.78 (s, 3H), 2.67 (t, J=7.5 Hz, 2H), 2.49 (s, 3H), 1.81-1.68 (m, 2H), 1.42 (d, J=6.3 Hz, 6H), 1.03 (t, J=7.5 Hz, 3H). MS: m/z 480.2 [M+H]$^+$.

Example 173

N-(3-(5-propyl-1H-imidazol-2-yl)-4-chlorophenyl)-2-chloro-4-(3S,5R)-3,4,5-trimethylpiperazin-1-yl)benzamide Off-white solid (18.05 mg, 12.0%). $^1$H NMR (CD$_3$OD): 7.94 (d, J=2.4 Hz, 1H), 7.85 (dd, J=9.0 and 2.4 Hz, 1H), 7.54-7.51 (m, 2H), 7.10 (d, J=2.4 Hz, 1H), 7.03 (dd, J=8.7 and 2.4 Hz, 1H), 6.95 (s, 1H), 3.87 (d, J=12.3 Hz, 2H), 2.96-2.87 (m, 2H), 2.81-2.73 (m, 2H), 2.66 (t, J=7.8 Hz, 2H), 2.62 (s, 3H), 1.80-1.68 (m, 2H), 1.35 (d, J=6.3 Hz, 6H), 1.03 (t, J=7.5 Hz, 3H). MS: m/z 500.2 [M+H]$^+$.

Example 174

N-(3-(5-tert-butyl-1H-imidazol-2-yl)-4-chlorophenyl)-2-methyl-4-((3S,5R)-3,4,5-trimethylpiperazin-1-yl)benzamide White solid (16.97 mg, 12.3%). $^1$H NMR (CD$_3$OD): 7.91 (d, J=2.7 Hz, 1H), 7.83 (dd, J=9.0 and 2.7 Hz, 1H), 7.53-7.46 (m, 2H), 6.91-6.88 (m, 3H), 3.81 (d, J=11.7 Hz, 2H), 2.85-2.76 (m, 2H), 2.74-2.64 (m, 2H), 2.57 (s, 3H), 2.48 (s, 3H), 1.38 (s, 9H), 1.32 (d, J=6.0 Hz, 6H). MS: m/z 494.3 [M+H]$^+$.

Example 175

N-(3-(5-tert-butyl-1H-imidazol-2-yl)-4-chlorophenyl)-2-chloro-4-((3S,5R)-3,4,5-trimethylpiperazin-1-yl)benzamide Off-white solid (18.02 mg, 12.5%). $^1$H NMR (CD$_3$OD): 7.91 (d, J=2.4 Hz, 1H), 7.84 (dd, J=8.7 and 2.1 Hz, 1H), 7.53-7.49 (m, 2H), 7.05 (d, J=2.1 Hz, 1H), 6.99 (dd, J=8.7 and 2.4 Hz, 1H), 6.89 (s, 1H), 3.76 (d, J=12.0 Hz, 2H), 2.71-2.63 (m, 2H), 2.60-2.50 (m, 2H), 2.44 (s, 3H), 1.38 (s, 9H), 1.27 (d, J=6.0 Hz, 6H). MS: m/z 514.2 [M+H]$^+$.

Example 176

N-(3-(5-cyclopropyl-1H-imidazol-2-yl)-4-chlorophenyl)-2-chloro-4-((3S,5R)-3,4,5-trimethylpiperazin-1-yl)benzamide Gray solid (9.74 mg, 3.9%). $^1$H NMR (CD$_3$OD): 7.90 (s, 1H), 7.82 (dd, J=8.4 and 1.5 Hz, 1H), 7.51-7.48 (m, 2H), 7.08 (d, J=1.8 Hz, 1H), 7.01 (dd, J=8.7 and 1.8 Hz, 1H), 6.86 (s, 1H), 3.85 (d, J=12.9 Hz, 2H), 2.96-2.84 (m, 2H), 2.75 (t, J=12.0 Hz, 2H), 2.61 (s, 3H), 1.96-1.85 (m, 1H), 1.33 (d, J=6.0 Hz, 6H), 0.94-0.87 (m, 2H), 0.74-0.69 (m, 2H). MS: m/z 498.2 [M+H]$^+$.

Example 177

N-(3-(5-cyclopropyl-1H-imidazol-2-yl)-4-chlorophenyl)-2-methyl-4-((3S,5R)-3,4,5-trimethylpiperazin-1-yl)benzamide Off-white solid (8.35 mg, 7.0%). $^1$H NMR (CD$_3$OD): 7.91 (d, J=2.7 Hz, 1H), 7.84 (dd, J=8.7 and 2.7 Hz, 1H), 7.52-7.47 (m, 2H), 6.92-6.88 (m, 3H), 3.86 (d, J=13.2 Hz, 2H), 3.02-2.91 (m, 2H), 2.80-2.72 (m, 2H), 2.66 (s, 3H), 2.48 (s, 3H), 1.97-1.87 (m, 1H), 1.37 (d, J=6.3 Hz, 6H), 0.94-0.91 (m, 2H), 0.74-0.73 (m, 2H). MS: m/z 478.2 [M+H]$^+$.

Example 178

N-(3-(5-cyclopropyl-1H-imidazol-2-yl)-4-chlorophenyl)-2-(trifluoro-methyl)-4-((3S,5R)-3,4,5-trimethylpiperazin-1-yl)benzamide Off-white solid (16.23 mg, 8.0%). $^1$H NMR (CD$_3$OD): 7.87 (d, J=2.4 Hz, 1H), 7.79 (dd, J=9.0 and 2.7 Hz, 1H), 7.56 (d, J=8.7 Hz, 1H), 7.50 (d, J=8.7 Hz, 1H), 7.32-7.25 (m, 2H), 6.86 (s, 1H), 3.86 (d, J=11.4 Hz, 2H), 2.86-2.72 (m, 4H), 2.57 (s, 3H), 1.95-1.86 (m, 1H), 1.33 (d, J=6.0 Hz, 6H), 0.94-0.88 (m, 2H), 0.74-0.69 (m, 2H). MS: m/z 532.2 [M+H]$^+$.

Example 179

N-(3-(5-cyclopropyl-1H-imidazol-2-yl)-4-chlorophenyl)-2-methyl-3-fluoro-4-((3S,5R)-3,4,5-trimethylpiperazin-1-yl)benzamide White solid (17.05 mg, 9.0%). $^1$H NMR (CD$_3$OD): 7.89 (d, J=2.4 Hz, 1H), 7.82 (dd, J=8.7 and 2.4 Hz, 1H), 7.49 (d, J=8.7 Hz, 1H), 7.29 (d, J=8.1 Hz, 1H), 6.98-6.93 (m, 1H), 6.85 (s, 1H), 3.47 (d, J=11.7 Hz, 2H), 2.88-2.77 (m, 2H), 2.73-2.66 (m, 2H), 2.54 (s, 3H), 2.35 (d, J=6.3 Hz, 3H), 1.95-1.86 (m, 1H), 1.26 (d, J=6.0 z, 6H), 0.93-0.87 (m, 1H), 0.73-0.68 (m, 2H). MS: m/z 496.2 [M+H]$^+$.

Example 180

N-(3-(5-cyclobutyl-1H-imidazol-2-yl)-4-chlorophenyl)-2-chloro-4-((3S,5R)-3,4,5-trimethylpiperazin-1-yl)benzamide Off-white solid (35.02 mg, 13.7%). $^1$H NMR (CD$_3$OD): 7.91 (d, J=2.4 Hz, 1H), 7.82 (dd, J=8.7 and 2.4 Hz, 1H), 7.51-7.48 (m, 2H), 7.07 (d, J=2.1 Hz, 1H), 6.99 (dd, J=8.7 and 2.4 Hz, 1H), 6.96 (s, 1H), 3.82 (d, J=11.4 Hz, 2H), 3.63-3.52 (m, 1H), 2.85-2.69 (m, 4H), 2.56 (s, 3H), 2.42-2.32 (m, 2H), 2.30-2.17 (m, 2H), 2.12-1.87 (m, 2H), 1.31 (d, J=5.7 Hz, 6H). MS: m/z 512.2 [M+H]$^+$.

Example 181

N-(3-(5-cyclobutyl-1H-imidazol-2-yl)-4-chlorophenyl)-2-methyl-4-((3S,5R)-3,4,5-trimethylpiperazin-1-yl)benzamide Off-white solid (3.11 mg, 1.26%). $^1$H NMR (CD$_3$OD): 7.89 (d, J=2.7 Hz, 1H), 7.81 (dd, J=8.7 and 2.4 Hz, 1H), 7.49-7.43 (m, 2H), 6.94 (s, 1H), 6.86-6.81 (m, 2H), 3.78-3.69 (m, 2H), 3.63-3.51 (m, 1H), 2.66-2.56 (m, 4H), 2.45 (s, 6H), 2.40-2.29 (m, 2H), 2.26-2.17 (m, 2H), 2.12-1.86 (m, 2H), 1.25 (d, J=5.4 Hz, 6H). MS: m/z 492.3 [M+H]$^+$.

Example 182

N-(3-(5-cyclopentyl-1H-imidazol-2-yl)-4-chlorophenyl)-2-chloro-4-((3S,5R)-3,4,5-trimethylpiperazin-1-yl)benzamide Off-white solid (13.03 mg, 8.2%). $^1$H NMR (CD$_3$OD): 7.91 (d, J=2.4 Hz, 1H), 7.82 (dd, J=9.0 and 2.4 Hz, 1H), 7.51-7.48 (m, 2H), 7.06 (d, J=2.4 Hz, 1H), 6.99 (dd, J=8.7 and 2.4 Hz, 1H), 6.91 (s, 1H), 3.84-3.75 (m, 2H), 3.18-3.05 (m, 1H), 2.75-2.66 (m, 4H), 2.51 (s, 3H), 2.12-2.06 (m, 2H), 1.85-1.69 (m, 6H), 1.29 (d, J=5.7 Hz, 6H). MS: m/z 526.2 [M+H]$^+$.

Example 183

N-(3-(5-cyclopentyl-1H-imidazol-2-yl)-4-chlorophenyl)-2-methyl-4-((3S,5R)-3,4,5-trimethylpiperazin-1-yl)benzamide Pink solid (6.40 mg, 3.7%). $^1$H NMR (CD$_3$OD): 7.90 (d, J=2.7 Hz, 1H), 7.81 (dd, J=9.0 and 2.4 Hz, 1H), 7.50-7.44 (m, 2H), 6.91-6.86 (m, 3H), 3.83 (d, J=12.3 Hz, 2H), 3.16-3.06 (m, 1H), 2.99-2.85 (m, 2H), 2.77-2.69 (m, 2H), 2.63 (s, 3H), 2.45 (s, 3H), 2.13-2.05 (m, 2H), 1.84-1.79 (m, 2H), 1.76-1.63 (m, 4H), 1.34 (d, J=6.3 Hz, 6H). MS: m/z 506.3 [M+H]$^+$.

Example 184

N-(3-(5-cyclohexyl-1H-imidazol-2-yl)-4-chlorophenyl)-2-chloro-4-((3S,5R)-3,4,5-trimethylpiperazin-1-yl)benzamide Brown solid (60.96 mg, 25.6%). $^1$H NMR (CD$_3$OD): 7.95 (d, J=2.7 Hz, 1H), 7.84 (dd, J=8.7 and 2.1 Hz, 1H), 7.54-7.51 (m, 2H), 7.12 (d, J=1.8 Hz, 1H), 7.04 (dd, J=8.7 and 2.1 Hz, 1H), 6.94 (s, 1H), 3.91 (d, J=12.6 Hz, 2H), 3.10-3.01 (m, 2H), 2.90-2.75 (m, 2H), 2.69 (s, 3H), 2.65-2.61 (m, 1H), 2.16-2.00 (m, 2H), 1.93-1.76 (m, 3H), 1.55-1.44 (m, 5H), 1.38 (d, J=6.0 Hz, 6H). MS: m/z 540.3 [M+H]$^+$.

Example 185

N-(3-(5-cyclohexyl-1H-imidazol-2-yl)-4-chlorophenyl)-2-methyl-4-((3S,5R)-3,4,5-trimethylpiperazin-1-yl)benzamide Pink solid (4.32 mg, 1.9%). $^1$H NMR (CD$_3$OD): 7.88 (d, J=2.7 Hz, 1H), 7.81 (dd, J=8.7 and 2.4 Hz, 1H), 7.49-7.43 (m, 2H), 6.88-6.85 (m, 3H), 3.78 (d, J=11.7 Hz, 2H), 2.78-2.62 (m, 5H), 2.53 (s, 3H), 2.45 (s, 3H), 2.08-1.99 (m, 2H), 1.89-1.80 (m, 2H), 1.78-1.73 (m, 1H), 1.55-1.35 (m, 5H), 1.29 (d, J=6.0 Hz, 6H). MS: m/z 520.3 [M+H]$^+$.

The following compounds were prepared from 2-chloro-5-nitrobenzimidamide hydrochloride, the corresponding 2-bromopropanal or 2-bromobutanol or 2-bromo-3-methylbutanal or 2-bromo-1-cyclopropylthanone and substituted 4-((3S,5R)-4-alkyl-3,5-dimethylpiperazin-1-yl)benzoic acid using a procedure similar to those described for the syntheses of compounds of Examples 135 and 131.

Example 186

N-(3-(5-methyl-1H-imidazol-2-yl)-4-chlorophenyl)-2-methyl-4-((3S,5R)-3,4,5-trimethylpiperazin-1-yl) benzamide Dihydrochloride White solid (1.66 mg, 0.7%). $^1$H NMR (CD$_3$OD): 7.89 (d, J=2.4 Hz, 1H), 7.81 (dd, J=8.9 and 2.6 Hz, 1H), 7.49-7.43 (m, 2H), 6.88-6.84 (m, 3H), 3.73 (d, J=9.6 Hz, 2H), 2.66-2.53 (m, 4H), 2.45-2.44 (m, 6H), 2.29 (s, 3H), 1.25 (d, J=5.7 Hz, 6H). MS: m/z 452.2 [M+H]$^+$.

Example 187

N-(3-(5-ethyl-1H-imidazol-2-yl)-4-chlorophenyl)-2-methyl-4-((3S,5R)-3,4,5-trimethylpiperazin-1-yl)benzamide Dihydrochloride Off-white solid (0.9 mg, 0.4%). $^1$H NMR (CD$_3$OD): 7.90 (d, J=2.7 Hz, 1H), 7.82 (dd, J=8.7 and 2.7 Hz, 1H), 7.50-7.44 (m, 2H), 6.93-6.86 (m, 3H), 3.80 (d, J=12.0 Hz, 2H), 2.84-2.75 (m, 2H), 2.72-2.64 (m, 4H), 2.56 (s, 3H), 2.46 (s, 3H), 1.32-1.27 (m, 9H). MS: m/z 466.2 [M+H]$^+$.

Example 188

N-(3-(5-ethyl-1H-imidazol-2-yl)-4-chlorophenyl)-2-chloro-4-((3S,5R)-3,4,5-trimethylpiperazin-1-yl)benzamide Dihydrochloride Off-white solid (9.98 mg, 4.4%). $^1$H NMR (CD$_3$OD): 7.93 (s, 1H), 7.85 (d, J=9.0 Hz, 1H), 7.53-7.50 (m, 2H), 7.08 (s, 1H), 7.01 (d, J=8.7 Hz, 1H), 6.93 (s, 1H), 3.86-3.76 (m, 2H), 2.76-2.67 (m, 6H), 2.52 (s, 3H), 1.34-1.24 (m, 9H). MS: m/z 486.3 [M+H]$^+$.

Example 189

N-(3-(5-isopropyl-1H-imidazol-2-yl)-4-chlorophenyl)-2-chloro-4-((3S,5R)-3,4,5-trimethylpiperazin-1-yl)benzamide Dihydrochloride Gray solid (14.63 mg, 6.7%). $^1$H NMR (CD$_3$OD): 8.29 (s, 1H), 7.82 (d, J=8.7 Hz, 1H), 7.68 (d, J=8.7 Hz, 1H), 7.54 (d, J=6.9 Hz, 1H), 7.47 (s, 1H), 7.18 (s, 1H), 7.09 (d, J=6.3 Hz, 1H), 4.07 (d, J=13.2 Hz, 2H), 3.57-3.42 (m, 2H), 3.20-3.06 (m, 3H), 2.99 (s, 3H), 1.52 (s, 6H), 1.40 (d, J=6.9 Hz, 6H). MS: m/z 500.3 [M+H]$^+$.

Example 190

N-(3-(5-isopropyl-1H-imidazol-2-yl)-4-chlorophenyl)-2-methyl-3-fluoro-4-((3S,5R)-3,4,5-trimethylpiperazin-1-yl)benzamide Dihydrochloride Orange red solid (23.03 mg, 10.6%). $^1$H NMR (CD$_3$OD): 7.94 (d, J=2.4 Hz, 1H), 7.82 (dd, J=8.7 and 2.7 Hz, 1H), 7.52 (d, J=8.7 Hz, 1H), 7.32 (d, J=7.8 Hz, 1H), 7.00 (t, J=8.4 Hz, 1H), 6.94 (s, 1H), 3.60 (d, J=12.9 Hz, 2H), 3.29-3.23 (m, 2H), 3.05-2.96 (m, 1H), 2.92-2.84 (m, 2H), 2.81 (s, 3H), 2.37 (d, J=2.7 Hz, 3H), 1.40 (d, J=6.6 Hz, 6H), 1.32 (d, J=6.9 Hz, 6H). MS: m/z 498.3 [M+H]$^+$.

Example 191

N-(3-(5-isopropyl-1H-imidazol-2-yl)-4-chlorophenyl)-2-chloro-5-fluoro-4-((3S,5R)-3,4,5-trimethylpiperazin-1-yl)benzamide Dihydrochloride Off-white solid (7.79 mg, 7.8%). $^1$H NMR (CD$_3$OD): 7.92 (d, J=2.4 Hz, 1H), 7.82 (dd, J=9.0 and 2.4 Hz, 1H), 7.52 (d, J=8.7 Hz, 1H), 7.37 (d, J=12.3 Hz, 1H), 7.14 (d, J=7.8 Hz, 1H), 6.91 (s, 1H), 3.56 (d, J=12.3 Hz, 2H), 3.04-2.89 (m, 3H), 2.83-2.75 (m, 2H), 2.62 (s, 3H), 1.33-1.30 (m, 12H). MS: m/z 518.2 [M+H]$^+$.

Example 192

N-(3-(5-isopropyl-1H-imidazol-2-yl)-4-chlorophenyl)-2-chloro-4-((3S,5R)-4-ethyl-3,5-dimethylpiperazin-1-yl)benzamide Dihydrochloride White solid (12.07 mg, 7.1%). $^1$H NMR (CD$_3$OD): 7.94 (d, J=2.4 Hz, 1H), 7.84 (dd, J=8.7 and 2.4 Hz, 1H), 7.53-7.50 (m, 2H), 7.11 (d, J=2.1 Hz, 1H), 7.03 (dd, J=8.7 and 2.1 Hz, 1H), 6.92 (s, 1H), 3.91 (d, J=12.0 Hz, 2H), 3.34-3.25 (m, 4H), 3.03-2.96 (m, 1H), 2.86-2.78 (m, 2H), 1.38-1.33 (m, 12H), 1.19 (t, J=7.2 Hz, 3H). MS: m/z 514.2 [M+H]$^+$.

Example 193

N-(3-(5-cyclopropyl-1H-imidazol-2-yl)-4-chlorophenyl)-2-chloro-5-fluoro-4-((3S,5R)-3,4,5-trimethylpiperazin-1-yl)benzamide Dihydrochloride White solid (0.86 mg, 0.3%). $^1$H NMR (CD$_3$OD): 7.92 (d, J=2.7 Hz, 1H), 7.83 (dd, J=8.7 and 2.7 Hz, 1H), 7.51 (d, J=8.7 Hz, 1H), 7.37 (d, J=12.9 Hz, 1H), 7.12 (d, J=7.8 Hz, 1H), 6.87 (s, 1H), 3.55-3.45 (m, 2H), 2.77-2.71 (m, 4H), 2.50 (s, 3H), 1.95-1.88 (m, 1H), 1.26 (d, J=5.4 Hz, 6H), 0.95-0.89 (m, 2H), 0.76-0.71 (m, 2H). MS: m/z 516.1 [M+H]$^+$.

Example 194

N-(3-(5-cyclopropyl-1H-imidazol-2-yl)-4-chlorophenyl)-2-chloro-4-((3S,5R)-4-ethyl-3,5-dimethylpiperazin-1-yl)benzamide Dihydrochloride Off-white solid (2.63 mg, 3.3%). $^1$H NMR (CD$_3$OD): 7.92 (s, 1H), 7.84 (d, J=6.6 Hz, 1H), 7.53-7.51 (m, 2H), 7.12 (s, 1H), 7.03 (d, J=8.1 Hz, 1H), 6.88 (s, 1H), 3.92 (d, J=12.6 Hz, 2H), 3.29-3.20 (m, 4H), 2.83 (t, J=11.7 Hz, 2H), 2.01-1.87 (m, 1H), 1.37 (d, J=5.7 Hz, 6H), 1.20 (t, J=6.9 Hz, 3H), 0.98-0.86 (m, 2H), 0.79-0.67 (m, 2H). MS: m/z 512.1 [M+H]$^+$.

Example 195

N-(3-(3H-imidazo[4,5-b]pyridin-2-yl)-4-chlorophenyl)-2-chloro-4-((3S,5R)-3,4,5-trimethylpiperazin-1-yl)benzamide a) N-(3-aminopyridin-2-yl)-2-chloro-5-nitrobenzamide. To a stirred solution of pyridine-2,3-diamine (0.90 g, 8.28 mmol), 2-chloro-5-nitrobenzoic acid (1.67 g, 8.28 mmol) and 2-(1H-benzotriazole-1-yl)-1,1,3,3-tetramethyluronium hexafluorophosphate (HBTU, 3.14 g, 8.28 mmol) in CH$_3$CN (30 mL) was added dropwise triethylamine (3.44 mL, 24.84 mmol) at 0° C., then was stirred at room temperature overnight. The mixture was concentrated. The residue was used for the next step without further purification. MS: m/z 293.1 [M+H]$^+$.

b) 3-(3H-imidazo[4,5-b]pyridin-2-yl)-4-chloroaniline. The title compound was prepared from N-(3-aminopyridin-2-yl)-2-chloro-5-nitrobenzamide using a procedure similar to those described for the syntheses of compounds of Examples 50b and 24. Yellow solid. MS: m/z 245.1 [M+H]$^+$.

c) N-(3-(3H-imidazo[4,5-b]pyridin-2-yl)-4-chlorophenyl)-2-chloro-4-((3S,5R)-3,4,5-trimethylpiperazin-1-yl)benzamide. The title compound was prepared from 3-(3H-imidazo[4,5-b]pyridin-2-yl)-4-chloroaniline and 2-chloro-4-((3S,5R)-3,4,5-trimethylpiperazin-1-yl)benzoic acid using a procedure similar to those described for the synthesis of compound of Example 83. Light-yellow solid (11.82 mg, 4.10%). ¹H NMR (CD₃OD): 8.44 (d, J=4.8 Hz, 1H), 8.20 (s, 1H), 8.09 (d, J=8.1 Hz, 1H), 7.93 (d, J=9.0 Hz, 1H), 7.60 (d, J=8.7 Hz, 1H), 7.51 (d, J=8.4 Hz, 1H), 7.38 (dd, J=8.1 and 4.8 Hz, 1H), 7.11 (d, J=2.1 Hz, 1H), 7.02 (dd, J=8.7 and 2.1 Hz, 1H), 3.93 (d, J=12.9 Hz, 2H), 3.28-3.15 (m, 2H), 2.93-2.85 (m, 2H), 2.79 (s, 3H), 1.41 (d, J=6.3 Hz, 3H). MS: m/z 509.2 [M+H]⁺.

The following compounds were prepared from pyridine-1,4-diamine, 2-chloro-5-nitrobenzoic acid, and the corresponding 2-substituted-4-((3S,5R)-3,4,5-trimethylpiperazin-1-yl)benzoic acid using a procedure similar to those described for the synthesis of compound of Example 195.

Example 196

N-(3-(3H-imidazo[4,5-c]pyridin-2-yl)-4-chlorophenyl)-2-chloro-4-((3S,5R)-3,4,5-trimethylpiperazin-1-yl)benzamide Off-white solid (35 mg, 15.3%). ¹H NMR (CD₃OD): 8.99 (s, 1H), 8.40 (d, J=6.0 Hz, 1H), 8.52 (d, J=2.4 Hz, 1H), 7.95 (dd, J=8.9 and 2.6 Hz, 1H), 7.74 (d, J=5.4 Hz, 1H), 7.65 (d, J=9.0 Hz, 1H), 7.53 (d, J=5.4 Hz, 1H), 7.10 (d, J=2.4 Hz, 1H), 7.03 (dd, J=8.9 and 2.3 Hz, 1H), 3.86 (d, J=11.7 Hz, 2H), 2.90-2.73 (m, 4H), 2.60 (s, 3H), 1.34 (d, J=6.0 Hz, 6H). MS: m/z 509.2 [M+H]⁺.

Example 197

N-(3-(3H-imidazo[4,5-c]pyridin-2-yl)-4-chlorophenyl)-2-methyl-4-((3S,5R)-3,4,5-trimethylpiperazin-1-yl)benzamide Off-white solid (35 mg, 15.3%). ¹H NMR (CD₃OD): 8.99 (s, 1H), 8.40 (d, J=5.7 Hz, 1H), 8.25 (d, J=2.4 Hz, 1H), 7.95 (dd, J=8.7 and 2.7 Hz, 1H), 7.74 (d, J=5.7 Hz, 1H), 7.64 (d, J=9.0 Hz, 1H), 7.52 (d, J=8.1 Hz, 1H), 6.95-6.92 (m, 2H), 3.92 (d, J=13.5 Hz, 2H), 3.18-3.11 (m, 2H), 2.88-2.79 (m, 2H), 2.77 (s, 3H), 2.50 (s, 3H), 1.42 (d, J=6.0 Hz, 6H). MS: m/z 489.3 [M+H]⁺.

Example 198

N-(3-(1H-thieno[3,4-d]imidazol-2-yl)-4-chlorophenyl)-2-methyl-4-(3S,5R)-3,4,5-trimethylpiperazin-1-yl)benzamide a) N-(4-aminothiophen-3-yl)-2-chloro-5-nitrobenzamide. A mixture of thiophene-3,4-diamine (0.90 g, 7.89 mmol), 2-chloro-5-nitrobenzoic acid (1.32 g, 6.57 mmol) and BOP (3.49 g, 7.89 mmol) in triethylamine (1.8 mL, 13.1 mmol) and MeCN (40 mL) was stirred at room temperature overnight under N₂. The mixture was concentrated. The residue was purified by the flash column chromatography (EA/PE) to give the title compound as a yellow solid (1.16 g, 49.5%). MS: m/z 298.0 [M+H]⁺.

b) 2-(2-Chloro-5-nitrophenyl)-1H-thieno[3,4-d]imidazole. The title compound was prepared from N-(4-aminothiophen-3-yl)-2-chloro-5-nitrobenzamide using a procedure similar to those described for the synthesis of compound of Example 52b. Black solid (1.0 g, 91.7%). MS: m/z 280.0 [M+H]⁺.

c) 3-(1H-thieno[3,4-d]imidazol-2-yl)-4-chloroaniline. The title compound was prepared from 2-(2-chloro-5-nitrophenyl)-1H-thieno[3,4-d]imidazole using a procedure similar to those described for the synthesis of compound of Example 24. Claybank solid (0.40 g, 44.7%). MS: m/z 250.0 [M+H]⁺.

d) N-(3-(1H-thieno[3,4-d]imidazol-2-yl)-4-chlorophenyl)-2-methyl-4-((3S,5R)-3,4,5-trimethylpiperazin-1-yl)benzamide. The title compound was prepared from 3-(1H-thieno[3,4-d]imidazol-2-yl)-4-chloroaniline and 2-methyl-4-((3S,5R)-3,4,5-trimethylpiperazin-1-yl)benzoic acid using a procedure similar to those described for the synthesis of compound of Example 83. Pale-yellow solid (2.0 mg, 2.5%). ¹H NMR (CD₃OD): 8.08 (d, J=2.4 Hz, 1H), 7.92 (dd, J=8.7 and 1.8 Hz, 1H), 7.57 (d, J=8.7 Hz, 1H), 7.48 (d, J=8.4 Hz, 1H), 7.07-6.94 (m, 2H), 6.91-6.89 (m, 2H), 3.86 (d, J=12.9 Hz, 2H), 3.04-2.92 (m, 2H), 2.79-2.75 (m, 2H), 2.67 (s, 3H), 2.47 (s, 3H), 1.36 (d, J=6.3 Hz, 3H). MS: m/z 494.2 [M+H]⁺.

The following compounds were prepared from 3-(1H-thieno[3,4-d]imidazol-2-yl)-4-chloroaniline (Example 198c) and the corresponding substituted 4-((3S,5R)-4-alkyl-3,5-dimethylpiperazin-1-yl)benzoic acid using a procedure similar to those described for the synthesis of compound of Example 83.

Example 199

N-(3-(1H-thieno[3,4-d]imidazol-2-yl)-4-chlorophenyl)-2-chloro-4-((3S,5R)-3,4,5-trimethylpiperazin-1-yl)benzamide Pale-yellow solid (1.88 mg, 3.5%). ¹H NMR (CD₃OD): 8.20 (s, 1H), 8.02 (d, J=8.4 Hz, 1H), 7.67 (d, J=8.7 Hz, 1H), 7.59 (d, J=8.7 Hz, 1H), 7.14-7.06 (m, 4H), 3.84 (d, J=11.7 Hz, 2H), 2.80-2.73 (m, 2H), 2.67-2.59 (m, 2H), 2.53 (s, 3H), 1.35 (d, J=6.0 Hz, 6H). MS: m/z 514.2 [M+H]⁺.

Example 200

N-(3-(1H-thieno[3,4-d]imidazol-2-yl)-4-chlorophenyl)-2-(trifluoromethyl)-4-((3S,5R)-3,4,5-trimethylpiperazin-1-yl) Benzamide Pale-yellow solid (5.99 mg, 6.8%). ¹H NMR (CD₃OD): 8.05 (d, J=2.7 Hz, 1H), 7.89 (dd, J=9.0 and 2.7 Hz, 1H), 7.60-7.55 (m, 2H), 7.30-7.24 (m, 2H), 7.08-6.92 (m, 2H), 3.85-3.77 (m, 2H), 2.75-2.61 (m, 4H), 2.48 (s, 3H), 1.28 (d, J=5.7 Hz, 6H). MS: m/z 548.2 [M+H]⁺.

Example 201

N-(3-(1H-thieno[3,4-d]imidazol-2-yl)-4-chlorophenyl)-2-methyl-3-fluoro-4-((3S,5R)-3,4,5-trimethylpiperazin-1-yl)benzamide Brown solid (2.55 mg, 3.13%). ¹H NMR (CD₃OD): 8.10 (d, J=2.4 Hz, 1H), 7.94 (dd, J=8.6 and 2.6 Hz, 1H), 7.60 (d, J=9.0 Hz, 1H), 7.33 (d, J=8.7 Hz, 1H), 7.01-6.95 (m, 3H), 3.47 (d, J=9.9 Hz, 2H), 2.72-2.65 (m, 4H), 2.51 (s, 3H), 2.39 (d, J=2.7 Hz, 3H), 1.26 (d, J=5.4 Hz, 6H). MS: m/z 512.1 [M+H]⁺.

Example 202

N-(3-(1H-thieno[3,4-d]imidazol-2-yl)-4-chlorophenyl)-2-chloro-5-fluoro-4-((3S,5R)-3,4,5-trimethylpiperazin-1-yl)benzamide Pale-yellow solid (1.5 mg, 2.3%). ¹H NMR (CD₃OD): 8.09 (d, J=2.4 Hz, 1H), 7.91 (dd, J=8.7 and 2.7 Hz, 1H), 7.58

(d, J=8.7 Hz, 1H), 7.36 (d, J=12.6 Hz, 1H), 7.09 (d, J=7.8 Hz, 1H), 7.05-6.93 (m, 2H), 3.46 (d, J=10.5 Hz, 2H), 2.72-2.58 (m, 4H), 2.43 (s, 3H), 1.22 (d, J=5.7 Hz, 6H). MS: m/z 532.0 [M+H]$^+$.

Example 203

N-(3-(1H-thieno[3,4-d]imidazol-2-yl)-4-chlorophenyl)-2-chloro-4-((3S,5R)-4-ethyl-3,5-dimethylpiperazin-1-yl)benzamide Pale-yellow solid (17.92 mg, 17.0%). $^1$H NMR (CD$_3$OD): 8.11 (d, J=2.4 Hz, 1H), 7.92 (dd, J=8.9 and 2.3 Hz, 1H), 7.58 (d, J=9.0 Hz, 1H), 7.52 (d, J=8.4 Hz, 1H), 7.10 (d, J=2.4 Hz, 1H), 7.03-7.00 (m, 3H), 3.89 (d, J=12.3 Hz, 2H), 3.38-3.26 (m, 4H), 2.91-2.77 (m, 2H), 1.35 (d, J=6.3 Hz, 6H), 1.18 (t, J=7.4 Hz, 3H). MS: m/z 528.0 [M+H]$^+$.

The following compounds were prepared from the corresponding 3-substituted-4-chloroaniline and 2-substituted-4-((3S,5R)-3,4,5-trimethylpiperazin-1-yl)benzoic acid using a procedure similar to those described for the synthesis of compound of Example 83.

Example 204

N-(3-(quinoxalin-2-yl)-4-chlorophenyl)-2-chloro-4-((3S,5R)-3,4,5-trimethylpiperazin-1-yl)benzamide Pale-yellow solid (26.2 mg, 18.6%). $^1$H NMR (CD$_3$OD): 9.22 (s, 1H), 8.22-8.13 (m, 3H), 7.97-7.89 (m, 3H), 7.63 (d, J=8.7 Hz, 1H), 7.52 (d, J=8.7 Hz, 1H), 7.07 (d, J=2.1 Hz, 1H), 7.00 (dd, J=8.7 and 2.4 Hz, 1H), 3.80 (d, J=9.9 Hz, 2H), 2.75-2.62 (m, 4H), 2.50 (s, 3H), 1.29 (d, J=5.7 Hz, 6H). MS: m/z 520.2 [M+H]$^+$.

Example 205

N-(3-(imidazo[2,1-b]thiazol-6-yl)-4-chlorophenyl)-2-chloro-4-((3S,5R)-3,4,5-trimethylpiperazin-1-yl)benzamide Off-white solid (19.3 mg, 18.8%). $^1$H NMR (CD$_3$OD): 8.32 (s, 1H), 8.14 (d, J=2.4 Hz, 1H), 7.84-7.79 (m, 2H), 7.54-7.48 (m, 2H), 7.20 (d, J=4.5 Hz, 1H), 7.08 (d, J=2.4 Hz, 1H), 7.01 (dd, J=8.7 and 2.7 Hz, 1H), 3.86-3.77 (m, 2H), 2.80-2.68 (m, 4H), 2.54 (s, 3H), 1.31 (d, J=5.4 Hz, 6H). MS: m/z 514.1 [M+H]$^+$.

Example 206

N-(3-(benzo[d]oxazol-2-yl)-4-chlorophenyl)-2-methyl-4-((3S,5R)-3,4,5-trimethylpiperazin-1-yl)benzamide Off-white solid (25.90 mg, 26.5%). $^1$H NMR (CD$_3$OD): 8.54 (d, J=2.7 Hz, 1H), 7.92 (dd, J=8.7 and 2.7 Hz, 1H), 7.86-7.83 (m, 1H), 7.77-7.74 (m, 1H), 7.64 (d, J=8.7 Hz, 1H), 7.53-7.48 (m, 3H), 6.94-6.91 (m, 2H), 3.87 (d, J=13.2 Hz, 2H), 2.95-2.94 (m, 2H), 2.79-2.71 (m, 2H), 2.66 (s, 3H), 2.51 (s, 3H), 1.37 (d, J=6.3 Hz, 3H). MS: m/z 489.2 [M+H]$^+$.

Example 207

N-(3-(benzo[d]thiazol-2-yl)-4-chlorophenyl)-2-chloro-4-((3S,5R)-3,4,5-trimethylpiperazin-1-yl)benzamide White solid (23.31 mg, 29.6%). $^1$H NMR (CD$_3$OD): 8.49 (d, J=2.1 Hz, 1H), 8.11-8.07 (m, 2H), 7.89 (dd, J=8.7 and 2.4 Hz, 1H), 7.62-7.49 (m, 4H), 7.07 (d, J=2.4 Hz, 1H), 7.00 (dd, J=8.7 and 2.4 Hz, 1H), 3.82 (d, J=10.5 Hz, 2H), 2.75-2.68 (m, 4H), 2.55 (s, 3H), 1.30 (d, J=5.7 Hz, 6H). MS: m/z 525.1 [M+H]$^+$.

Example 208

N-(3-(pyridin-2-yl)-4-chlorophenyl)-2-chloro-4-((3S,5R)-3,4,5-trimethylpiperazin-1-yl)benzamide Off-white solid (75.13 mg, 29%). $^1$H NMR (CD$_3$OD): 8.64 (d, J=4.8 Hz, 1H), 7.99-7.93 (m, 1H), 7.87 (d, J=1.8 Hz, 1H), 7.79 (dd, J=8.7 and 2.1 Hz, 1H), 7.68 (d, J=8.1 Hz, 1H), 7.54-7.45 (m, 3H), 7.16 (d, J=2.1 Hz, 1H), 7.06 (dd, J=8.6 and 2.2 Hz, 1H), 4.03 (d, J=13.2 Hz, 2H), 3.56-3.40 (m, 2H), 3.01-2.97 (m, 2H), 2.94 (s, 3H), 1.47 (d, J=6.6 Hz, 6H). MS: m/z 469.1 [M+H]$^+$.

Example 209

N-(3-(pyrimidin-2-yl)-4-chlorophenyl)-2-chloro-4-((3S,5R)-3,4,5-trimethylpiperazin-1-yl)benzamide Pale-yellow solid (54.07 mg, 20.9%). $^1$H NMR (CD$_3$OD): 8.95 (d, J=5.1 Hz, 2H), 8.06 (d, J=2.4 Hz, 1H), 7.84 (dd, J=8.7 and 2.4 Hz, 1H), 7.57-7.49 (m, 3H), 7.05 (d, J=2.4 Hz, 1H), 6.98 (dd, J=8.7 and 2.4 Hz, 1H), 3.74 (d, J=12.0 Hz, 2H), 2.70-2.62 (m, 2H), 2.56-2.45 (m, 2H), 2.41 (s, 3H), 1.25 (d, J=6.0 Hz, 6H). MS: m/z 470.1 [M+H]$^+$.

Example 210

The Application of SAG to Induce Pluripotent Mesenchymal Mouse Embryonic Cell C3H/10T1/2 to Differentiate into Osteoblastic Cells for the Determination of the Inhibitory Activity of N-(3-(1H-benzo[d]imidazol-2-yl)-4-chlorophenyl)-2-methyl-4-((2S,6R)-2,6-dimethylmorpholino)benzamide and Analogs on Hedgehog Signaling Pathway The pluripotent mesenchymal mouse embryonic cellline C3H10T1/2 (C3H/10T1/2, Clone 8 from Chinese Cellbank, Shanghai) can be induced to differentiate into osteoblastic cells with stimulation of the hedgehog pathway. The intracellular alkaline phosphatase activity is a reliable indication of the differentiation process. Therefore this enzymatic activity can be used to monitor the activity of hedgehog pathway inhibitors.

The C3H10T1/2 cells were grown in DMEM medium supplemented with 10% fetal bovine serum (FBS, Hyclone) at 37° C. with 5% CO$_2$. 10000 cells were sown to each well of a 96-well microplate a day before the experiment and grown overnight. At the day of experiment, the inducing medium and inhibitor solutions were prepared as follows: the reference compound and testing compounds were serially diluted 1 to 3 and 1 to 10 in DMSO to seven concentrations with the eighth concentration being DMSO. A 10-fold dilution was prepared by mixing 10 µL of the DMSO dilution with 90 µL of fresh growing medium. The inducing medium was prepared by diluting 1 mM DMSO stock solution of hedgehog pathway activator SAG (Yang, H. et al. J. Biol. Chem. 2009, 284, 20876-84) 1000-fold into fresh growth medium (DMEM with 10% FBS) with the final SAG concentration being 1 µM and DMSO 0.1%. Pre-sown cells were taken out from incubator and the medium was removed. To each well, 180 µL inducing medium was added and followed immediately with 20 μL of testing or reference compound dilutions. The testing compound concentrations are between 10 μM and 1 nM. The cells were then return to $CO_2$ incubator to grow additional 5 days at 37° C.

After incubating for 5 days, the cells were taken out and intracellular alkaline phosphatase activity was tested. The alkaline phosphatase activity was measured as follows:

1) Preparation of Substrate Solution:

Solution A: A 0.5 mM $MgCl_2$ (Sigma Prod. No. M-0250) solution was prepared.

Solution B: A 1 M diethanol amine solution was prepared as follows: weigh out 10.51 g diethanol amine (Sigma Prod. No. D-8885) and dissolved in 80 mL double distilled water. After the pH value was adjusted to 9.8 with 5 M HCl at 37° C., the total volume was adjusted to 100 mL.

Solution C: Weigh out 3.71 mg p-NPP (molecular weight 371.14) and dissolved in double distilled water. After it is completely dissolved the total volume was adjusted to 10 mL with the final concentration being 1 mM.

Substrate reaction medium: To 10 mL of solution B, 250 μL of solution A and 200 μL of solution C were added, and mixed well.

2) the Measurement of Intracellular Alkaline Phosphatase Activity:

After taking out the cells from the incubator, the cell culture medium was removed and cells were washed twice with PBS. 20 μL of lysis solution (0.2% Triton solution) was added to each well. After being shaken for 30 min at room temperature, each well of cells received 80 μL of substrate reaction medium. The microplate was placed immediately into a VariSkan Flashplate reader and absorbance at $OD_{405}$ was read as background reading. The plate was replaced back to cell culture incubator at 37° C. for additional 30 min and the absorbance was read again using VariSkan Flash plate reader at $OD_{405}$.

Data Analysis:

The data were analyzed by subtracting the background reading from the reading at 30 min, and the obtained numbers were plotted and analyzed with Prism 5 software (GraphPad). The phosphatase activity (calculated $OD_{405}$) was plotted against the log concentration of testing compound, and the obtained plot was fitted with non-linear curve fitting equation to calculate $IC_{50}$ values. The curve fitting equation is Y=Bottom+(Top−Bottom)/(1+10^((X−Log $IC_{50}$))). X is the logarithm of concentration. Y is the measure of alkaline phosphatase activity ($OD_{405}$).

The calculated $IC_{50}$ value is a measurement of the inhibitory activity of compound to Hh pathway. The data are listed in Table 1.

TABLE 1

$IC_{50}$ values of compounds that inhibit Hh pathway

| | Example | | | | | | |
|---|---|---|---|---|---|---|---|
| | 2 | 3 | 4 | 5 | 6 | 7 | 8 |
| $IC_{50}$ (nM) | 74 | 111 | 86 | 26 | 19 | 25 | 86 |
| | Example | | | | | | |
| | 9 | 10 | 11 | 12 | 13 | 14 | 15 |
| $IC_{50}$ (nM) | 156 | 74 | 31 | 153 | 86 | 80 | >10000 |
| | Example | | | | | | |
| | 16 | 17 | 18 | 19 | 20 | 21 | 22 |
| $IC_{50}$ (nM) | >10000 | 81 | 60 | 161 | >10000 | 30 | 124 |
| | Example | | | | | | |
| | 23 | 24 | 25 | 26 | 27 | 28 | 29 |
| $IC_{50}$ (nM) | 163 | 255 | 191 | >10000 | 151 | 228 | >10000 |
| | Example | | | | | | |
| | 30 | 31 | 32 | 33 | 34 | 35 | 36 |
| $IC_{50}$ (nM) | 88 | 229 | 53 | 83 | 263 | 56 | 362 |
| | Example | | | | | | |
| | 37 | 38 | 39 | 40 | 41 | 42 | 43 |
| $IC_{50}$ (nM) | 167 | 28 | 40 | 27 | 99 | 230 | 16 |
| | Example | | | | | | |
| | 44 | 45 | 46 | 47 | 48 | 49 | 50 |
| $IC_{50}$ (nM) | 139 | 284 | 89 | 102 | >10000 | 261 | 125 |

TABLE 1-continued

IC$_{50}$ values of compounds that inhibit Hh pathway

| | \multicolumn{7}{c}{Example} |
|---|---|---|---|---|---|---|---|
| | 51 | 52 | 53 | 54 | 55 | 56 | 57 |
| IC$_{50}$ (nM) | >10000 | 740 | >10000 | >10000 | >10000 | 2369 | >10000 |
| | \multicolumn{7}{c}{Example} |
| | 58 | 59 | 60 | 61 | 62 | 63 | 64 |
| IC$_{50}$ (nM) | >10000 | 232 | 141 | >10000 | >10000 | 1345 | 636 |
| | \multicolumn{7}{c}{Example} |
| | 65 | 66 | 67 | 68 | 69 | 70 | 71 |
| IC$_{50}$ (nM) | 522 | 24 | >10000 | 69 | 33 | 34 | 181 |
| | \multicolumn{7}{c}{Example} |
| | 72 | 73 | 74 | 75 | 76 | 77 | 78 |
| IC$_{50}$ (nM) | >10000 | 163 | 191 | 17 | >10000 | 139 | 166 |
| | \multicolumn{7}{c}{Example} |
| | 79 | 80 | 81 | 82 | 83 | 84 | 85 |
| IC$_{50}$ (nM) | 100 | 28 | 6.4 | 12 | 43 | 44 | 49 |
| | \multicolumn{7}{c}{Example} |
| | 86 | 87 | 88 | 89 | 90 | 91 | 92 |
| IC$_{50}$ (nM) | 40 | 21 | 119 | 381 | 461 | 52 | 312 |
| | \multicolumn{7}{c}{Example} |
| | 93 | 94 | 95 | 96 | 97 | 98 | 99 |
| IC$_{50}$ (nM) | 32 | 16 | 111 | 106 | 32 | 24 | 81 |
| | \multicolumn{7}{c}{Example} |
| | 100 | 101 | 102 | 103 | 104 | 105 | 106 |
| IC$_{50}$ (nM) | 33 | 46 | 47 | 449 | 58 | 58 | 58 |
| | \multicolumn{7}{c}{Example} |
| | 107 | 108 | 109 | 110 | 111 | 112 | 113 |
| IC$_{50}$ (nM) | 47 | 698 | 96 | 28 | 68 | 83 | 1042 |
| | \multicolumn{7}{c}{Example} |
| | 114 | 115 | 116 | 117 | 118 | 119 | 120 |
| IC$_{50}$ (nM) | 77 | 145 | 68 | 27 | 260 | 39 | 57 |
| | \multicolumn{7}{c}{Example} |
| | 121 | 122 | 123 | 124 | 125 | 126 | 127 |
| IC$_{50}$ (nM) | 29 | 29 | 53 | 38 | 23 | 81 | 34 |
| | \multicolumn{7}{c}{Example} |
| | 128 | 129 | 130 | 131 | 132 | 133 | 134 |
| IC$_{50}$ (nM) | 60 | 82 | 178 | 81 | 28 | 54 | >10000 |
| | \multicolumn{7}{c}{Example} |
| | 135 | 136 | 137 | 138 | 139 | 140 | 141 |
| IC$_{50}$ (nM) | 67 | 9.2 | 51 | 39 | 44 | 4.8 | 9.4 |

TABLE 1-continued

IC$_{50}$ values of compounds that inhibit Hh pathway

| Example | | | | | | |
|---|---|---|---|---|---|---|
| 143 | 144 | 145 | 146 | 147 | 148 | 149 |

| | | | | | | |
|---|---|---|---|---|---|---|
| IC$_{50}$ (nM) | 108 | 17 | 3.3 | 25 | >10000 | 15 | 15 |

| Example | | | | | | |
|---|---|---|---|---|---|---|
| 153 | 154 | 155 | 156 | 157 | 158 | 159 |

| | | | | | | |
|---|---|---|---|---|---|---|
| IC$_{50}$ (nM) | 280 | 178 | 13 | 7.0 | 10 | 8.2 | 10 |

| Example | | | | | | |
|---|---|---|---|---|---|---|
| 160 | 166 | 170 | 172 | 173 | 174 | 175 |

| | | | | | | |
|---|---|---|---|---|---|---|
| IC$_{50}$ (nM) | 66 | 347 | 30 | 127 | 165 | 91 | 176 |

| Example | | | | | | |
|---|---|---|---|---|---|---|
| 176 | 177 | 178 | 179 | 180 | 181 | 182 |

| | | | | | | |
|---|---|---|---|---|---|---|
| IC$_{50}$ (nM) | 7.2 | 23 | 26 | 21 | 47 | 70 | 100 |

| Example | | | | | | |
|---|---|---|---|---|---|---|
| 183 | 184 | 185 | 189 | 195 | 196 | 197 |

| | | | | | | |
|---|---|---|---|---|---|---|
| IC$_{50}$ (nM) | 90 | 184 | 169 | 30 | 258 | 157 | 306 |

| Example | | | | | | |
|---|---|---|---|---|---|---|
| 198 | 199 | 204 | 205 | 206 | 207 | 208 |

| | | | | | | |
|---|---|---|---|---|---|---|
| IC$_{50}$ (nM) | 26 | 11 | 201 | 250 | 244 | 158 | 52 |

| Example | |
|---|---|
| 209 | GDC-0449 |

| | | |
|---|---|---|
| IC$_{50}$ (nM) | 1800 | 108 |

Therefore, compounds of the present invention, including N-(3-(1H-benzo[d]imidazol-2-yl)-4-chlorophenyl)-2-methyl-4-((2S,6R)-2,6-dimethylmorpholino)benzamide (Example 32) and analogs, show strong inhibitory effects on hedgehog pathway.

Example 211

The Application of SHH to Induce Pluripotent Mesenchymal Mouse Embryonic Cell C3H10T1/2 to Differentiate into Osteoblastic Cells for the Determination of the Inhibitory Activity of N-(3-(1H-benzo[d]imidazol-2-yl)-4-chlorophenyl)-2-methyl-4-((2S,6R)-2,6-dimethylmorpholino)benzamide and Analogs on Hedgehog Signaling Pathway The C3H10T1/2 cells were grown in DMEM medium supplemented with 10% fetal bovine serum (FBS, Hyclone) at 37° C. with 5% CO$_2$. 10000 cells were sown to each well of a 96-well microplate a day before the experiment and grown overnight. At the day of experiment, the inducing medium and inhibitor solutions were prepared as follows: the conditioned medium containing recombinant mouse SHH-N (N-terminal 1-198 aa) was taken out of −80° C. freezer, thawed and diluted to the concentration of 10 nM in complete growth medium. The reference compound and testing compounds were serially diluted 1 to 3 and 1 to 10 in DMSO to seven concentrations with the eighth concentration being DMSO. A 10-fold dilution was prepared by mixing 10 μL of the DMSO dilutions with 90 μL of fresh growing medium. Pre-sown cells were taken out from incubator and the medium was removed. To each well, 180 μL of inducing medium containing 10 nM of SHH-N was added and followed immediately with 20 μL of 10× testing or reference compound dilutions. The testing compound concentrations are between 10 μM and 10 nM. The cells were then returned to CO$_2$ incubator to grow additional 5 days at 37° C.

After incubating for 5 days, the cells were taken out and intracellular alkaline phosphatase activity was tested. The alkaline phosphatase activity was measured as follows:

3) Preparation of Substrate Solution:

Solution A: A 0.5 mM MgCl$_2$ (Sigma Prod. No. M-0250) solution was prepared.

Solution B: A 1 M diethanol amine solution was prepared as follows: weigh out 10.51 g diethanol amine (Sigma Prod. No. D-8885) and dissolved in 80 mL double distilled water. After the pH value was adjusted to 9.8 with 5 M HCl at 37° C., the total volume was adjusted to 100 mL.

Solution C: weigh out 3.71 mg p-NPP (molecular weight 371.14) and dissolved in double distilled water. After it is completely dissolved the total volume was adjusted to 10 mL with the final concentration being 1 mM.

Substrate reaction medium: to 10 mL of solution B, 250 μL of solution A and 200 μL of solution C were added, and mixed well.

4) The Measurement of Intracellular Alkaline Phosphatase Activity:

After taking out the cells from the incubator, the cell culture medium was removed and cells were washed twice with PBS. 20 μL of lysis solution (0.2% Triton solution) was added to each well. After being shaken for 30 min at room temperature, each well of cells received 80 μL of substrate reaction medium. The microplate was placed immediately into a VariSkan Flashplate reader and absorbance at $OD_{405}$ was read as background reading. The plate was replaced back to cell culture incubator at 37° C. for additional 30 min and the absorbance was read again using VariSkan Flash plate reader at $OD_{405}$.

Data Analysis:

The data were analyzed by subtracting the background reading from the reading at 30 min, and the obtained numbers were plotted and analyzed with Prism 5 software (GraphPad). The phosphatase activity (calculated $OD_{405}$) was plotted against the log concentration of testing compound, and the obtained plot was fitted with non-linear curve fitting equation to calculate $IC_{50}$ values. The curve fitting equation is $Y=Bottom+(Top-Bottom)/(1+10^{\wedge}(X-Log\ IC_{50}))$. X is the logarithm of concentration. Y is the measure of alkaline phosphatase activity ($OD_{405}$).

The calculated $IC_{50}$ value is a measurement of the inhibitory activity of compound to Hh pathway. These data are listed in Table 2.

TABLE 2

$IC_{50}$ values of compounds that inhibit Hh pathway

| | Example | | | | | | |
|---|---|---|---|---|---|---|---|
| | 2 | 3 | 4 | 5 | 6 | 7 | 8 |
| $IC_{50}$ (nM) | 14 | 39 | 7.8 | 5.9 | 2.6 | 3.5 | 3.6 |

| | Example | | | | | | |
|---|---|---|---|---|---|---|---|
| | 9 | 10 | 11 | 12 | 13 | 14 | 15 |
| $IC_{50}$ (nM) | 43 | 6.3 | 1.7 | 18 | 14.6 | 5.5 | 40 |

| | Example | | | | | | |
|---|---|---|---|---|---|---|---|
| | 16 | 17 | 18 | 19 | 20 | 21 | 22 |
| $IC_{50}$ (nM) | >10000 | 15 | 3.7 | 23 | 59 | 2.3 | 15 |

| | Example | | | | | | |
|---|---|---|---|---|---|---|---|
| | 23 | 24 | 25 | 26 | 27 | 28 | 29 |
| $IC_{50}$ (nM) | 24 | 62 | 5.5 | >10000 | 57 | 59 | 72 |

| | Example | | | | | | |
|---|---|---|---|---|---|---|---|
| | 30 | 31 | 32 | 33 | 34 | 35 | 36 |
| $IC_{50}$ (nM) | 31 | 44 | 7.9 | 22 | 162 | 10 | 95 |

| | Example | | | | | | |
|---|---|---|---|---|---|---|---|
| | 37 | 38 | 39 | 40 | 41 | 42 | 43 |
| $IC_{50}$ (nM) | 52 | 4.9 | 15 | 13 | 32 | 337 | 8.5 |

| | Example | | | | | | |
|---|---|---|---|---|---|---|---|
| | 44 | 45 | 46 | 47 | 48 | 49 | 50 |
| $IC_{50}$ (nM) | 18 | 20 | 5.1 | 3.3 | >10000 | 2.4 | 7.9 |

| | Example | | | | | | |
|---|---|---|---|---|---|---|---|
| | 51 | 52 | 53 | 54 | 55 | 56 | 57 |
| $IC_{50}$ (nM) | 77 | 465 | >10000 | >10000 | >10000 | 189 | >10000 |

| | Example | | | | | | |
|---|---|---|---|---|---|---|---|
| | 58 | 59 | 60 | 61 | 62 | 63 | 64 |
| $IC_{50}$ (nM) | >10000 | 7.5 | 18 | >10000 | 409 | 39 | 1131 |

| | Example | | | | | | |
|---|---|---|---|---|---|---|---|
| | 65 | 66 | 67 | 68 | 69 | 70 | 71 |
| $IC_{50}$ (nM) | 501 | 7.1 | 68 | 4.0 | 0.55 | 2.8 | 3.6 |

TABLE 2-continued

IC$_{50}$ values of compounds that inhibit Hh pathway

| | Example | | | | | | |
|---|---|---|---|---|---|---|---|
| | 72 | 73 | 74 | 75 | 76 | 77 | 78 |
| IC$_{50}$ (nM) | 467 | 134 | 4.5 | 2.9 | >10000 | 1.9 | 4.8 |

| | Example | | | | | | |
|---|---|---|---|---|---|---|---|
| | 79 | 80 | 81 | 82 | 83 | 84 | 85 |
| IC$_{50}$ (nM) | 2.7 | 2.7 | 0.16 | 0.21 | 9.2 | 7.1 | 5.6 |

| | Example | | | | | | |
|---|---|---|---|---|---|---|---|
| | 86 | 87 | 88 | 89 | 90 | 91 | 92 |
| IC$_{50}$ (nM) | 1.7 | 1.7 | 11 | 55 | 35 | 6.8 | 45 |

| | Example | | | | | | |
|---|---|---|---|---|---|---|---|
| | 93 | 94 | 95 | 96 | 97 | 98 | 99 |
| IC$_{50}$ (nM) | 0.69 | 0.81 | 13 | 5.0 | 0.59 | 1.4 | 2.6 |

| | Example | | | | | | |
|---|---|---|---|---|---|---|---|
| | 100 | 101 | 102 | 103 | 104 | 105 | 106 |
| IC$_{50}$ (nM) | 2.3 | 0.64 | 3.9 | 40 | 0.61 | 2.2 | 19 |

| | Example | | | | | | |
|---|---|---|---|---|---|---|---|
| | 107 | 108 | 109 | 110 | 111 | 112 | 113 |
| IC$_{50}$ (nM) | 2.3 | 76 | 6.4 | 0.66 | 0.94 | 8.6 | >10000 |

| | Example | | | | | | |
|---|---|---|---|---|---|---|---|
| | 114 | 115 | 116 | 117 | 118 | 119 | 120 |
| IC$_{50}$ (nM) | 9.0 | 31 | 2.1 | 4.6 | 13 | 0.76 | 7.4 |

| | Example | | | | | | |
|---|---|---|---|---|---|---|---|
| | 121 | 122 | 123 | 124 | 125 | 126 | 127 |
| IC$_{50}$ (nM) | 23 | 0.52 | 0.97 | 0.49 | 1.2 | 25 | 1.1 |

| | Example | | | | | | |
|---|---|---|---|---|---|---|---|
| | 128 | 129 | 130 | 131 | 132 | 133 | 134 |
| IC$_{50}$ (nM) | 5.3 | 7.5 | 18 | 7.2 | 0.53 | 6.3 | >10000 |

| | Example | | | | | | |
|---|---|---|---|---|---|---|---|
| | 135 | 136 | 137 | 138 | 139 | 140 | 141 |
| IC$_{50}$ (nM) | 1.5 | 4.0 | 15 | 1.6 | 1.8 | 0.20 | 0.24 |

| | Example | | | | | | |
|---|---|---|---|---|---|---|---|
| | 143 | 144 | 145 | 146 | 147 | 148 | 149 |
| IC$_{50}$ (nM) | 15 | 0.82 | 0.93 | 0.49 | >10000 | 0.33 | 0.27 |

| | Example | | | | | | |
|---|---|---|---|---|---|---|---|
| | 153 | 154 | 155 | 156 | 157 | 158 | 159 |
| IC$_{50}$ (nM) | 34 | 22 | 0.11 | 0.20 | 0.15 | 0.42 | 0.36 |

| | Example | | | | | | |
|---|---|---|---|---|---|---|---|
| | 160 | 166 | 170 | 172 | 173 | 174 | 175 |
| IC$_{50}$ (nM) | >10000 | 47 | 0.22 | 45 | 60 | 11 | 6.1 |

TABLE 2-continued

IC$_{50}$ values of compounds that inhibit Hh pathway

| | Example | | | | | | |
|---|---|---|---|---|---|---|---|
| | 176 | 177 | 178 | 179 | 180 | 181 | 182 |
| IC$_{50}$ (nM) | 3.9 | 1.0 | 0.30 | 0.39 | 9.9 | 19 | 9.0 |

| | Example | | | | | | |
|---|---|---|---|---|---|---|---|
| | 183 | 184 | 185 | 189 | 195 | 196 | 197 |
| IC$_{50}$ (nM) | 22 | 28 | 6.1 | 5.2 | 8.1 | 54 | 115 |

| | Example | | | | | | |
|---|---|---|---|---|---|---|---|
| | 198 | 199 | 204 | 205 | 206 | 207 | 208 |
| IC$_{50}$ (nM) | 0.30 | 0.19 | 49 | 94 | 46 | 31 | 1.3 |

| | Example | |
|---|---|---|
| | 209 | GDC-0449 |
| IC$_{50}$ (nM) | >10000 | 38 |

Therefore, compounds of the present invention, including N-(3-(1H-benzo[d]imidazol-2-yl)-4-chlorophenyl)-2-methyl-4-((2S,6R)-2,6-dimethylmorpholino)benzamide (Example 32) and analogs, show strong inhibitory effects on hedgehog pathway.

Example 212

The Application of Reporter Gene Cell Assay for the Determination of the Inhibitory Activity of N-(3-(1H-benzo[d]imidazol-2-yl)-4-chlorophenyl)-2-methyl-4-((2S,6R)-2,6-dimethylmorpholino) benzamide and Analogs on Hedgehog Signaling Pathway The binding of Sonic hedgehog (Shh) to its receptor Patched 1 initiates numerous intracellular signal transmission, and leads to the nuclear translocation of Gli and the elevated transcription of Gli target genes. When C3H10T1/2 cells are stably transfected with the Gli-Luc plasmids containing the luciferase gene under the control of Gli response element and stimulated with Shh, the expression of luciferase is elevated. Luciferase activity is indicative of the hedgehog signaling pathway activity. Therefore, the inhibitory activity of compounds on hedgehog signaling pathway can be measured using the luciferase activity when the transfected cells are stimulated with Shh.

The day before experiment, C3H10T1/2/Gli-Luc cells in log phase of growth were seeded into 96 well plate at a density of 20000 cells per well. The cells were maintained in DMEM (Hyclone) supplemented with 10% FBS (Hyclone) and incubated at 37° C. with 5% CO$_2$ overnight. The compounds to be examined were diluted into 7 different concentrations by series of dilutions (⅓ and ¹/₁₀), and the eighth point of concentration is the DMSO control. Those solutions were diluted 100-fold in the fresh growth medium. The cells were taken out of the incubator and the medium of cultured cells were removed. Then, each well was added in an orderly manner with 80 µL of fresh growth medium, 20 µL of medium pre-dilution of positive compound and compounds to be tested, as well as 100 µL of growth medium containing 30 nM of Shh. The cells are returned to the incubator, and incubated for 24 hours.

Measurement of luciferase activity: After taking the 96 well plate out of the incubator, the supernatants were discarded and the cells were washed twice with PBS. Thereafter, each well was dispensed with 20 µL of lysis buffer (Promega E1531), and the plate was shaken for 30 min at room temperature. Following transferring 5 µL of cell lysate into 384 well plate (Greiner 781074), adding 25 µL of luciferase reaction buffer (Promega E1501) into each well and mixing the plate, the relative light unit (RLU) was immediately captured by VarioSkan Flash.

The data were analyzed with Prism 5 software (Graph-Pad). The relative light unit (RLU) was plotted against the log concentration of testing compound, and the obtained plot was fitted with non-linear curve fitting equation to calculate IC$_{50}$ values. The curve fitting equation is Y (RLU)=Bottom+ (Top−Bottom)/(1+10^((X−Log IC$_{50}$))). X is the logarithm of concentration. Y is the measure of relative light unit (RLU).

The calculated IC$_{50}$ value is a measurement of the inhibitory activity of compound to Hh pathway. These data are listed in Table 3.

TABLE 3

IC$_{50}$ values of compounds that inhibit Hh pathway

| | Example | | | | | | |
|---|---|---|---|---|---|---|---|
| | 6 | 7 | 8 | 14 | 18 | 21 | 22 |
| IC$_{50}$ (nM) | 3.3 | 4.6 | 4.6 | 9.5 | 8.2 | 5.8 | 16 |

| | Example | | | | | | |
|---|---|---|---|---|---|---|---|
| | 25 | 32 | 35 | 38 | 39 | 43 | 46 |
| IC$_{50}$ (nM) | 4.0 | 7.2 | 7.8 | 8.4 | 8.2 | 12 | 5.5 |

| | Example | | | | | | |
|---|---|---|---|---|---|---|---|
| | 47 | 49 | 50 | 59 | 60 | 66 | 68 |
| IC$_{50}$ (nM) | 8.7 | 7.2 | 10 | 9.1 | 23 | 6.1 | 9.9 |

TABLE 3-continued

IC$_{50}$ values of compounds that inhibit Hh pathway

| Example | | | | | | |
|---|---|---|---|---|---|---|
| 69 | 70 | 71 | 77 | 78 | 79 | 80 |
| IC$_{50}$ (nM) 4.2 | 1.7 | 7.1 | 7.1 | 15 | 6.6 | 1.8 |

| Example | | | | | | |
|---|---|---|---|---|---|---|
| 81 | 82 | 83 | 84 | 85 | 86 | 87 |
| IC$_{50}$ (nM) 0.15 | 0.16 | 6.3 | 10 | 7.1 | 0.94 | 0.53 |

| Example | | | | | | |
|---|---|---|---|---|---|---|
| 88 | 89 | 90 | 91 | 93 | 94 | 95 |
| IC$_{50}$ (nM) 6.7 | 21 | 25 | 7.8 | 0.50 | 0.63 | 3.3 |

| Example | | | | | | |
|---|---|---|---|---|---|---|
| 96 | 97 | 98 | 99 | 100 | 101 | 103 |
| IC$_{50}$ (nM) 3.3 | 1.7 | 0.96 | 1.6 | 0.58 | 0.67 | 9.4 |

| Example | | | | | | |
|---|---|---|---|---|---|---|
| 104 | 105 | 107 | 109 | 110 | 111 | 112 |
| IC$_{50}$ (nM) 0.94 | 1.1 | 0.75 | 3.8 | 0.57 | 2.2 | 5.5 |

| Example | | | | | | |
|---|---|---|---|---|---|---|
| 113 | 114 | 115 | 116 | 117 | 118 | 119 |
| IC$_{50}$ (nM) 27 | 0.85 | 3.4 | 1.4 | 1.2 | 5.1 | 0.45 |

| Example | | | | | | |
|---|---|---|---|---|---|---|
| 120 | 121 | 122 | 123 | 124 | 125 | 126 |
| IC$_{50}$ (nM) 1.7 | 1.6 | 0.39 | 0.39 | 0.80 | 0.57 | 2.3 |

| Example | | | | | | |
|---|---|---|---|---|---|---|
| 127 | 128 | 129 | 130 | 131 | 132 | 133 |
| IC$_{50}$ (nM) 1.1 | 5.2 | 4.0 | 8.5 | 1.2 | 0.74 | 1.6 |

| Example | | | | | | |
|---|---|---|---|---|---|---|
| 134 | 135 | 136 | 137 | 138 | 139 | 140 |
| IC$_{50}$ (nM) >10000 | 1.2 | 0.97 | 2.3 | 0.58 | 1.1 | 0.21 |

| Example | | | | | | |
|---|---|---|---|---|---|---|
| 141 | 142 | 143 | 144 | 145 | 146 | 147 |
| IC$_{50}$ (nM) 0.35 | 0.28 | 2.3 | 0.15 | 0.38 | 0.39 | >10000 |

| Example | | | | | | |
|---|---|---|---|---|---|---|
| 148 | 149 | 150 | 151 | 152 | 153 | 154 |
| IC$_{50}$ (nM) 0.26 | 0.28 | 0.50 | 2.0 | 1.2 | 8.7 | 6.7 |

| Example | | | | | | |
|---|---|---|---|---|---|---|
| 155 | 156 | 157 | 158 | 159 | 160 | 161 |
| IC$_{50}$ (nM) 0.22 | 0.21 | 0.23 | 0.30 | 0.31 | 6.5 | 0.38 |

| Example | | | | | | |
|---|---|---|---|---|---|---|
| 162 | 164 | 165 | 166 | 167 | 168 | 169 |
| IC$_{50}$ (nM) 0.30 | 0.24 | 0.19 | 11 | 28 | 0.38 | 0.67 |

| Example | | | | | | |
|---|---|---|---|---|---|---|
| 170 | 171 | 172 | 173 | 174 | 175 | 176 |
| IC$_{50}$ (nM) 0.22 | 0.46 | 17 | 15 | 5.7 | 7.6 | 0.97 |

| Example | | | | | | |
|---|---|---|---|---|---|---|
| 177 | 178 | 179 | 180 | 181 | 182 | 183 |
| IC$_{50}$ (nM) 0.67 | 1.0 | 0.43 | 2.4 | 3.2 | 4.5 | 6.6 |

| Example | | | | | | |
|---|---|---|---|---|---|---|
| 184 | 185 | 186 | 187 | 188 | 189 | 190 |
| IC$_{50}$ (nM) 10 | 17 | 3.4 | 0.45 | 1.0 | 0.82 | 0.20 |

| Example | | | | | | |
|---|---|---|---|---|---|---|
| 191 | 192 | 193 | 194 | 195 | 196 | 197 |
| IC$_{50}$ (nM) 0.34 | 0.52 | 0.56 | 0.63 | 8.9 | 5.7 | 9.5 |

| Example | | | | | | |
|---|---|---|---|---|---|---|
| 198 | 199 | 200 | 203 | 204 | 205 | 206 |
| IC$_{50}$ (nM) 0.29 | 0.27 | 0.28 | 0.29 | 9.6 | 29 | 27 |

| Example | | | GDC-0449 |
|---|---|---|---|
| 207 | 208 | 209 | |
| IC$_{50}$ (nM) 8.5 | 3.7 | >10000 | 43 |

Therefore, compounds of the present invention, including N-(3-(1H-benzo[d]imidazol-2-yl)-4-chlorophenyl)-2-methyl-4-((2S,6R)-2,6-dimethylmorpholino)benzamide (Example 32) and analogs, show strong inhibitory effects on hedgehog pathway.

Having now fully described this invention, it will be understood by those of ordinary skill in the art that the same can be performed within a wide and equivalent range of conditions, formulations and other parameters without affecting the scope of the invention or any embodiment thereof. All patents, patent applications and publications cited herein are fully incorporated by reference herein in their entirety.

What is claimed is:

1. A compound or a pharmaceutically acceptable salt thereof that is selected from the group consisting of:
   N-(3-(1H-benzo[d]imidazol-2-yl)-4-chlorophenyl)-3-methylbiphenyl-4-carboxamide;
   N-(3-(1H-benzo[d]imidazol-2-yl)-4-chlorophenyl)-3-methyl-4'-methoxybiphenyl-4-carboxamide;
   N-(3-(1H-benzo[d]imidazol-2-yl)-4-chlorophenyl)-3-methyl-4'-fluorobiphenyl-4-carboxamide;
   N-(3-(1H-benzo[d]imidazol-2-yl)-4-chlorophenyl)-3-methyl-4'-(methylsulfonyl)biphenyl-4-carboxamide;
   N-(3-(1H-benzo[d]imidazol-2-yl)-4-chlorophenyl)-3-methyl-4'-cyanobiphenyl-4-carboxamide;
   N-(3-(1H-benzo[d]imidazol-2-yl)-4-chlorophenyl)-3-methyl-4'-nitrobiphenyl-4-carboxamide;
   N-(3-(1H-benzo[d]imidazol-2-yl)-4-chlorophenyl)-3-methyl-4'-chlorobiphenyl-4-carboxamide;
   N-(3-(1H-benzo[d]imidazol-2-yl)-4-chlorophenyl)-3-methyl-4'-acetylbiphenyl-4-carboxamide;
   N-(3-(1H-benzo[d]imidazol-2-yl)-4-chlorophenyl)-3-methyl-3'-fluorobiphenyl-4-carboxamide;

N-(3-(1H-benzo[d]imidazol-2-yl)-4-chlorophenyl)-3-methyl-3'-cyanobiphenyl-4-carboxamide;
N-(3-(1H-benzo[d]imidazol-2-yl)-4-chlorophenyl)-4'-fluorobiphenyl-4-carboxamide;
N-(3-(1H-benzo[d]imidazol-2-yl)-4-chlorophenyl)-3'-fluorobiphenyl-4-carboxamide;
N-(3-(1H-benzo[d]imidazol-2-yl)-4-chlorophenyl)-2-methyl-4'-(trifluoromethyl)biphenyl-4-carboxamide;
N-(3-(1H-benzo[d]imidazol-2-yl)-4-chlorophenyl)-3-methoxy-4'-(trifluoromethyl)biphenyl-4-carboxamide;
N-(3-(1H-benzo[d]imidazol-2-yl)-4-chlorophenyl)-3-hydroxy-4'-(trifluoromethyl)biphenyl-4-carboxamide;
N-(3-(1H-benzo[d]imidazol-2-yl)-4-chlorophenyl)-3-fluoro-4'-(trifluoromethyl)biphenyl-4-carboxamide;
N-(3-(1H-benzo[d]imidazol-2-yl)-4-chlorophenyl)-3-chloro-4'-(trifluoromethyl)biphenyl-4-carboxamide;
N-(3-(1H-benzo[d]imidazol-2-yl)-4-chlorophenyl)-3-nitro-4'-(trifluoromethyl)biphenyl-4-carboxamide;
N-(3-(1H-benzo[d]imidazol-2-yl)-4-chlorophenyl)-3,5-dimethyl-4'-(trifluoromethyl)biphenyl-4-carboxamide;
N-(3-(1H-benzo[d]imidazol-2-yl)-4-chlorophenyl)-3-methyl-4'-(trifluoromethyl)biphenyl-4-carboxamide;
N-(3-(1H-benzo[d]imidazol-2-yl)-4-chlorophenyl)-4'-(trifluoromethyl)biphenyl-4-carboxamide;
N-(3-(1H-benzo[d]imidazol-2-yl)-4-chlorophenyl)biphenyl-4-carboxamide;
N-(3-(1H-benzo[d]imidazol-2-yl)-4-chlorophenyl)-3-methyl-4'-aminobiphenyl-4-carboxamide;
N-(3-(1H-benzo[d]imidazol-2-yl)-4-chlorophenyl)-3-amino-4'-(trifluoromethyl)biphenyl-4-carboxamide;
3-(3-(1H-benzo[d]imidazol-2-yl)-4-chlorophenyl)-7-(4-(trifluoromethyl)phenyl)quinazoline-2,4(1H,3H)-dione;
3-(3-(1H-benzo[d]imidazol-2-yl)-4-chlorophenyl)-7-(4-(trifluoromethyl)phenyl)quinazolin-4(3H)-one;
3-(3-(1H-benzo[d]imidazol-2-yl)-4-chlorophenyl)-7-(4-(trifluoromethyl)phenyl)-2H-benzo[e][1,3]oxazin-4(3H)-one;
2-(3-(1H-benzo[d]imidazol-2-yl)-4-chlorophenyl)-6-phenyl-3,4-dihydroisoquinolin-1(2H)-one;
N-(3-(1H-benzo[d]imidazol-2-yl)-4-chlorophenyl)-2-methyl-4-morpholinobenzamide;
N-(3-(1H-benzo[d]imidazol-2-yl)-4-chlorophenyl)-2-methyl-4-(piperidin-1-yl)benzamide;
N-(3-(1H-benzo[d]imidazol-2-yl)-4-chlorophenyl)-2-methyl-4-((2S,6R)-2,6-dimethylmorpholino)benzamide;
N-(3-(1H-benzo[d]imidazol-2-yl)-4-chlorophenyl)-2-amino-4-((2S,6R)-2,6-dimethylmorpholino)benzamide;
3-(3-(1H-benzo[d]imidazol-2-yl)-4-chlorophenyl)-7-((2S,6R)-2,6-dimethylmorpholino)quinazolin-4(3H)-one;
N-(3-(1H-benzo[d]imidazol-2-yl)-4-chlorophenyl)-6-((2S,6R)-2,6-dimethylmorpholino)nicotinamide;
N-(3-(1H-benzo[d]imidazol-2-yl)-4-chlorophenyl)-4-chloro-6-((2S,6R)-2,6-dimethylmorpholino)nicotinamide;
N-(3-(1H-benzo[d]imidazol-2-yl)-4-chlorophenyl)-5-methyl-6-((2S,6R)-2,6-dimethylmorpholino)nicotinamide;
N-(3-(1H-benzo[d]imidazol-2-yl)-4-chlorophenyl)-2-methyl-6-((2S,6R)-2,6-dimethylmorpholino)nicotinamide;
N-(3-(1H-benzo[d]imidazol-2-yl)-4-chlorophenyl)-2-methyl-4-(2-methoxypyrimidin-5-yl)benzamide;
N-(3-(1H-benzo[d]imidazol-2-yl)-4-chlorophenyl)-2-methyl-4-(pyridin-3-yl)benzamide;
N-(3-(1H-benzo[d]imidazol-2-yl)-4-chlorophenyl)-2-methyl-4-(furan-3-yl)benzamide;
N-(3-(1H-benzo[d]imidazol-2-yl)-4-chlorophenyl)-2-methyl-4-(thiophen-3-yl)benzamide;
N-(3-(1H-benzo[d]imidazol-2-yl)-4-chlorophenyl)-2-methyl-4-(pyrimidin-5-yl)benzamide;
N-(3-(1H-benzo[d]imidazol-2-yl)-4-chlorophenyl)-4-phenylcyclohexanecarboxamide;
N-(3-(1H-benzo[d]imidazol-2-yl)phenyl)-3-methyl-4'-(trifluoromethyl)biphenyl-4-carboxamide;
N-(3-(1H-benzo[d]imidazol-2-yl)-4-methylphenyl)-3-methyl-4'-(trifluoromethyl)biphenyl-4-carboxamide;
N-(3-(1-methyl-1H-benzo[d]imidazol-2-yl)-4-chlorophenyl)-3-methyl-4'-(trifluoromethyl)biphenyl-4-carboxamide;
N-(3-(1H-benzo[d]imidazol-2-yl)-4-chlorophenyl)-N,3-dimethyl-4'-(trifluoromethyl)biphenyl-4-carboxamide;
N-(3-(1H-imidazo[4,5-c]pyridin-2-yl)-4-chlorophenyl)-3-methyl-4'-(trifluoromethyl)biphenyl-4-carboxamide;
N-(3-(5-phenyl-1H-imidazol-2-yl)-4-chlorophenyl)-3-methyl-4'-(trifluoromethyl)biphenyl-4-carboxamide;
N-(3-(5-(pyridin-3-yl)-1H-imidazol-2-yl)-4-chlorophenyl)-3-methyl-4'-(trifluoromethyl)biphenyl-4-carboxamide;
N-(3-([1,2,4]triazolo[4,3-a]pyridin-3-yl)-4-chlorophenyl)-3-methyl-4'-(trifluoromethyl)biphenyl-4-carboxamide;
N-(3-([1,2,4]triazolo[4,3-a]pyrimidin-3-yl)-4-chlorophenyl)-3-methyl-4'-(trifluoromethyl)biphenyl-4-carboxamide;
N-(3-([1,2,4]triazolo[4,3-a]pyrazin-3-yl)-4-chlorophenyl)-3-methyl-4'-(trifluoromethyl)biphenyl-4-carboxamide;
N-(3-(imidazo[1,2-a]pyrimidin-2-yl)phenyl)-3-methyl-4'-(trifluoromethyl)biphenyl-4-carboxamide;
N-(3-(imidazo[1,2-a]pyrimidin-2-yl)phenyl)-3-methyl-4'-(trifluoromethyl)biphenyl-4-carboxamide;
N-(3-(imidazo[1,2-a]pyrimidin-2-yl)phenyl)-6-((2S,6R)-2,6-dimethylmorpholino)nicotinamide;
N-(3-([1,2,4]triazolo[4,3-a]pyrazin-3-yl)-4-chlorophenyl)-6-((2S,6R)-2,6-dimethylmorpholino)nicotinamide;
N-(3-(pyridin-2-yl)-4-chlorophenyl)-3-methyl-4'-(trifluoromethyl)biphenyl-4-carboxamide;
N-(5-(1H-benzo[d]imidazol-2-yl)pyridin-3-yl)-3-methyl-4'-(trifluoromethyl)biphenyl-4-carboxamide;
N-(4-(1H-benzo[d]imidazol-2-yl)pyridin-2-yl)-3-methyl-4'-(trifluoromethyl)biphenyl-4-carboxamide;
N-(3-(1H-benzo[d]imidazol-2-yl)-5-(trifluoromethyl)phenyl)-3-methyl-4'-(trifluoromethyl)biphenyl-4-carboxamide;
N-(3-(1H-benzo[d]imidazol-2-yl)-5-chlorophenyl)-3-methyl-4'-(trifluoromethyl)biphenyl-4-carboxamide;
N-(3-(1H-benzo[d]imidazol-2-yl)-2-chlorophenyl)-3-methyl-4'-(trifluoromethyl)biphenyl-4-carboxamide;
N-(3-(1H-benzo[d]imidazol-2-yl)-2-methylphenyl)-6-((2S,6R)-2,6-dimethylmorpholino)nicotinamide;
N-(3-(1H-benzo[d]imidazol-2-yl)-4-chlorophenyl)-2-methyl-4-(6-methoxypyridin-3-yl)benzamide;
N-(3-(imidazo[1,2-a]pyridin-2-yl)-4-chlorophenyl)-3-methyl-4'-(trifluoromethyl)biphenyl-4-carboxamide;
N-(3-(5-(thiophen-2-yl)-1H-imidazol-2-yl)-4-chlorophenyl)-3-methyl-4'-(trifluoromethyl)biphenyl-4-carboxamide;

N-(5-(1H-benzo[d]imidazol-2-yl)-6-chloropyridin-3-yl)-3-methyl-4'-(trifluoromethyl)biphenyl-4-carboxamide;
N-(5-(1H-benzo[d]imidazol-2-yl)-6-chloropyridin-3-yl)-3-methyl-4'-cyanobiphenyl-4-carboxamide;
N-(5-(1H-benzo[d]imidazol-2-yl)-6-methylpyridin-3-yl)-3-methyl-4'-(trifluoromethyl)biphenyl-4-carboxamide;
N-(6-(1H-benzo[d]imidazol-2-yl)pyridin-2-yl)-3-methyl-4'-(trifluoromethyl)biphenyl-4-carboxamide;
N-(3-([1,2,4]triazolo[1,5-a]pyridin-2-yl)phenyl)-3-methyl-4'-(trifluoromethyl)biphenyl-4-carboxamide;
N-(3-(1H-benzo[d]imidazol-2-yl)-4-fluorophenyl)-3-methyl-4'-(trifluoromethyl)biphenyl-4-carboxamide;
N-(3-(1H-benzo[d]imidazol-2-yl)-4-bromophenyl)-3-methyl-4'-(trifluoromethyl)biphenyl-4-carboxamide;
N-(3-(1H-benzo[d]imidazol-2-yl)-4-methoxyphenyl)-3-methyl-4'-(trifluoromethyl)biphenyl-4-carboxamide;
N-(3-(5-p-tolyl-1H-imidazol-2-yl)-4-chlorophenyl)-3-methyl-4'-(trifluoromethyl)biphenyl-4-carboxamide;
N-(3-(5-(4-fluorophenyl)-1H-imidazol-2-yl)-4-chlorophenyl)-3-methyl-4'-(trifluoromethyl)biphenyl-4-carboxamide;
N-(3-(5-(furan-2-yl)-1H-imidazol-2-yl)-4-chlorophenyl)-3-methyl-4'-(trifluoromethyl)biphenyl-4-carboxamide;
N-(3-(5-p-tolyl-1H-imidazol-2-yl)-4-chlorophenyl)-2-methyl-4-((2S,6R)-2,6-dimethylmorpholino)benzamide;
N-(3-(5-(thiophen-2-yl)-1H-imidazol-2-yl)-4-chlorophenyl)-2-methyl-4-((3S,5R)-3,4,5-trimethylpiperazin-1-yl)benzamide;
N-(3-(5-(thiophen-2-yl)-1H-imidazol-2-yl)-4-chlorophenyl)-2-chloro-4-((3S,5R)-3,4,5-trimethylpiperazin-1-yl)benzamide;
N-(5-(1H-benzo[d]imidazol-2-yl)-6-chloropyridin-3-yl)-2-methyl-4-((2S,6R)-2,6-dimethylmorpholino)benzamide;
N-(5-(1H-benzo[d]imidazol-2-yl)-6-chloropyridin-3-yl)-2-methyl-6-((2S,6R)-2,6-dimethylmorpholino)nicotinamide;
N-(5-(1H-benzo[d]imidazol-2-yl)-6-chloropyridin-3-yl)-4-methyl-6-((2S,6R)-2,6-dimethylmorpholino)nicotinamide;
N-(5-(1H-benzo[d]imidazol-2-yl)-6-chloropyridin-3-yl)-6-((3S,5R)-3,4,5-trimethylpiperazin-1-yl)nicotinamide;
N-(5-(1H-benzo[d]imidazol-2-yl)-6-chloropyridin-3-yl)-2-methyl-4-((3S,5R)-3,4,5-trimethylpiperazin-1-yl)benzamide;
N-(5-(1H-benzo[d]imidazol-2-yl)-6-methylpyridin-3-yl)-2-methyl-4-((3S,5R)-3,4,5-trimethylpiperazin-1-yl)benzamide;
N-(5-(1H-benzo[d]imidazol-2-yl)-6-methylpyridin-3-yl)-3-methyl-4-((3S,5R)-3,4,5-trimethylpiperazin-1-yl)benzamide;
N-(5-(1H-benzo[d]imidazol-2-yl)-6-methylpyridin-3-yl)-6-((3S,5R)-3,4,5-trimethylpiperazin-1-yl)nicotinamide;
N-(3-(1H-benzo[d]imidazol-2-yl)-4-chlorophenyl)-4-methyl-6-((2S,6R)-2,6-dimethylmorpholino)nicotinamide;
N-(3-(1H-benzo[d]imidazol-2-yl)-4-chlorophenyl)-2-methyl-4-(4-methylpiperazin-1-yl)benzamide;
N-(3-(1H-benzo[d]imidazol-2-yl)-4-chlorophenyl)-2-methyl-4-((3S,5R)-3,4,5-trimethylpiperazin-1-yl)benzamide;
N-(3-(1H-benzo[d]imidazol-2-yl)-4-chlorophenyl)-2-chloro-4-((3S,5R)-3,4,5-trimethylpiperazin-1-yl)benzamide;
N-(3-(1H-benzo[d]imidazol-2-yl)-4-chlorophenyl)-2-fluoro-4-((3S,5R)-3,4,5-trimethylpiperazin-1-yl)benzamide;
N-(3-(6-chloro-1H-benzo[d]imidazol-2-yl)-4-chlorophenyl)-2-chloro-4-((3S,5R)-3,4,5-trimethylpiperazin-1-yl)benzamide;
N-(3-(6-chloro-1H-benzo[d]imidazol-2-yl)-4-chlorophenyl)-2-methyl-4-((3S,5R)-3,4,5-trimethylpiperazin-1-yl)benzamide;
N-(3-(6-fluoro-1H-benzo[d]imidazol-2-yl)-4-chlorophenyl)-2-methyl-4-((3S,5R)-3,4,5-trimethylpiperazin-1-yl)benzamide;
N-(3-(6-fluoro-1H-benzo[d]imidazol-2-yl)-4-chlorophenyl)-2-chloro-4-((3S,5R)-3,4,5-trimethylpiperazin-1-yl)benzamide;
N-(3-(1H-benzo[d]imidazol-2-yl)-4-chlorophenyl)-2-methyl-4-((3S,5R)-4-ethyl-3,5-dimethylpiperazin-1-yl)benzamide;
N-(3-(1H-benzo[d]imidazol-2-yl)-4-chlorophenyl)-2-methyl-4-((3S,5R)-4-isopropyl-3,5-dimethylpiperazin-1-yl)benzamide;
N-(3-(1H-benzo[d]imidazol-2-yl)-4-methylphenyl)-2-chloro-4-((3S,5R)-3,4,5-trimethylpiperazin-1-yl)benzamide;
N-(3-(1H-benzo[d]imidazol-2-yl)-4-chlorophenyl)-6-(4-methylpiperazin-1-yl)nicotinamide;
N-(3-(1H-benzo[d]imidazol-2-yl)-4-chlorophenyl)-6-((3S,5R)-3,4,5-trimethylpiperazin-1-yl)nicotinamide;
N-(3-(1H-benzo[d]imidazol-2-yl)-4-chlorophenyl)-6-((3S,5R)-4-ethyl-3,5-dimethylpiperazin-1-yl)nicotinamide;
N-(5-(1H-benzo[d]imidazol-2-yl)-6-chloropyridin-3-yl)-6-((2S,6R)-2,6-dimethylmorpholino)nicotinamide;
N-(3-(1H-benzo[d]imidazol-2-yl)-4-chlorophenyl)-4-methyl-6-((3S,5R)-3,4,5-trimethylpiperazin-1-yl)nicotinamide;
N-(3-(1H-benzo[d]imidazol-2-yl)-4-chlorophenyl)-2-methyl-4-(piperazin-1-yl)benzamide;
N-(3-(1H-benzo[d]imidazol-2-yl)-4-chlorophenyl)-2-methyl-4-((3S,5R)-3,5-dimethylpiperazin-1-yl)benzamide;
N-(3-(1-methyl-1H-benzo[d]imidazol-2-yl)-4-chlorophenyl)-2-chloro-4-((3S,5R)-3,4,5-trimethylpiperazin-1-yl)benzamide;
N-(3-(6-methyl-1H-benzo[d]imidazol-2-yl)-4-chlorophenyl)-2-chloro-4-((3S,5R)-3,4,5-trimethylpiperazin-1-yl)benzamide;
N-(3-(6-methyl-1H-benzo[d]imidazol-2-yl)-4-chlorophenyl)-2-methyl-4-((3S,5R)-3,4,5-trimethylpiperazin-1-yl)benzamide;
N-(3-(6-chloro-1H-benzo[d]imidazol-2-yl)-4-methylphenyl)-2-chloro-4-((3S,5R)-3,4,5-trimethylpiperazin-1-yl)benzamide;
N-(3-(6-fluoro-1H-benzo[d]imidazol-2-yl)-4-chlorophenyl)-2-chloro-4-((3S,5R)-4-ethyl-3,5-dimethylpiperazin-1-yl)benzamide;
N-(3-(6-fluoro-1H-benzo[d]imidazol-2-yl)-4-methylphenyl)-2-chloro-4-((3S,5R)-3,4,5-trimethylpiperazin-1-yl)benzamide;
N-(3-(1H-benzo[d]imidazol-2-yl)-4-chlorophenyl)-2-methyl-6-((3S,5R)-3,4,5-trimethylpiperazin-1-yl)nicotinamide;
N-(3-(1H-benzo[d]imidazol-2-yl)-4-chlorophenyl)-2-chloro-6-((3S,5R)-3,4,5-trimethylpiperazin-1-yl)nicotinamide;
N-(3-(1H-benzo[d]imidazol-2-yl)-4-chlorophenyl)-4-((3S,5R)-3,4,5-trimethylpiperazin-1-yl)benzamide;

N-(3-(1H-benzo[d]imidazol-2-yl)-4-chlorophenyl)-2-(trifluoromethyl)-4-((3S,5R)-3,4,5-trimethylpiperazin-1-yl)benzamide;

N-(3-(1H-benzo[d]imidazol-2-yl)-4-chlorophenyl)-3-chloro-4-((3S,5R)-3,4,5-trimethylpiperazin-1-yl)benzamide;

N-(3-(1H-benzo[d]imidazol-2-yl)-4-chlorophenyl)-3-methyl-4-((3S,5R)-3,4,5-trimethylpiperazin-1-yl)benzamide;

N-(3-(1H-benzo[d]imidazol-2-yl)-4-chlorophenyl)-2-methyl-3-fluoro-4-((3S,5R)-3,4,5-trimethylpiperazin-1-yl)benzamide;

N-(3-(1H-benzo[d]imidazol-2-yl)-4-chlorophenyl)-2-chloro-5-fluoro-4-((3S,5R)-3,4,5-trimethylpiperazin-1-yl)benzamide;

N-(3-(1H-benzo[d]imidazol-2-yl)-4-chlorophenyl)-2-chloro-4-((3S,5R)-4-ethyl-3,5-dimethylpiperazin-1-yl)benzamide;

N-(3-(1H-benzo[d]imidazol-2-yl)-4-chlorophenyl)-2-chloro-4-((3S,5R)-4-isopropyl-3,5-dimethylpiperazin-1-yl)benzamide;

(S)—N-(3-(1H-benzo[d]imidazol-2-yl)-4-chlorophenyl)-2-chloro-4-(3,4-dimethylpiperazin-1-yl)benzamide;

N-(5-(1H-benzo[d]imidazol-2-yl)-6-chloropyridin-3-yl)-2-chloro-4-((3S,5R)-3,4,5-trimethylpiperazin-1-yl)benzamide;

N-(5-(1H-benzo[d]imidazol-2-yl)-6-chloropyridin-3-yl)-2-chloro-4-((2S,6R)-2,6-dimethylmorpholino)benzamide;

N-(5-(6-fluoro-1H-benzo[d]imidazol-2-yl)-6-chloropyridin-3-yl)-2-chloro-4-((3S,5R)-3,4,5-trimethylpiperazin-1-yl)benzamide;

N-(5-(6-chloro-1H-benzo[d]imidazol-2-yl)-6-chloropyridin-3-yl)-2-chloro-4-((3S,5R)-3,4,5-trimethylpiperazin-1-yl)benzamide;

N-(3-(6-fluoro-1H-benzo[d]imidazol-2-yl)-4-chlorophenyl)-2-chloro-4-((3S,5R)-3,4,5-trimethylpiperazin-1-yl)benzamide dihydrochloride;

N-(3-(1H-benzo[d]imidazol-2-yl)-4-chlorophenyl)-2-chloro-4-((3S,5R)-3,4,5-trimethylpiperazin-1-yl)benzamide dihydrochloride;

N-(3-(1H-benzo[d]imidazol-2-yl)-4-chlorophenyl)-3-chloro-4-((3S,5R)-3,4,5-trimethylpiperazin-1-yl)benzamide dihydrochloride;

N-(3-(1H-benzo[d]imidazol-2-yl)-4-chlorophenyl)-2-cyano-4-((3S,5R)-3,4,5-trimethylpiperazin-1-yl)benzamide dihydrochloride;

N-(3-(5-(4-methylthiophen-2-yl)-1H-imidazol-2-yl)-4-chlorophenyl)-2-methyl-4-((3S,5R)-3,4,5-trimethylpiperazin-1-yl)benzamide;

N-(3-(5-(4-methylthiophen-2-yl)-1H-imidazol-2-yl)-4-chlorophenyl)-2-chloro-4-((3S,5R)-3,4,5-trimethylpiperazin-1-yl)benzamide;

N-(3-(5-(5-chlorothiophen-2-yl)-1H-imidazol-2-yl)-4-chlorophenyl)-3-chloro-4-((3S,5R)-3,4,5-trimethylpiperazin-1-yl)benzamide;

N-(3-(5-(5-chlorothiophen-2-yl)-1H-imidazol-2-yl)-4-chlorophenyl)-2-chloro-4-((3S,5R)-3,4,5-trimethylpiperazin-1-yl)benzamide;

N-(3-(5-(thiophen-3-yl)-1H-imidazol-2-yl)-4-chlorophenyl)-2-methyl-4-((3S,5R)-3,4,5-trimethylpiperazin-1-yl)benzamide;

N-(3-(5-(thiophen-3-yl)-1H-imidazol-2-yl)-4-chlorophenyl)-2-chloro-4-((3S,5R)-3,4,5-trimethylpiperazin-1-yl)benzamide;

N-(3-(5-(thiophen-3-yl)-1H-imidazol-2-yl)-4-chlorophenyl)-2-methyl-3-fluoro-4-((3S,5R)-3,4,5-trimethylpiperazin-1-yl)benzamide;

N-(3-(5-(thiophen-3-yl)-1H-imidazol-2-yl)-4-chlorophenyl)-2-chloro-5-fluoro-4-((3S,5R)-3,4,5-trimethylpiperazin-1-yl)benzamide;

N-(3-(4-methyl-5-(thiophen-2-yl)-1H-imidazol-2-yl)-4-chlorophenyl)-2-methyl-4-((3S,5R)-3,4,5-trimethylpiperazin-1-yl)benzamide;

N-(3-(5-(furan-2-yl)-1H-imidazol-2-yl)-4-chlorophenyl)-2-chloro-4-((3S,5R)-3,4,5-trimethylpiperazin-1-yl)benzamide;

N-(3-(5-(furan-2-yl)-1H-imidazol-2-yl)-4-chlorophenyl)-2-methyl-4-((3S,5R)-3,4,5-trimethylpiperazin-1-yl)benzamide;

N-(3-(5-(furan-2-yl)-1H-imidazol-2-yl)-4-chlorophenyl)-2-(trifluoromethyl)-4-((3S,5R)-3,4,5-trimethylpiperazin-1-yl)benzamide;

N-(3-(5-(furan-2-yl)-1H-imidazol-2-yl)-4-chlorophenyl)-2-cyano-4-((3S,5R)-3,4,5-trimethylpiperazin-1-yl)benzamide;

N-(3-(5-(furan-2-yl)-1H-imidazol-2-yl)-4-chlorophenyl)-2-methyl-3-fluoro-4-((3S,5R)-3,4,5-trimethylpiperazin-1-yl)benzamide;

N-(3-(5-(furan-2-yl)-1H-imidazol-2-yl)-4-chlorophenyl)-2-chloro-5-fluoro-4-((3S,5R)-3,4,5-trimethylpiperazin-1-yl)benzamide;

N-(3-(5-(furan-2-yl)-1H-imidazol-2-yl)-4-chlorophenyl)-2-chloro-4-((3S,5R)-4-ethyl-3,5-dimethylpiperazin-1-yl)benzamide;

N-(3-(5-(5-methylfuran-2-yl)-1H-imidazol-2-yl)-4-chlorophenyl)-2-chloro-4-((3S,5R)-3,4,5-trimethylpiperazin-1-yl)benzamide;

N-(3-(5-(5-methylfuran-2-yl)-1H-imidazol-2-yl)-4-chlorophenyl)-2-methyl-4-((3S,5R)-3,4,5-trimethylpiperazin-1-yl)benzamide;

N-(3-(5-(thiazol-2-yl)-1H-imidazol-2-yl)-4-chlorophenyl)-2-chloro-4-((3S,5R)-3,4,5-trimethylpiperazin-1-yl)benzamide;

N-(3-(5-(thiazol-2-yl)-1H-imidazol-2-yl)-4-chlorophenyl)-2-methyl-4-((3S,5R)-3,4,5-trimethylpiperazin-1-yl)benzamide;

N-(3-(5-(thiophen-2-yl)-1H-imidazol-2-yl)-4-chlorophenyl)-2-(trifluoromethyl)-4-((3S,5R)-3,4,5-trimethylpiperazin-1-yl)benzamide;

N-(3-(5-(thiophen-2-yl)-1H-imidazol-2-yl)-4-chlorophenyl)-2-methyl-3-fluoro-4-((3S,5R)-3,4,5-trimethylpiperazin-1-yl)benzamide;

N-(3-(5-(thiophen-2-yl)-1H-imidazol-2-yl)-4-chlorophenyl)-2-chloro-5-fluoro-4-((3S,5R)-3,4,5-trimethylpiperazin-1-yl)benzamide;

N-(3-(5-(thiophen-2-yl)-1H-imidazol-2-yl)-4-chlorophenyl)-2-chloro-4-((3S,5R)-4-ethyl-3,5-dimethylpiperazin-1-yl)benzamide;

N-(3-(5-(thiophen-2-yl)-1H-imidazol-2-yl)-4-chlorophenyl)-2-chloro-4-((3S,5R)-4-isopropyl-3,5-dimethylpiperazin-1-yl)benzamide;

N-(3-(5-(thiophen-2-yl)-1H-imidazol-2-yl)-4-chlorophenyl)-2-chloro-4-(methylsulfonyl)benzamide;

N-(3-(5-(1-methyl-1H-pyrrol-2-yl)-1H-imidazol-2-yl)-4-chlorophenyl)-2-methyl-4-((3S,5R)-3,4,5-trimethylpiperazin-1-yl)benzamide;

N-(3-(5-(1-methyl-1H-pyrrol-2-yl)-1H-imidazol-2-yl)-4-chlorophenyl)-2-chloro-4-((3S,5R)-3,4,5-trimethylpiperazin-1-yl)benzamide;

N-(3-(5-(1-methyl-1H-pyrrol-2-yl)-1H-imidazol-2-yl)-4-chlorophenyl)-2-(trifluoromethyl)-4-((3S,5R)-3,4,5-trimethylpiperazin-1-yl)benzamide;
N-(3-(5-(thiophen-3-yl)-1H-imidazol-2-yl)-4-chlorophenyl)-2-(trifluoromethyl)-4-((3S,5R)-3,4,5-trimethylpiperazin-1-yl)benzamide dihydrochloride;
N-(3-(5-(thiophen-3-yl)-1H-imidazol-2-yl)-4-chlorophenyl)-2-chloro-4-((3S,5R)-4-ethyl-3,5-dimethylpiperazin-1-yl)benzamide dihydrochloride;
N-(3-(1H-imidazol-2-yl)-4-chlorophenyl)-2-methyl-4-((3S,5R)-3,4,5-trimethylpiperazin-1-yl)benzamide;
N-(3-(5-ethyl-1H-imidazol-2-yl)-4-chlorophenyl)-2-(trifluoromethyl)-4-((3S,5R)-3,4,5-trimethylpiperazin-1-yl)benzamide;
N-(3-(5-ethyl-1H-imidazol-2-yl)-4-chlorophenyl)-2-methyl-3-fluoro-4-((3S,5R)-3,4,5-trimethylpiperazin-1-yl)benzamide;
N-(3-(5-ethyl-1H-imidazol-2-yl)-4-chlorophenyl)-2-chloro-4-((3S,5R)-4-ethyl-3,5-dimethylpiperazin-1-yl)benzamide;
N-(3-(5-isopropyl-1H-imidazol-2-yl)-4-chlorophenyl)-2-methyl-4-((3S,5R)-3,4,5-trimethylpiperazin-1-yl)benzamide;
N-(3-(5-isopropyl-1H-imidazol-2-yl)-4-chlorophenyl)-2-(trifluoromethyl)-4-((3S,5R)-3,4,5-trimethylpiperazin-1-yl)benzamide;
N-(3-(5-propyl-1H-imidazol-2-yl)-4-chlorophenyl)-2-methyl-4-((3S,5R)-3,4,5-trimethylpiperazin-1-yl)benzamide;
N-(3-(5-propyl-1H-imidazol-2-yl)-4-chlorophenyl)-2-chloro-4-((3S,5R)-3,4,5-trimethylpiperazin-1-yl)benzamide;
N-(3-(5-tert-butyl-1H-imidazol-2-yl)-4-chlorophenyl)-2-methyl-4-((3S,5R)-3,4,5-trimethylpiperazin-1-yl)benzamide;
N-(3-(5-tert-butyl-1H-imidazol-2-yl)-4-chlorophenyl)-2-chloro-4-((3S,5R)-3,4,5-trimethylpiperazin-1-yl)benzamide;
N-(3-(5-cyclopropyl-1H-imidazol-2-yl)-4-chlorophenyl)-2-chloro-4-((3S,5R)-3,4,5-trimethylpiperazin-1-yl)benzamide;
N-(3-(5-cyclopropyl-1H-imidazol-2-yl)-4-chlorophenyl)-2-methyl-4-((3S,5R)-3,4,5-trimethylpiperazin-1-yl)benzamide;
N-(3-(5-cyclopropyl-1H-imidazol-2-yl)-4-chlorophenyl)-2-(trifluoromethyl)-4-((3S,5R)-3,4,5-trimethylpiperazin-1-yl)benzamide;
N-(3-(5-cyclopropyl-1H-imidazol-2-yl)-4-chlorophenyl)-2-methyl-3-fluoro-4-((3S,5R)-3,4,5-trimethylpiperazin-1-yl)benzamide;
N-(3-(5-cyclobutyl-1H-imidazol-2-yl)-4-chlorophenyl)-2-chloro-4-((3S,5R)-3,4,5-trimethylpiperazin-1-yl)benzamide;
N-(3-(5-cyclobutyl-1H-imidazol-2-yl)-4-chlorophenyl)-2-methyl-4-((3S,5R)-3,4,5-trimethylpiperazin-1-yl)benzamide;
N-(3-(5-cyclopentyl-1H-imidazol-2-yl)-4-chlorophenyl)-2-chloro-4-((3S,5R)-3,4,5-trimethylpiperazin-1-yl)benzamide;
N-(3-(5-cyclopentyl-1H-imidazol-2-yl)-4-chlorophenyl)-2-methyl-4-((3S,5R)-3,4,5-trimethylpiperazin-1-yl)benzamide;
N-(3-(5-cyclohexyl-1H-imidazol-2-yl)-4-chlorophenyl)-2-chloro-4-((3S,5R)-3,4,5-trimethylpiperazin-1-yl)benzamide;
N-(3-(5-cyclohexyl-1H-imidazol-2-yl)-4-chlorophenyl)-2-methyl-4-((3S,5R)-3,4,5-trimethylpiperazin-1-yl)benzamide;
N-(3-(5-methyl-1H-imidazol-2-yl)-4-chlorophenyl)-2-methyl-4-((3S,5R)-3,4,5-trimethylpiperazin-1-yl)benzamide dihydrochloride;
N-(3-(5-ethyl-1H-imidazol-2-yl)-4-chlorophenyl)-2-methyl-4-((3S,5R)-3,4,5-trimethylpiperazin-1-yl)benzamide dihydrochloride;
N-(3-(5-ethyl-1H-imidazol-2-yl)-4-chlorophenyl)-2-chloro-4-((3S,5R)-3,4,5-trimethylpiperazin-1-yl)benzamide dihydrochloride;
N-(3-(5-isopropyl-1H-imidazol-2-yl)-4-chlorophenyl)-2-chloro-4-((3S,5R)-3,4,5-trimethylpiperazin-1-yl)benzamide dihydrochloride;
N-(3-(5-isopropyl-1H-imidazol-2-yl)-4-chlorophenyl)-2-methyl-3-fluoro-4-((3S,5R)-3,4,5-trimethylpiperazin-1-yl)benzamide dihydrochloride;
N-(3-(5-isopropyl-1H-imidazol-2-yl)-4-chlorophenyl)-2-chloro-5-fluoro-4-((3S,5R)-3,4,5-trimethylpiperazin-1-yl)benzamide dihydrochloride;
N-(3-(5-isopropyl-1H-imidazol-2-yl)-4-chlorophenyl)-2-chloro-4-((3S,5R)-4-ethyl-3,5-dimethylpiperazin-1-yl)benzamide dihydrochloride;
N-(3-(5-cyclopropyl-1H-imidazol-2-yl)-4-chlorophenyl)-2-chloro-5-fluoro-4-((3S,5R)-3,4,5-trimethylpiperazin-1-yl)benzamide dihydrochloride;
N-(3-(5-cyclopropyl-1H-imidazol-2-yl)-4-chlorophenyl)-2-chloro-4-((3S,5R)-4-ethyl-3,5-dimethylpiperazin-1-yl)benzamide dihydrochloride;
N-(3-(3H-imidazo[4,5-b]pyridin-2-yl)-4-chlorophenyl)-2-chloro-4-((3S,5R)-3,4,5-trimethylpiperazin-1-yl)benzamide;
N-(3-(3H-imidazo[4,5-c]pyridin-2-yl)-4-chlorophenyl)-2-chloro-4-((3S,5R)-3,4,5-trimethylpiperazin-1-yl)benzamide;
N-(3-(3H-imidazo[4,5-c]pyridin-2-yl)-4-chlorophenyl)-2-methyl-4-((3S,5R)-3,4,5-trimethylpiperazin-1-yl)benzamide;
N-(3-(1H-thieno[3,4-d]imidazol-2-yl)-4-chlorophenyl)-2-methyl-4-((3S,5R)-3,4,5-trimethylpiperazin-1-yl)benzamide;
N-(3-(1H-thieno[3,4-d]imidazol-2-yl)-4-chlorophenyl)-2-chloro-4-((3S,5R)-3,4,5-trimethylpiperazin-1-yl)benzamide;
N-(3-(1H-thieno[3,4-d]imidazol-2-yl)-4-chlorophenyl)-2-(trifluoromethyl)-4-((3S,5R)-3,4,5-trimethylpiperazin-1-yl)benzamide;
N-(3-(1H-thieno[3,4-d]imidazol-2-yl)-4-chlorophenyl)-2-methyl-3-fluoro-4-((3S,5R)-3,4,5-trimethylpiperazin-1-yl)benzamide;
N-(3-(1H-thieno[3,4-d]imidazol-2-yl)-4-chlorophenyl)-2-chloro-5-fluoro-4-((3S,5R)-3,4,5-trimethylpiperazin-1-yl)benzamide;
N-(3-(1H-thieno[3,4-d]imidazol-2-yl)-4-chlorophenyl)-2-chloro-4-((3S,5R)-4-ethyl-3,5-dimethylpiperazin-1-yl)benzamide;
N-(3-(quinoxalin-2-yl)-4-chlorophenyl)-2-chloro-4-((3S,5R)-3,4,5-trimethylpiperazin-1-yl)benzamide;
N-(3-(imidazo[2,1-b]thiazol-6-yl)-4-chlorophenyl)-2-chloro-4-((3S,5R)-3,4,5-trimethylpiperazin-1-yl)benzamide;
N-(3-(benzo[d]oxazol-2-yl)-4-chlorophenyl)-2-methyl-4-((3S,5R)-3,4,5-trimethylpiperazin-1-yl)benzamide;
N-(3-(benzo[d]thiazol-2-yl)-4-chlorophenyl)-2-chloro-4-((3S,5R)-3,4,5-trimethylpiperazin-1-yl)benzamide;

N-(3-(pyridin-2-yl)-4-chlorophenyl)-2-chloro-4-((3S, 5R)-3,4,5-trimethylpiperazin-1-yl)benzamide; and
N-(3-(pyrimidin-2-yl)-4-chlorophenyl)-2-chloro-4-((3S, 5R)-3,4,5-trimethylpiperazin-1-yl)benzamide;
or a pharmaceutically acceptable salt thereof.

2. A method of treating a disease responsive to the inhibition of hedgehog activity in a mammal in need thereof, comprising administering a compound of claim 1, or a pharmaceutically acceptable salt thereof, to the mammal, wherein the disease is selected from the group consisting of basal cell carcinoma, medulloblastoma, melanoma, acute or chronic lymphocytic leukemia, multiple myeloma, breast carcinoma, ovarian carcinoma, lung carcinoma, cervical carcinoma, stomach carcinoma, colon carcinoma, pancreatic carcinoma, rhabdomyosarcoma, and prostatic carcinoma.

3. The method according to claim 2, wherein said disease is basal cell carcinoma, melanoma, acute or chronic lymphocytic leukemia, breast carcinoma, ovarian carcinoma, lung carcinoma, cervical carcinoma, stomach carcinoma, colon carcinoma, pancreatic carcinoma, rhabdomyosarcoma, or prostatic carcinoma.

4. The method of claim 3, further comprising administering at least one anticancer agent, or a pharmaceutically acceptable salt thereof, wherein the anticancer agent is selected from the group consisting of busulfan, melphalan, chlorambucil, cyclophosphamide, ifosfamide, temozolomide, bendamustine, cis-platin, mitomycin C, bleomycin, carboplatin, camptothecin, irinotecan, topotecan, doxorubicin, epirubicin, aclarubicin, mitoxantrone, elliptinium, etoposide, 5-azacytidine, gemcitabine, 5-fluorouracil, methotrexate, 5-fluoro-2'-deoxyuridine, fludarabine, nelarabine, ara-C, alanosine, pralatrexed, pemetrexed, hydroxyurea, thioguanine, colchicine, vinblastine, vincristine, vinorelbine, paclitaxel, ixabepilone, cabazitaxel, docetaxel, campath, Panitumumab, Ofatumumab, bevacizumab, trastuzumab, rituximab, imatinib, gefitinib, erlotinib, lapatinib, sorafenib, sunitinib, nilotinib, dasatinib, pazopanib, temsirolimus, everolimus, vorinostat, romidepsin, tamoxifen, letrozole, fulvestrant, mitoguazone, octreotide, retinoic acid, arsenic trioxide, zoledronic acid, bortezomib, thalidomide and lenalidomide.

5. The method according to claim 4, wherein optionally, the method further comprises treating said mammal with a radiation-therapy.

6. A pharmaceutical composition comprising a compound of claim 1, or a pharmaceutically acceptable salt thereof, and a pharmaceutically acceptable carrier.

7. The pharmaceutical composition according to claim 6, further comprising at least one anticancer agent, or a pharmaceutically acceptable salt thereof, wherein the anticancer agent is selected from the group consisting of busulfan, melphalan, chlorambucil, cyclophosphamide, ifosfamide, temozolomide, bendamustine, cis-platin, mitomycin C, bleomycin, carboplatin, camptothecin, irinotecan, topotecan, doxorubicin, epirubicin, aclarubicin, mitoxantrone, elliptinium, etoposide, 5-azacytidine, gemcitabine, 5-fluorouracil, methotrexate, 5-fluoro-2'-deoxyuridine, fludarabine, nelarabine, ara-C, alanosine, pralatrexed, pemetrexed, hydroxyurea, thioguanine, colchicine, vinblastine, vincristine, vinorelbine, paclitaxel, ixabepilone, cabazitaxel, docetaxel, campath, Panitumumab, Ofatumumab, bevacizumab, trastuzumab, rituximab, imatinib, gefitinib, erlotinib, lapatinib, sorafenib, sunitinib, nilotinib, dasatinib, pazopanib, temsirolimus, everolimus, vorinostat, romidepsin, tamoxifen, letrozole, fulvestrant, mitoguazone, octreotide, retinoic acid, arsenic trioxide, zoledronic acid, bortezomib, thalidomide and lenalidomide.

8. A compound having the structure of Formula IVa

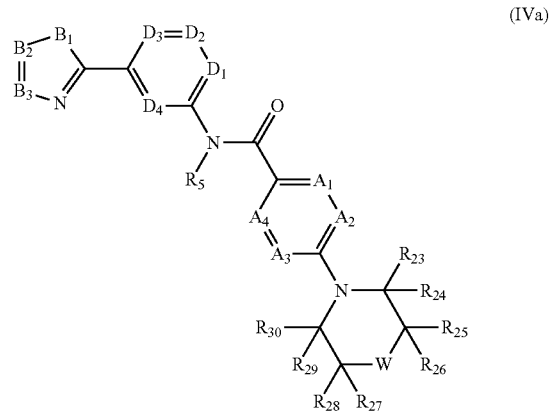

(IVa)

or pharmaceutically acceptable salts thereof, wherein:

$A_1$ is N or $CR_1$; $A_2$ is N or $CR_2$; $A_3$ is N or $CR_3$; $A_4$ is N or $CR_4$;

$R_1$-$R_4$ independently are hydrogen, halo, optionally substituted amino, alkoxy, $C_{1-10}$ alkyl, $C_{3-8}$ cycloalkyl, haloalkyl, optionally substituted aryl, a carbocyclic group, a heterocyclic group, optionally substituted heteroaryl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, hydroxyalkoxy, aminoalkyl, aminoalkoxy, carboxyalkyl, carboxyalkoxy, nitro, cyano, acylamino, aminocarbonyl, hydroxy, thiol, acyloxy, azido, carboxy, hydroxyacylamino, alkylsulfonyl, aminosulfonyl, acyl, dialkylaminosulfonyl, alkylsulfinyl, or alkylthiol;

$B_1$ is O, S, $CR_{10}$ or $NR_{14}$; $B_2$ is $CR_{11}$ or $NR_{15}$; $B_3$ is $CR_{12}$ or $NR_{16}$;

$R_{10}$-$R_{12}$ independently are hydrogen, halo, optionally substituted amino, alkoxy, $C_{1-10}$ alkyl, $C_{3-8}$ cycloalkyl, haloalkyl, optionally substituted aryl, a carbocyclic group, a heterocyclic group, optionally substituted heteroaryl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, hydroxyalkoxy, aminoalkyl, aminoalkoxy, carboxyalkyl, carboxyalkoxy, nitro, cyano, acylamino, aminocarbonyl, hydroxy, thiol, acyloxy, azido, carboxy, hydroxyacylamino, alkylsulfonyl, aminosulfonyl, acyl, dialkylaminosulfonyl, alkylsulfinyl, or alkylthiol;

$R_{14}$ is hydrogen;

$R_{15}$ and $R_{16}$ independently are hydrogen, $C_{1-10}$ alkyl, $C_{3-8}$ cycloalkyl, haloalkyl, optionally substituted aryl, a carbocyclic group, a heterocyclic group, optionally substituted heteroaryl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl; or $R_{10}$ or $R_{14}$ and $R_{11}$ or $R_{15}$, or $R_{11}$ or $R_{15}$ and $R_{12}$ or $R_{16}$, are taken together with C or N atom to which they are attached to form a five- or six-member aryl or heteroaryl;

$D_1$ is N or $CR_6$; $D_2$ is N or $CR_7$; $D_3$ is N or $CR_8$; $D_4$ is N or $CR_9$;

$R_6$-$R_9$ independently are hydrogen, halo, alkoxy, $C_{1-10}$ alkyl, $C_{3-8}$ cycloalkyl, haloalkyl, aryl, a carbocyclic group, a heterocyclic group, heteroaryl, alkenyl, alkynyl, arylalkyl, arylalkenyl, arylalkynyl, heteroarylalkyl, heteroarylalkenyl, heteroarylalkynyl, carbocycloalkyl, heterocycloalkyl, hydroxyalkyl, hydroxyalkoxy, aminoalkyl, aminoalkoxy, carboxyalkyl, carboxyalkoxy, nitro, cyano, acylamino, aminocarbonyl, thiol, acyloxy, azido, carboxy, hydroxyacylamino, alkylsulfonyl, aminosulfonyl, dialkylaminosulfonyl, alkylsulfinyl, or alkylthiol;

W is $NR_{33}$;

$R_5$ is hydrogen;

$R_{23}$, $R_{24}$, $R_{29}$ and $R_{30}$ independently are hydrogen or $C_{1-6}$ alkyl;

$R_{25}$ and $R_{27}$ are H;

$R_{26}$ is $C_{1-6}$ alkyl;

$R_{28}$ is $C_{1-6}$ alkyl; and $R_{33}$ is optionally substituted $C_{1-10}$ alkyl, haloalkyl, $C_{3-8}$ cycloalkyl, aryl, heteroaryl, a carbocyclic group, a heterocyclic group, alkenyl, alkynyl, acyl, arylalkyl, arylalkenyl, arylalkynyl, heteroarylalkyl, heteroarylalkenyl, heteroarylalkynyl, carbocycloalkyl, heterocycloalkyl, hydroxyalkyl, aminoalkyl, carboxyalkyl, alkylcarbonyl, cycloalkylcarbonyl, arylcarbonyl, heteroarylcarbonyl, heterocyclocarbonyl, aminocarbonyl, alkylsulfonyl, cycloalkylsulfonyl, or aminosulfonyl.

9. The compound of claim 8, wherein the compound has the structure of formula IVa, wherein:

$B_1$ is $NR_{14}$;

$B_2$ is $CR_{11}$;

$B_3$ is $CR_{12}$;

$R_{11}$ and $R_{12}$ independently are hydrogen; halo; $C_{1-6}$ alkyl; $C_{3-8}$ cycloalkyl; phenyl optionally substituted by 1-4 substituents selected from the group consisting of $C_{1-6}$ alkyl and halo; thienyl optionally substituted by 1-4 substituents selected from the group consisting of $C_{1-6}$ alkyl and halo; thiazolyl; pyrrolyl optionally substituted by 1-4 $C_{1-6}$ alkyl; or furyl optionally substituted by 1-4 $C_{1-6}$ alkyl; or $R_{11}$ and $R_{12}$ are taken together with the C atoms to which they are attached to form phenyl, pyridinyl or thienyl optionally substituted by one or two substituents selected from the group consisting of halo and $C_{1-6}$ alkyl;

$R_{14}$ is H;

$D_1$ is N or $CR_6$; $D_2$ is N or $CR_7$; $D_3$ is N or $CR_8$; $D_4$ is N or $CR_9$; with the proviso that (1) $D_1$ is $CR_6$, $D_2$ is $CR_7$, $D_3$ is $CR_8$, and $D_4$ is $CR_9$, or (2) at least one of $D_1$ to $D_4$ is N; wherein $R_6$-$R_9$ independently are hydrogen, halo, $C_{1-6}$ alkoxy, $C_{1-6}$ alkyl, and halo-$C_{1-6}$ alkyl;

$A_1$ is N or $CR_1$; $A_2$ is N or $CR_2$; $A_3$ is N or $CR_3$; $A_4$ is N or $CR_4$; with the proviso that (1) $A_1$ is $CR_1$, $A_2$ is $CR_2$, $A_3$ is $CR_3$, and $A_4$ is $CR_4$, or (2) at least one of $A_1$ to $A_4$ is N; wherein $R_1$-$R_4$ independently are hydrogen, halo, amino, $C_{1-6}$ alkoxy, $C_{1-6}$ alkyl, halo-$C_{1-6}$ alkyl, nitro, hydroxy, or $C_{1-6}$ alkylsulfonyl;

W is $NR_{33}$;

$R_{23}$, $R_{24}$, $R_{29}$ and $R_{30}$ independently are hydrogen or $C_{1-6}$ alkyl;

$R_{25}$ and $R_{27}$ are H;

$R_{26}$ and $R_{28}$ independently are $C_{1-6}$ alkyl; and $R_{33}$ is $C_{1-6}$ alkyl.

10. The compound of claim 8, wherein:

the cyclic group containing $B_1$-$B_3$ is imidazolyl substituted by one or two substituents selected from the group consisting of: thienyl optionally substituted by 1-4 substituents selected from the group consisting of $C_{1-6}$ alkyl and halo; thiazolyl; pyrrolyl optionally substituted by 1-4 $C_{1-6}$ alkyl; furyl optionally substituted by 1-4 $C_{1-6}$ alkyl; and $C_{3-8}$ cycloalkyl;

the cyclic group containing $D_1$-$D_4$ is phenyl optionally substituted by halo or $C_{1-6}$ alkyl;

the cyclic group containing $A_1$-$A_4$ is phenyl optionally substituted by $C_{1-6}$ alkyl, halo-$C_{1-6}$ alkyl or halo; and the W-containing cyclic group is piperazinyl substituted by $C_{1-6}$ alkyl at positions 3, 4 and 5.

11. A compound selected from the group consisting of:

N-(3-(5-isopropyl-1H-imidazol-2-yl)-4-chlorophenyl)-2-methyl-4-((3S,5R)-3,4,5-trimethylpiperazin-1-yl)benzamide;

N-(3-(5-isopropyl-1H-imidazol-2-yl)-4-chlorophenyl)-2-(trifluoromethyl)-4-((3S,5R)-3,4,5-trimethylpiperazin-1-yl)benzamide;

N-(3-(5-isopropyl-1H-imidazol-2-yl)-4-chlorophenyl)-2-chloro-4-((3S,5R)-3,4,5-trimethylpiperazin-1-yl)benzamide dihydrochloride;

N-(3-(5-isopropyl-1H-imidazol-2-yl)-4-chlorophenyl)-2-methyl-3-fluoro-4-((3S,5R)-3,4,5-trimethylpiperazin-1-yl)benzamide dihydrochloride;

N-(3-(5-isopropyl-1H-imidazol-2-yl)-4-chlorophenyl)-2-chloro-5-fluoro-4-((3S,5R)-3,4,5-trimethylpiperazin-1-yl)benzamide dihydrochloride;

N-(3-(5-isopropyl-1H-imidazol-2-yl)-4-chlorophenyl)-2-chloro-4-((3S,5R)-4-ethyl-3,5-dimethylpiperazin-1-yl)benzamide dihydrochloride;

N-(3-(5-cyclopropyl-1H-imidazol-2-yl)-4-chlorophenyl)-2-chloro-4-((3S,5R)-3,4,5-trimethylpiperazin-1-yl)benzamide;

N-(3-(5-cyclopropyl-1H-imidazol-2-yl)-4-chlorophenyl)-2-methyl-4-((3S,5R)-3,4,5-trimethylpiperazin-1-yl)benzamide;

N-(3-(5-cyclopropyl-1H-imidazol-2-yl)-4-chlorophenyl)-2-(trifluoromethyl)-4-((3S,5R)-3,4,5-trimethylpiperazin-1-yl)benzamide;

N-(3-(5-cyclopropyl-1H-imidazol-2-yl)-4-chlorophenyl)-2-methyl-3-fluoro-4-((3S,5R)-3,4,5-trimethylpiperazin-1-yl)benzamide;

N-(3-(5-cyclopropyl-1H-imidazol-2-yl)-4-chlorophenyl)-2-chloro-5-fluoro-4-((3S,5R)-3,4,5-trimethylpiperazin-1-yl)benzamide dihydrochloride; and N-(3-(5-cyclopropyl-1H-imidazol-2-yl)-4-chlorophenyl)-2-chloro-4-((3S,5R)-4-ethyl-3,5-dimethylpiperazin-1-yl)benzamide dihydrochloride;

or a pharmaceutically acceptable salt thereof.

12. A pharmaceutical composition comprising a compound of claim 8, or a pharmaceutically acceptable salt thereof, and a pharmaceutically acceptable carrier.

13. The pharmaceutical composition according to claim 12, further comprising at least one anticancer agent, or a pharmaceutically acceptable salt thereof, wherein the anticancer agent is selected from the group consisting of busulfan, melphalan, chlorambucil, cyclophosphamide, ifosfamide, temozolomide, bendamustine, cis-platin, mitomycin C, bleomycin, carboplatin, camptothecin, irinotecan, topotecan, doxorubicin, epirubicin, aclarubicin, mitoxantrone, elliptinium, etoposide, 5-azacytidine, gemcitabine, 5-fluorouracil, methotrexate, 5-fluoro-2'-deoxyuridine, fludarabine, nelarabine, ara-C, alanosine, pralatrexate, pemetrexed, hydroxyurea, thioguanine, colchicine, vinblastine, vincristine, vinorelbine, paclitaxel, ixabepilone, cabazitaxel, docetaxel, campath, Panitumumab, Ofatumumab, bevacizumab, trastuzumab, rituximab, imatinib, gefitinib, erlotinib, lapatinib, sorafenib, sunitinib, nilotinib, dasatinib, pazopanib, temsirolimus, everolimus, vorinostat, romidepsin, tamoxifen, letrozole, fulvestrant, mitoguazone, octreotide, retinoic acid, arsenic trioxide, zoledronic acid, bortezomib, thalidomide and lenalidomide.

14. A method of treating a disease responsive to the inhibition of hedgehog activity in a mammal in need thereof, comprising administering a compound of claim 8, or a pharmaceutically acceptable salt thereof, to the mammal, wherein the disease is selected from the group consisting of basal cell carcinoma, medulloblastoma, melanoma, acute or chronic lymphocytic leukemia, multiple myeloma, breast carcinoma, ovarian carcinoma, lung carcinoma, cervical carcinoma, stomach carcinoma, colon carcinoma, pancreatic carcinoma, rhabdomyosarcoma, and prostatic carcinoma.

15. The method according to claim 14, wherein said disease is basal cell carcinoma, melanoma, acute or chronic lymphocytic leukemia, multiple myeloma, breast carcinoma, ovarian carcinoma, lung carcinoma, cervical carcinoma, stomach carcinoma, colon carcinoma, pancreatic carcinoma, rhabdomyosarcoma, or prostatic carcinoma.

16. The method of claim 14, further comprising administering at least one anticancer agent, or a pharmaceutically acceptable salt thereof, wherein the anticancer agent is selected from the group consisting of busulfan, melphalan, chlorambucil, cyclophosphamide, ifosfamide, temozolomide, bendamustine, cis-platin, mitomycin C, bleomycin, carboplatin, camptothecin, irinotecan, topotecan, doxorubicin, epirubicin, aclarubicin, mitoxantrone, elliptinium, etoposide, 5-azacytidine, gemcitabine, 5-fluorouracil, methotrexate, 5-fluoro-2'-deoxyuridine, fludarabine, nelarabine, ara-C, alanosine, pralatrexate, pemetrexed, hydroxyurea, thioguanine, colchicine, vinblastine, vincristine, vinorelbine, paclitaxel, ixabepilone, cabazitaxel, docetaxel, campath, Panitumumab, Ofatumumab, bevacizumab, trastuzumab, rituximab, imatinib, gefitinib, erlotinib, lapatinib, sorafenib, sunitinib, nilotinib, dasatinib, pazopanib, temsirolimus, everolimus, vorinostat, romidepsin, tamoxifen, letrozole, fulvestrant, mitoguazone, octreotide, retinoic acid, arsenic trioxide, zoledronic acid, bortezomib, thalidomide and lenalidomide.

17. The method according to claim 16, wherein optionally, the method further comprises treating said mammal with a radiation-therapy.

* * * * *